US010961230B2

(12) United States Patent
Parham et al.

(10) Patent No.: US 10,961,230 B2
(45) Date of Patent: Mar. 30, 2021

(54) MATERIALS FOR ORGANIC ELECTROLUMINESCENT DEVICES

(71) Applicant: Merck Patent GmbH, Darmstadt (DE)

(72) Inventors: Amir Hossain Parham, Frankfurt am Main (DE); Thomas Eberle, Landau (DE); Anja Jatsch, Frankfurt am Main (DE); Tobias Grossmann, Darmstadt (DE); Jonas Valentin Kroeber, Frankfurt am Main (DE); Elvira Montenegro, Weinheim (DE); Dominik Joosten, Frankfurt am Main (DE); Caroline Wern, Darmstadt (DE)

(73) Assignee: Merck Patent GmbH, Darmstadt (DE)

( * ) Notice: Subject to any disclaimer, the term of this patent is extended or adjusted under 35 U.S.C. 154(b) by 237 days.

(21) Appl. No.: 16/081,463

(22) PCT Filed: Feb. 6, 2017

(86) PCT No.: PCT/EP2017/000155
§ 371 (c)(1),
(2) Date: Aug. 31, 2018

(87) PCT Pub. No.: WO2017/148565
PCT Pub. Date: Sep. 8, 2017

(65) Prior Publication Data
US 2019/0119260 A1 Apr. 25, 2019

(30) Foreign Application Priority Data

Mar. 3, 2016 (EP) .................................... 16158460
Mar. 11, 2016 (EP) .................................... 16159829

(51) Int. Cl.
| | | |
|---|---|---|
| *H01L 51/50* | (2006.01) | |
| *C07D 405/04* | (2006.01) | |
| *C07D 405/14* | (2006.01) | |
| *C07D 409/04* | (2006.01) | |
| *C07D 409/14* | (2006.01) | |
| *C07D 495/04* | (2006.01) | |
| *H01L 51/00* | (2006.01) | |
| *C09K 11/06* | (2006.01) | |

(52) U.S. Cl.
CPC ......... *C07D 405/04* (2013.01); *C07D 405/14* (2013.01); *C07D 409/04* (2013.01); *C07D 409/14* (2013.01); *C07D 495/04* (2013.01); *C09K 11/06* (2013.01); *H01L 51/006* (2013.01); *H01L 51/0058* (2013.01); *H01L 51/0061* (2013.01); *H01L 51/0072* (2013.01); *H01L 51/0073* (2013.01); *H01L 51/0074* (2013.01); *H01L 51/5016* (2013.01); *H01L 51/5096* (2013.01); *C09K 2211/1007* (2013.01); *C09K 2211/1011* (2013.01); *C09K 2211/1029* (2013.01); *C09K 2211/1088* (2013.01); *C09K 2211/1092* (2013.01); *H01L 51/5056* (2013.01)

(58) Field of Classification Search
None
See application file for complete search history.

(56) References Cited

U.S. PATENT DOCUMENTS

| | | |
|---|---|---|
| 9,145,363 B2 | 9/2015 | Yabunouchi et al. |
| 2016/0028014 A1 | 1/2016 | Kim et al. |
| 2016/0028020 A1 | 1/2016 | Lee et al. |
| 2017/0125689 A1 | 5/2017 | Lee et al. |
| 2017/0207399 A1 | 7/2017 | Parham et al. |
| 2019/0047992 A1* | 2/2019 | Park .................... H01L 51/0067 |
| 2019/0088878 A1 | 3/2019 | Parham et al. |

FOREIGN PATENT DOCUMENTS

| | | | |
|---|---|---|---|
| JP | 2019-512476 A | 5/2019 | |
| KR | 2014-103697 | * 8/2014 | ............. H01L 51/50 |
| KR | 10-2015-0001101 A | 1/2015 | |
| KR | 10-2015-0006199 A | 1/2015 | |
| KR | 2015-0004099 A | 1/2015 | |
| KR | 10-1512059 B1 | 4/2015 | |
| KR | 10-2015-0133998 A | 12/2015 | |
| WO | 2010/095621 A1 | 8/2010 | |
| WO | 2014/129764 A1 | 8/2014 | |
| WO | 2015/041428 A1 | 3/2015 | |
| WO | WO-2015041492 A1 | 3/2015 | |
| WO | WO-2015194791 A2 | 12/2015 | |
| WO | WO-2016015810 A1 | 2/2016 | |
| WO | WO-2017012687 A1 | 1/2017 | |
| WO | WO-2017016632 A1 | 2/2017 | |
| WO | 2017/148564 A1 | 9/2017 | |

OTHER PUBLICATIONS

International Search Report for PCT/EP2017/000154 dated Apr. 12, 2017.
International Search Report for PCT/EP2017/000155 dated Apr. 28, 2017.
Written Opinion of the International Searching Authority for PCT/EP2017/000154 dated Apr. 12, 2017.
Written Opinion of the International Searching Authority for PCT/EP2017/000155 dated Apr. 28, 2017.
International Preliminary Report on Patentability received for PCT Patent Application No. PCT/EP2017/000155, dated Sep. 13, 2018, 13 pages (8 pages of English Translation and 5 pages of Original Document).
International Search Report and Written Opinion received for PCT Patent Application No. PCT/EP2017/000155, dated Apr. 28, 2017, 15 pages (7 pages of English Translation and 8 pages of Original Document).

* cited by examiner

*Primary Examiner* — Gregory D Clark
(74) *Attorney, Agent, or Firm* — Faegre Drinker Biddle & Reath LLP

(57) ABSTRACT

The present invention describes amines with dibenzofuran or dibenzothiophene groups in combination with carbazole, especially for use as triplet matrix materials in organic electroluminescent devices. The invention further relates to a process for preparing the compounds of the invention and to electronic devices comprising these compounds.

7 Claims, No Drawings

MATERIALS FOR ORGANIC ELECTROLUMINESCENT DEVICES

CROSS-REFERENCE TO RELATED APPLICATIONS

This application is a national stage application (under 35 U.S.C. § 371) of PCT/EP2017/000155, filed Feb. 6, 2017, which claims benefit of European Application Nos. 16158460.2, filed Mar. 3, 2016, and 16159829.7, filed Mar. 11, 2016, all of which are incorporated herein by reference in their entirety.

The present invention describes amines with dibenzofuran or dibenzothiophene groups in combination with carbazole, especially for use as triplet matrix materials in organic electroluminescent devices. The invention further relates to a process for preparing the compounds of the invention and to electronic devices comprising these compounds.

BACKGROUND OF THE INVENTION

The structure of organic electroluminescent devices (OLEDs) in which organic semiconductors are used as functional materials is described, for example, in U.S. Pat. Nos. 4,539,507, 5,151,629, EP 0676461 and WO 98/27136. Emitting materials used are frequently organometallic complexes which exhibit phosphorescence. For quantum-mechanical reasons, up to four times the energy efficiency and power efficiency is possible using organometallic compounds as phosphorescent emitters. In general terms, there is still a need for improvement in OLEDs, especially also in OLEDs which exhibit phosphorescence, for example with regard to efficiency, operating voltage and lifetime.

The properties of phosphorescent OLEDs are not just determined by the triplet emitters used. More particularly, the other materials used, for example matrix materials, are also of particular significance here. Improvements to these materials can thus also lead to distinct improvements in the OLED properties.

In general terms, in the case of these materials for use as matrix materials, there is still need for improvement, particularly in relation to lifetime and oxidation sensitivity, but also in relation to the efficiency and operating voltage of the device.

BRIEF SUMMARY OF THE INVENTION

It is an object of the present invention to provide compounds suitable for use in a phosphorescent or fluorescent OLED, especially as matrix material. More particularly, it is an object of the present invention to provide matrix materials which are suitable for red-, yellow- and green-phosphorescing OLEDs and possibly also for blue-phosphorescing OLEDs, and which lead to long lifetime, good efficiency and low operating voltage. Particularly the properties of the matrix materials too have an essential influence on the lifetime and efficiency of the organic electroluminescent device.

It has been found that, surprisingly, electroluminescent devices containing compounds of the formula (1) or (2) below have improvements over the prior art, especially when used as matrix material for phosphorescent dopants.

JP 2012-049518 discloses a dibenzofuran which is substituted by a diphenylamine and is also substituted by a carbazole.

WO 2013/120577 discloses 9,9-spirobifluorenes substituted by at least one amine which may bear dibenzofurans as groups.

DETAILED DESCRIPTION OF THE INVENTION

The present invention therefore provides a compound of the following formulae (1) or (2):

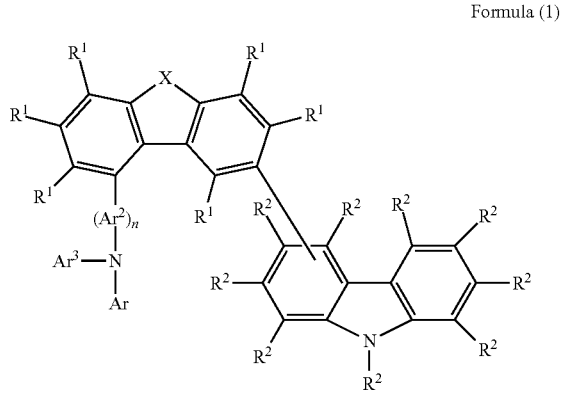

Formula (1)

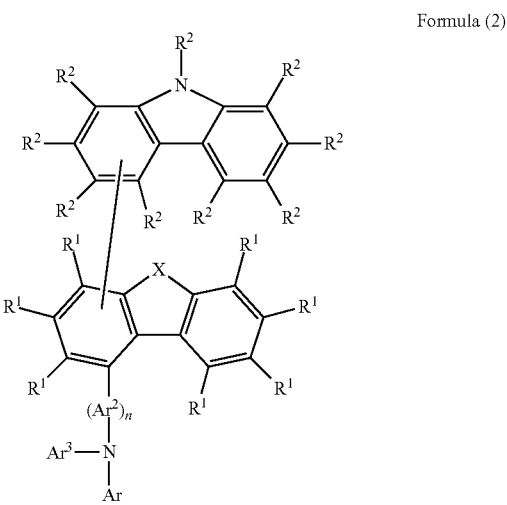

Formula (2)

where the symbols used are as follows:

X is O or S;

Ar is an aromatic or heteroaromatic ring system which has 5 to 40 aromatic ring atoms and may be substituted by one or more R radicals;

$Ar^1$ is the same or different at each instance and is an aromatic or heteroaromatic ring system which has 5 to 40 aromatic ring atoms and may be substituted by one or more $R^4$ radicals;

$Ar^2$ is a divalent aromatic or heteroaromatic ring system which has 5 to 40 aromatic ring atoms and may be substituted by one or more R radicals;

$Ar^3$ is an aromatic or heteroaromatic ring system which has 5 to 40 aromatic ring atoms and may be substituted by one or more R radicals;

R is the same or different at each instance and is selected from the group consisting of H, D, F, Cl, Br, I, CN, $NO_2$, $C(=O)R^4$, $C(=O)Ar^1$, $P(=O)(Ar^1)_2$, $P(Ar^1)_2$, $B(Ar^1)_2$, $N(R^4)_2$, $N(Ar^1)_2$, a straight-chain alkyl, alkoxy or thioalkyl group having 1 to 20 carbon atoms or a branched or cyclic alkyl, alkoxy or thioalkyl group having 3 to 20 carbon atoms or an alkenyl group having 2 to 20 carbon atoms, each of which may be substituted by one or more $R^4$ radicals, where one or more non-adjacent $CH_2$ groups may be replaced by $R^4C=CR^4$, $C=O$, $C=S$, $C=NR^4$, $P(=O)(R^4)$, $SO$, $SO_2$, $NR^4$, $O$, $S$ or $CONR^4$ and where one or more hydrogen atoms may be replaced by D, F, Cl, Br, I, CN or $NO_2$, an aromatic or heteroaromatic ring system which has 5 to 40 aromatic ring atoms and may be substituted in each case by one or more $R^4$ radicals, an aryloxy or heteroaryloxy group which has 5 to 40 aromatic ring atoms and may be substituted by one or more $R^4$ radicals, or an aralkyl or heteroaralkyl group which has 5 to 40 aromatic ring atoms and may be substituted by one or more $R^4$ radicals; at the same time, it is optionally possible for two R substituents bonded to the same carbon atom or to adjacent carbon atoms to form a monocyclic or polycyclic aliphatic or aromatic ring system which may be substituted by one or more $R^4$ radicals;

$R^1$ is the same or different at each instance and is selected from the group consisting of H, D, F, Cl, Br, I, CN, $NO_2$, $C(=O)R^4$, $C(=O)Ar^1$, $P(=O)(Ar^1)_2$, $P(Ar^1)_2$, $B(Ar^1)_2$, a straight-chain alkyl, alkoxy or thioalkyl group having 1 to 20 carbon atoms or a branched or cyclic alkyl, alkoxy or thioalkyl group having 3 to 20 carbon atoms or an alkenyl group having 2 to 20 carbon atoms, each of which may be substituted by one or more $R^4$ radicals, where one or more nonadjacent $CH_2$ groups may be replaced by $R^4C=CR^4$, $C=O$, $C=S$, $C=NR^4$, $P(=O)(R^4)$, $SO$, $SO_2$, $NR^4$, $O$, $S$ or $CONR^4$ and where one or more hydrogen atoms may be replaced by D, F, Cl, Br, I, CN or $NO_2$, an aromatic or heteroaromatic ring system which has 5 to 40 aromatic ring atoms and may be substituted in each case by one or more $R^4$ radicals, an aryloxy or heteroaryloxy group which has 5 to 40 aromatic ring atoms and may be substituted by one or more $R^4$ radicals, or an aralkyl or heteroaralkyl group which has 5 to 40 aromatic ring atoms and may be substituted by one or more $R^4$ radicals; at the same time, it is optionally possible for two $R^1$ substituents bonded to adjacent carbon atoms to form a monocyclic or polycyclic, aliphatic, aromatic or heteroaromatic ring system which may be substituted by one or more $R^4$ radicals;

$R^2$ is the same or different at each instance and is selected from the group consisting of H, D, F, Cl, Br, I, ON, $NO_2$, $C(=O)Ar^1$, $C(=O)R^4$, $P(=O)(Ar^1)_2$, $P(Ar^1)_2$, $B(Ar^1)_2$, $N(R^4)_2$, a straight-chain alkyl, alkoxy or thioalkyl group having 1 to 20 carbon atoms or a branched or cyclic alkyl, alkoxy or thioalkyl group having 3 to 20 carbon atoms or an alkenyl group having 2 to 20 carbon atoms, each of which may be substituted by one or more $R^4$ radicals, where one or more nonadjacent $CH_2$ groups may be replaced by $R^4C=CR^4$, $C=O$, $C=S$, $C=NR^4$, $P(=O)(R^4)$, $SO$, $SO_2$, $NR^4$, $O$, $S$ or $CONR^4$ and where one or more hydrogen atoms may be replaced by D, F, Cl, Br, I, CN or $NO_2$, an aromatic or heteroaromatic ring system which has 5 to 40 aromatic ring atoms and may be substituted in each case by one or more $R^4$ radicals, an aryloxy or heteroaryloxy group which has 5 to 40 aromatic ring atoms and may be substituted by one or more $R^4$ radicals, or an aralkyl or heteroaralkyl group which has 5 to 40 aromatic ring atoms and may be substituted by one or more $R^4$ radicals; at the same time, it is optionally possible for two $R^2$ substituents bonded to adjacent carbon atoms to form a monocyclic or polycyclic, aliphatic, aromatic or heteroaromatic ring system which may be substituted by one or more $R^4$ radicals;

$R^4$ is the same or different at each instance and is selected from the group consisting of H, D, F, Cl, Br, I, ON, $NO_2$, $N(R^5)_2$, $C(=O)R^5$, a straight-chain alkyl, alkoxy or thioalkyl group having 1 to 20 carbon atoms or a branched or cyclic alkyl, alkoxy or thioalkyl group having 3 to 20 carbon atoms or an alkenyl group having 2 to 20 carbon atoms, each of which may be substituted by one or more $R^5$ radicals, where one or more nonadjacent $CH_2$ groups may be replaced by $R^5C=CR^5$, $C=O$, $C=S$, $C=NR^5$, $P(=O)(R^5)$, $SO$, $SO_2$, $NR^5$, $O$, $S$ or $CONR^5$ and where one or more hydrogen atoms may be replaced by D, F, Cl, Br, I, CN or $NO_2$, an aromatic or heteroaromatic ring system which has 5 to 40 aromatic ring atoms and may be substituted in each case by one or more $R^5$ radicals, an aryloxy or heteroaryloxy group which has 5 to 40 aromatic ring atoms and may be substituted by one or more $R^5$ radicals, or an aralkyl or heteroaralkyl group which has 5 to 40 aromatic ring atoms and may be substituted by one or more $R^5$ radicals; at the same time, it is optionally possible for two $R^4$ substituents bonded to the same carbon atom or adjacent carbon atoms to form a monocyclic or polycyclic, aliphatic, aromatic or heteroaromatic ring system which may be substituted by one or more $R^5$ radicals;

$R^5$ is the same or different at each instance and is selected from the group consisting of H, D, F, CN, an aliphatic hydrocarbyl radical having 1 to 20 carbon atoms, or an aromatic or heteroaromatic ring system having 5 to 30 aromatic ring atoms in which one or more hydrogen atoms may be replaced by D, F, Cl, Br, I or CN and which may be substituted by one or more alkyl groups each having 1 to 4 carbon atoms; at the same time, it is possible for two or more adjacent $R^5$ substituents together to form a mono- or polycyclic, aliphatic ring system;

n is 0 or 1;

where one $R^2$ in formula (1), and one $R^2$ and one $R^1$ bonded to a carbon atom in formula (2) are substituted by the single bond, i.e. the one radical $R^2$ in formula (1) and one radical $R^2$ and one radical $R^1$ bonded to a carbon atom in formula (2) are not present and are replaced by the single bond.

Adjacent carbon atoms in the context of the present invention are carbon atoms bonded directly to one another.

The wording that two or more radicals together may form a ring, in the context of the present description, shall be understood to mean, inter alia, that the two radicals are joined to one another by a chemical bond with formal elimination of two hydrogen atoms. This is illustrated by the following scheme:

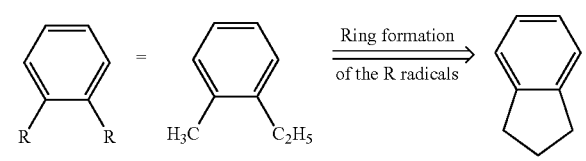

In addition, however, the abovementioned wording shall also be understood to mean that, if one of the two radicals is hydrogen, the second radical binds to the position to which the hydrogen atom was bonded, forming a ring. This shall be illustrated by the following scheme;

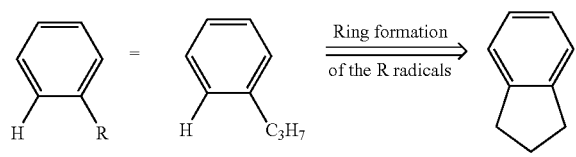

A fused aryl group in the context of the present invention is a group in which two or more aromatic groups are fused, i.e. annellated, to one another along a common edge, as, for example, in naphthalene. By contrast, for example, fluorene is not a fused aryl group in the context of the present invention, since the two aromatic groups in fluorene do not have a common edge.

An aryl group in the context of this invention contains 6 to 40 carbon atoms; a heteroaryl group in the context of this invention contains 2 to 40 carbon atoms and at least one heteroatom, with the provision that the sum total of carbon atoms and heteroatoms is at least 5. The heteroatoms are preferably selected from N, O and/or S. An aryl group or heteroaryl group is understood here to mean either a simple aromatic cycle, i.e. benzene, or a simple heteroaromatic cycle, for example pyridine, pyrimidine, thiophene, etc., or a fused aryl or heteroaryl group, for example naphthalene, anthracene, phenanthrene, quinoline, isoquinoline, etc.

An aromatic ring system in the context of this invention contains 6 to 40 carbon atoms in the ring system. A heteroaromatic ring system in the context of this invention contains 1 to 40 carbon atoms and at least one heteroatom in the ring system, with the proviso that the sum total of carbon atoms and heteroatoms is at least 5. The heteroatoms are preferably selected from N, O and/or S. An aromatic or heteroaromatic ring system in the context of this invention shall be understood to mean a system which does not necessarily contain only aryl or heteroaryl groups, but in which it is also possible for two or more aryl or heteroaryl groups to be interrupted by a nonaromatic unit (preferably less than 10% of the atoms other than H), for example a carbon, nitrogen or oxygen atom or a carbonyl group. For example, systems such as 9,9'-spirobifluorene, 9,9-diarylfluorene, triarylamine, diaryl ethers, stilbene, etc. shall thus also be regarded as aromatic ring systems in the context of this invention, and likewise systems in which two or more aryl groups are interrupted, for example, by a linear or cyclic alkyl group or by a silyl group. In addition, systems in which two or more aryl or heteroaryl groups are bonded directly to one another, for example biphenyl, terphenyl, quaterphenyl or bipyridine, shall likewise be regarded as an aromatic or heteroaromatic ring system.

A cyclic alkyl, alkoxy or thioalkoxy group in the context of this invention is understood to mean a monocyclic, bicyclic or polycyclic group.

In the context of the present invention, a $C_1$ to $C_{20}$-alkyl group in which individual hydrogen atoms or $CH_2$ groups may also be substituted by the abovementioned groups is understood to mean, for example, the methyl, ethyl, n-propyl, i-propyl, cyclopropyl, n-butyl, i-butyl, s-butyl, t-butyl, cyclobutyl, 2-methylbutyl, n-pentyl, s-pentyl, t-pentyl, 2-pentyl, neopentyl, cyclopentyl, n-hexyl, s-hexyl, t-hexyl, 2-hexyl, 3-hexyl, neohexyl, cyclohexyl, 1-methylcyclopentyl, 2-methylpentyl, n-heptyl, 2-heptyl, 3-heptyl, 4-heptyl, cycloheptyl, 1-methylcyclohexyl, n-octyl, 2-ethylhexyl, cyclooctyl, 1-bicyclo[2.2.2]octyl, 2-bicyclo[2.2.2]octyl, 2-(2,6-dimethyl)octyl, 3-(3,7-dimethyl)octyl, adamantyl, trifluoromethyl, pentafluoroethyl, 2,2,2-trifluoroethyl, 1,1-dimethyl-n-hex-1-yl, 1,1-dimethyl-n-hept-1-yl, 1,1-dimethyl-n-oct-1-yl, 1,1-dimethyl-n-dec-1-yl, 1,1-dimethyl-n-dodec-1-yl, 1,1-dimethyl-n-tetradec-1-yl, 1,1-dimethyl-n-hexadec-1-yl, 1,1-dimethyl-n-octadec-1-yl, 1,1-diethyl-n-hex-1-yl, 1,1-diethyl-n-hept-1-yl, 1,1-diethyl-n-oct-1-yl, 1,1-diethyl-n-dec-1-yl, 1,1-diethyl-n-dodec-1-yl, 1,1-diethyl-n-tetradec-1-yl, 1,1-diethyl-n-hexadec-1-yl, 1,1-diethyl-n-octadec-1-yl, 1-(n-propyl)cyclohex-1-yl, 1-(n-butyl)cyclohex-1-yl, 1-(n-hexyl)cyclohex-1-yl, 1-(n-octyl)cyclohex-1-yl and 1-(n-decyl)cyclohex-1-yl radicals. An alkenyl group is understood to mean, for example, ethenyl, propenyl, butenyl, pentenyl, cyclopentenyl, hexenyl, cyclohexenyl, heptenyl, cycloheptenyl, octenyl, cyclooctenyl or cyclooctadienyl. An alkynyl group is understood to mean, for example, ethynyl, propynyl, butynyl, pentynyl, hexynyl, heptynyl or octynyl. A $C_1$- to $C_{40}$-alkoxy group is understood to mean, for example, methoxy, trifluoromethoxy, ethoxy, n-propoxy, i-propoxy, n-butoxy, i-butoxy, s-butoxy, t-butoxy or 2-methylbutoxy.

An aromatic or heteroaromatic ring system which has 5-40 aromatic ring atoms and may also be substituted in each case by the abovementioned radicals and which may be joined to the aromatic or heteroaromatic system via any desired positions is understood to mean, for example, groups derived from benzene, naphthalene, anthracene, benzanthracene, phenanthrene, benzophenanthrene, pyrene, chrysene, perylene, fluoranthene, benzofluoranthene, naphthacene, pentacene, benzopyrene, biphenyl, biphenylene, terphenyl, terphenylene, fluorene, spirobifluorene, dihydrophenanthrene, dihydropyrene, tetrahydropyrene, cis- or trans-indenofluorene, cis- or trans-monobenzoindenofluorene, cis- or trans-dibenzoindenofluorene, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, indolocarbazole, indenocarbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

In one embodiment of the invention, when n is 0, Ar and $Ar^3$ are not both phenyl.

The Ar and $Ar^3$ groups are not joined to one another by bonds other than via the nitrogen atom.

In one embodiment of the invention, the carbazolyl group in formula (1) is not bonded to the dibenzofuran or dibenzothiophene via the 2 position thereof.

In a preferred embodiment of the invention, the compound is a compound of the formula (1-1) or formula (2-1)

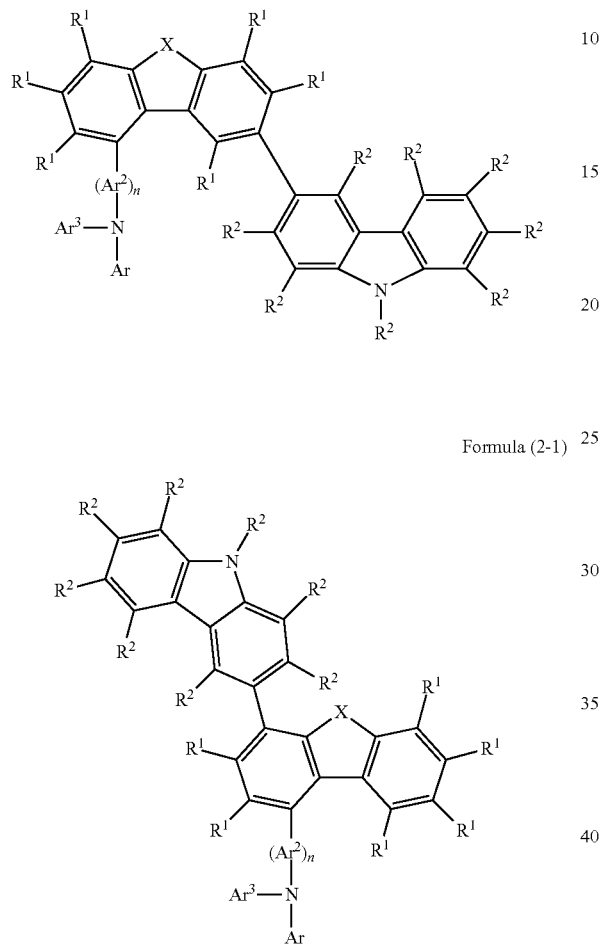

Formula (1-1)

Formula (2-1)

where the indices and symbols correspond to the indices and symbols of formula (1) and (2).

In a further preferred embodiment of the invention, Ar and/or $Ar^3$ is/are the same or different at each instance and is an aromatic or heteroaromatic ring system having 6 to 24 aromatic ring atoms, preferably 6 to 18 aromatic ring atoms, and is more preferably an aromatic ring system having 6 to 12 aromatic ring atoms or a heteroaromatic ring system having 6 to 13 aromatic ring atoms, each of which may be substituted by one or more R radicals, but is preferably unsubstituted. Examples of suitable Ar and $Ar^3$ groups are the same or different at each instance and are selected from the group consisting of phenyl, ortho-, meta- or para-biphenyl, terphenyl, especially branched terphenyl, quaterphenyl, especially branched quaterphenyl, 1-, 2-, 3- or 4-fluorenyl, pyridyl, pyrimidinyl, 1-, 2-, 3- or 4-dibenzofuranyl and 1-, 2-, 3- or 4-dibenzothienyl, each of which may be substituted by one or more R radicals, but are preferably unsubstituted.

In a preferred embodiment of the invention, Ar and $Ar^3$ are the same or different at each instance and are selected from the structures of the formulae (Ar-1) to (Ar-16):

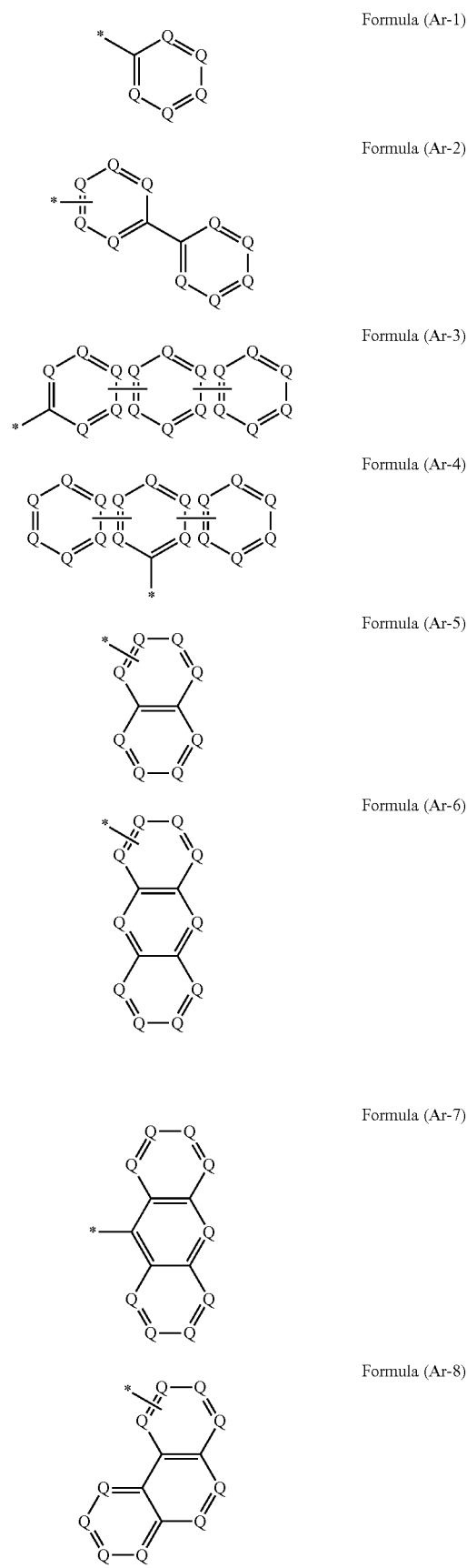

-continued

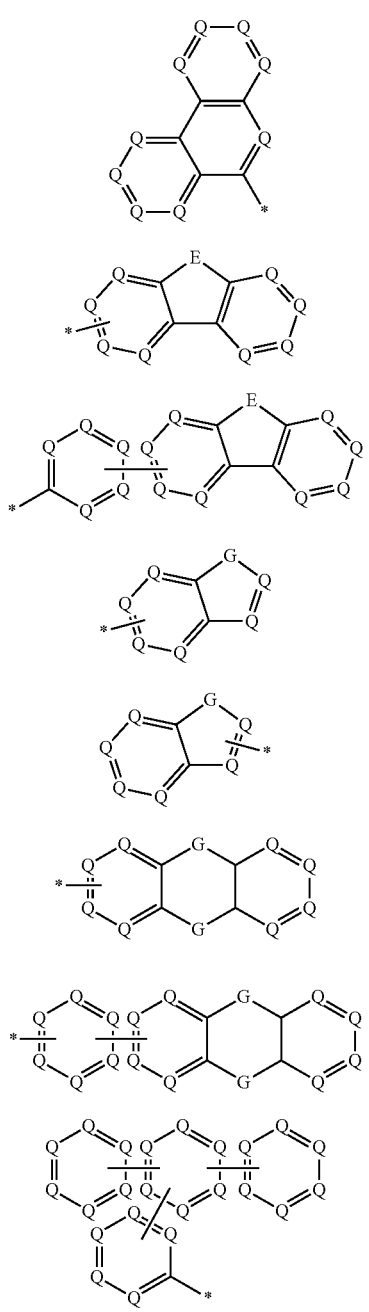

Formula (Ar-9)

Formula (Ar-10)

Formula (Ar-11)

Formula (Ar-12)

Formula (Ar-13)

Formula (Ar-14)

Formula (Ar-15)

Formula (Ar-16)

where the symbols correspond to the symbols of the formula (1) and, in, addition, Q is the same or different at each instance and is $CR^4$ or N, where not more than 3 Q symbols per cycle are N;

E is the same or different at each instance and is $NR^4$, $C(R^4)_2$, O, S or C=O;

G at each instance is $NR^4$, $C(R^4)_2$, O, S or C=O; and

* represents the bond to the nitrogen atom

Preferably, a maximum of one Q is N. More preferably, no Q is N.

In a further preferred embodiment, the Ar and $Ar^3$ groups at each instance are selected from the groups having the structures of formulae (Ar-1) to (Ar-16), where the general formulae are replaced by the respective particularly preferred embodiments of the following formulae (Ar-1-1) to (Ar-16-6) (for example, formula (Ar-1) is replaced by one of the formulae (Ar-1-1) to (Ar-1-9)):

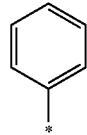

Formula (Ar-1-1)

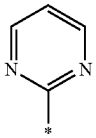

Formula (Ar-1-2)

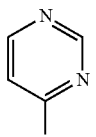

Formula (Ar-1-3)

Formula (Ar-1-4)

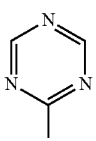

Formula (Ar-1-5)

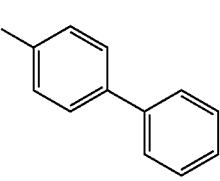

Formula (Ar-2-1)

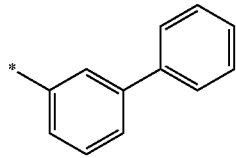

Formula (Ar-2-2)

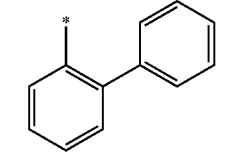

Formula (Ar-2-3)

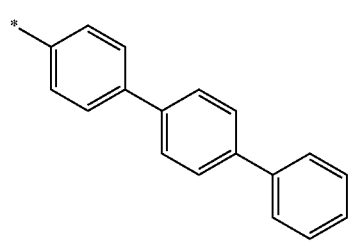

Formula (Ar-3-1)

Formula (Ar-3-2)
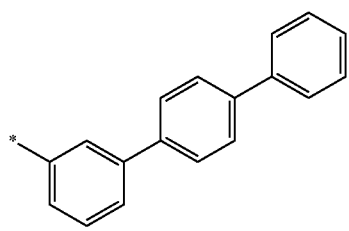
Formula (Ar-3-3)
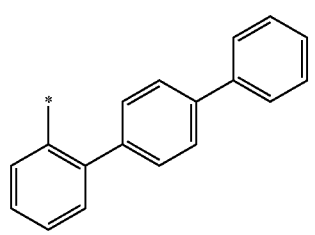
Formula (Ar-3-4)
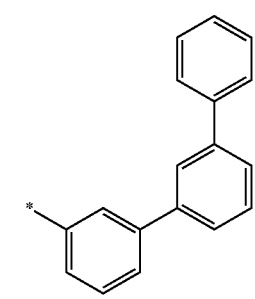
Formula (Ar-3-5)
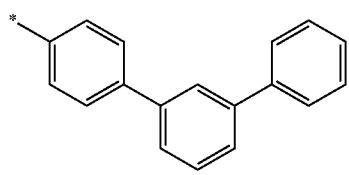
Formula (Ar-3-6)
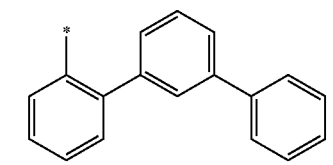
Formula (Ar-3-7)
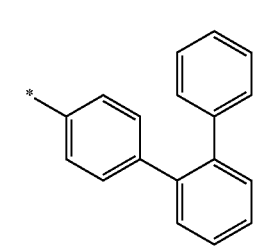
Formula (Ar-3-8)
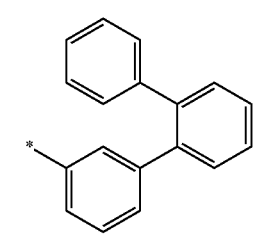
Formula (Ar-3-9)
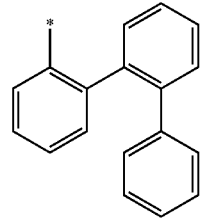
Formula (Ar-4-1)
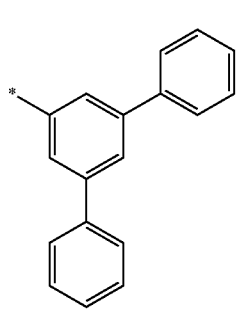
Formula (Ar-4-2)
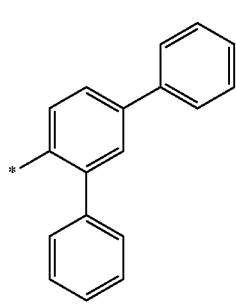
Formula (Ar-4-3)
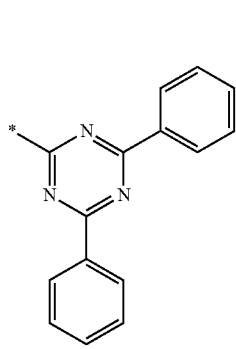
Formula (Ar-4-4)
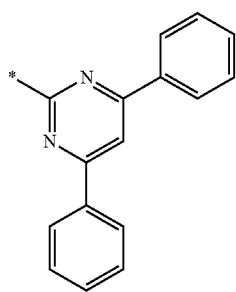

-continued
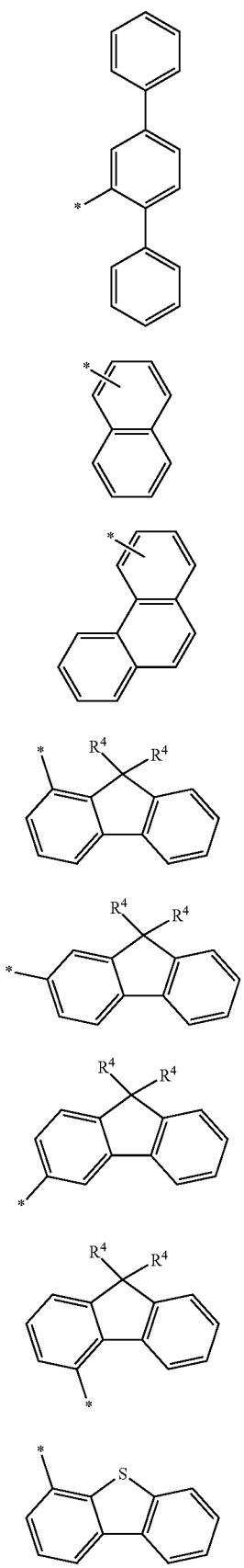
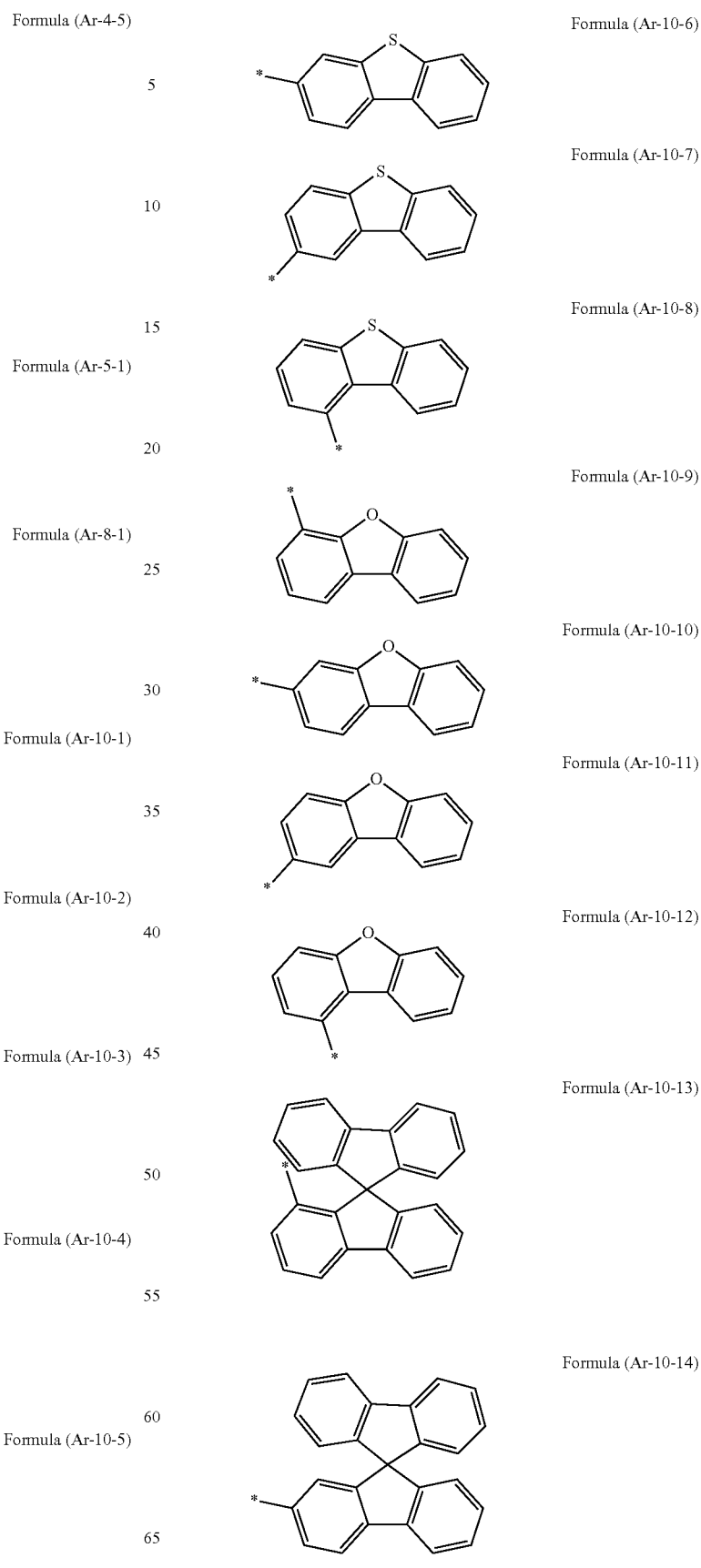

-continued
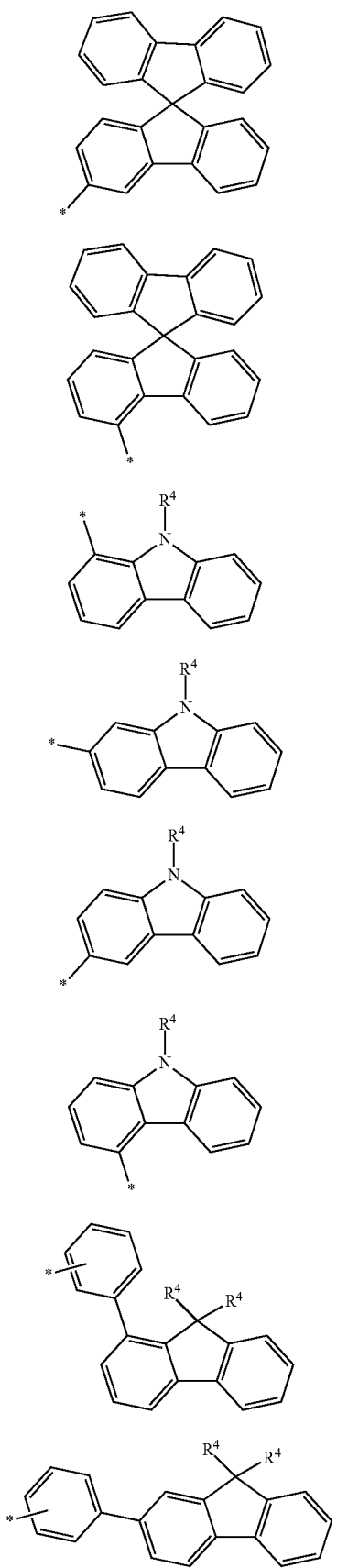
Formula (Ar-10-15)
Formula (Ar-10-16)
Formula (Ar-10-17)
Formula (Ar-10-18)
Formula (Ar-10-19)
Formula (Ar-10-20)
Formula (Ar-11-1)
Formula (Ar-11-2)
-continued
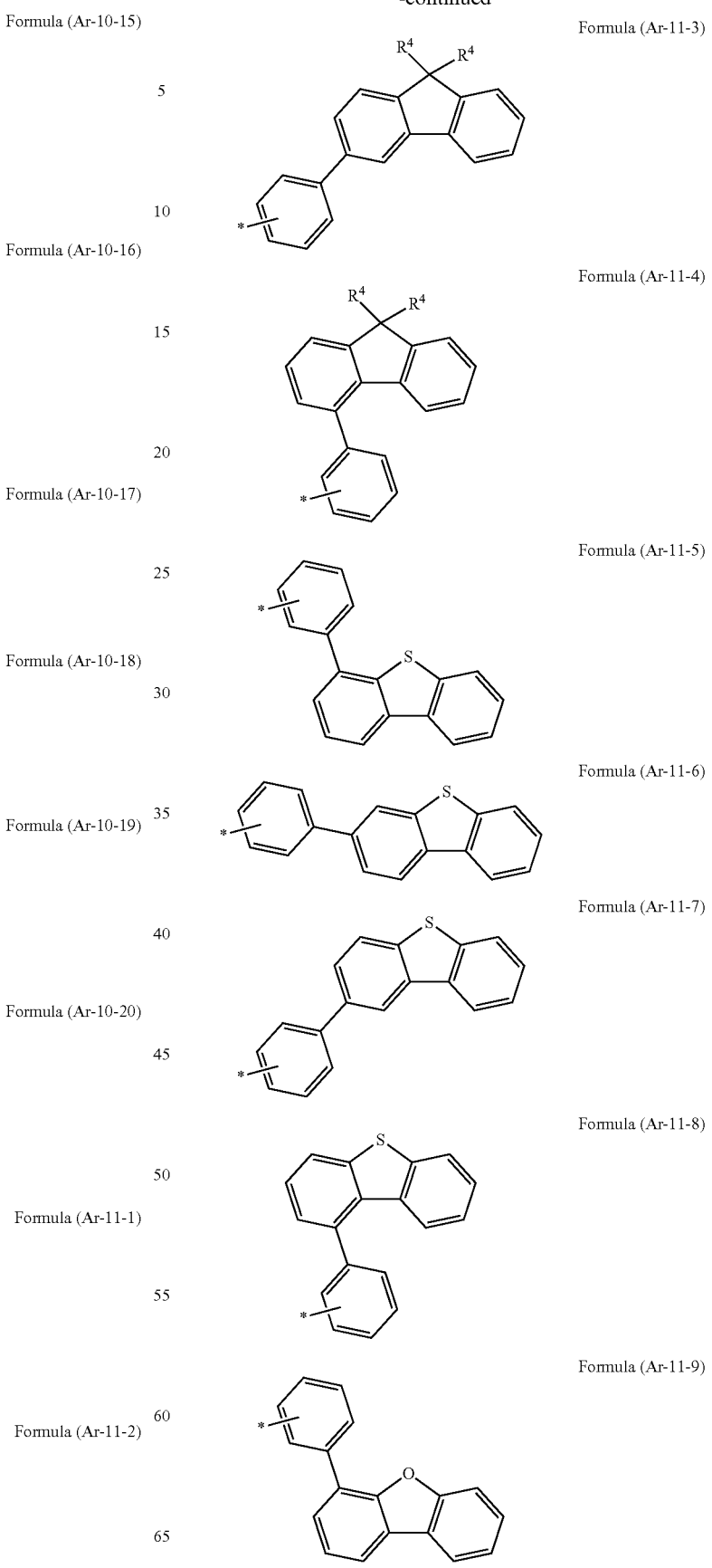
Formula (Ar-11-3)
Formula (Ar-11-4)
Formula (Ar-11-5)
Formula (Ar-11-6)
Formula (Ar-11-7)
Formula (Ar-11-8)
Formula (Ar-11-9)

-continued
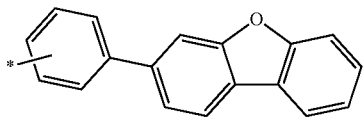
Formula (Ar-11-10)
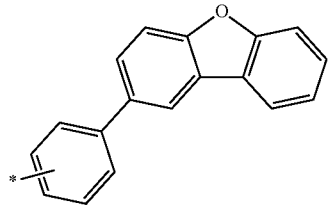
Formula (Ar-11-11)
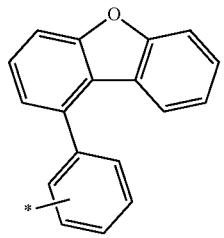
Formula (Ar-11-12)
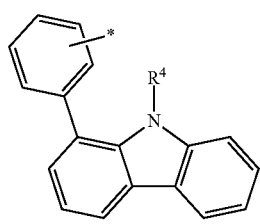
Formula (Ar-11-13)
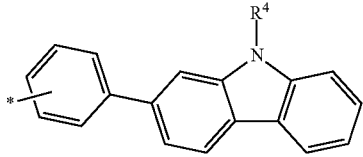
Formula (Ar-11-14)
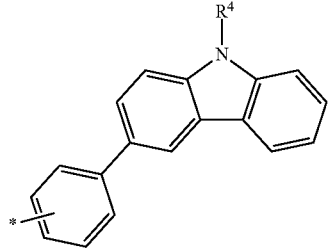
Formula (Ar-11-15)
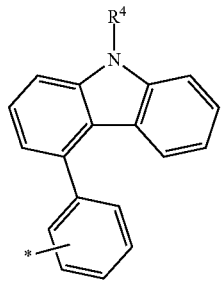
Formula (Ar-11-16)
-continued
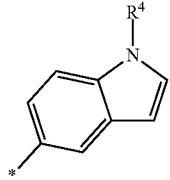
Formula (Ar-12-1)
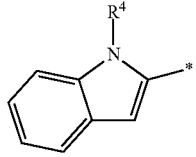
Formula (Ar-13-1)
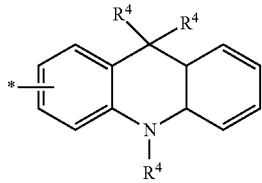
Formula (Ar-14-1)
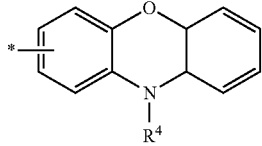
Formula (Ar-14-2)
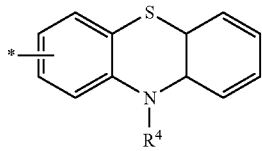
Formula (Ar-14-3)
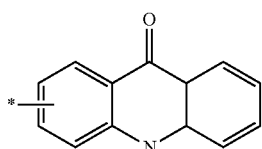
Formula (Ar-14-4)
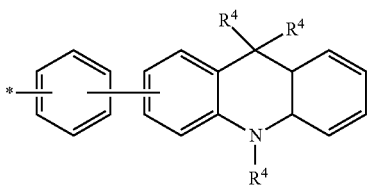
Formula (Ar-15-1)
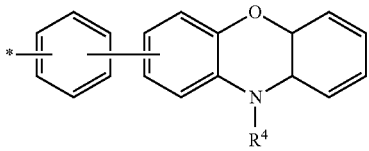
Formula (Ar-15-2)
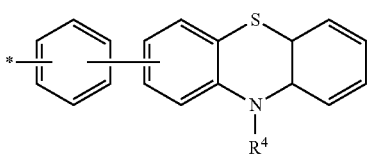
Formula (Ar-15-3)

Formula (Ar-15-4)
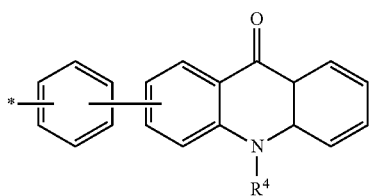
Formula (Ar-16-1)
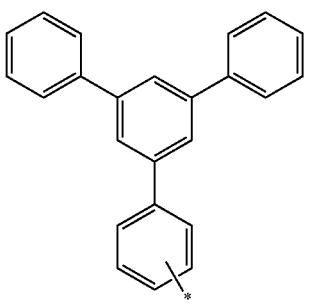
Formula (Ar-16-2)
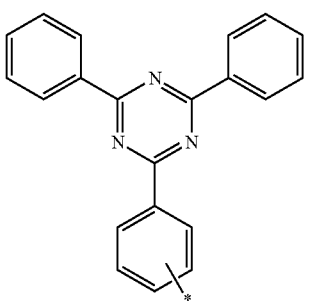
Formula (Ar-16-3)
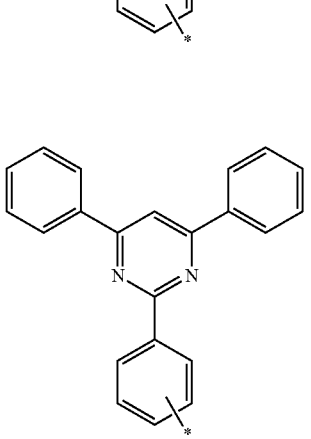
Formula (Ar-16-4)
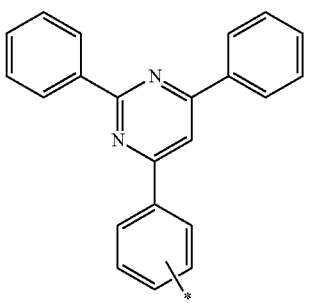
Formula (Ar-16-5)
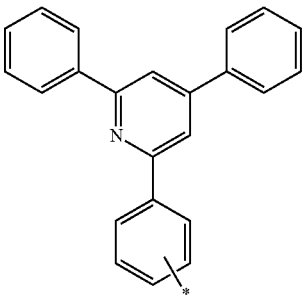
Formula (Ar-16-6)
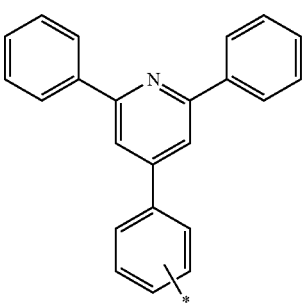
where the symbols correspond to the symbols in formula (Ar-1) to (Ar-16). The formulae may be substituted by $R^4$ at the free positions.
In a further preferred embodiment of the invention, Ar is selected from the formulae (Ar-1-1) to (Ar-11-16a):
Formula (Ar1-1)
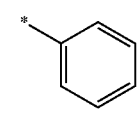
Formula (Ar-2-1)
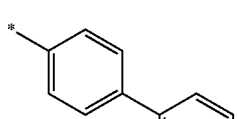
Formula (Ar-2-3)
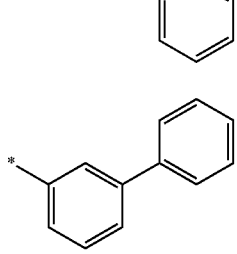
Formula (Ar-4-1)
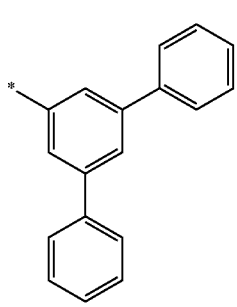

Formula (Ar-4-2)

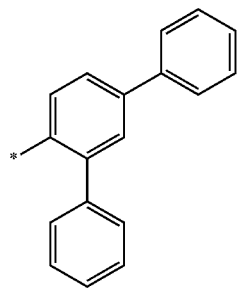

Formula (Ar-4-5)

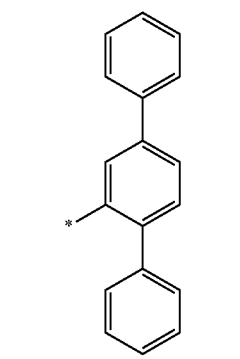

Formula (Ar-10-2a)

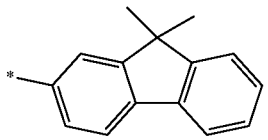

Formula (Ar-10-2b)

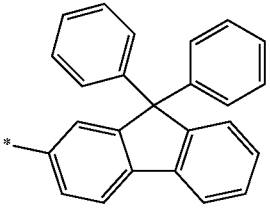

Formula (Ar-10-2c)

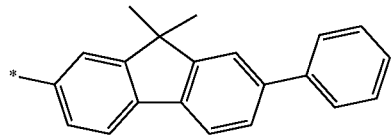

Formula (Ar-11-2a)

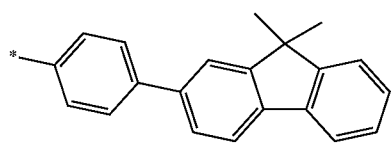

Formula (Ar-11-2b)

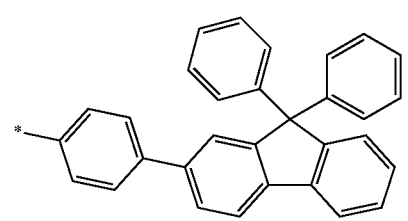

Formula (Ar-11-9a)

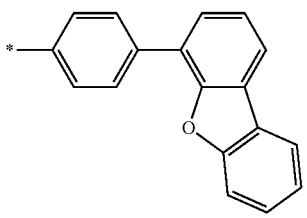

Formula (Ar-11-16a)

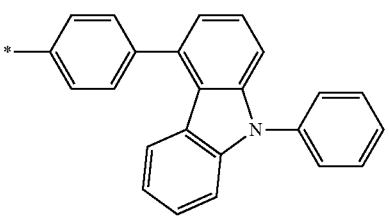

Where the symbols correspond to the symbols in formula (Ar-1) to (Ar-16). The formulae may be substituted at the free positions by $R^4$; they are preferably unsubstituted.

In a further embodiment of the invention, $Ar^3$ is selected from the formulae (Ar-10-2a) to (Ar-11-16a):

Formula (Ar-10-2a)

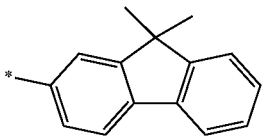

Formula (Ar-10-2b)

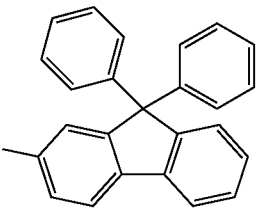

Formula (Ar-10-2c)

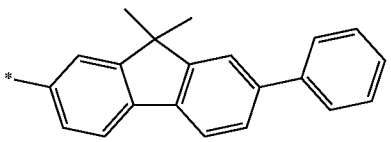

Formula (Ar-10-2d)

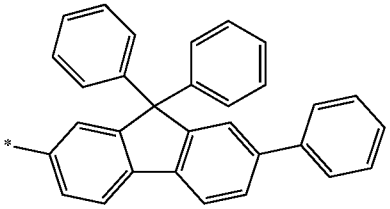

Formula (Ar-10-2e)

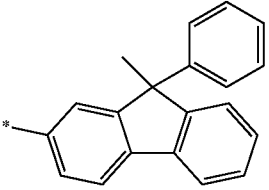

Formula (Ar-10-14)
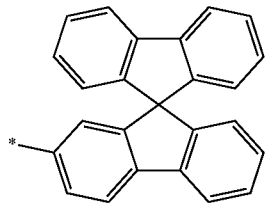
Formula (Ar-10-14a)
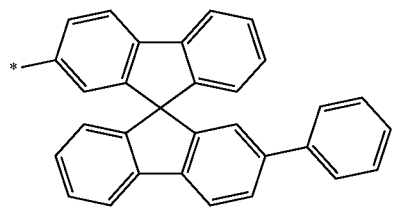
Formula (Ar-10-14b)
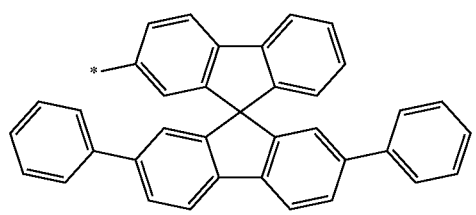
Formula (Ar-10-14c)
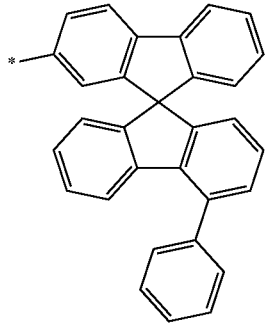
Formula (Ar-11-2b)
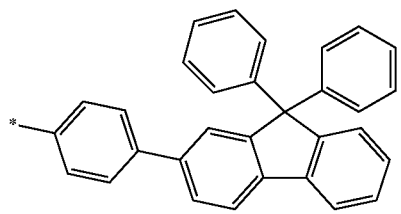
Formula (Ar-11-2c)
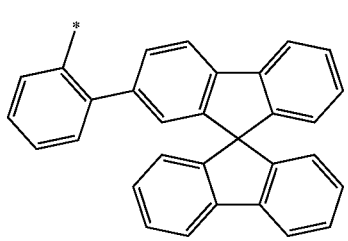
Formula (Ar-11-2d)
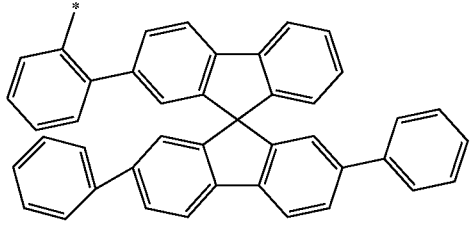
Formula (Ar-11-2e)
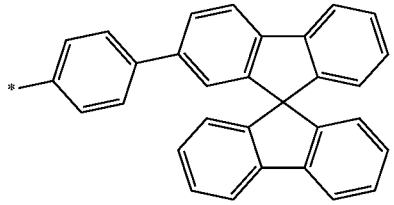
Formula (Ar-11-2f)
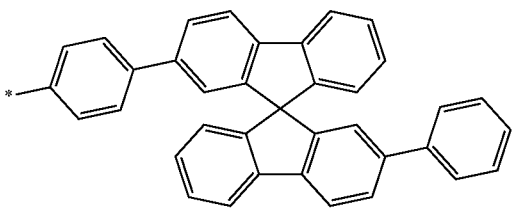
Formula (Ar-11-2g)
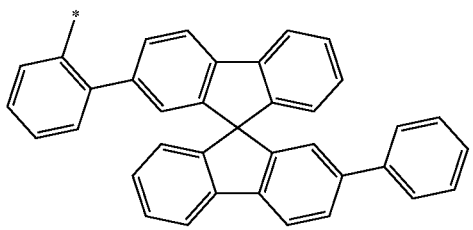
Formula (Ar-11-2h)
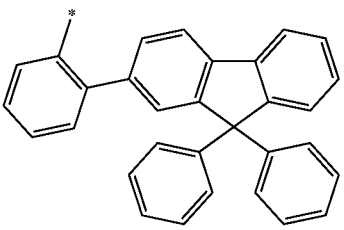
Formula (Ar-11-2i)
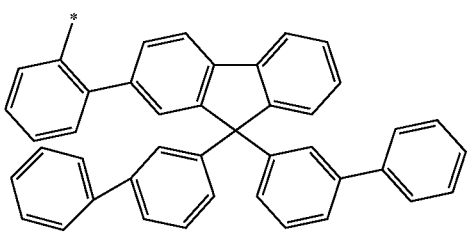

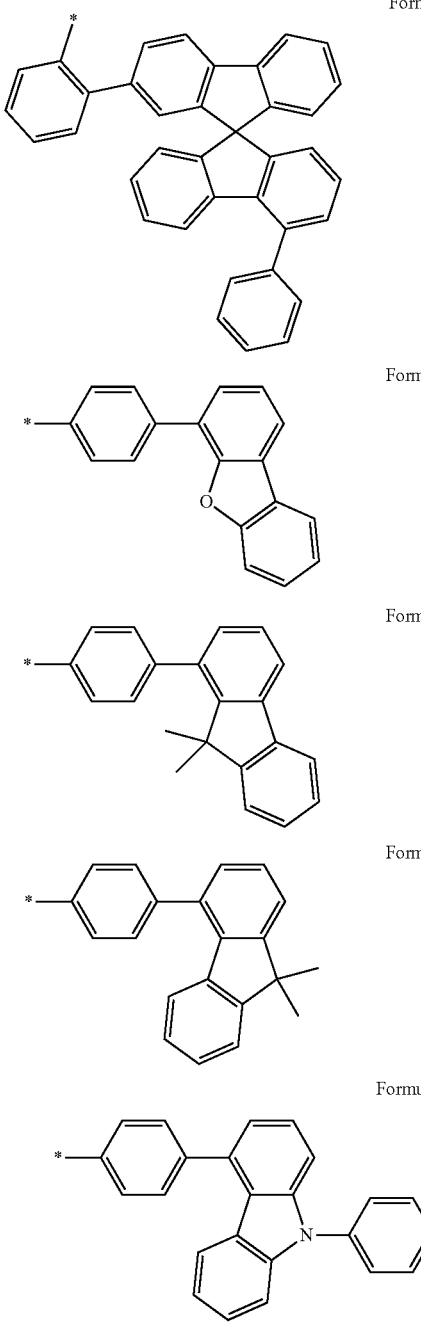

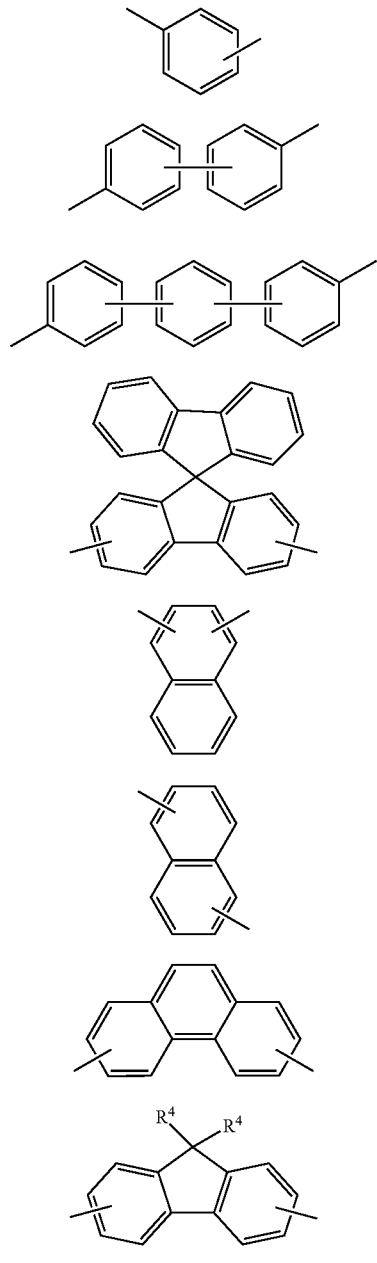

where the symbols correspond to the symbols in formula (Ar-1) to (Ar-16). The formulae may be substituted at the free positions by $R^4$; they are preferably unsubstituted.

In a further embodiment, $Ar^2$ is a divalent aromatic ring system which has 5 to 40 aromatic ring atoms and may be substituted by one or more R radicals, preferably having 5 to 30 aromatic ring atoms and more preferably having 6 to 18 aromatic ring atoms.

In a further embodiment of the invention, the index n is 1 and the $Ar^2$ group is a group of one of the following formulae (Ar2-1) to (Ar2-8):

where the symbols used have the definitions given for formula (1) and the two terminal single bonds are the bonds to the adjacent groups. The groups may be substituted by $R^4$ at the free positions. They are preferably unsubstituted.

Preferably, $Ar^2$ at each instance is selected from the structures of the formulae (Ar2-1) and (Ar2-2).

Preferred embodiments of the formulae are shown by the following formulae (Ar2-1a) to (Ar2-8b):

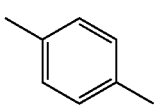

Formula (Ar2-1a)

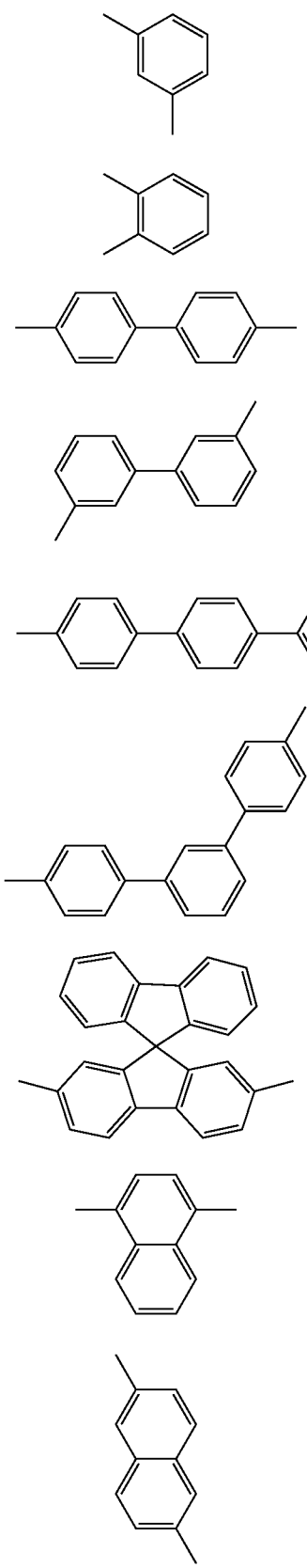

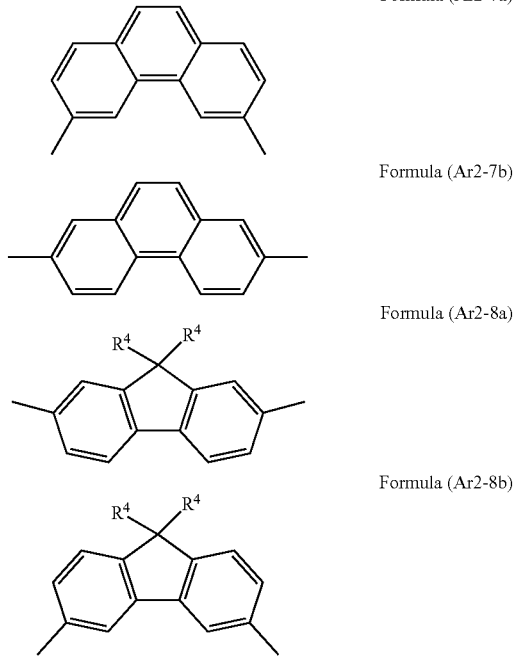

where the symbols used have the definitions given and the two terminal single bonds represent the bonds to the adjacent groups. The groups may be substituted by $R^4$ at the free positions. They are preferably unsubstituted.

In one embodiment of the invention, Ar or $Ar^3$, preferably when n=0, are a group of one of the formulae (Ar-10-13), (Ar-10-14), (Ar-10-15), (Ar-10-16); in particular, Ar or $Ar^3$ comprise a 9,9'-spirobifluorene group.

In one embodiment, if $Ar^3$ is a group of the formula (Ar-10) where E is $C(R^4)_2$, the bond to the nitrogen atom is according to the formula (Ar-10a):

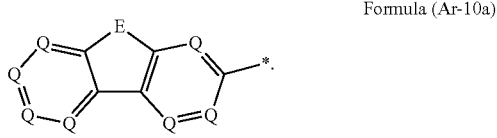

In a further embodiment of the invention, for Ar and $Ar^3$, in the case of a group of the formula (Ar-10), the bond to the nitrogen atom in each case is according to the formula (Ar-10a).

In a further embodiment of the invention, when $Ar^3$ is a group of the formula (Ar-10) or (Ar-11), $Ar^3$ is a group of one of the formulae (Ar-10-2), (Ar-10-14) and (Ar-11-2).

In a further embodiment of the invention, when $Ar^3$ and Ar are a group of the formula (Ar-10) or (Ar-11), $Ar^3$ and Ar are a group of one of the formulae (Ar-10-2), (Ar-10-14) and (Ar-11-2).

In a further embodiment of the invention, $Ar^3$ and Ar, when n is 0, are each not a group of the formula (Ar-10) where E is O or S.

In a further embodiment of the invention, when n is 0, $Ar^3$ and Ar are each not a compound of the formula (Ar-10) where E is O, S and, in the case of $C(R^4)_2$, a group of the formula (Ar-10a) when the two $R^4$ do not form an aromatic or heteroaromatic ring system, and are otherwise, in the case of C(R$^4$)$_2$, a group of the formula (Ar-10).

In a further embodiment of the invention Ar$^3$ or Ar, when n is 0, comprises at least one carbazolyl group or at least one 9,9'-spirobifluorene group, preferably at least one 9,9'-spirobifluorene group.

In a further embodiment of the invention, R$^1$ and R$^2$ are the same or different at each instance and, in the case of an aromatic or heteroaromatic ring system, are selected from one of the formulae (Ar-1) to (Ar-16), where the definition of the symbols corresponds to the symbols as defined for Ar and * is the bond to the carbazole or dibenzofuran or dibenzothiophene.

Preferably, the R substituents bonded to Ar, Ar$^2$ and Ar$^3$ are selected from the group consisting of H, D, F, CN, N(Ar$^1$)$_2$, a straight-chain alkyl group having 1 to 8 carbon atoms, preferably having 1, 2, 3 or 4 carbon atoms, or a branched or cyclic alkyl group having 3 to 8 carbon atoms, preferably having 3, 4, 5 or 6 carbon atoms, or an alkenyl group having 2 to 8 carbon atoms, preferably having 2, 3 or 4 carbon atoms, which may be substituted in each case by one or more R$^4$ radicals, but is preferably unsubstituted, or an aromatic or heteroaromatic ring system having 6 to 24 aromatic ring atoms, preferably having 6 to 18 aromatic ring atoms, more preferably having 6 to 13 aromatic ring atoms, each of which may be substituted by one or more R$^4$ radicals, but is preferably unsubstituted; at the same time, it is optionally possible for two R substituents bonded to adjacent carbon atoms to form a monocyclic or polycyclic aliphatic ring system which may be substituted by one or more R$^4$ radicals, but is preferably unsubstituted.

Preferably, the R$^1$ substituents are selected from the group consisting of H, D, F, CN, a straight-chain alkyl group having 1 to 8 carbon atoms, preferably having 1, 2, 3 or 4 carbon atoms, or a branched or cyclic alkyl group having 3 to 8 carbon atoms, preferably having 3, 4, 5 or 6 carbon atoms, or an alkenyl group having 2 to 8 carbon atoms, preferably having 2, 3 or 4 carbon atoms, which in each case may be substituted by one or more R$^4$ radicals, but is preferably unsubstituted, or an aromatic or heteroaromatic ring system having 6 to 24 aromatic ring atoms, preferably having 6 to 18 aromatic ring atoms, more preferably having 6 to 13 aromatic ring atoms, each of which may be substituted by one or more R$^4$ radicals, but is preferably unsubstituted; at the same time, it is optionally possible for two R$^1$ substituents bonded to adjacent carbon atoms to form a monocyclic or polycyclic aliphatic ring system which may be substituted by one or more R$^4$ radicals, but is preferably unsubstituted.

Preferably, the R$^2$ substituents are selected from the group consisting of H, D, F, CN, a straight-chain alkyl group having 1 to 8 carbon atoms, preferably having 1, 2, 3 or 4 carbon atoms, or a branched or cyclic alkyl group having 3 to 8 carbon atoms, preferably having 3, 4, 5 or 6 carbon atoms, or an alkenyl group having 2 to 8 carbon atoms, preferably having 2, 3 or 4 carbon atoms, which in each case may be substituted by one or more R$^4$ radicals, but is preferably unsubstituted, or an aromatic or heteroaromatic ring system having 6 to 24 aromatic ring atoms, preferably having 6 to 18 aromatic ring atoms, more preferably having 6 to 13 aromatic ring atoms, each of which may be substituted by one or more R$^4$ radicals, but is preferably unsubstituted; at the same time, it is optionally possible for two R$^2$ substituents bonded to adjacent carbon atoms to form a monocyclic or polycyclic aliphatic ring system which may be substituted by one or more R$^4$ radicals, but is preferably unsubstituted.

In a further embodiment of the invention, R, R$^1$ or R$^2$ are the same or different at each instance and, in the case of an aromatic or heteroaromatic ring system, are selected from the structures of the formulae (Ar-1) to (Ar-16), or the preferred embodiments thereof, and structures of the formulae (Ar-17) and (Ar-18):

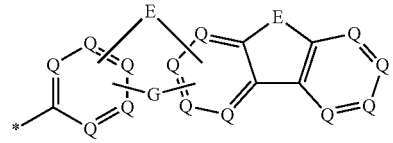

Formula (Ar-17)

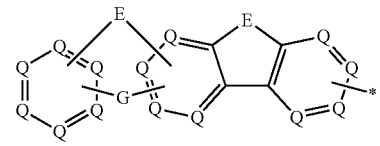

Formula (Ar-18)

where the symbols correspond to the symbols of formula (1) and, in addition, for formulae (Ar-17) and (Ar-18):

Q is the same or different at each instance and is CR$^4$ or N, where not more than 3 Q symbols per cycle are N;

E is the same or different at each instance and is NR$^4$, C(R$^4$)$_2$, O, S or C=O;

G at each instance is NR$^4$, C(R$^4$)$_2$, O, S or C=O; and

* represents the bond to the aromatic ring system,

Preferably, no Q is N.

In a further preferred embodiment, the R, R$^1$ or R$^2$ group at each instance, in the case of an aromatic or heteroaromatic ring system, are selected from the groups having the structures of formulae (Ar-1) to (Ar-18), where the general formulae are replaced by the respective particularly preferred embodiments of the following formulae (Ar-1-1) to (Ar-16-6) (for example, formula (Ar-1) is replaced by one of the formulae (Ar-1-1) to (Ar-1-9)), preference being given additionally to the following formulae:

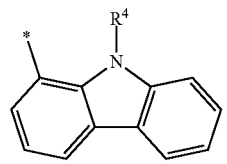

Formula (Ar-10-17)

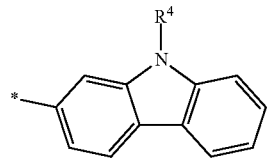

Formula (Ar-10-18)

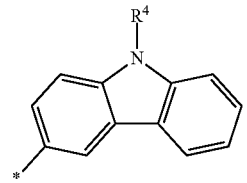

Formula (Ar-10-19)

-continued

Formula (Ar-10-20)

Formula (Ar-10-21)

Formula (Ar-10-22)

Formula (Ar-10-23)

Formula (Ar-10-24)

Formula (Ar-10-25)

Formula (Ar-11-13)

Formula (Ar-11-14)

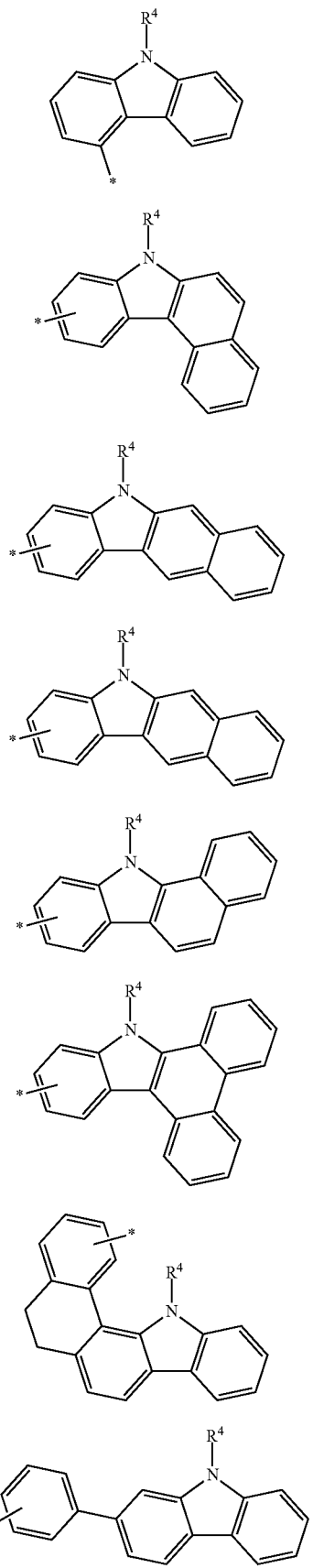

Formula (Ar-11-15)

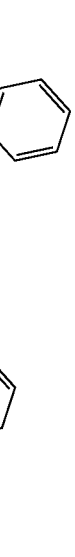

Formula (Ar-11-16)

where the symbols correspond to the symbols of formula (1).

Preferably, the $R^4$ substituents are selected from the group consisting of H, D, F, CN, a straight-chain alkyl group having 1 to 8 carbon atoms, preferably having 1, 2, 3 or 4 carbon atoms, or a branched or cyclic alkyl group having 3 to 8 carbon atoms, preferably having 3, 4, 5 or 6 carbon atoms, or an alkenyl group having 2 to 8 carbon atoms, preferably having 2, 3 or 4 carbon atoms, which in each case may be substituted by one or more $R^4$ radicals, but is preferably unsubstituted, or an aromatic or heteroaromatic ring system having 6 to 24 aromatic ring atoms, preferably having 6 to 18 aromatic ring atoms, more preferably having 6 to 13 aromatic ring atoms, each of which may be substituted by one or more nonaromatic $R^5$ radicals, but is preferably unsubstituted; at the same time, it is optionally possible for two $R^4$ substituents bonded to the same carbon atom or to adjacent carbon atoms to form a monocyclic or polycyclic aliphatic or aromatic ring system which may be substituted by one or more $R^4$ radicals, but is preferably unsubstituted.

When E or G is $NR^4$, it is preferable when the $R^4$ radical bonded to this nitrogen atom is the same or different at each instance and is an aromatic or heteroaromatic ring system which has 5 to 24 aromatic ring atoms and may be substituted in each case by one or more $R^5$ radicals, more preferably an aromatic or heteroaromatic ring system which has 6 to 18 aromatic ring atoms and may be substituted by one or more $R^5$ radicals. Examples of suitable $R^4$ substituents are selected from the group consisting of phenyl, ortho-, meta- or para-biphenyl, terphenyl, especially branched terphenyl, quaterphenyl, especially branched quaterphenyl, 1-, 2-, 3- or 4-fluorenyl, 1-, 2-, 3- or 4-spirobifluorenyl, pyridyl, pyrimidinyl, 1,3,5-triazinyl, 4,6-diphenyl-1,3,5-triazinyl, 1-, 2-, 3- or 4-dibenzofuranyl, 1-, 2-, 3- or 4-dibenzothienyl and 1-, 2-, 3- or 4-carbazolyl, where the carbazolyl group is substituted on the nitrogen atom by an $R^5$ radical other than H or D. These groups may each be substituted by one or more $R^5$ radicals, but are preferably unsubstituted.

When E is $C(R^4)_2$, it is preferable when the $R^4$ radicals bonded to this carbon atom are the same or different at each instance and are a straight-chain alkyl group having 1 to 8 carbon atoms, preferably having 1, 2, 3 or 4 carbon atoms, or a branched or cyclic alkyl group having 3 to 8 carbon atoms, preferably having 3, 4, 5 or 6 carbon atoms, or an alkenyl group having 2 to 8 carbon atoms, preferably having 2, 3 or 4 carbon atoms, which may be substituted in each case by one or more $R^5$ radicals, where one or more nonadjacent $CH_2$ groups may be replaced by O and where one or more hydrogen atoms may be replaced by D or F, or an aromatic or heteroaromatic ring system having 6 to 24 aromatic ring atoms, preferably having 6 to 18 aromatic ring atoms, more preferably having 6 to 13 aromatic ring atoms, each of which may be substituted by one or more $R^5$ radicals; at the same time, it is optionally possible for the two $R^4$ substituents to form a monocyclic or polycyclic aliphatic or aromatic ring system which may be substituted by one or more $R^5$ radicals. Ring formation between the two $R^4$ substituents forms a spiro system.

In a further embodiment of the invention, the compound does not comprise any further unbridged amines apart from the central nitrogen atom. This means that, for example, no radical is $N(R^4)_2$.

In a further embodiment of the invention, no radical in the compound is $N(R^4)_2$ or $N(R^5)_2$. The compound therefore does not comprise any further unbridged or bridged amines which—on the basis of formula (1) or (2)—are bonded via the nitrogen atom.

The abovementioned preferences can occur individually or together. It is preferable when the abovementioned preferences occur together.

Examples of suitable compounds of the invention are the structures shown below.

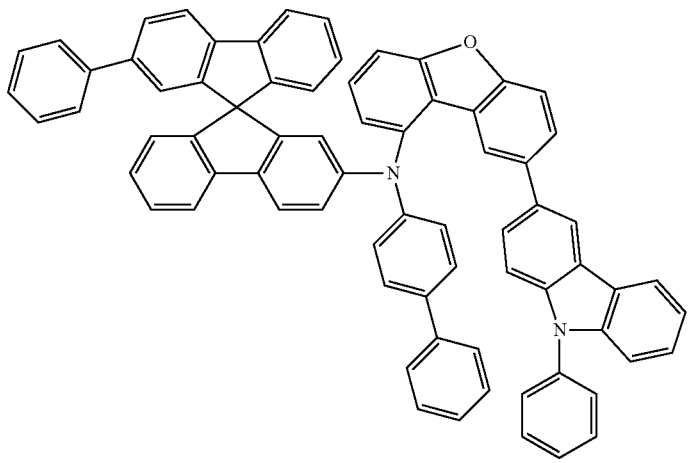 [SMILES: c1ccc(-c2ccc(N(c3ccc4c(c3)C3(c5ccccc5-c5ccc(-c6ccccc6)cc53)c3ccccc3-4)c3cccc4oc5ccc(-c6ccc7c(c6)c6ccccc6n7-c6ccccc6)cc5c34)cc2)cc1]

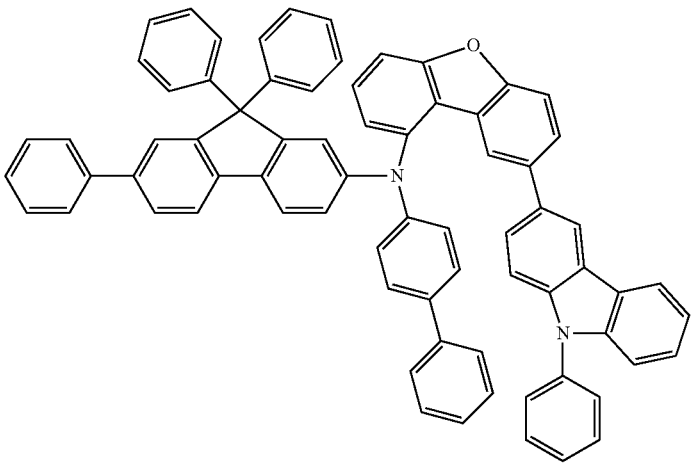 [SMILES: c1ccc(-c2ccc(N(c3ccc4c(c3)C(c3ccccc3)(c3ccccc3)c3cc(-c5ccccc5)ccc3-4)c3cccc4oc5ccc(-c6ccc7c(c6)c6ccccc6n7-c6ccccc6)cc5c34)cc2)cc1]

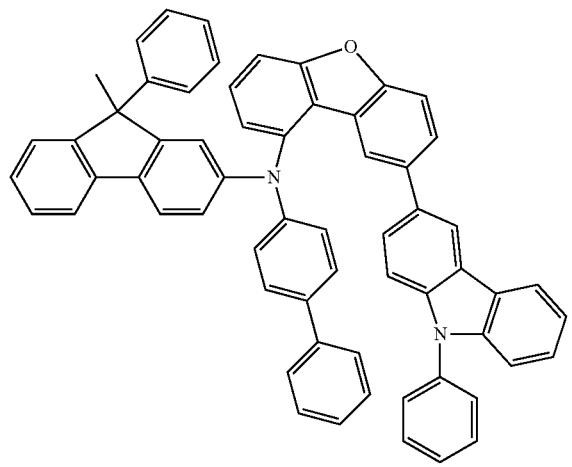 [SMILES: CC1(c2ccccc2)c2ccccc2-c2ccc(N(c3ccc(-c4ccccc4)cc3)c3cccc4oc5ccc(-c6ccc7c(c6)c6ccccc6n7-c6ccccc6)cc5c34)cc21]
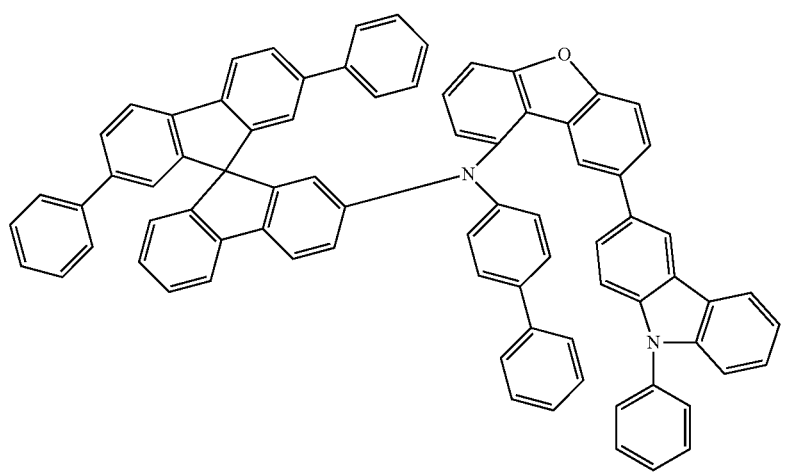 [SMILES: c1ccc(-c2ccc(N(c3ccc4c(c3)C3(c5ccccc5-4)c4cc(-c5ccccc5)ccc4-c4ccc(-c5ccccc5)cc43)c3cccc4oc5ccc(-c6ccc7c(c6)c6ccccc6n7-c6ccccc6)cc5c34)cc2)cc1]
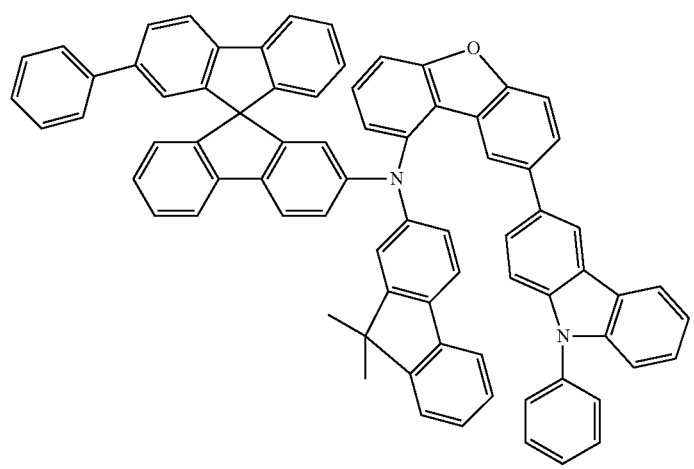 [SMILES: CC1(C)c2ccccc2-c2ccc(N(c3ccc4c(c3)C3(c5ccccc5-c5ccc(-c6ccccc6)cc53)c3ccccc3-4)c3cccc4oc5ccc(-c6ccc7c(c6)c6ccccc6n7-c6ccccc6)cc5c34)cc21]

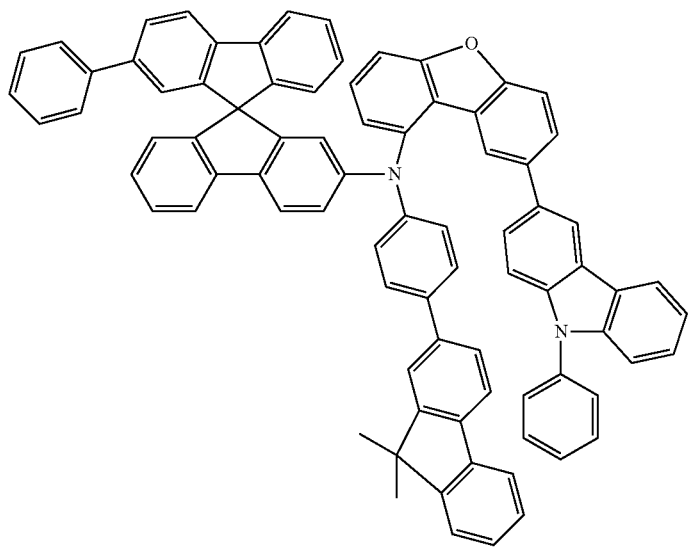 [SMILES: CC1(C)c2ccccc2-c2ccc(-c3ccc(N(c4ccc5c(c4)C4(c6ccccc6-c6ccc(-c7ccccc7)cc64)c4ccccc4-5)c4cccc5oc6ccc(-c7ccc8c(c7)c7ccccc7n8-c7ccccc7)cc6c45)cc3)cc21]
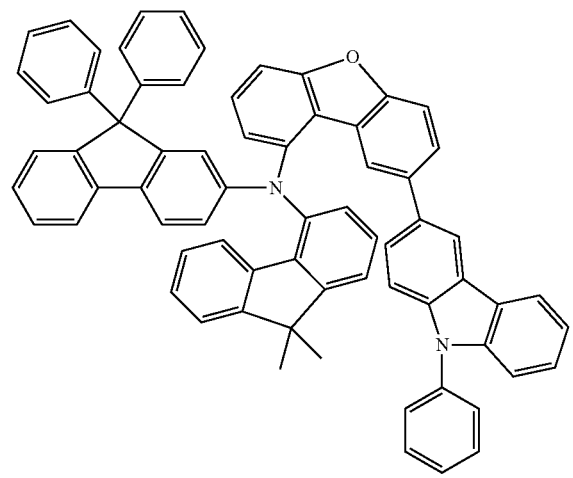 [SMILES: CC1(C)c2ccccc2-c2c(N(c3ccc4c(c3)C(c3ccccc3)(c3ccccc3)c3ccccc3-4)c3cccc4oc5ccc(-c6ccc7c(c6)c6ccccc6n7-c6ccccc6)cc5c34)cccc21]
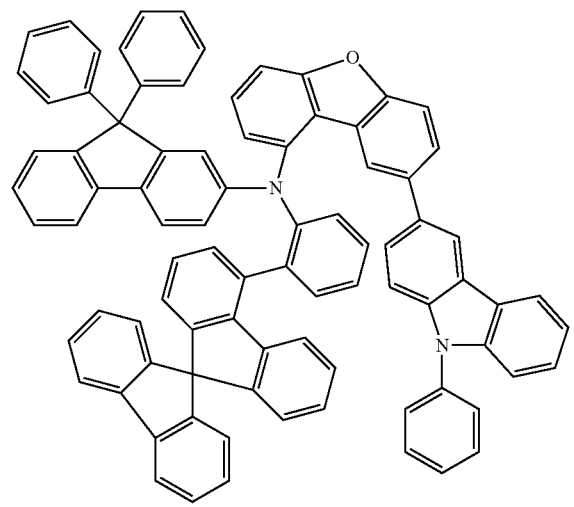 [SMILES: c1ccc(-n2c3ccccc3c3cc(-c4ccc5oc6cccc(N(c7ccc8c(c7)C(c7ccccc7)(c7ccccc7)c7ccccc7-8)c7ccccc7-c7cccc8c7-c7ccccc7C87c8ccccc8-c8ccccc87)c6c5c4)ccc32)cc1]

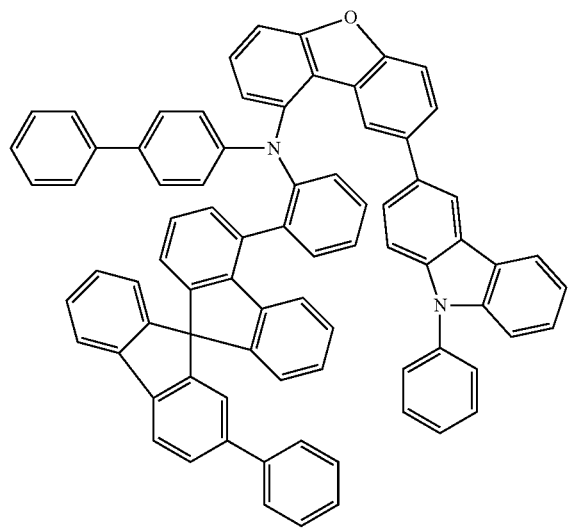 [SMILES: c1ccc(-c2ccc(N(c3ccccc3-c3cccc4c3-c3ccccc3C43c4ccccc4-c4ccc(-c5ccccc5)cc43)c3cccc4oc5ccc(-c6ccc7c(c6)c6ccccc6n7-c6ccccc6)cc5c34)cc2)cc1]
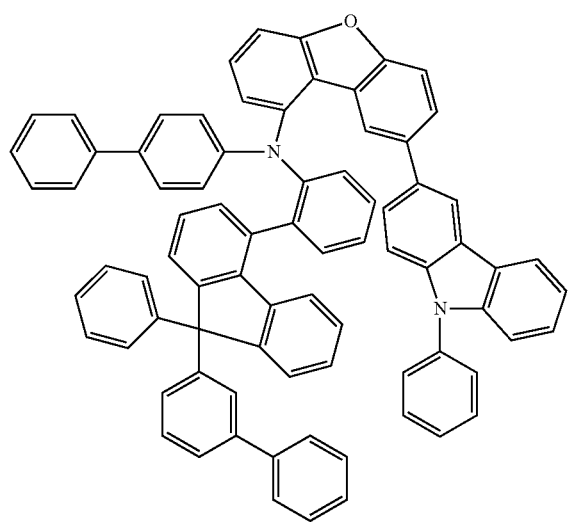 [SMILES: c1ccc(-c2ccc(N(c3ccccc3-c3cccc4c3-c3ccccc3C4(c3ccccc3)c3cccc(-c4ccccc4)c3)c3cccc4oc5ccc(-c6ccc7c(c6)c6ccccc6n7-c6ccccc6)cc5c34)cc2)cc1]
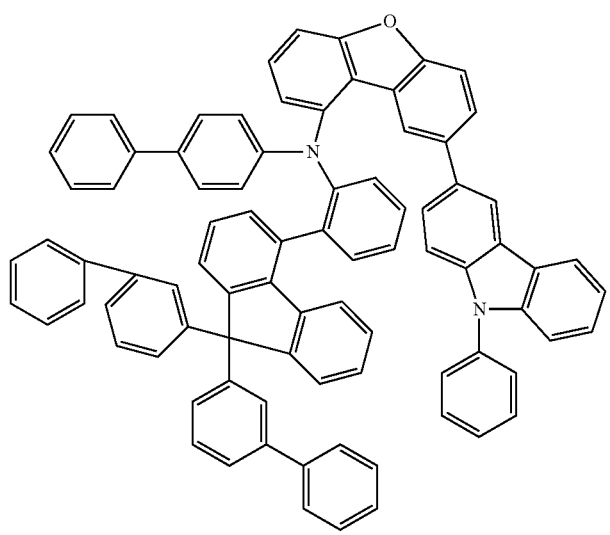 [SMILES: c1ccc(-c2ccc(N(c3ccccc3-c3cccc4c3-c3ccccc3C4(c3cccc(-c4ccccc4)c3)c3cccc(-c4ccccc4)c3)c3cccc4oc5ccc(-c6ccc7c(c6)c6ccccc6n7-c6ccccc6)cc5c34)cc2)cc1]

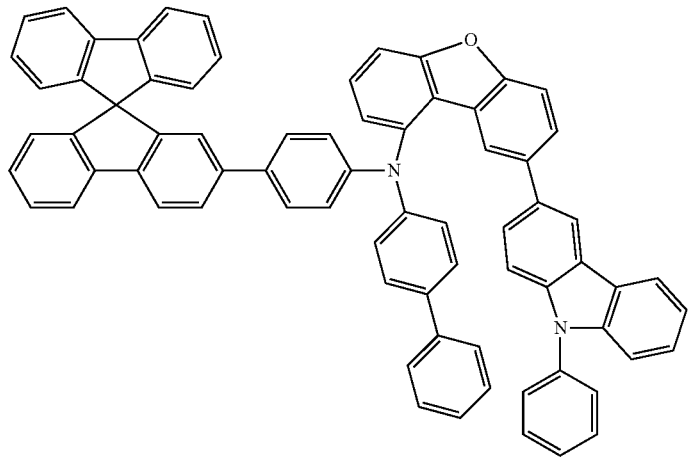 [SMILES: c1ccc(-c2ccc(N(c3ccc(-c4ccc5c(c4)C4(c6ccccc6-c6ccccc64)c4ccccc4-5)cc3)c3cccc4oc5ccc(-c6ccc7c(c6)c6ccccc6n7-c6ccccc6)cc5c34)cc2)cc1]
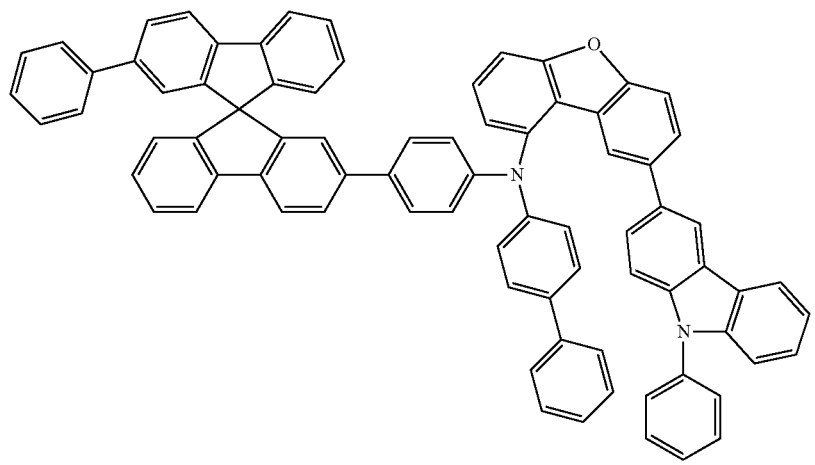 [SMILES: c1ccc(-c2ccc(N(c3ccc(-c4ccc5c(c4)C4(c6ccccc6-c6ccc(-c7ccccc7)cc64)c4ccccc4-5)cc3)c3cccc4oc5ccc(-c6ccc7c(c6)c6ccccc6n7-c6ccccc6)cc5c34)cc2)cc1]
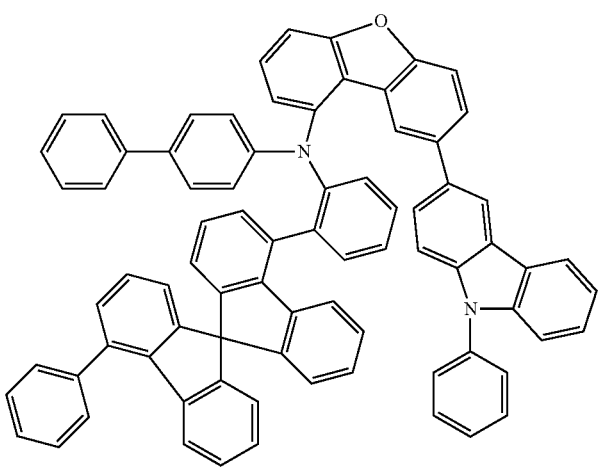 [SMILES: c1ccc(-c2ccc(N(c3ccccc3-c3cccc4c3-c3ccccc3C43c4ccccc4-c4c(-c5ccccc5)cccc43)c3cccc4oc5ccc(-c6ccc7c(c6)c6ccccc6n7-c6ccccc6)cc5c34)cc2)cc1]

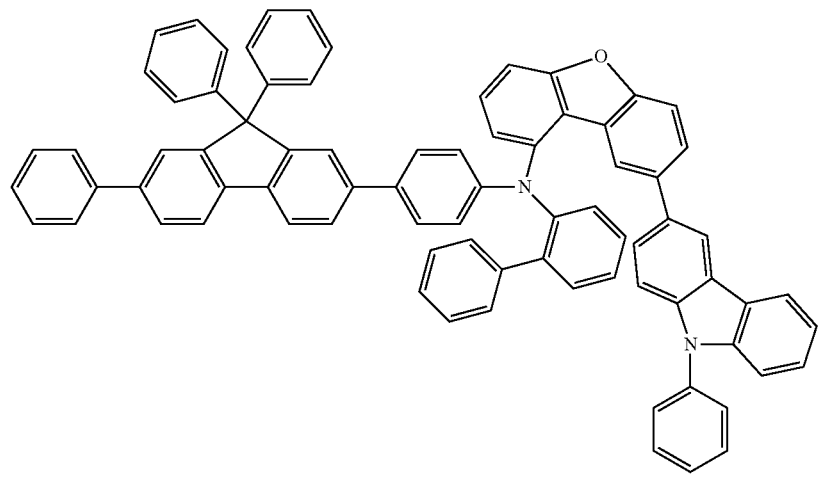 [SMILES: c1ccc(-c2ccc3c(c2)C(c2ccccc2)(c2ccccc2)c2cc(-c4ccc(N(c5ccccc5-c5ccccc5)c5cccc6oc7ccc(-c8ccc9c(c8)c8ccccc8n9-c8ccccc8)cc7c56)cc4)ccc2-3)cc1]

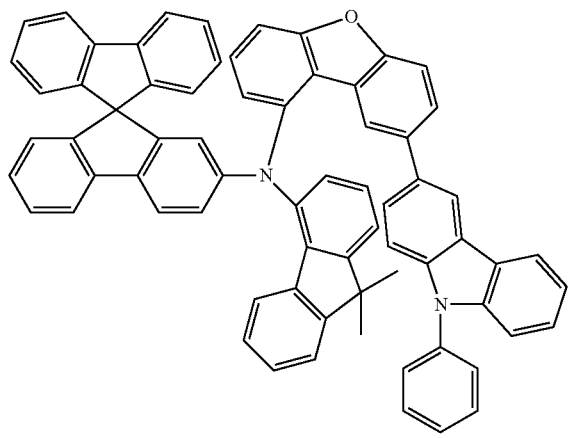 [SMILES: CC1(C)c2ccccc2-c2c(N(c3ccc4c(c3)C3(c5ccccc5-c5ccccc53)c3ccccc3-4)c3cccc4oc5ccc(-c6ccc7c(c6)c6ccccc6n7-c6ccccc6)cc5c34)cccc21]
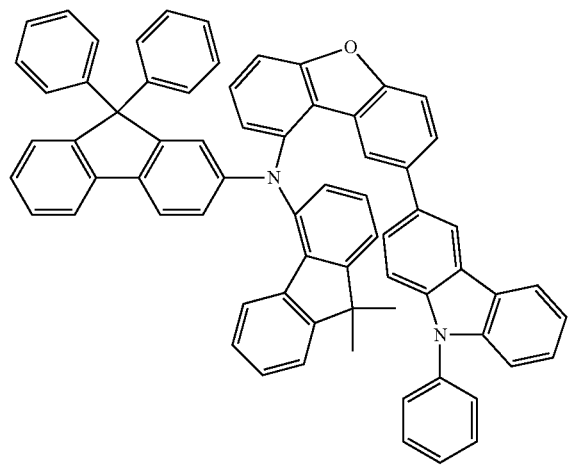 [SMILES: CC1(C)c2ccccc2-c2c(N(c3ccc4c(c3)C(c3ccccc3)(c3ccccc3)c3ccccc3-4)c3cccc4oc5ccc(-c6ccc7c(c6)c6ccccc6n7-c6ccccc6)cc5c34)cccc21]
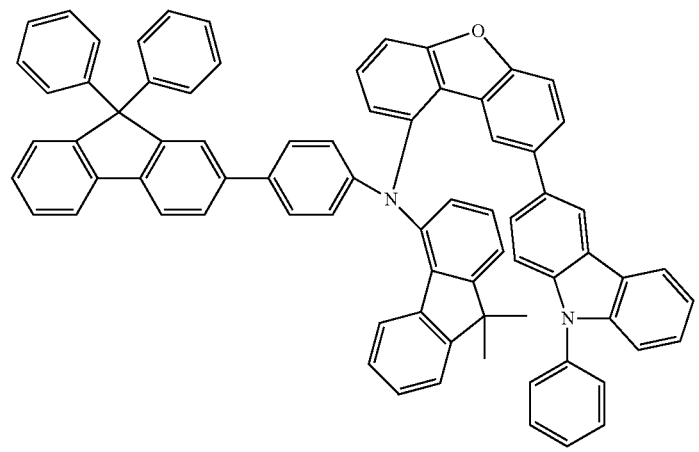 [SMILES: CC1(C)c2ccccc2-c2c(N(c3ccc(-c4ccc5c(c4)C(c4ccccc4)(c4ccccc4)c4ccccc4-5)cc3)c3cccc4oc5ccc(-c6ccc7c(c6)c6ccccc6n7-c6ccccc6)cc5c34)cccc21]

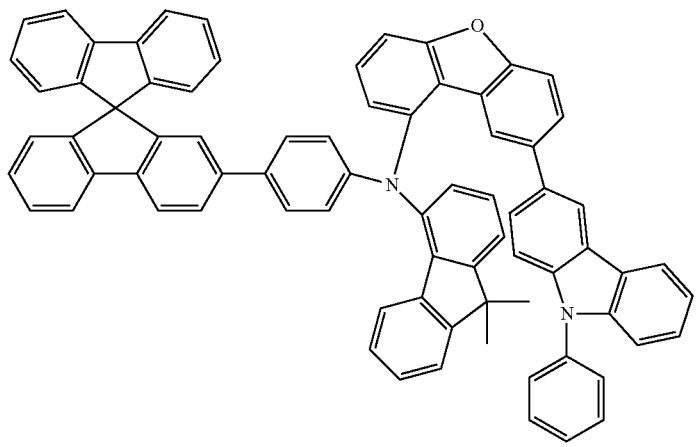 [SMILES: CC1(C)c2ccccc2-c2c(N(c3ccc(-c4ccc5c(c4)C4(c6ccccc6-c6ccccc64)c4ccccc4-5)cc3)c3cccc4oc5ccc(-c6ccc7c(c6)c6ccccc6n7-c6ccccc6)cc5c34)cccc21]
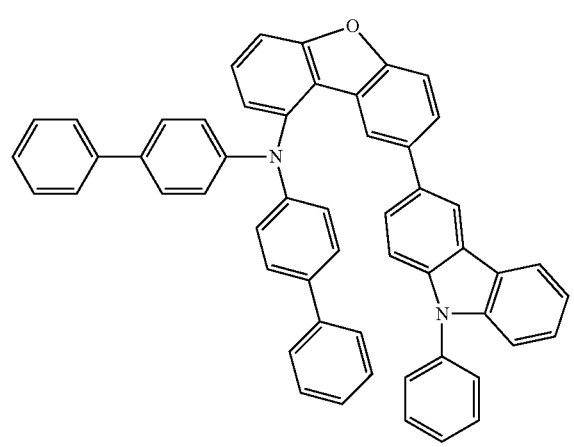 [SMILES: c1ccc(-c2ccc(N(c3ccc(-c4ccccc4)cc3)c3cccc4oc5ccc(-c6ccc7c(c6)c6ccccc6n7-c6ccccc6)cc5c34)cc2)cc1]
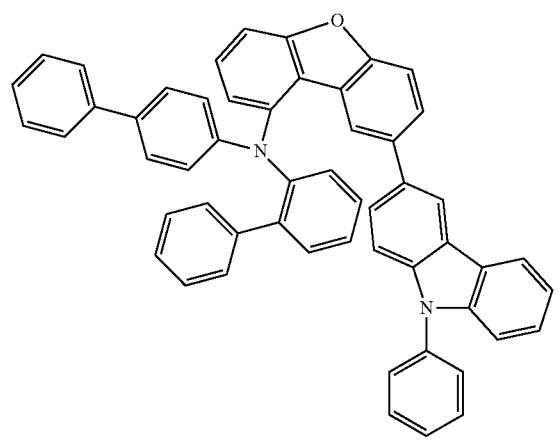 [SMILES: c1ccc(-c2ccc(N(c3ccccc3-c3ccccc3)c3cccc4oc5ccc(-c6ccc7c(c6)c6ccccc6n7-c6ccccc6)cc5c34)cc2)cc1]

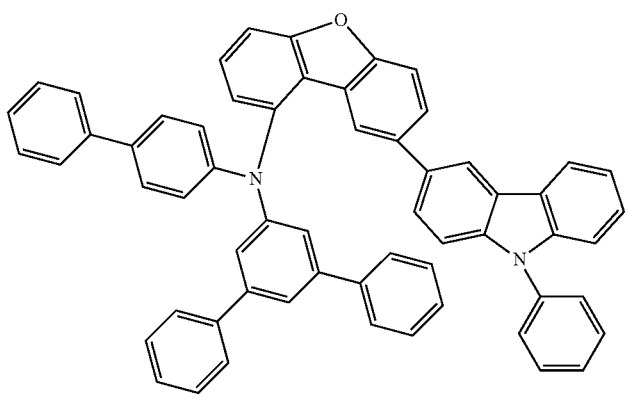 [SMILES: c1ccc(-c2ccc(N(c3cc(-c4ccccc4)cc(-c4ccccc4)c3)c3cccc4oc5ccc(-c6ccc7c(c6)c6ccccc6n7-c6ccccc6)cc5c34)cc2)cc1]
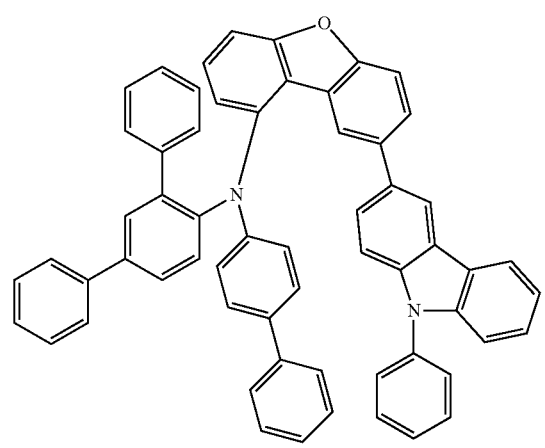 [SMILES: c1ccc(-c2ccc(N(c3ccc(-c4ccccc4)cc3-c3ccccc3)c3cccc4oc5ccc(-c6ccc7c(c6)c6ccccc6n7-c6ccccc6)cc5c34)cc2)cc1]
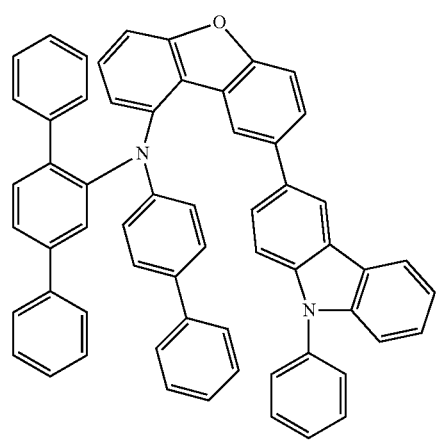

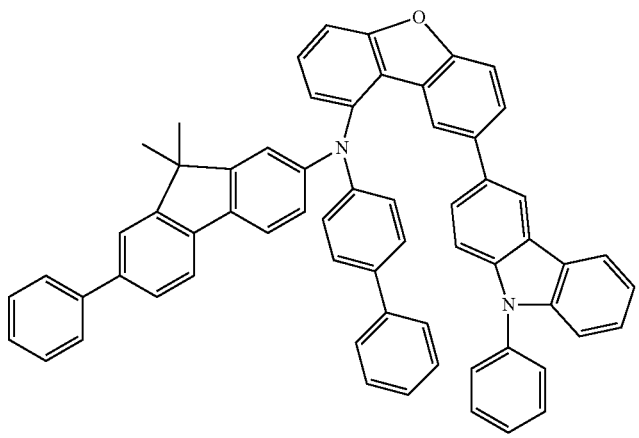 [SMILES: CC1(C)c2cc(-c3ccccc3)ccc2-c2ccc(N(c3ccc(-c4ccccc4)cc3)c3cccc4oc5ccc(-c6ccc7c(c6)c6ccccc6n7-c6ccccc6)cc5c34)cc21]
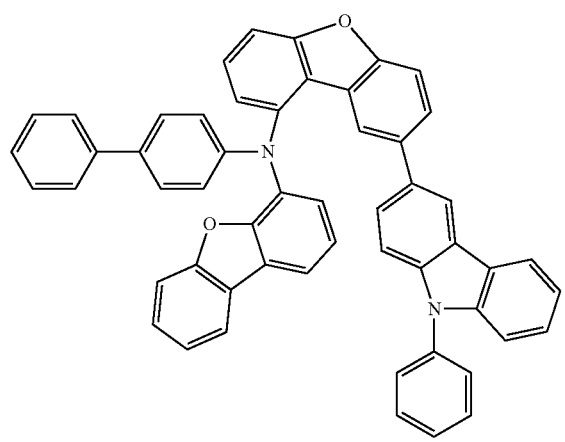 [SMILES: c1ccc(-c2ccc(N(c3cccc4c3oc3ccccc34)c3cccc4oc5ccc(-c6ccc7c(c6)c6ccccc6n7-c6ccccc6)cc5c34)cc2)cc1]
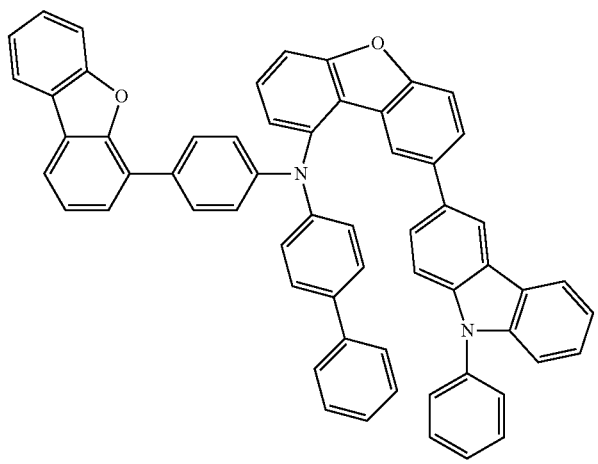 [SMILES: c1ccc(-c2ccc(N(c3ccc(-c4cccc5c4oc4ccccc45)cc3)c3cccc4oc5ccc(-c6ccc7c(c6)c6ccccc6n7-c6ccccc6)cc5c34)cc2)cc1]

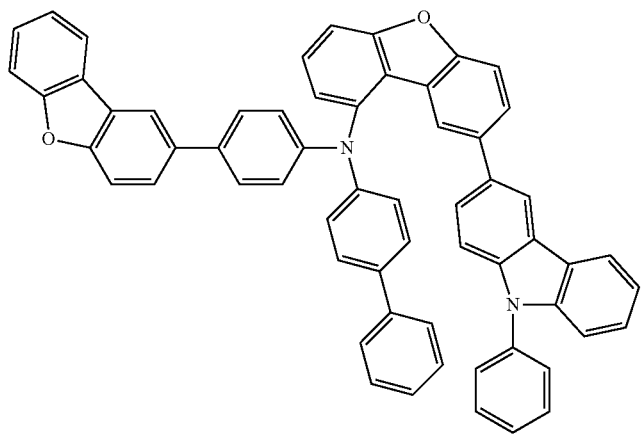 [SMILES: c1ccc(-c2ccc(N(c3ccc(-c4ccc5oc6ccccc6c5c4)cc3)c3cccc4oc5ccc(-c6ccc7c(c6)c6ccccc6n7-c6ccccc6)cc5c34)cc2)cc1]
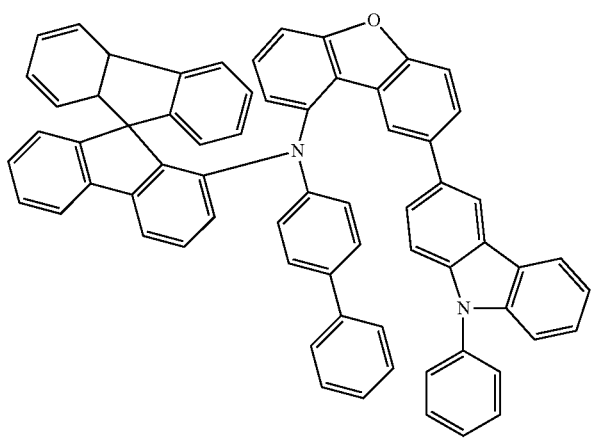 [SMILES: C1=CC2c3ccccc3C3(c4ccccc4-c4cccc(N(c5ccc(-c6ccccc6)cc5)c5cccc6oc7ccc(-c8ccc9c(c8)c8ccccc8n9-c8ccccc8)cc7c56)c43)C2C=C1]
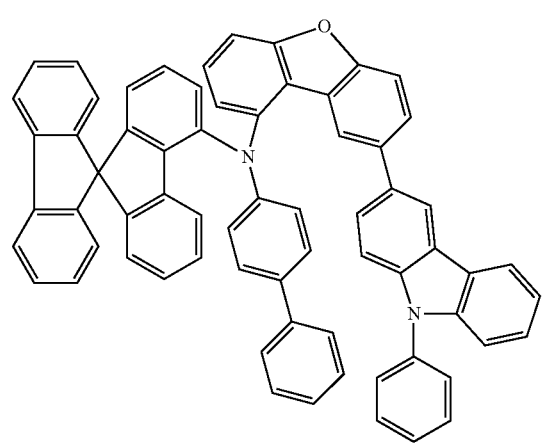 [SMILES: c1ccc(-c2ccc(N(c3cccc4c3-c3ccccc3C43c4ccccc4-c4ccccc43)c3cccc4oc5ccc(-c6ccc7c(c6)c6ccccc6n7-c6ccccc6)cc5c34)cc2)cc1]

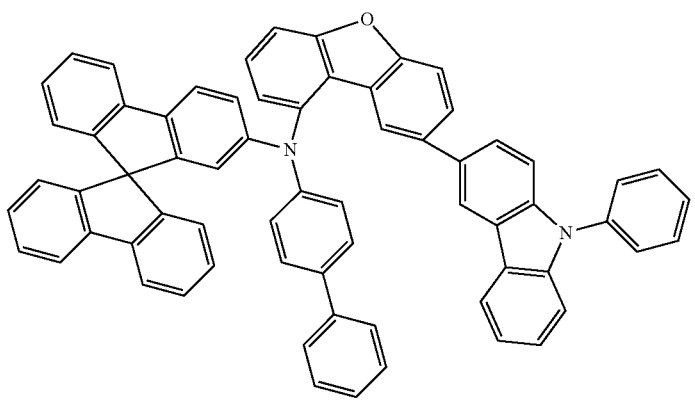 [SMILES: c1ccc(-c2ccc(N(c3ccc4c(c3)C3(c5ccccc5-c5ccccc53)c3ccccc3-4)c3cccc4oc5ccc(-c6ccc7c(c6)c6ccccc6n7-c6ccccc6)cc5c34)cc2)cc1]
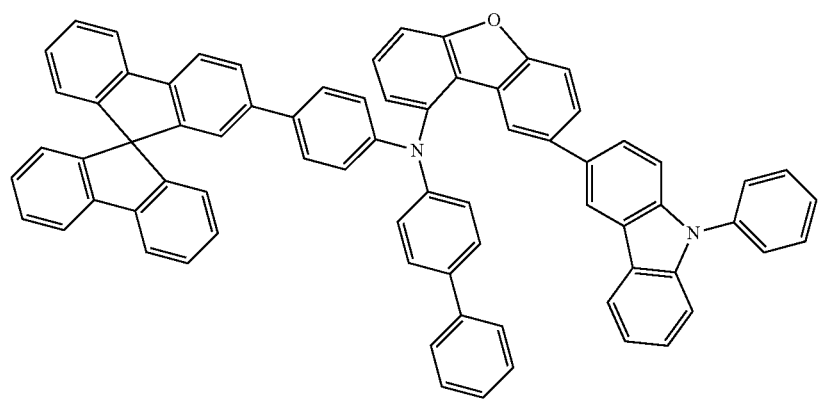 [SMILES: c1ccc(-c2ccc(N(c3ccc(-c4ccc5c(c4)C4(c6ccccc6-c6ccccc64)c4ccccc4-5)cc3)c3cccc4oc5ccc(-c6ccc7c(c6)c6ccccc6n7-c6ccccc6)cc5c34)cc2)cc1]
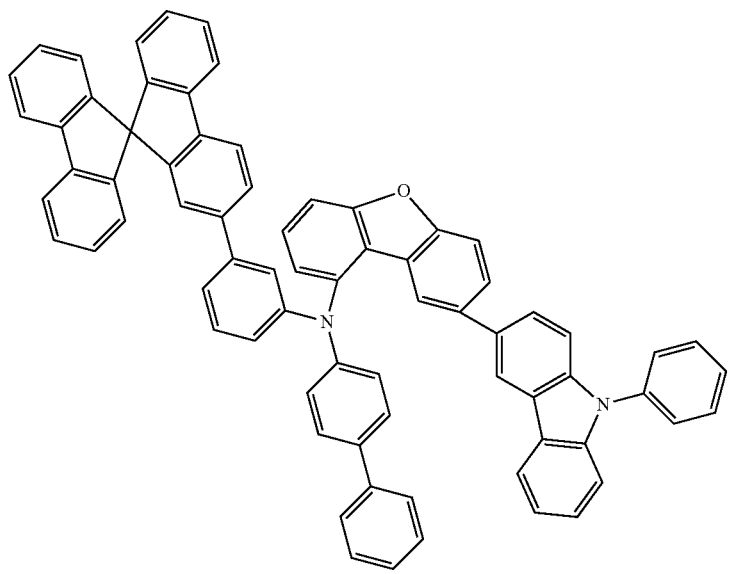 [SMILES: c1ccc(-c2ccc(N(c3cccc(-c4ccc5c(c4)C4(c6ccccc6-c6ccccc64)c4ccccc4-5)c3)c3cccc4oc5ccc(-c6ccc7c(c6)c6ccccc6n7-c6ccccc6)cc5c34)cc2)cc1]

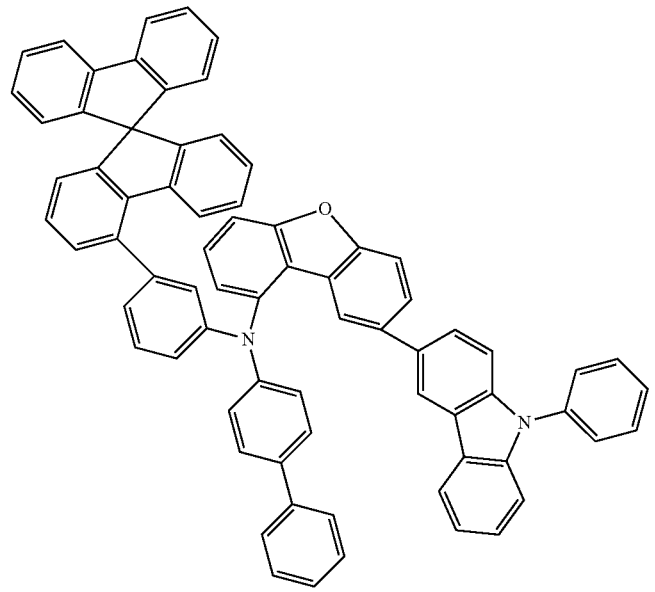
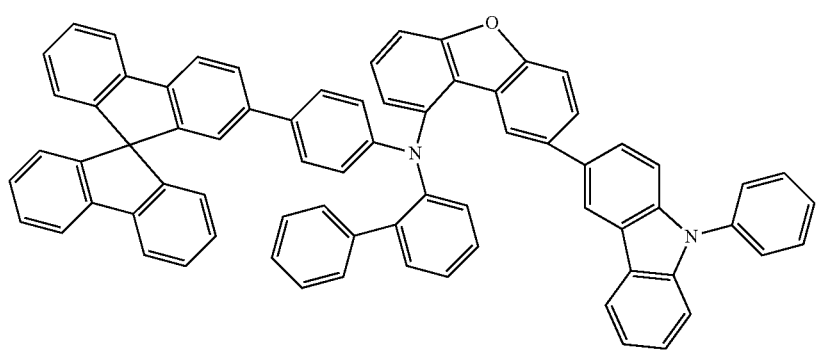 [SMILES: c1ccc(-c2ccccc2N(c2ccc(-c3ccc4c(c3)C3(c5ccccc5-c5ccccc53)c3ccccc3-4)cc2)c2cccc3oc4ccc(-c5ccc6c(c5)c5ccccc5n6-c5ccccc5)cc4c23)cc1]
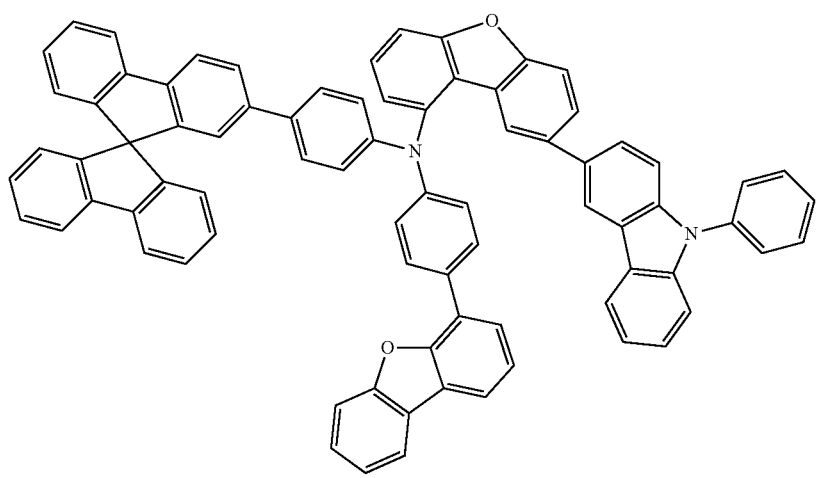 [SMILES: c1ccc(-n2c3ccccc3c3cc(-c4ccc5oc6cccc(N(c7ccc(-c8ccc9c(c8)C8(c%10ccccc%10-c%10ccccc%108)c8ccccc8-9)cc7)c7ccc(-c8cccc9c8oc8ccccc89)cc7)c6c5c4)ccc32)cc1]

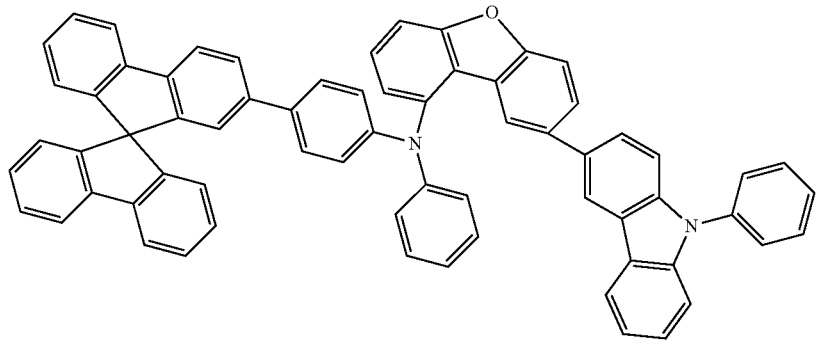 [SMILES: c1ccc(N(c2ccc(-c3ccc4c(c3)C3(c5ccccc5-c5ccccc53)c3ccccc3-4)cc2)c2cccc3oc4ccc(-c5ccc6c(c5)c5ccccc5n6-c5ccccc5)cc4c23)cc1]
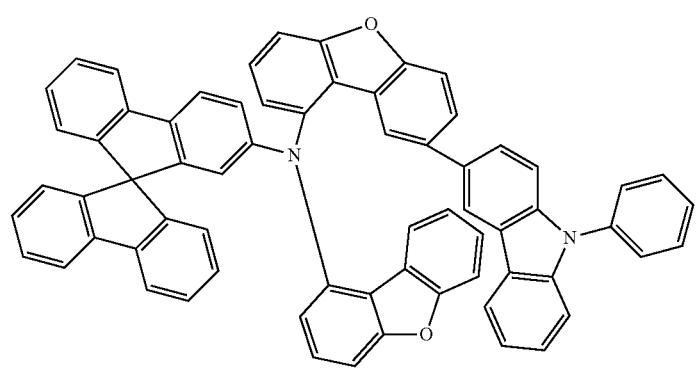 [SMILES: c1ccc(-n2c3ccccc3c3cc(-c4ccc5oc6cccc(N(c7ccc8c(c7)C7(c9ccccc9-c9ccccc97)c7ccccc7-8)c7cccc8oc9ccccc9c78)c6c5c4)ccc32)cc1]
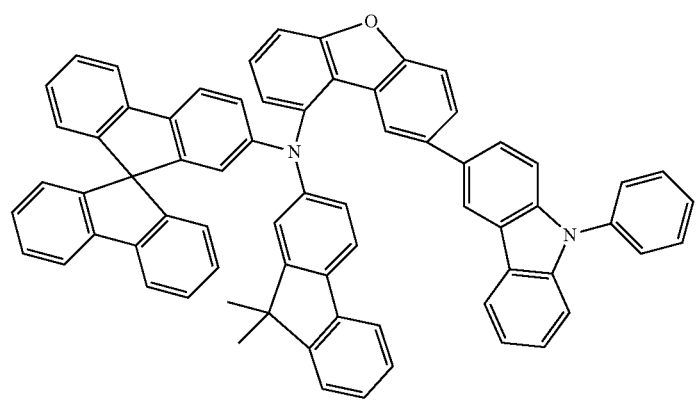 [SMILES: CC1(C)c2ccccc2-c2ccc(N(c3ccc4c(c3)C3(c5ccccc5-c5ccccc53)c3ccccc3-4)c3cccc4oc5ccc(-c6ccc7c(c6)c6ccccc6n7-c6ccccc6)cc5c34)cc21]
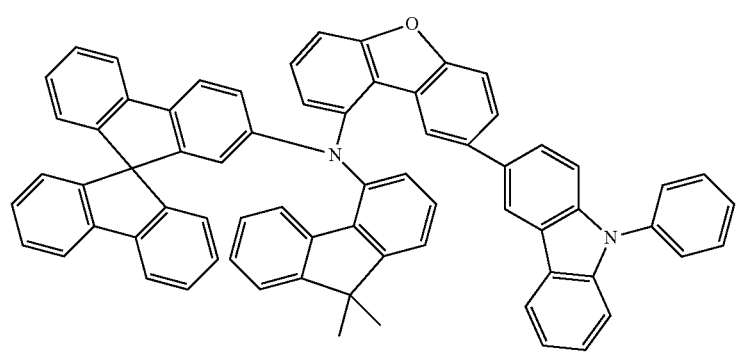 [SMILES: CC1(C)c2ccccc2-c2c(N(c3ccc4c(c3)C3(c5ccccc5-c5ccccc53)c3ccccc3-4)c3cccc4oc5ccc(-c6ccc7c(c6)c6ccccc6n7-c6ccccc6)cc5c34)cccc21]

-continued
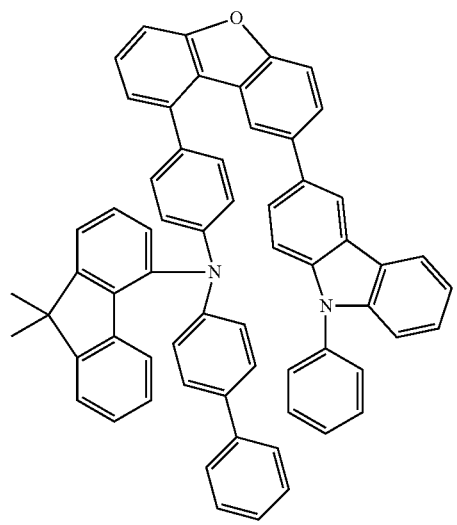 [SMILES: CC1(C)c2ccccc2-c2c(N(c3ccc(-c4ccccc4)cc3)c3ccc(-c4cccc5oc6ccc(-c7ccc8c(c7)c7ccccc7n8-c7ccccc7)cc6c45)cc3)cccc21]
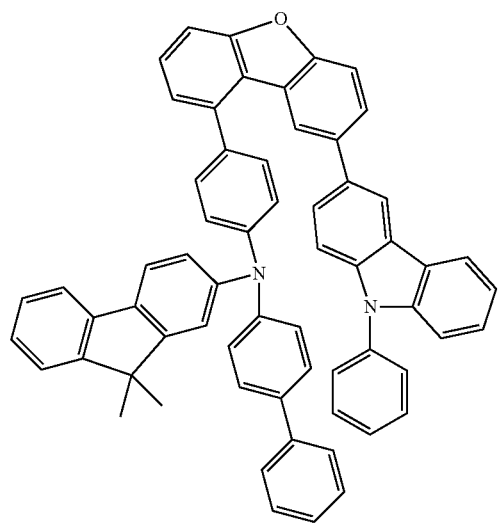 [SMILES: CC1(C)c2ccccc2-c2ccc(N(c3ccc(-c4ccccc4)cc3)c3ccc(-c4cccc5oc6ccc(-c7ccc8c(c7)c7ccccc7n8-c7ccccc7)cc6c45)cc3)cc21]
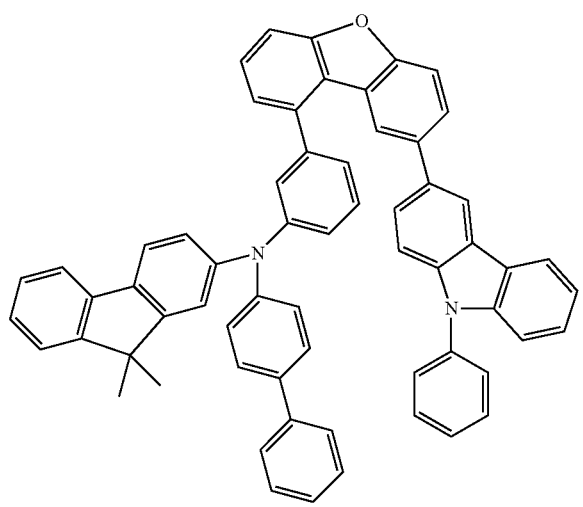 [SMILES: CC1(C)c2ccccc2-c2ccc(N(c3ccc(-c4ccccc4)cc3)c3cccc(-c4cccc5oc6ccc(-c7ccc8c(c7)c7ccccc7n8-c7ccccc7)cc6c45)c3)cc21]

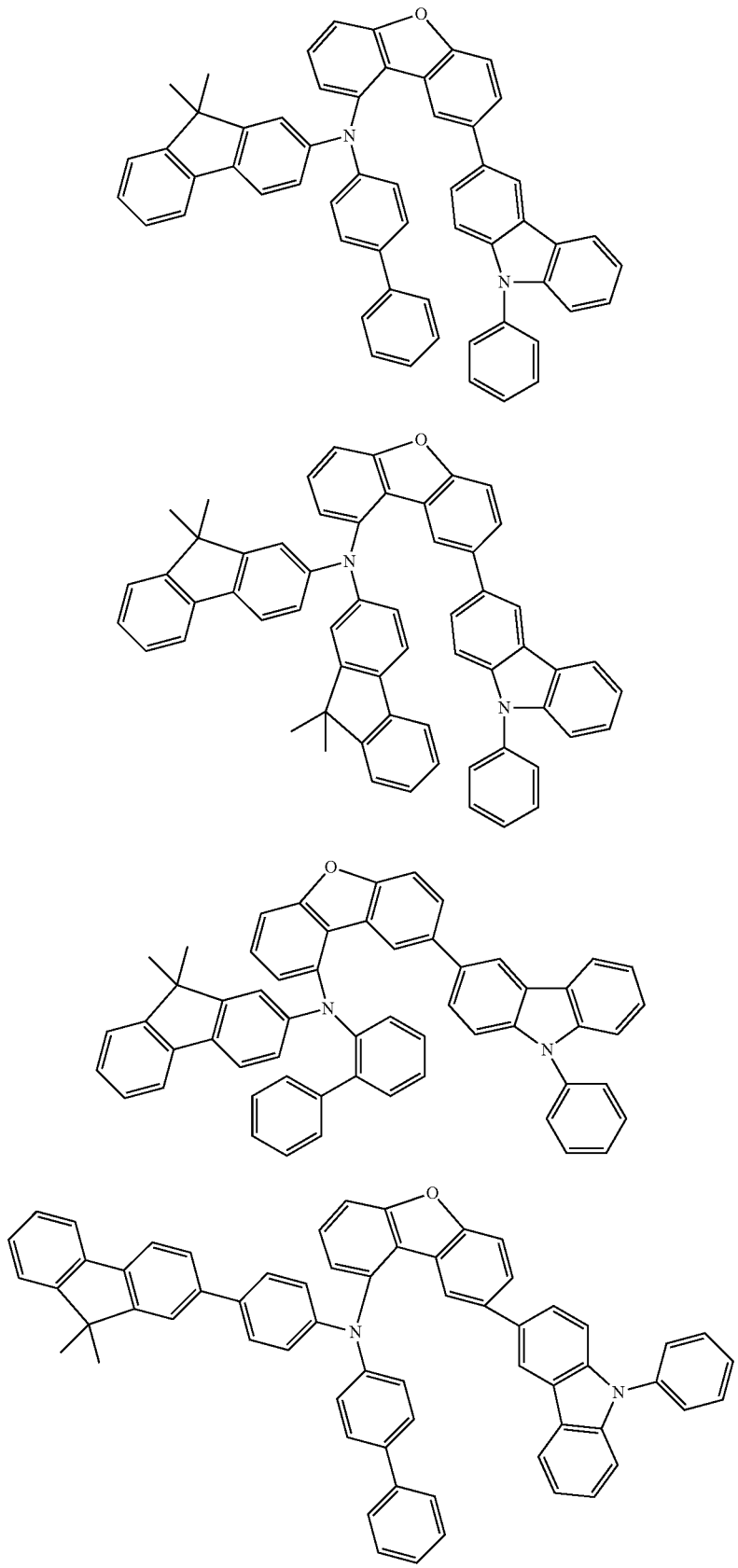

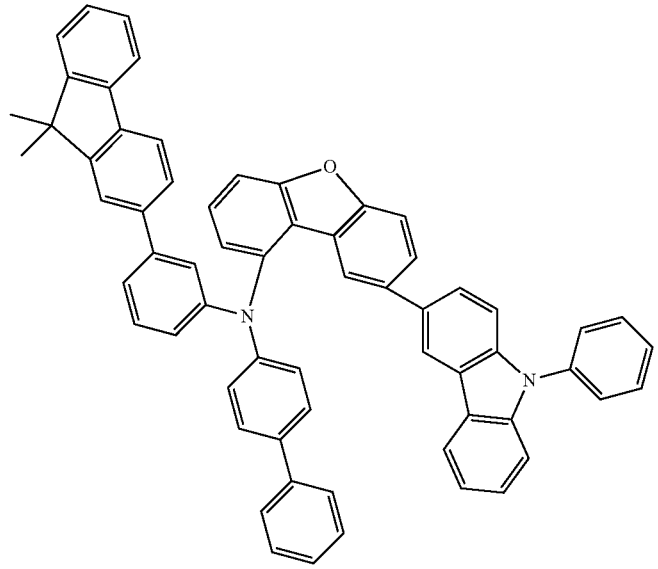
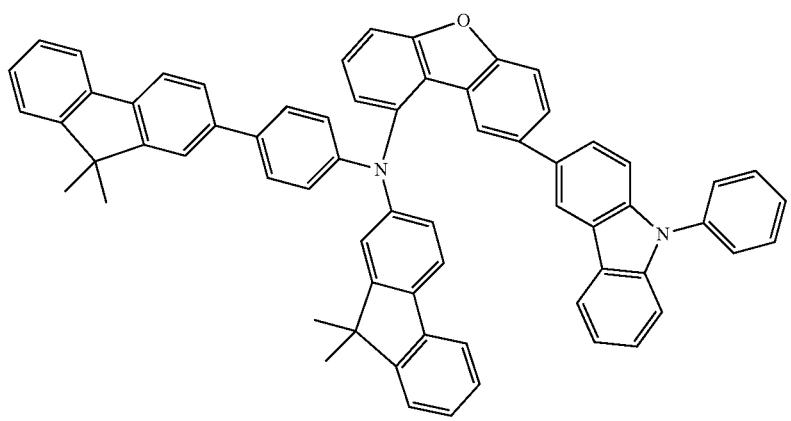
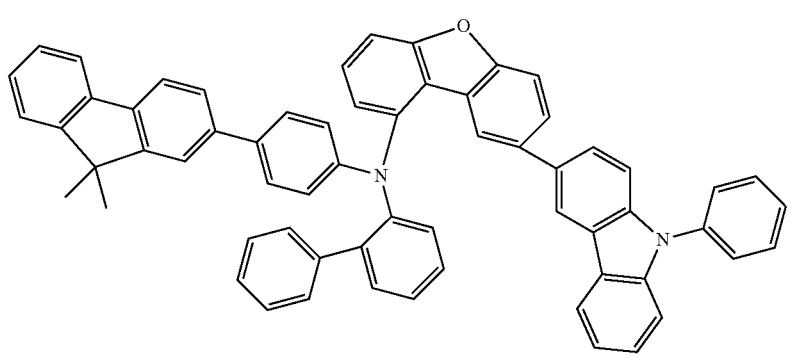

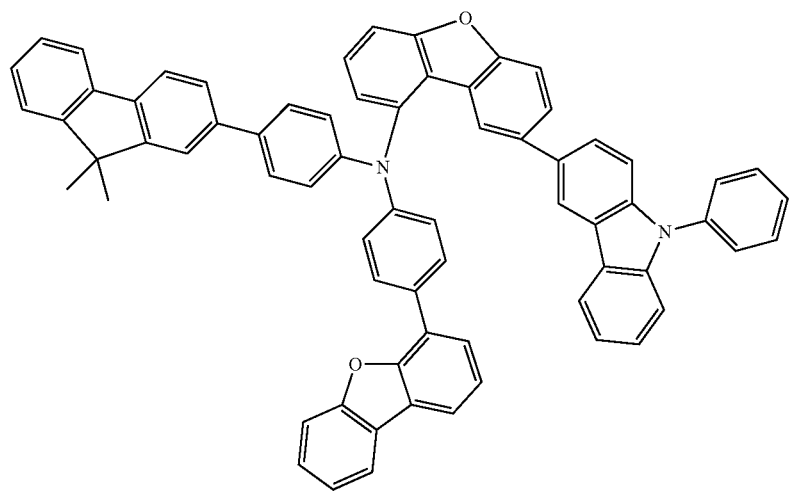
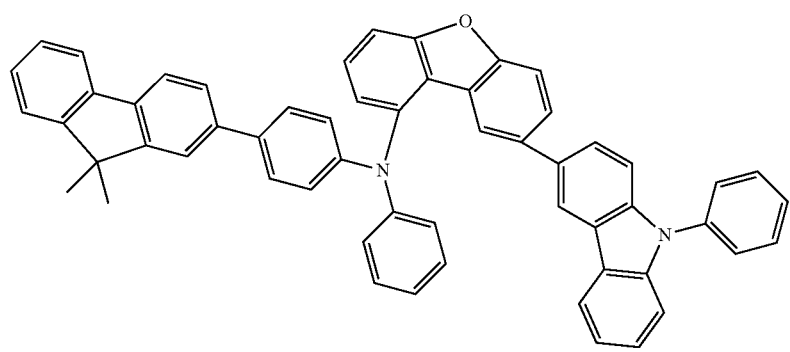
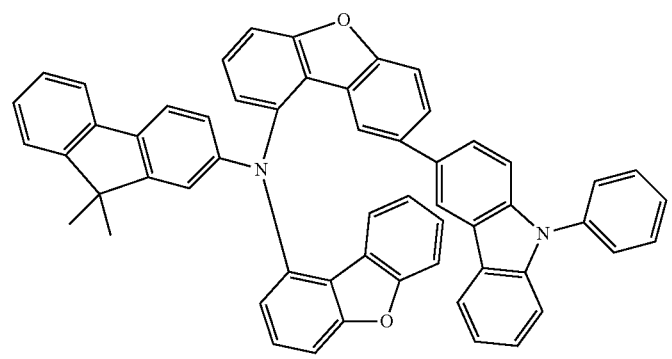
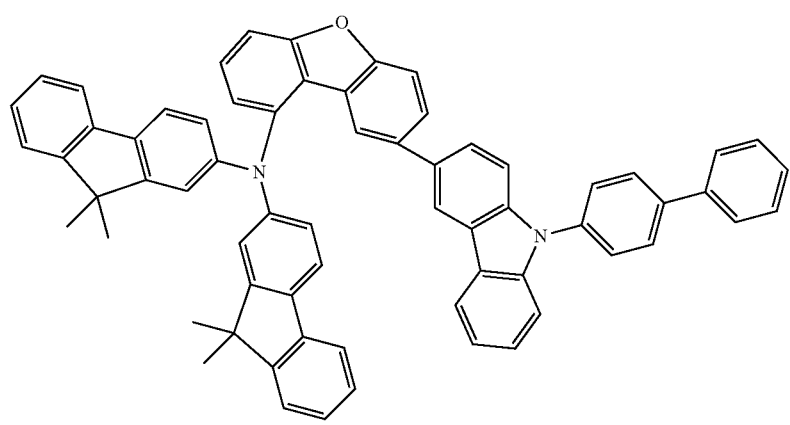

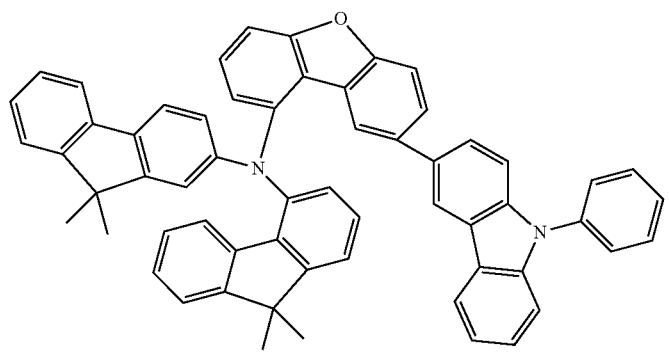
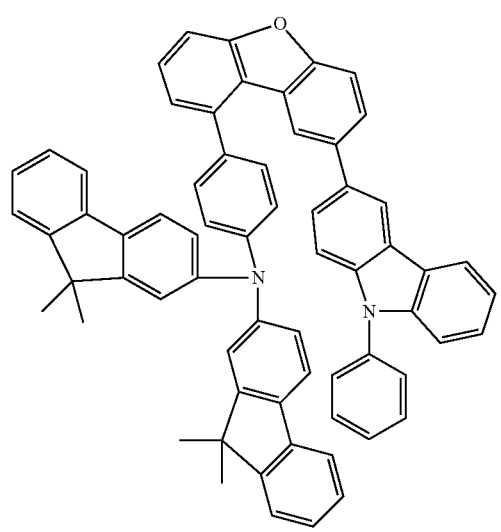 [SMILES: CC1(C)c2ccccc2-c2ccc(CN(c3ccc(-c4cccc5oc6ccc(-c7ccc8c(c7)c7ccccc7n8-c7ccccc7)cc6c45)cc3)c3ccc4c(c3)C(C)(C)c3ccccc3-4)cc21]
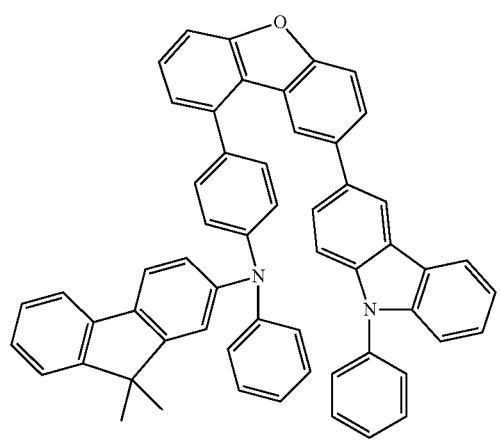

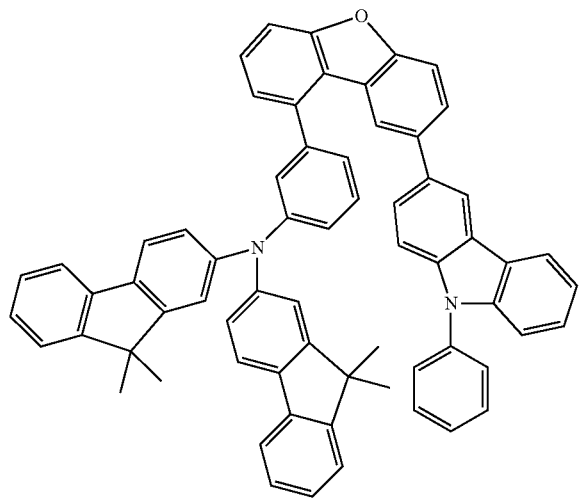
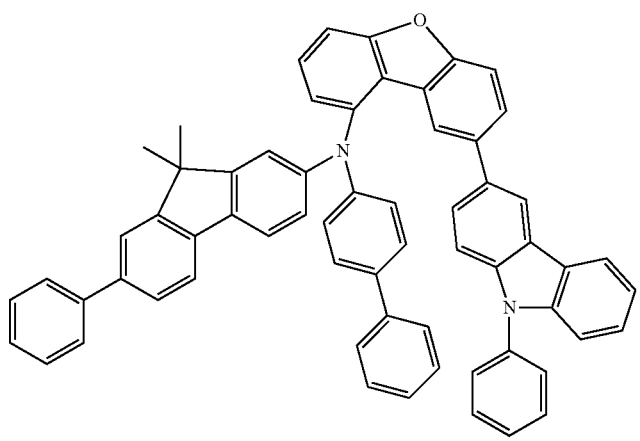 [SMILES: CC1(C)c2cc(-c3ccccc3)ccc2-c2ccc(N(c3ccc(-c4ccccc4)cc3)c3cccc4oc5ccc(-c6ccc7c(c6)c6ccccc6n7-c6ccccc6)cc5c34)cc21]
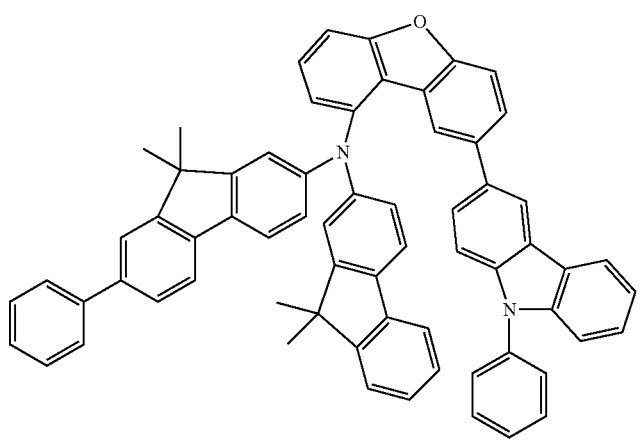 [SMILES: CC1(C)c2ccccc2-c2ccc(N(c3ccc4c(c3)C(C)(C)c3cc(-c5ccccc5)ccc3-4)c3cccc4oc5ccc(-c6ccc7c(c6)c6ccccc6n7-c6ccccc6)cc5c34)cc21]

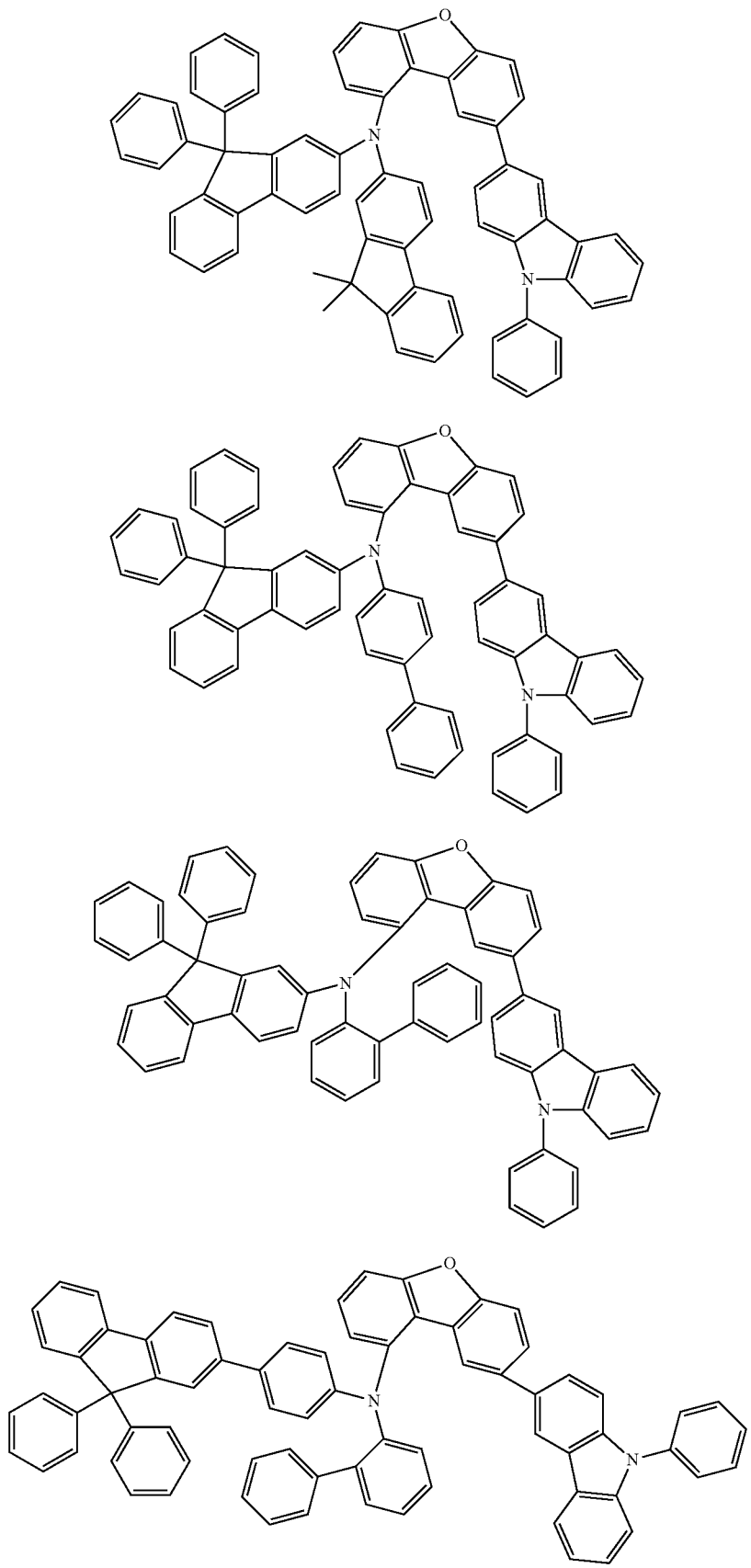

-continued
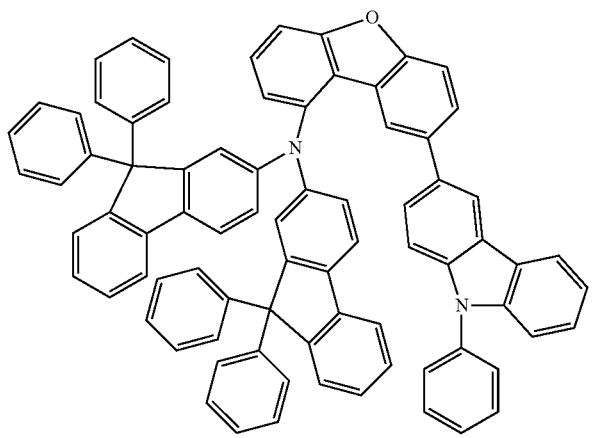 [SMILES: c1ccc(-n2c3ccccc3c3cc(-c4ccc5oc6cccc(N(c7ccc8c(c7)C(c7ccccc7)(c7ccccc7)c7ccccc7-8)c7ccc8c(c7)C(c7ccccc7)(c7ccccc7)c7ccccc7-8)c6c5c4)ccc32)cc1]
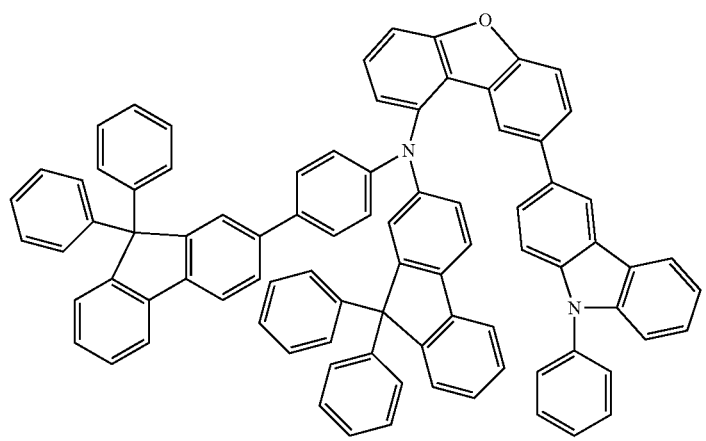 [SMILES: c1ccc(-n2c3ccccc3c3cc(-c4ccc5oc6cccc(N(c7ccc(-c8ccc9c(c8)C(c8ccccc8)(c8ccccc8)c8ccccc8-9)cc7)c7ccc8c(c7)C(c7ccccc7)(c7ccccc7)c7ccccc7-8)c6c5c4)ccc32)cc1]
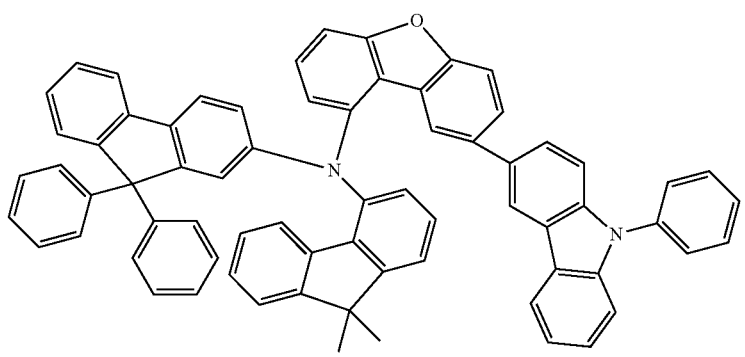 [SMILES: CC1(C)c2ccccc2-c2c(N(c3ccc4c(c3)C(c3ccccc3)(c3ccccc3)c3ccccc3-4)c3cccc4oc5ccc(-c6ccc7c(c6)c6ccccc6n7-c6ccccc6)cc5c34)cccc21]

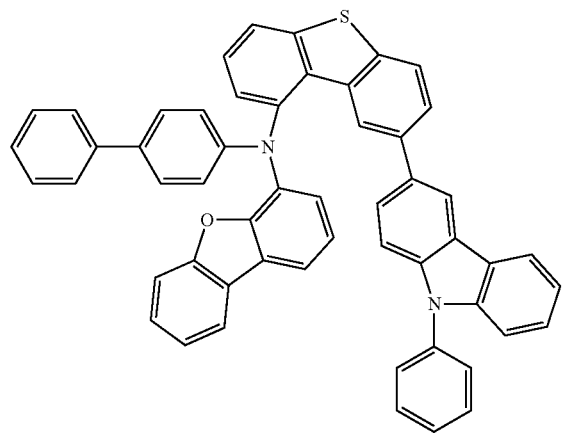 [SMILES: c1ccc(-c2ccc(N(c3cccc4c3oc3ccccc34)c3cccc4sc5ccc(-c6ccc7c(c6)c6ccccc6n7-c6ccccc6)cc5c34)cc2)cc1]
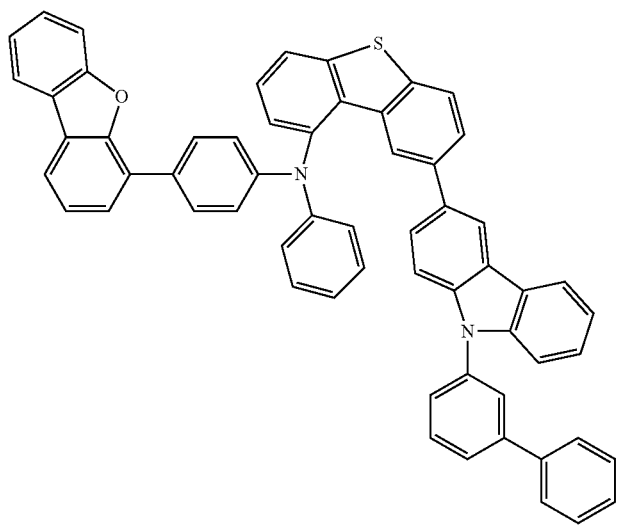 [SMILES: c1ccc(-c2cccc(-n3c4ccccc4c4cc(-c5ccc6sc7cccc(N(c8ccccc8)c8ccc(-c9cccc%10c9oc9ccccc9%10)cc8)c7c6c5)ccc43)c2)cc1]
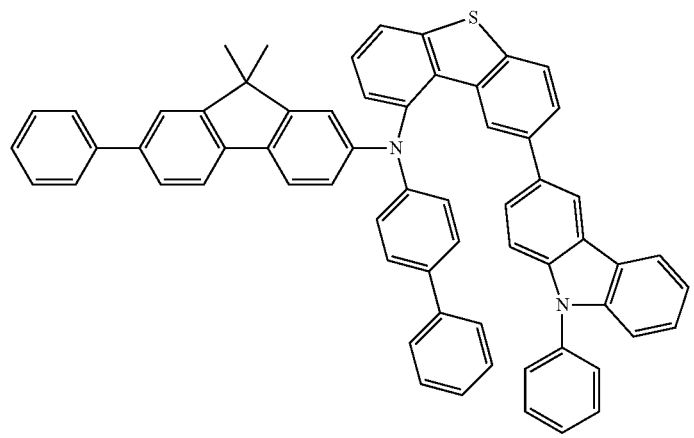 [SMILES: CC1(C)c2cc(-c3ccccc3)ccc2-c2ccc(N(c3ccc(-c4ccccc4)cc3)c3cccc4sc5ccc(-c6ccc7c(c6)c6ccccc6n7-c6ccccc6)cc5c34)cc21]

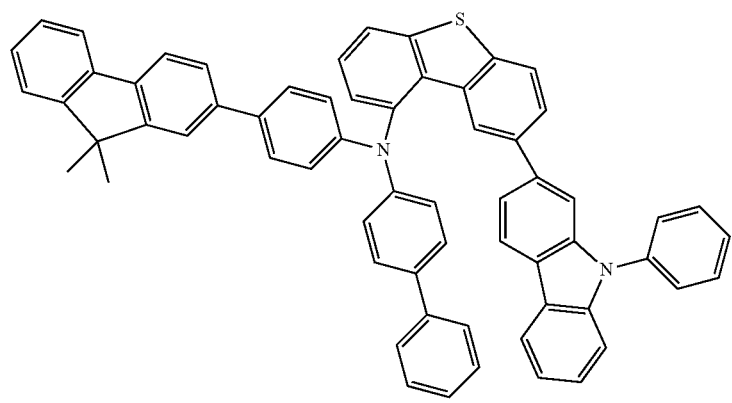 [SMILES: CC1(C)c2ccccc2-c2ccc(-c3ccc(N(c4ccc(-c5ccccc5)cc4)c4cccc5sc6ccc(-c7ccc8c9ccccc9n(-c9ccccc9)c8c7)cc6c45)cc3)cc21]
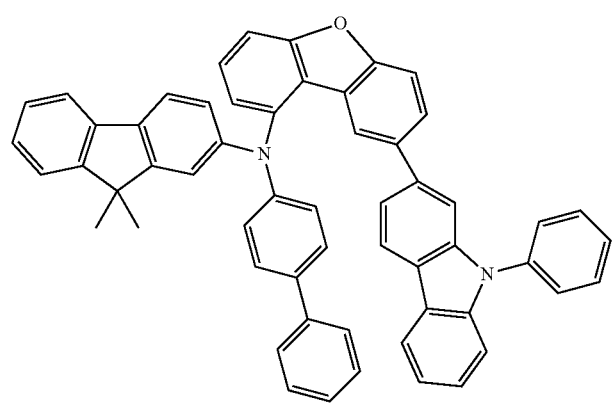 [SMILES: CC1(C)c2ccccc2-c2ccc(N(c3ccc(-c4ccccc4)cc3)c3cccc4oc5ccc(-c6ccc7c8ccccc8n(-c8ccccc8)c7c6)cc5c34)cc21]
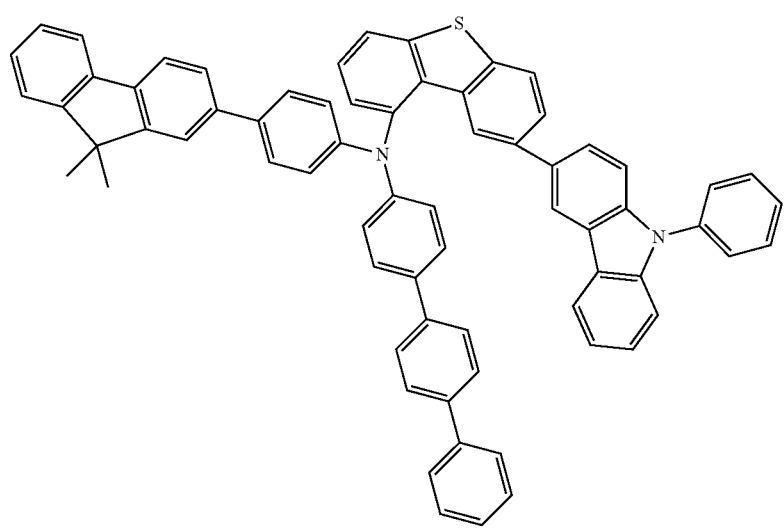 [SMILES: CC1(C)c2ccccc2-c2ccc(-c3ccc(N(c4ccc(-c5ccc(-c6ccccc6)cc5)cc4)c4cccc5sc6ccc(-c7ccc8c(c7)c7ccccc7n8-c7ccccc7)cc6c45)cc3)cc21]

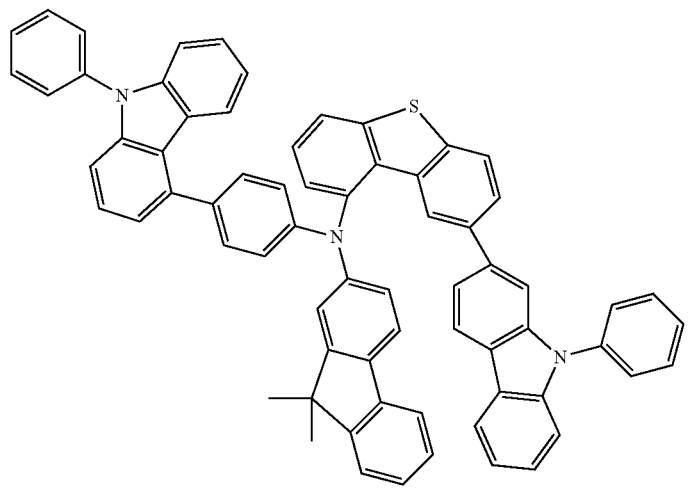 [SMILES: CC1(C)c2ccccc2-c2ccc(N(c3ccc(-c4cccc5c4c4ccccc4n5-c4ccccc4)cc3)c3cccc4sc5ccc(-c6ccc7c8ccccc8n(-c8ccccc8)c7c6)cc5c34)cc21]
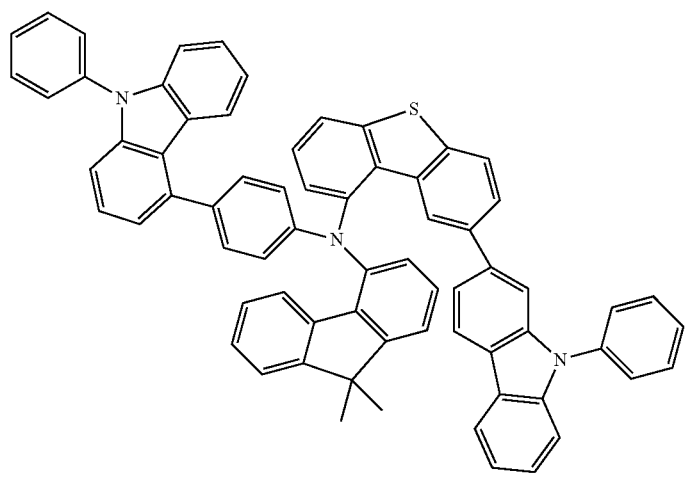 [SMILES: CC1(C)c2ccccc2-c2c(N(c3ccc(-c4cccc5c4c4ccccc4n5-c4ccccc4)cc3)c3cccc4sc5ccc(-c6ccc7c8ccccc8n(-c8ccccc8)c7c6)cc5c34)cccc21]
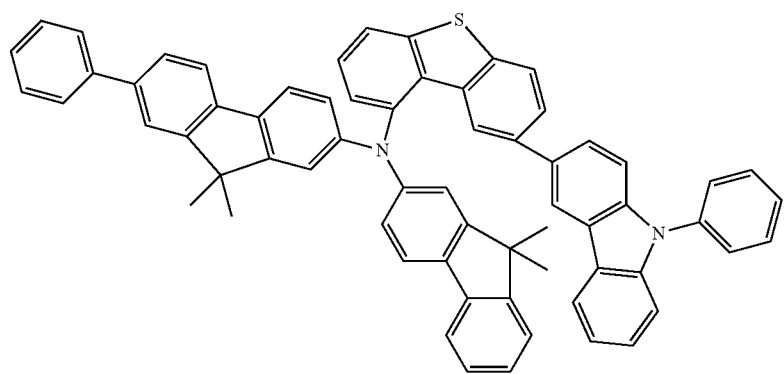 [SMILES: CC1(C)c2ccccc2-c2ccc(N(c3ccc4c(c3)C(C)(C)c3cc(-c5ccccc5)ccc3-4)c3cccc4sc5ccc(-c6ccc7c(c6)c6ccccc6n7-c6ccccc6)cc5c34)cc21]

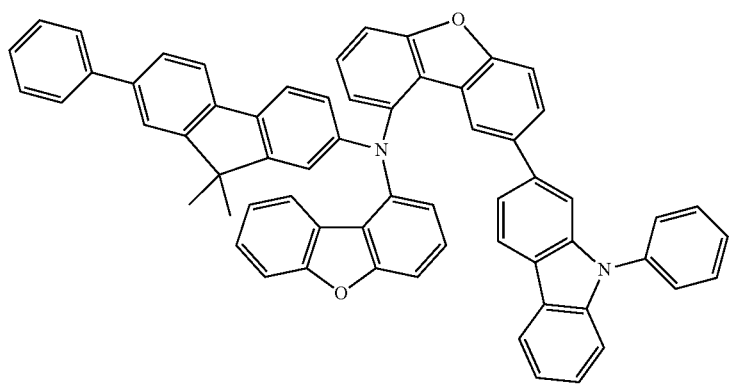 [SMILES: CC1(C)c2cc(-c3ccccc3)ccc2-c2ccc(N(c3cccc4oc5ccccc5c34)c3cccc4oc5ccc(-c6ccc7c8ccccc8n(-c8ccccc8)c7c6)cc5c34)cc21]
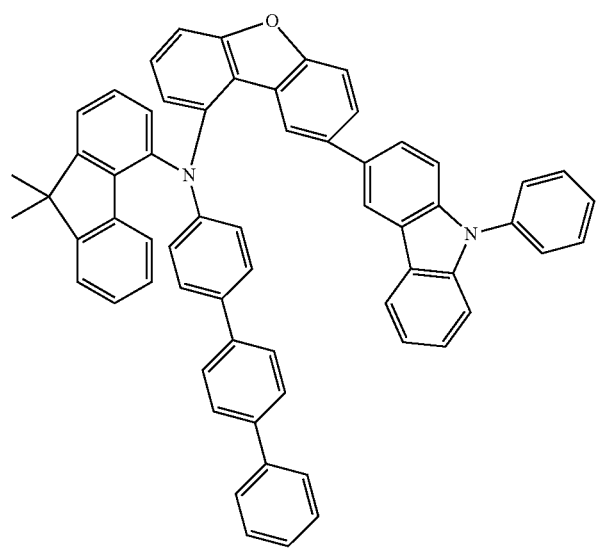 [SMILES: CC1(C)c2ccccc2-c2c(N(c3ccc(-c4ccc(-c5ccccc5)cc4)cc3)c3cccc4oc5ccc(-c6ccc7c(c6)c6ccccc6n7-c6ccccc6)cc5c34)cccc21]
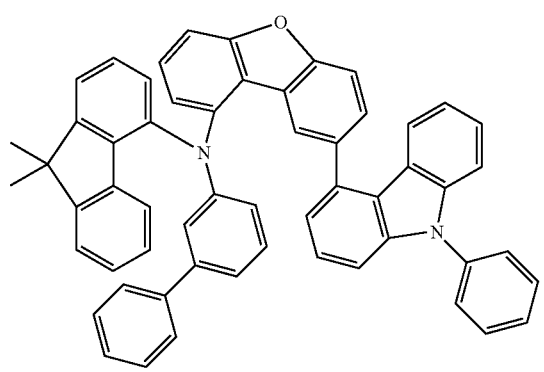 [SMILES: CC1(C)c2ccccc2-c2c(N(c3cccc(-c4ccccc4)c3)c3cccc4oc5ccc(-c6cccc7c6c6ccccc6n7-c6ccccc6)cc5c34)cccc21]

-continued
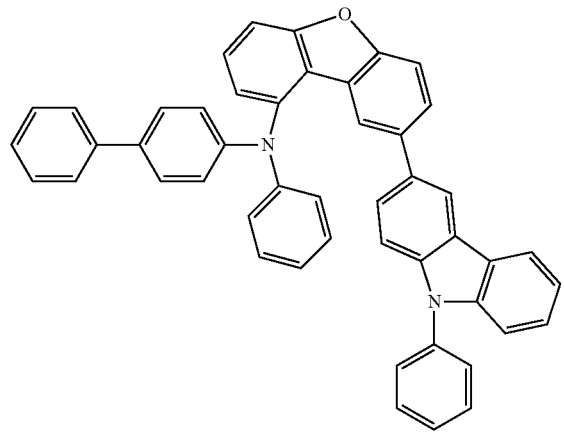
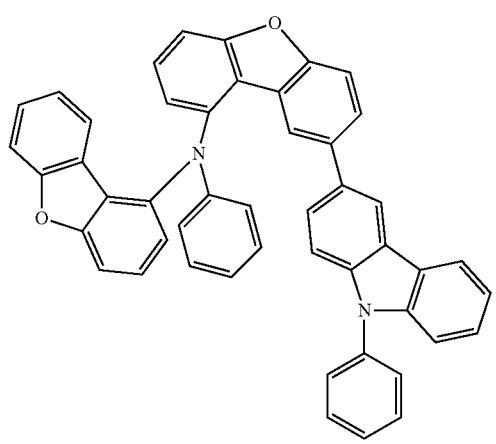
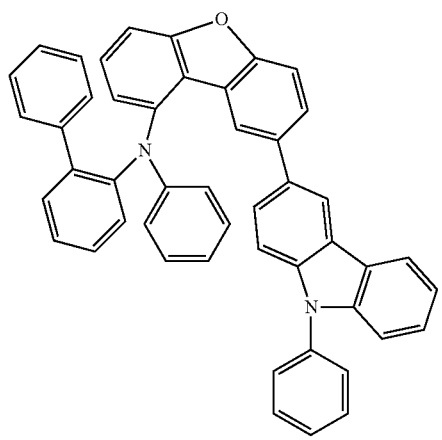 [SMILES: c1ccc(-c2ccccc2N(c2ccccc2)c2cccc3oc4ccc(-c5ccc6c(c5)c5ccccc5n6-c5ccccc5)cc4c23)cc1]

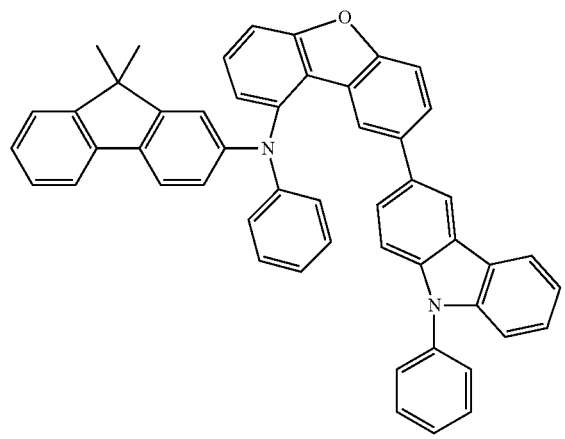
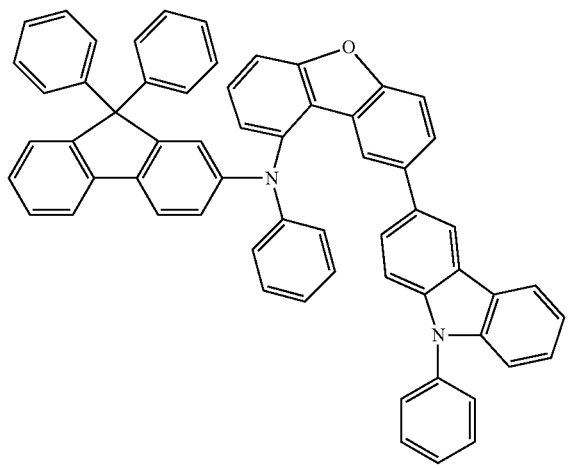 [SMILES: c1ccc(N(c2ccc3c(c2)C(c2ccccc2)(c2ccccc2)c2ccccc2-3)c2cccc3oc4ccc(-c5ccc6c(c5)c5ccccc5n6-c5ccccc5)cc4c23)cc1]
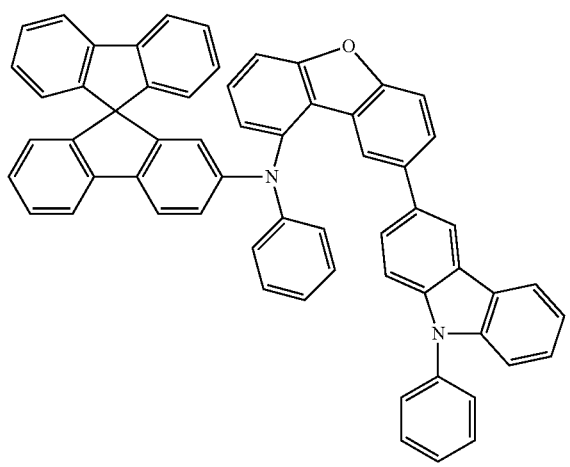 [SMILES: c1ccc(N(c2ccc3c(c2)C2(c4ccccc4-c4ccccc42)c2ccccc2-3)c2cccc3oc4ccc(-c5ccc6c(c5)c5ccccc5n6-c5ccccc5)cc4c23)cc1]

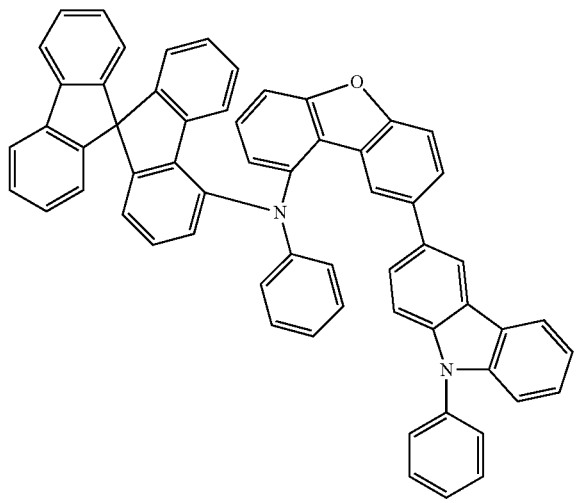
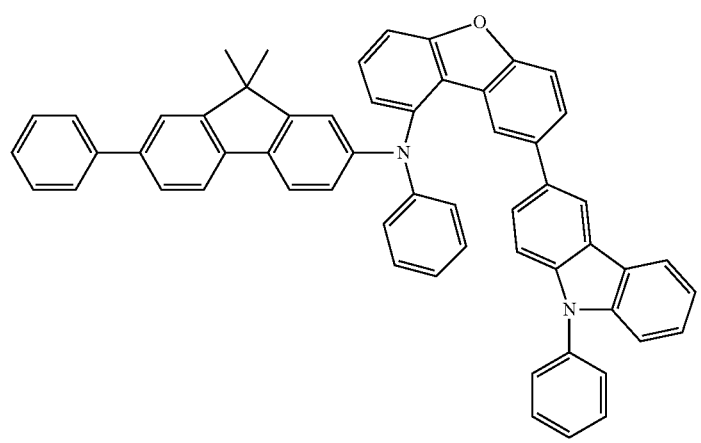 [SMILES: CC1(C)c2cc(-c3ccccc3)ccc2-c2ccc(N(c3ccccc3)c3cccc4oc5ccc(-c6ccc7c(c6)c6ccccc6n7-c6ccccc6)cc5c34)cc21]
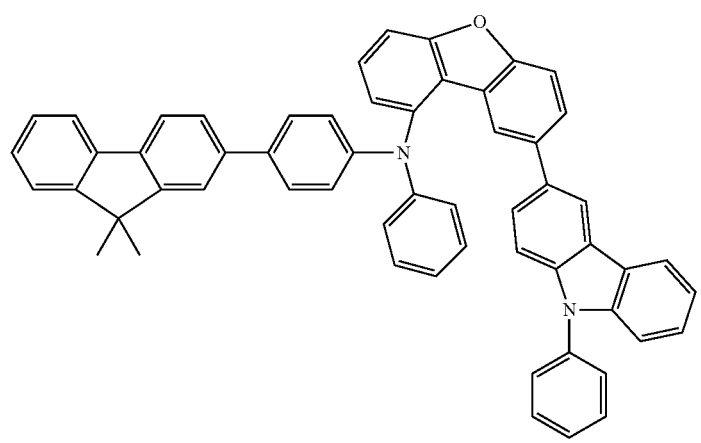 [SMILES: CC1(C)c2ccccc2-c2ccc(-c3ccc(N(c4ccccc4)c4cccc5oc6ccc(-c7ccc8c(c7)c7ccccc7n8-c7ccccc7)cc6c45)cc3)cc21]

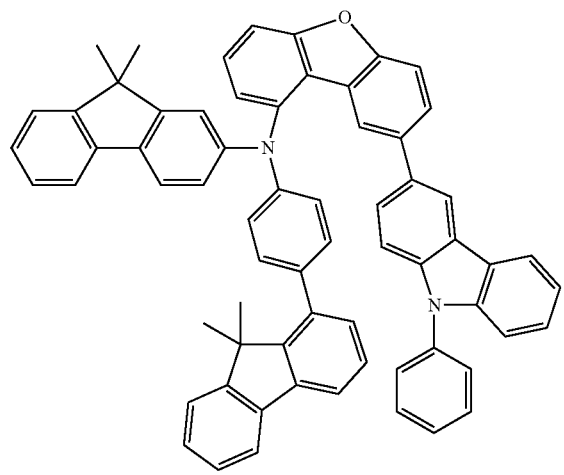
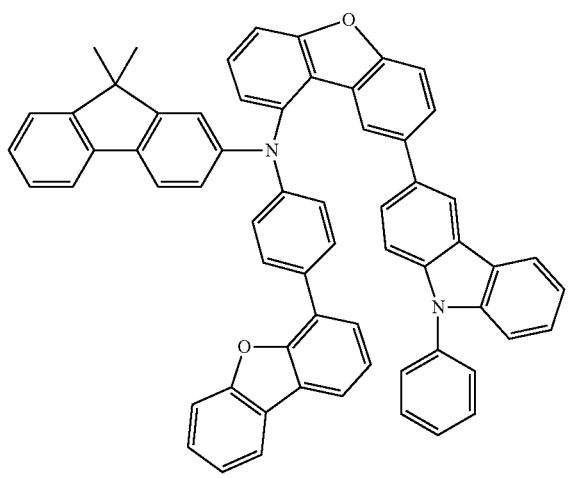 [SMILES: CC1(C)c2ccccc2-c2ccc(N(c3ccc(-c4cccc5c4oc4ccccc45)cc3)c3cccc4oc5ccc(-c6ccc7c(c6)c6ccccc6n7-c6ccccc6)cc5c34)cc21]
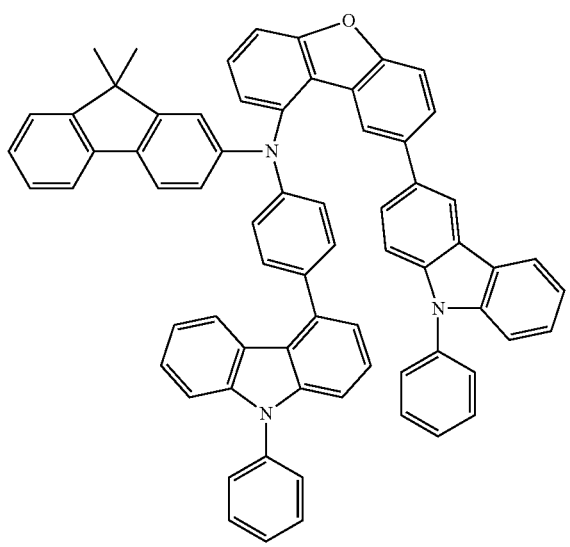 [SMILES: CC1(C)c2ccccc2-c2ccc(N(c3ccc(-c4cccc5c4c4ccccc4n5-c4ccccc4)cc3)c3cccc4oc5ccc(-c6ccc7c(c6)c6ccccc6n7-c6ccccc6)cc5c34)cc21]

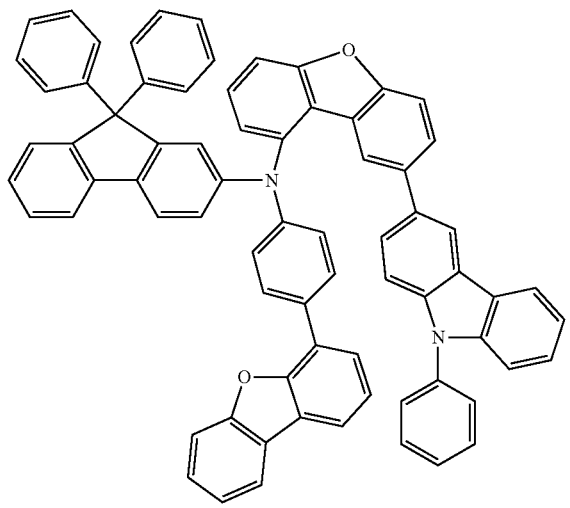 [SMILES: c1ccc(-n2c3ccccc3c3cc(-c4ccc5oc6cccc(N(c7ccc(-c8cccc9c8oc8ccccc89)cc7)c7ccc8c(c7)C(c7ccccc7)(c7ccccc7)c7ccccc7-8)c6c5c4)ccc32)cc1]
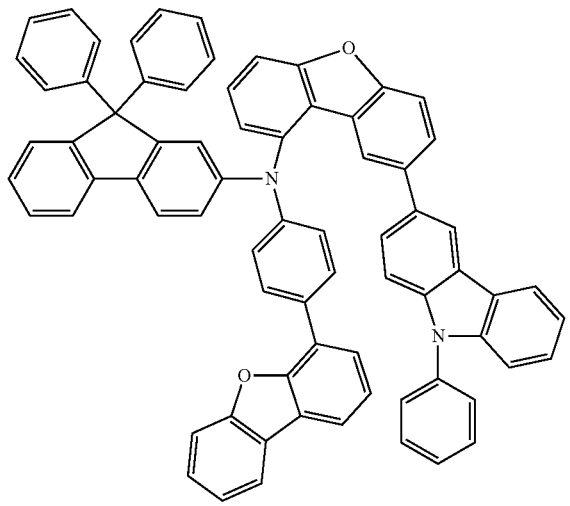 [SMILES: c1ccc(-n2c3ccccc3c3cc(-c4ccc5oc6cccc(N(c7ccc(-c8cccc9c8oc8ccccc89)cc7)c7ccc8c(c7)C(c7ccccc7)(c7ccccc7)c7ccccc7-8)c6c5c4)ccc32)cc1]
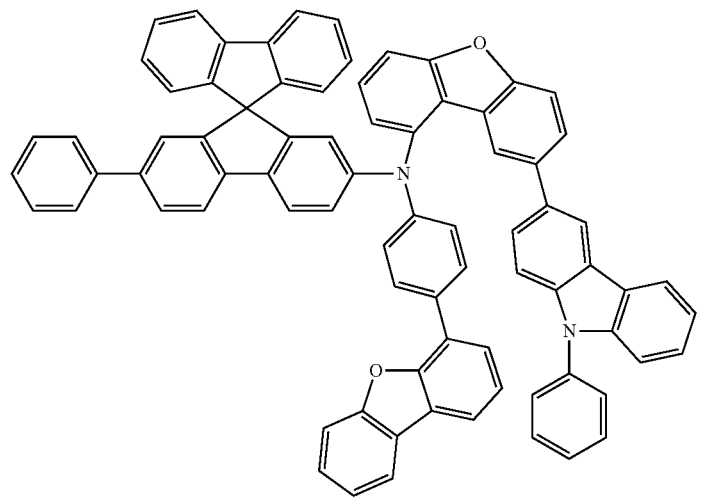 [SMILES: c1ccc(-c2ccc3c(c2)C2(c4ccccc4-c4ccccc42)c2cc(N(c4ccc(-c5cccc6c5oc5ccccc56)cc4)c4cccc5oc6ccc(-c7ccc8c(c7)c7ccccc7n8-c7ccccc7)cc6c45)ccc2-3)cc1]

-continued
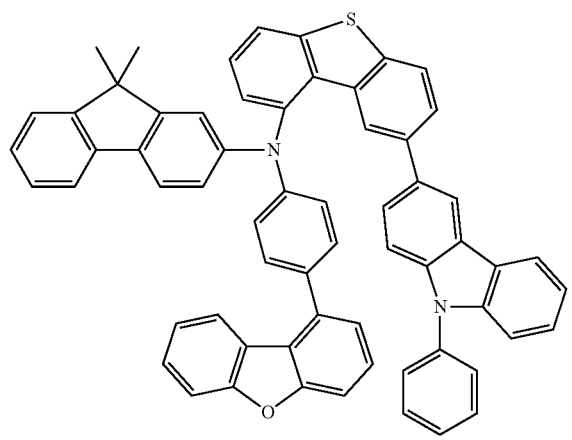 [SMILES: CC1(C)c2ccccc2-c2ccc(N(c3ccc(-c4cccc5oc6ccccc6c45)cc3)c3cccc4sc5ccc(-c6ccc7c(c6)c6ccccc6n7-c6ccccc6)cc5c34)cc21]
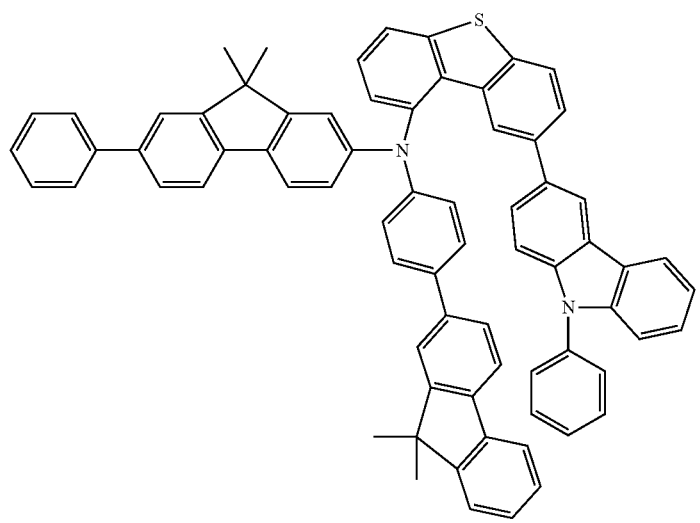 [SMILES: CC1(C)c2ccccc2-c2ccc(-c3ccc(N(c4ccc5c(c4)C(C)(C)c4cc(-c6ccccc6)ccc4-5)c4cccc5sc6ccc(-c7ccc8c(c7)c7ccccc7n8-c7ccccc7)cc6c45)cc3)cc21]
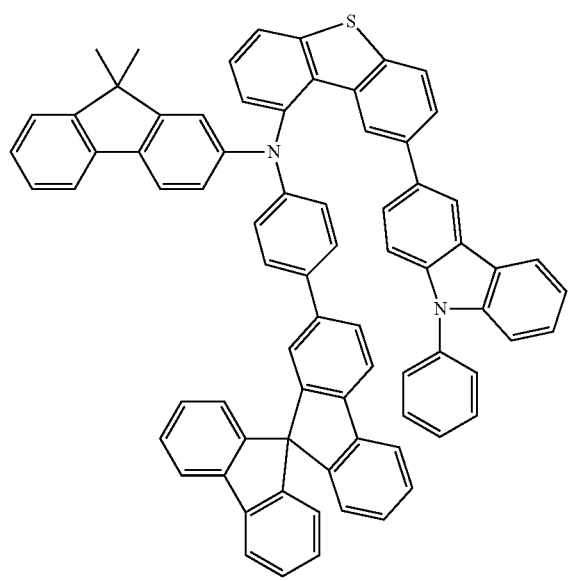 [SMILES: CC1(C)c2ccccc2-c2ccc(N(c3ccc(-c4ccc5c(c4)C4(c6ccccc6-c6ccccc64)c4ccccc4-5)cc3)c3cccc4sc5ccc(-c6ccc7c(c6)c6ccccc6n7-c6ccccc6)cc5c34)cc21]

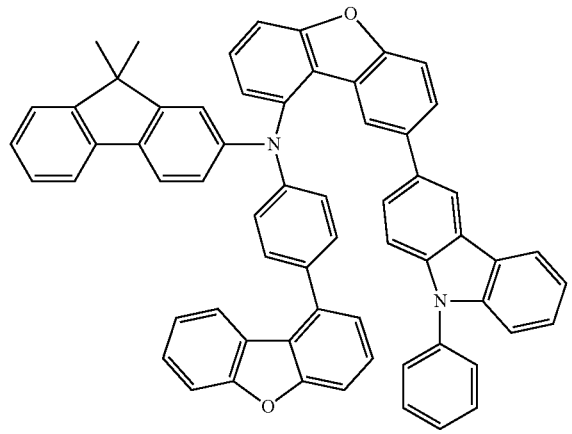 [SMILES: CC1(C)c2ccccc2-c2ccc(N(c3ccc(-c4cccc5oc6ccccc6c45)cc3)c3cccc4oc5ccc(-c6ccc7c(c6)c6ccccc6n7-c6ccccc6)cc5c34)cc21]
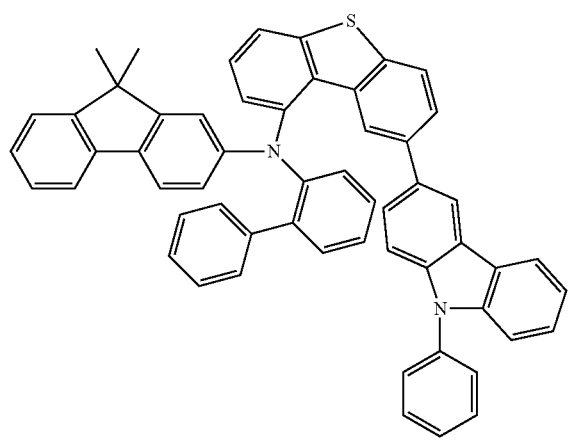 [SMILES: CC1(C)c2ccccc2-c2ccc(N(c3ccccc3-c3ccccc3)c3cccc4sc5ccc(-c6ccc7c(c6)c6ccccc6n7-c6ccccc6)cc5c34)cc21]
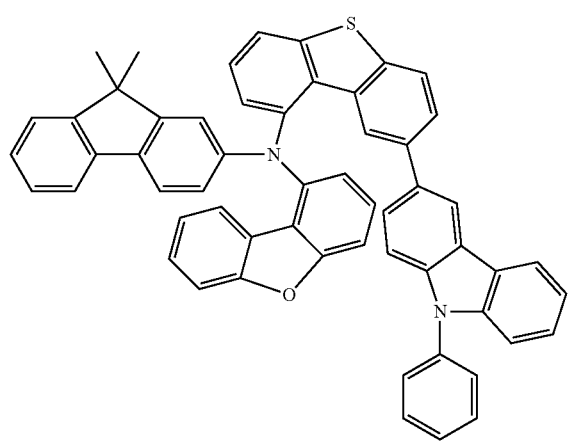 [SMILES: CC1(C)c2ccccc2-c2ccc(N(c3cccc4oc5ccccc5c34)c3cccc4sc5ccc(-c6ccc7c(c6)c6ccccc6n7-c6ccccc6)cc5c34)cc21]

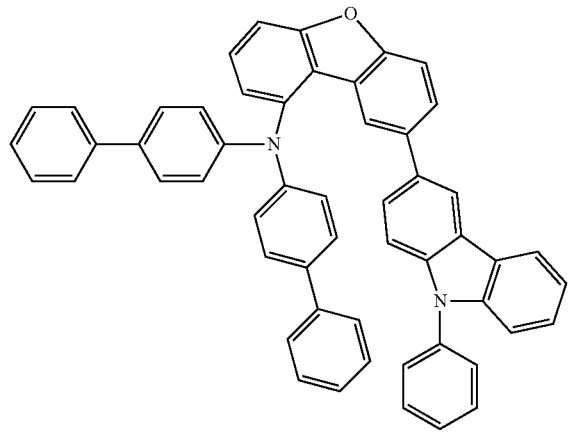 [SMILES: c1ccc(-c2ccc(N(c3ccc(-c4ccccc4)cc3)c3cccc4oc5ccc(-c6ccc7c(c6)c6ccccc6n7-c6ccccc6)cc5c34)cc2)cc1]
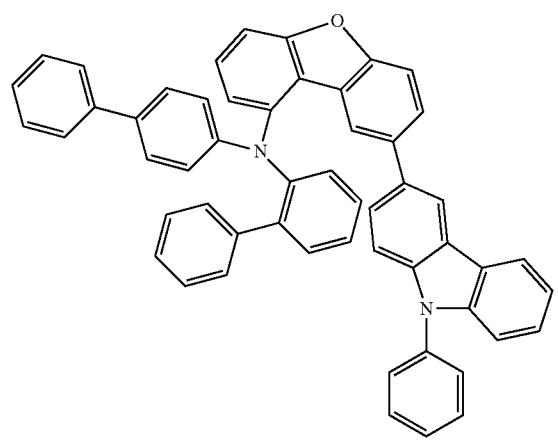 [SMILES: c1ccc(-c2ccc(N(c3ccccc3-c3ccccc3)c3cccc4oc5ccc(-c6ccc7c(c6)c6ccccc6n7-c6ccccc6)cc5c34)cc2)cc1]
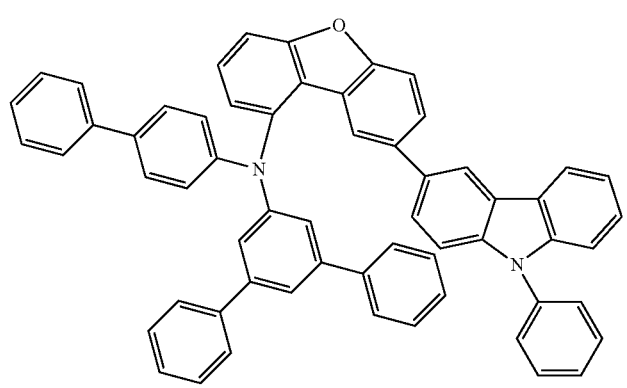 [SMILES: c1ccc(-c2ccc(N(c3cc(-c4ccccc4)cc(-c4ccccc4)c3)c3cccc4oc5ccc(-c6ccc7c(c6)c6ccccc6n7-c6ccccc6)cc5c34)cc2)cc1]

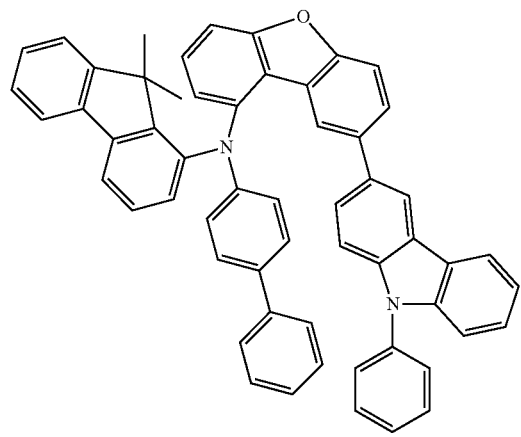 [SMILES: CC1(C)c2ccccc2-c2cccc(N(c3ccc(-c4ccccc4)cc3)c3cccc4oc5ccc(-c6ccc7c(c6)c6ccccc6n7-c6ccccc6)cc5c34)c21]
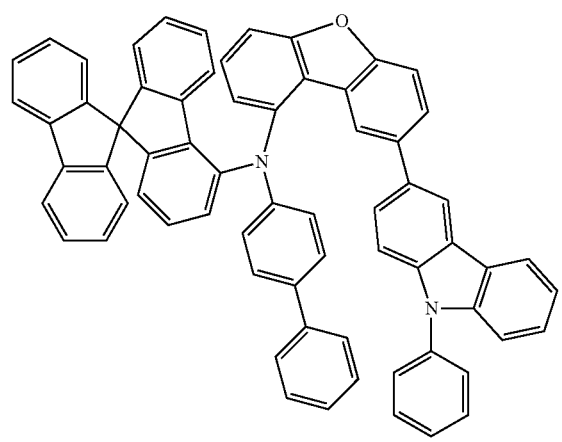 [SMILES: c1ccc(-c2ccc(N(c3cccc4c3-c3ccccc3C43c4ccccc4-c4ccccc43)c3cccc4oc5ccc(-c6ccc7c(c6)c6ccccc6n7-c6ccccc6)cc5c34)cc2)cc1]
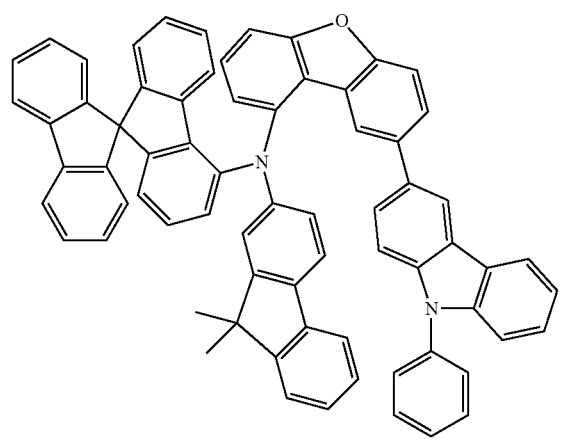 [SMILES: CC1(C)c2ccccc2-c2ccc(N(c3cccc4c3-c3ccccc3C43c4ccccc4-c4ccccc43)c3cccc4oc5ccc(-c6ccc7c(c6)c6ccccc6n7-c6ccccc6)cc5c34)cc21]

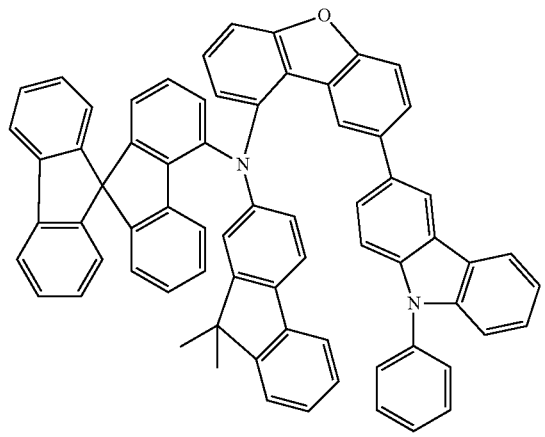 [SMILES: CC1(C)c2ccccc2-c2ccc(N(c3cccc4c3-c3ccccc3C43c4ccccc4-c4ccccc43)c3cccc4oc5ccc(-c6ccc7c(c6)c6ccccc6n7-c6ccccc6)cc5c34)cc21]
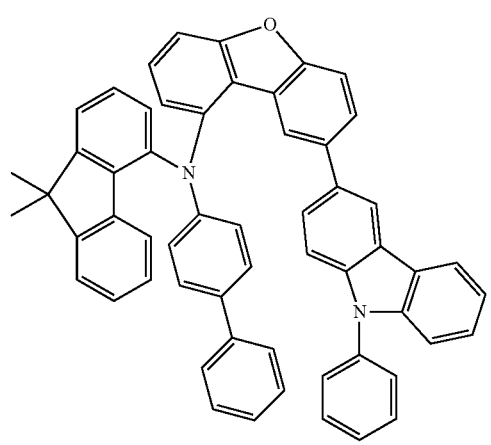 [SMILES: CC1(C)c2ccccc2-c2c(N(c3ccc(-c4ccccc4)cc3)c3cccc4oc5ccc(-c6ccc7c(c6)c6ccccc6n7-c6ccccc6)cc5c34)cccc21]
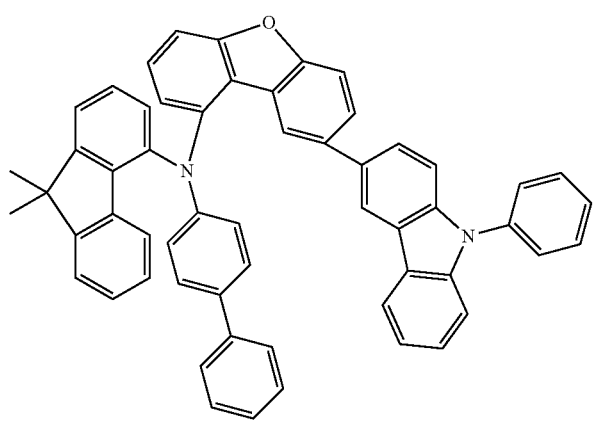 [SMILES: CC1(C)c2ccccc2-c2c(N(c3ccc(-c4ccccc4)cc3)c3cccc4oc5ccc(-c6ccc7c(c6)c6ccccc6n7-c6ccccc6)cc5c34)cccc21]

-continued
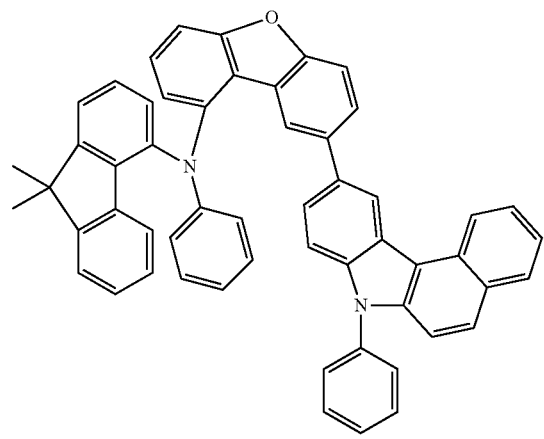 [SMILES: CC1(C)c2ccccc2-c2c(N(c3ccccc3)c3cccc4oc5ccc(-c6ccc7c(c6)c6c8ccccc8ccc6n7-c6ccccc6)cc5c34)cccc21]
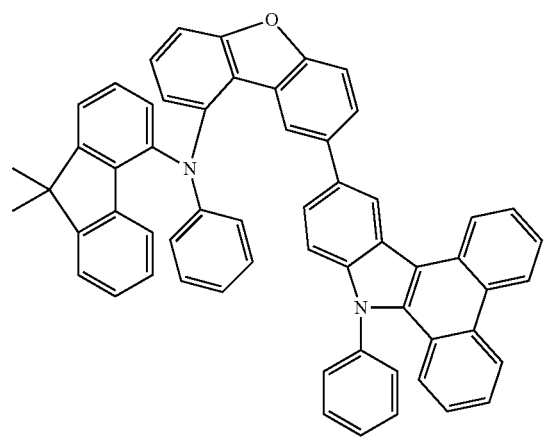 [SMILES: CC1(C)c2ccccc2-c2c(N(c3ccccc3)c3cccc4oc5ccc(-c6ccc7c(c6)c6c8ccccc8c8ccccc8c6n7-c6ccccc6)cc5c34)cccc21]
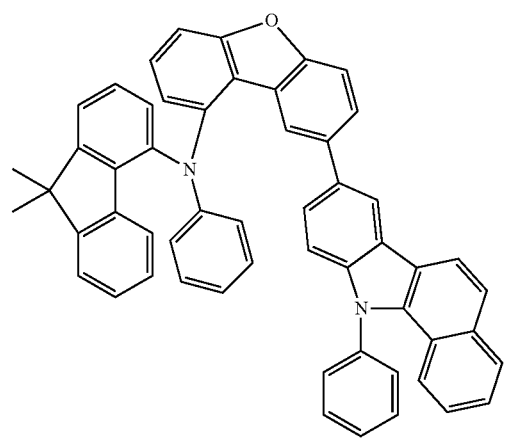 [SMILES: CC1(C)c2ccccc2-c2c(N(c3ccccc3)c3cccc4oc5ccc(-c6ccc7c(c6)c6ccc8ccccc8c6n7-c6ccccc6)cc5c34)cccc21]

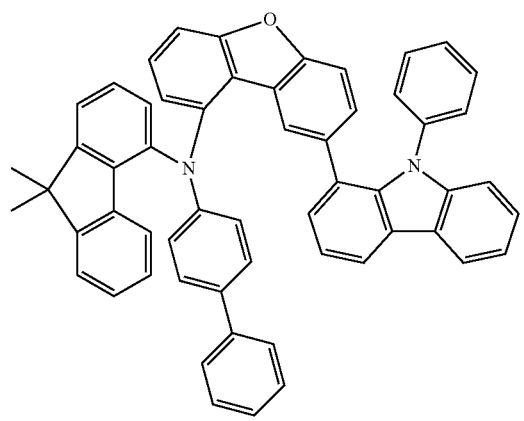 [SMILES: CC1(C)c2ccccc2-c2c(N(c3ccc(-c4ccccc4)cc3)c3cccc4oc5ccc(-c6cccc7c8ccccc8n(-c8ccccc8)c67)cc5c34)cccc21]
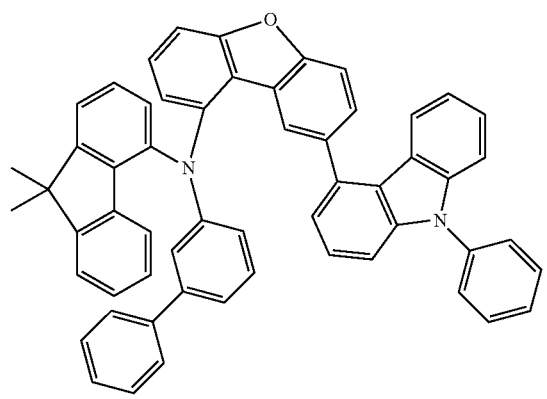 [SMILES: CC1(C)c2ccccc2-c2c(N(c3cccc(-c4ccccc4)c3)c3cccc4oc5ccc(-c6cccc7c6c6ccccc6n7-c6ccccc6)cc5c34)cccc21]
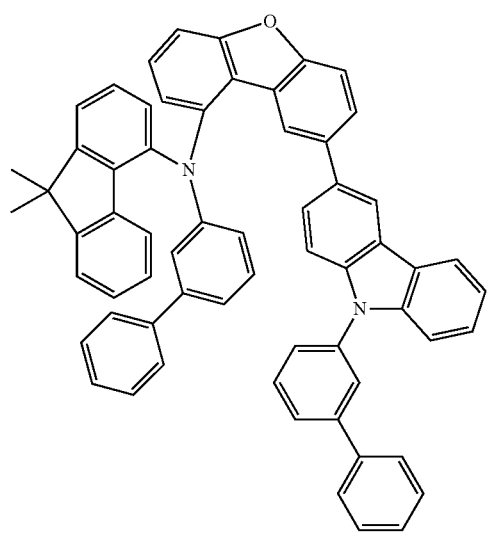 [SMILES: CC1(C)c2ccccc2-c2c(N(c3cccc(-c4ccccc4)c3)c3cccc4oc5ccc(-c6ccc7c(c6)c6ccccc6n7-c6cccc(-c7ccccc7)c6)cc5c34)cccc21]

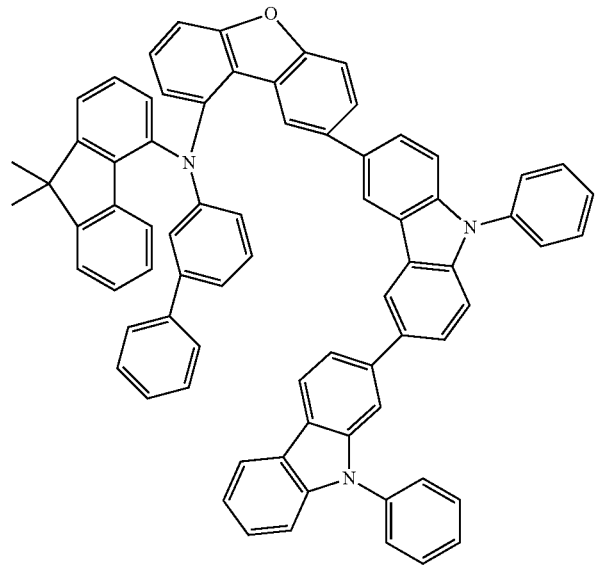 [SMILES: CC1(C)c2ccccc2-c2c(N(c3cccc(-c4ccccc4)c3)c3cccc4oc5ccc(-c6ccc7c(c6)c6cc(-c8ccc9c%10ccccc%10n(-c%10ccccc%10)c9c8)ccc6n7-c6ccccc6)cc5c34)cccc21]
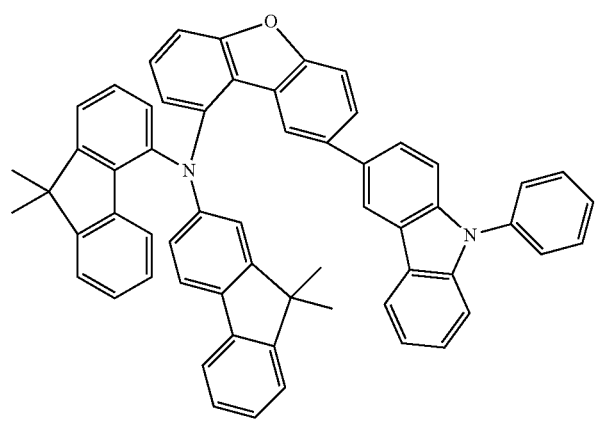 [SMILES: CC1(C)c2ccccc2-c2ccc(N(c3cccc4c3-c3ccccc3C4(C)C)c3cccc4oc5ccc(-c6ccc7c(c6)c6ccccc6n7-c6ccccc6)cc5c34)cc21]
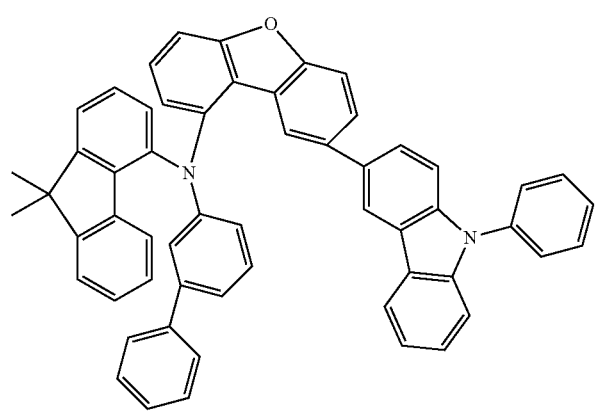 [SMILES: CC1(C)c2ccccc2-c2c(N(c3cccc(-c4ccccc4)c3)c3cccc4oc5ccc(-c6ccc7c(c6)c6ccccc6n7-c6ccccc6)cc5c34)cccc21]

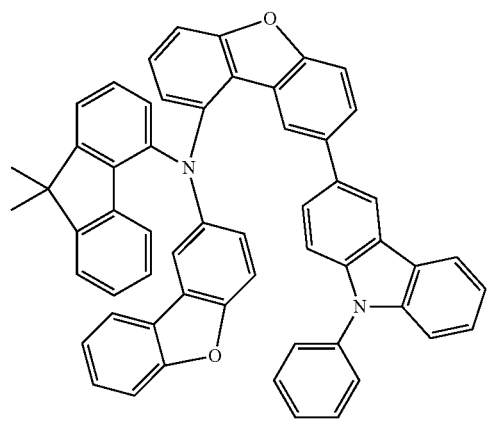 [SMILES: CC1(C)c2ccccc2-c2c(N(c3ccc4oc5ccccc5c4c3)c3cccc4oc5ccc(-c6ccc7c(c6)c6ccccc6n7-c6ccccc6)cc5c34)cccc21]
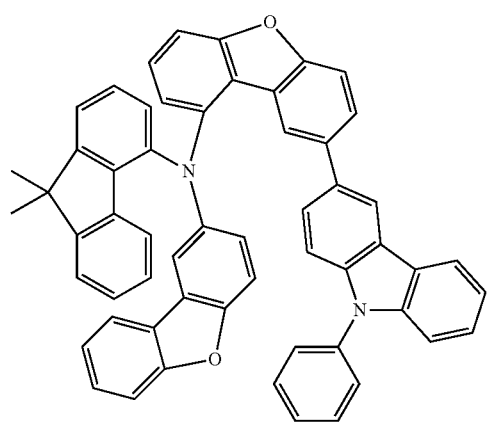 [SMILES: CC1(C)c2ccccc2-c2c(N(c3ccc4oc5ccccc5c4c3)c3cccc4oc5ccc(-c6ccc7c(c6)c6ccccc6n7-c6ccccc6)cc5c34)cccc21]
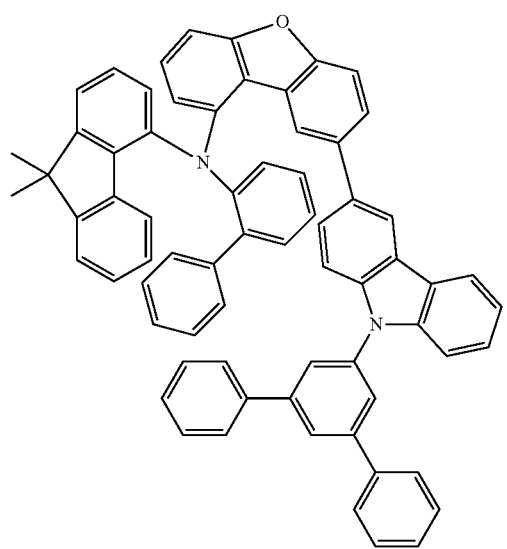 [SMILES: CC1(C)c2ccccc2-c2c(N(c3ccccc3-c3ccccc3)c3cccc4oc5ccc(-c6ccc7c(c6)c6ccccc6n7-c6cc(-c7ccccc7)cc(-c7ccccc7)c6)cc5c34)cccc21]

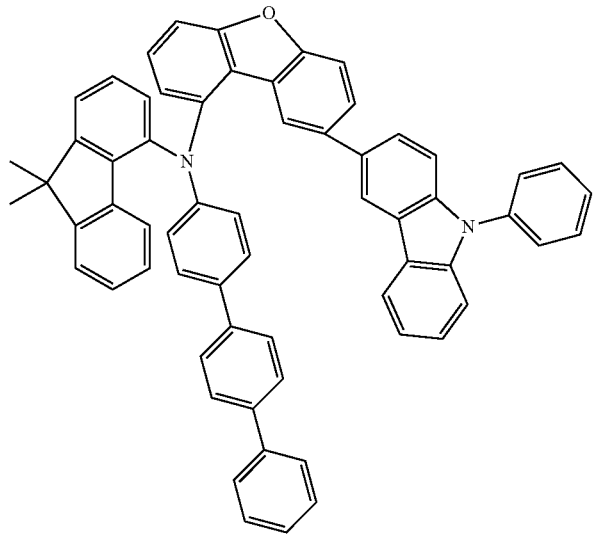 [SMILES: CC1(C)c2ccccc2-c2c(N(c3ccc(-c4ccc(-c5ccccc5)cc4)cc3)c3cccc4oc5ccc(-c6ccc7c(c6)c6ccccc6n7-c6ccccc6)cc5c34)cccc21]
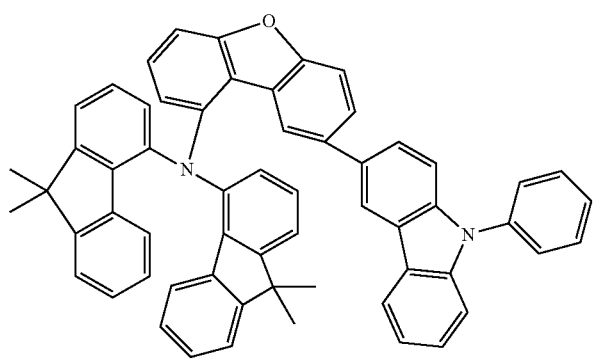 [SMILES: CC1(C)c2ccccc2-c2c(N(c3cccc4c3-c3ccccc3C4(C)C)c3cccc4oc5ccc(-c6ccc7c(c6)c6ccccc6n7-c6ccccc6)cc5c34)cccc21]
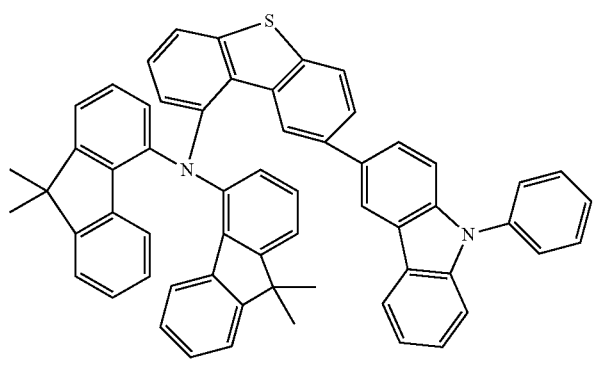 [SMILES: CC1(C)c2ccccc2-c2c(N(c3cccc4c3-c3ccccc3C4(C)C)c3cccc4sc5ccc(-c6ccc7c(c6)c6ccccc6n7-c6ccccc6)cc5c34)cccc21]

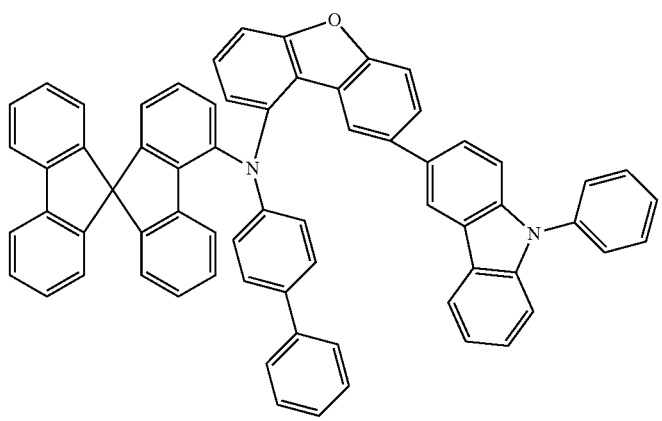 [SMILES: c1ccc(-c2ccc(N(c3cccc4c3-c3ccccc3C43c4ccccc4-c4ccccc43)c3cccc4oc5ccc(-c6ccc7c(c6)c6ccccc6n7-c6ccccc6)cc5c34)cc2)cc1]
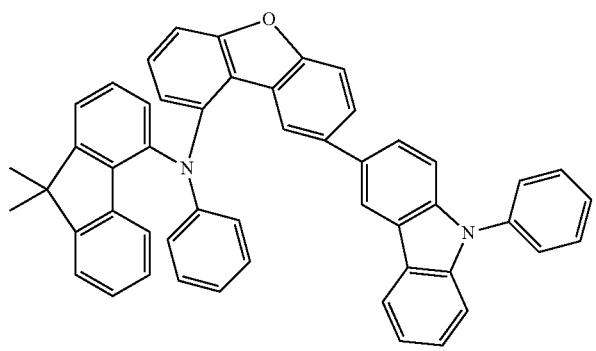 [SMILES: CC1(C)c2ccccc2-c2c(N(c3ccccc3)c3cccc4oc5ccc(-c6ccc7c(c6)c6ccccc6n7-c6ccccc6)cc5c34)cccc21]
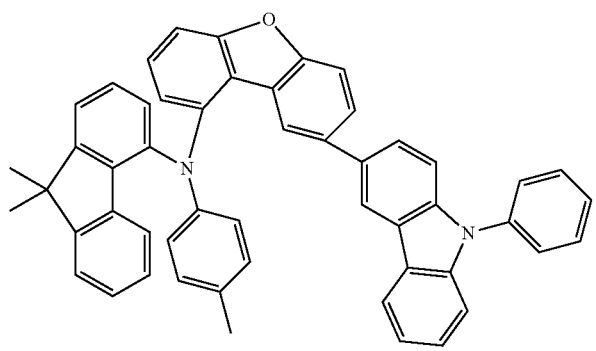 [SMILES: Cc1ccc(N(c2cccc3c2-c2ccccc2C3(C)C)c2cccc3oc4ccc(-c5ccc6c(c5)c5ccccc5n6-c5ccccc5)cc4c23)cc1]
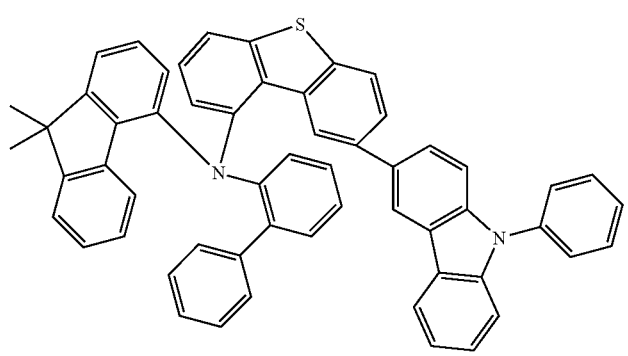 [SMILES: CC1(C)c2ccccc2-c2c(N(c3ccccc3-c3ccccc3)c3cccc4sc5ccc(-c6ccc7c(c6)c6ccccc6n7-c6ccccc6)cc5c34)cccc21]

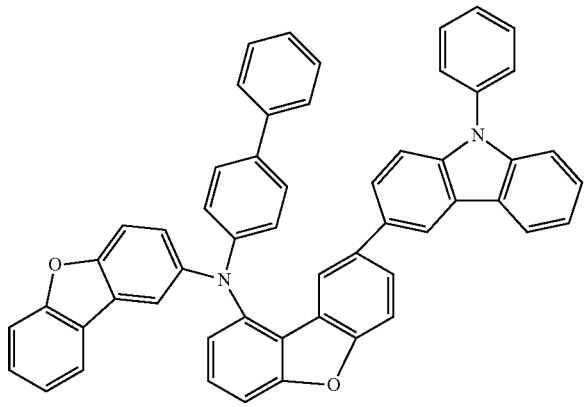 [SMILES: c1ccc(-c2ccc(N(c3ccc4oc5ccccc5c4c3)c3cccc4oc5ccc(-c6ccc7c(c6)c6ccccc6n7-c6ccccc6)cc5c34)cc2)cc1]
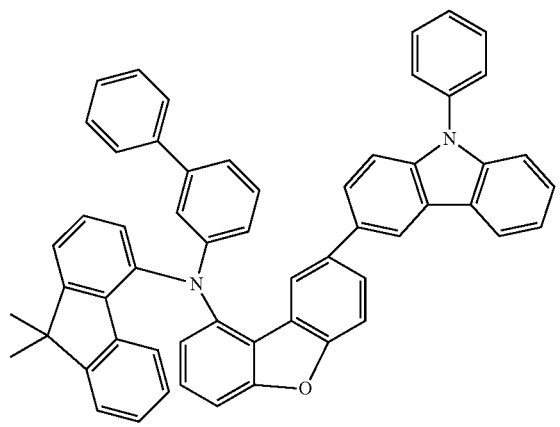 [SMILES: CC1(C)c2ccccc2-c2c(N(c3cccc(-c4ccccc4)c3)c3cccc4oc5ccc(-c6ccc7c(c6)c6ccccc6n7-c6ccccc6)cc5c34)cccc21]
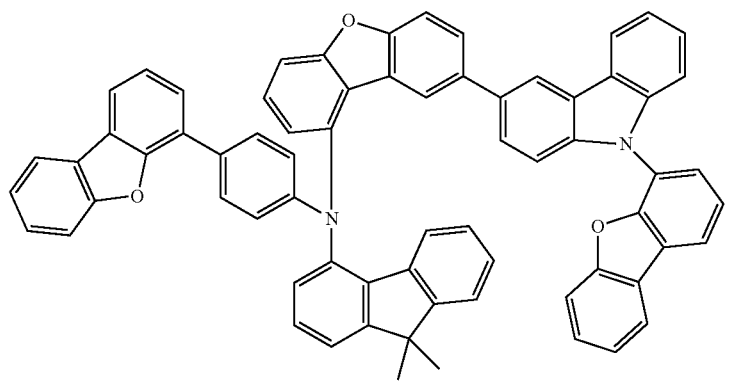 [SMILES: CC1(C)c2ccccc2-c2c(N(Cc3cccc4oc5ccc(-c6ccc7c(c6)c6ccccc6n7-c6cccc7c6oc6ccccc67)cc5c34)c3ccc(-c4cccc5c4oc4ccccc45)cc3)cccc21]

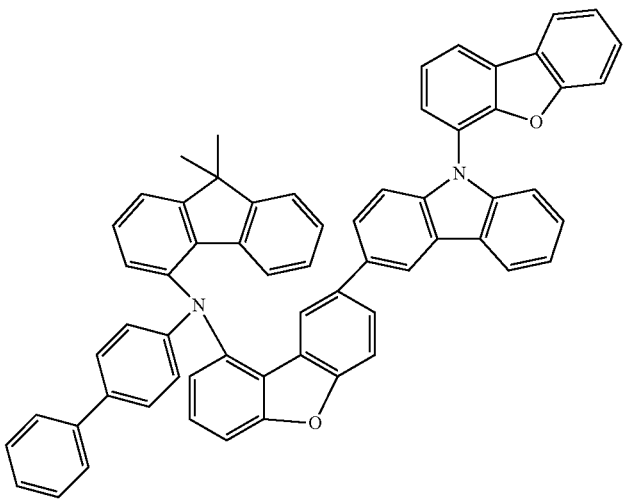 [SMILES: CC1(C)c2ccccc2-c2c(N(c3ccc(-c4ccccc4)cc3)c3cccc4oc5ccc(-c6ccc7c(c6)c6ccccc6n7-c6cccc7c6oc6ccccc67)cc5c34)cccc21]
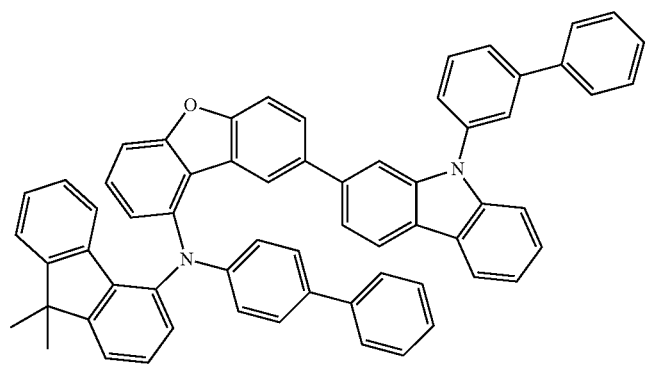 [SMILES: CC1(C)c2ccccc2-c2c(N(c3ccc(-c4ccccc4)cc3)c3cccc4oc5ccc(-c6ccc7c8ccccc8n(-c8cccc(-c9ccccc9)c8)c7c6)cc5c34)cccc21]
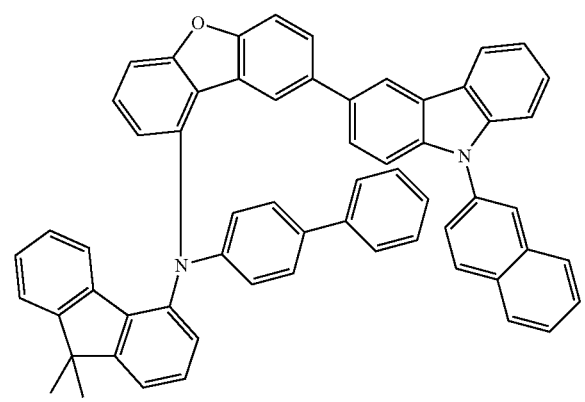 [SMILES: CC1(C)c2ccccc2-c2c(N(Cc3cccc4oc5ccc(-c6ccc7c(c6)c6ccccc6n7-c6ccc7ccccc7c6)cc5c34)c3ccc(-c4ccccc4)cc3)cccc21]

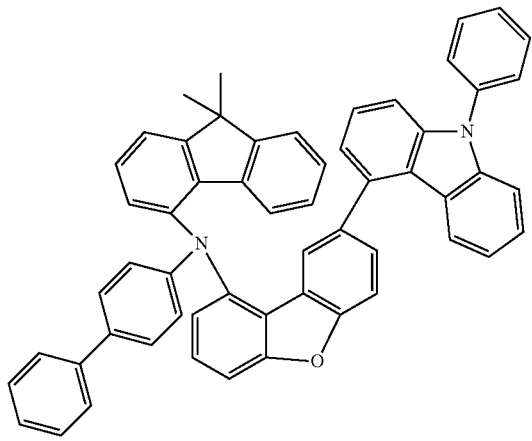 [SMILES: CC1(C)c2ccccc2-c2c(N(c3ccc(-c4ccccc4)cc3)c3cccc4oc5ccc(-c6cccc7c6c6ccccc6n7-c6ccccc6)cc5c34)cccc21]
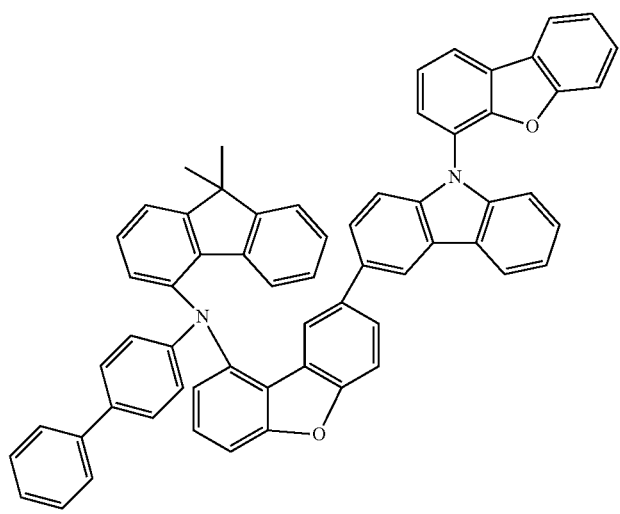 [SMILES: CC1(C)c2ccccc2-c2c(N(c3ccc(-c4ccccc4)cc3)c3cccc4oc5ccc(-c6ccc7c(c6)c6ccccc6n7-c6cccc7c6oc6ccccc67)cc5c34)cccc21]
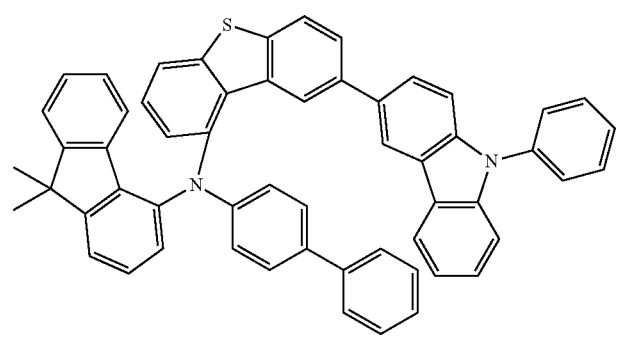 [SMILES: CC1(C)c2ccccc2-c2c(N(c3ccc(-c4ccccc4)cc3)c3cccc4sc5ccc(-c6ccc7c(c6)c6ccccc6n7-c6ccccc6)cc5c34)cccc21]

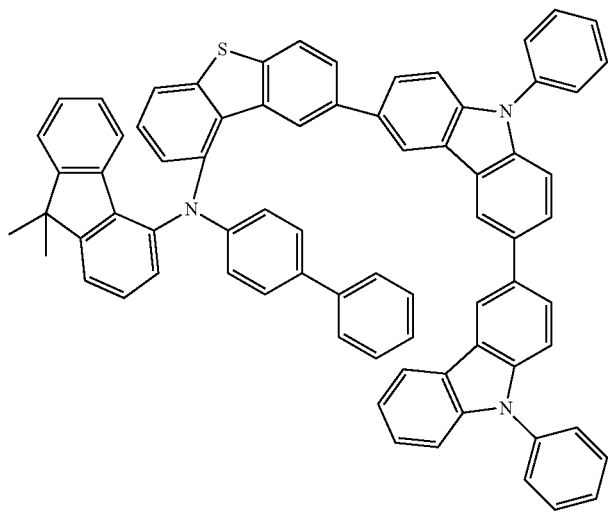 [SMILES: CC1(C)c2ccccc2-c2c(N(c3ccc(-c4ccccc4)cc3)c3cccc4sc5ccc(-c6ccc7c(c6)c6cc(-c8ccc9c(c8)c8ccccc8n9-c8ccccc8)ccc6n7-c6ccccc6)cc5c34)cccc21]
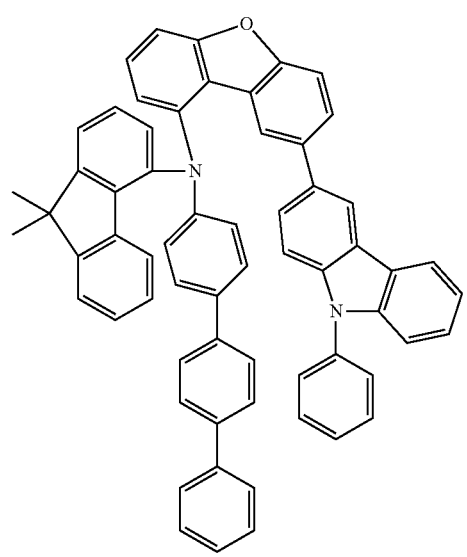 [SMILES: CC1(C)c2ccccc2-c2c(N(c3ccc(-c4ccc(-c5ccccc5)cc4)cc3)c3cccc4oc5ccc(-c6ccc7c(c6)c6ccccc6n7-c6ccccc6)cc5c34)cccc21]
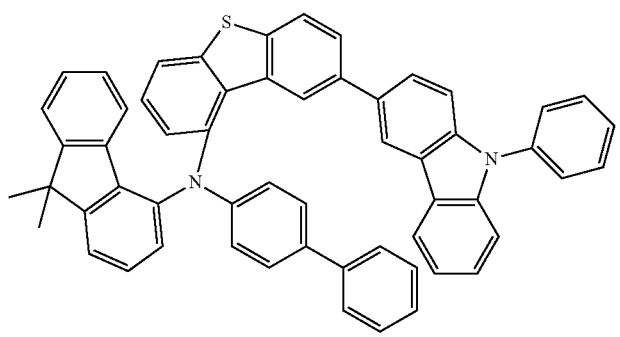 [SMILES: CC1(C)c2ccccc2-c2c(N(c3ccc(-c4ccccc4)cc3)c3cccc4sc5ccc(-c6ccc7c(c6)c6ccccc6n7-c6ccccc6)cc5c34)cccc21]

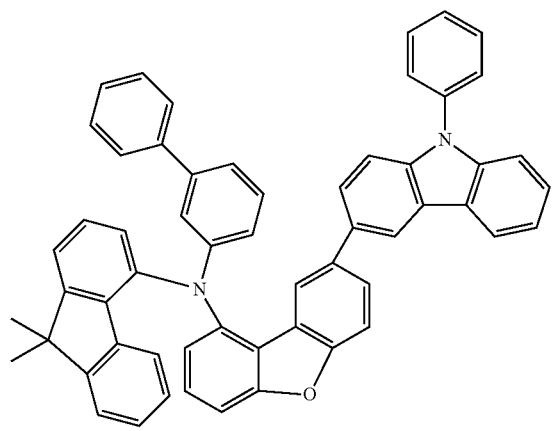 [SMILES: CC1(C)c2ccccc2-c2c(N(c3cccc(-c4ccccc4)c3)c3cccc4oc5ccc(-c6ccc7c(c6)c6ccccc6n7-c6ccccc6)cc5c34)cccc21]
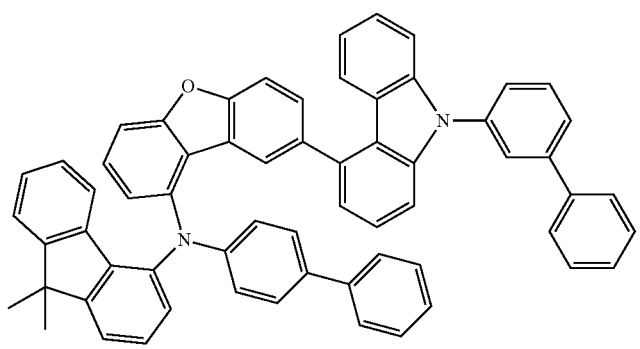 [SMILES: CC1(C)c2ccccc2-c2c(N(c3ccc(-c4ccccc4)cc3)c3cccc4oc5ccc(-c6cccc7c6c6ccccc6n7-c6cccc(-c7ccccc7)c6)cc5c34)cccc21]
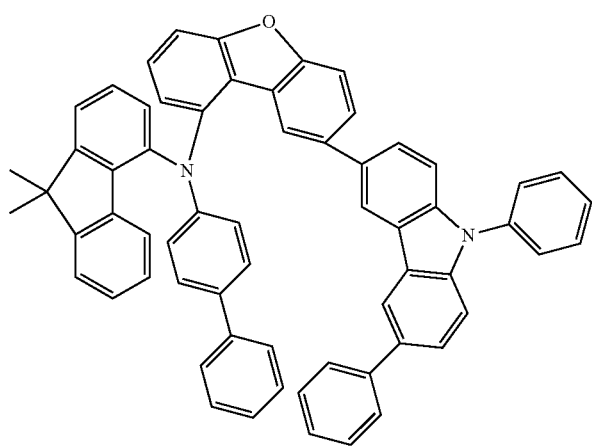 [SMILES: CC1(C)c2ccccc2-c2c(N(c3ccc(-c4ccccc4)cc3)c3cccc4oc5ccc(-c6ccc7c(c6)c6cc(-c8ccccc8)ccc6n7-c6ccccc6)cc5c34)cccc21]

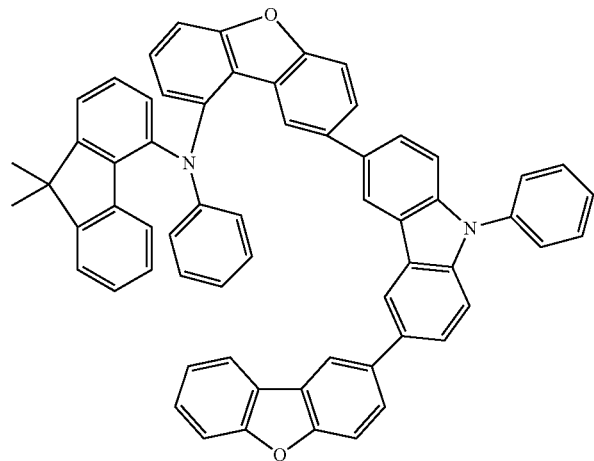 [SMILES: CC1(C)c2ccccc2-c2c(N(c3ccccc3)c3cccc4oc5ccc(-c6ccc7c(c6)c6cc(-c8ccc9oc%10ccccc%10c9c8)ccc6n7-c6ccccc6)cc5c34)cccc21]
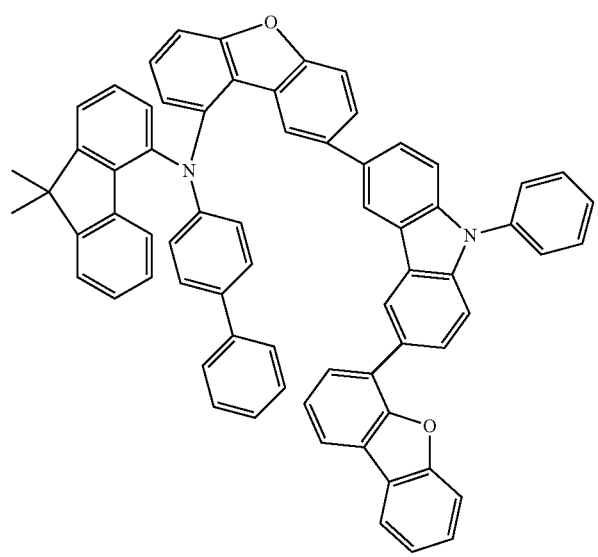 [SMILES: CC1(C)c2ccccc2-c2c(N(c3ccc(-c4ccccc4)cc3)c3cccc4oc5ccc(-c6ccc7c(c6)c6cc(-c8cccc9c8oc8ccccc89)ccc6n7-c6ccccc6)cc5c34)cccc21]
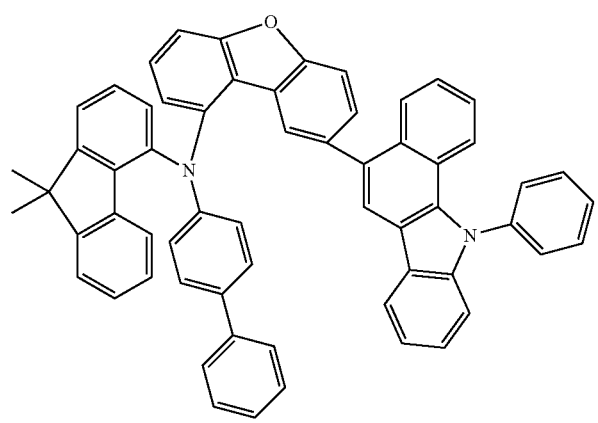 [SMILES: CC1(C)c2ccccc2-c2c(N(c3ccc(-c4ccccc4)cc3)c3cccc4oc5ccc(-c6cc7c8ccccc8n(-c8ccccc8)c7c7ccccc67)cc5c34)cccc21]

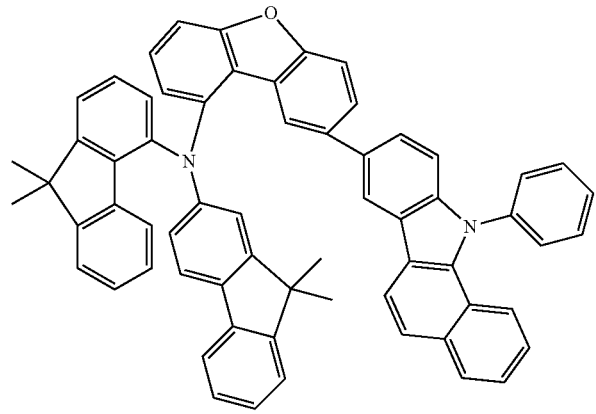 [SMILES: CC1(C)c2ccccc2-c2ccc(N(c3cccc4c3-c3ccccc3C4(C)C)c3cccc4oc5ccc(-c6ccc7c(c6)c6ccc8ccccc8c6n7-c6ccccc6)cc5c34)cc21]
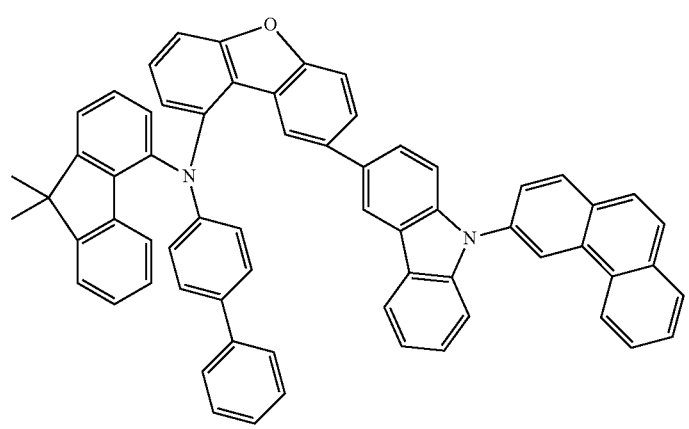 [SMILES: CC1(C)c2ccccc2-c2c(N(c3ccc(-c4ccccc4)cc3)c3cccc4oc5ccc(-c6ccc7c(c6)c6ccccc6n7-c6ccc7ccc8ccccc8c7c6)cc5c34)cccc21]
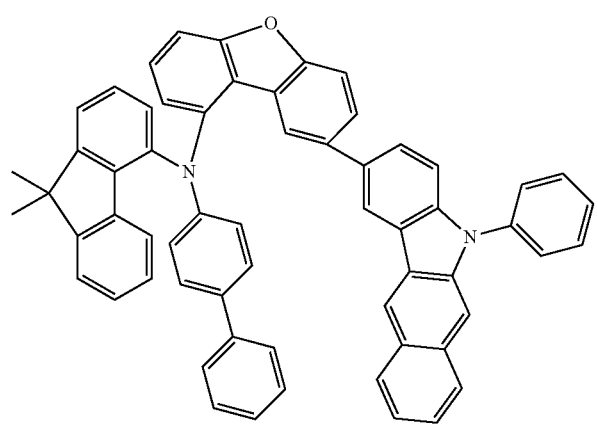 [SMILES: CC1(C)c2ccccc2-c2c(N(c3ccc(-c4ccccc4)cc3)c3cccc4oc5ccc(-c6ccc7c(c6)c6cc8ccccc8cc6n7-c6ccccc6)cc5c34)cccc21]

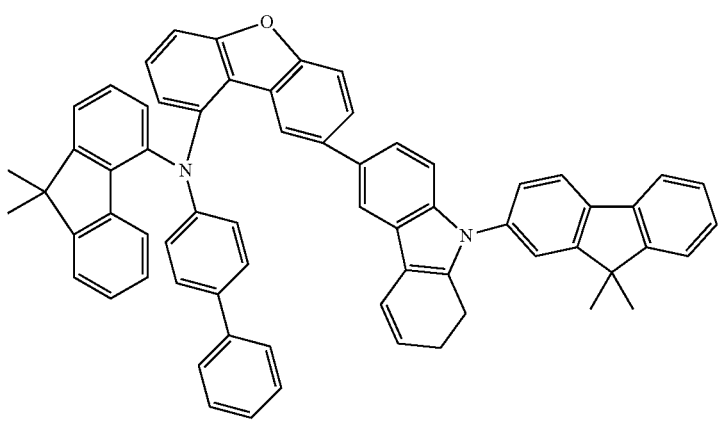 [SMILES: CC1(C)c2ccccc2-c2ccc(-n3c4c(c5cc(-c6ccc7oc8cccc(N(c9ccc(-c%10ccccc%10)cc9)c9cccc%10c9-c9ccccc9C%10(C)C)c8c7c6)ccc53)C=CCC4)cc21]
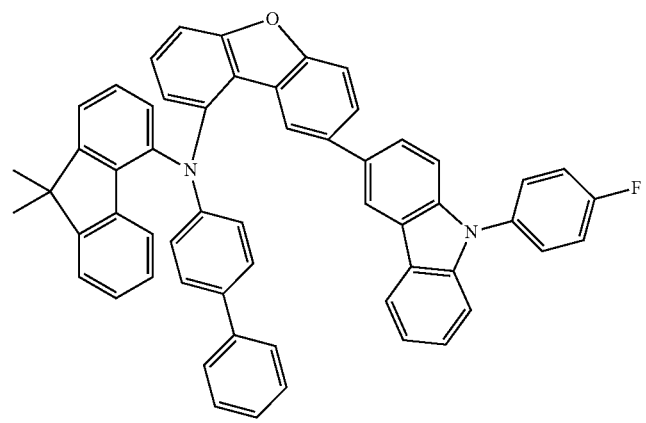 [SMILES: CC1(C)c2ccccc2-c2c(N(c3ccc(-c4ccccc4)cc3)c3cccc4oc5ccc(-c6ccc7c(c6)c6ccccc6n7-c6ccc(F)cc6)cc5c34)cccc21]
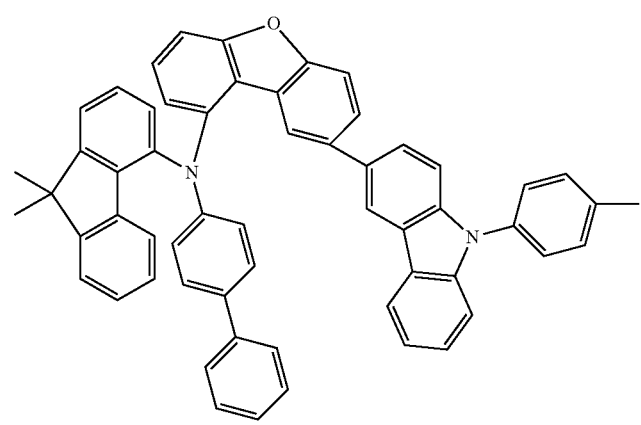

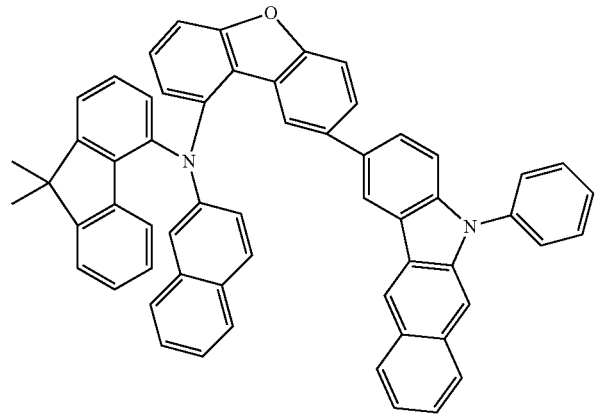 [SMILES: CC1(C)c2ccccc2-c2c(N(c3ccc4ccccc4c3)c3cccc4oc5ccc(-c6ccc7c(c6)c6cc8ccccc8cc6n7-c6ccccc6)cc5c34)cccc21]
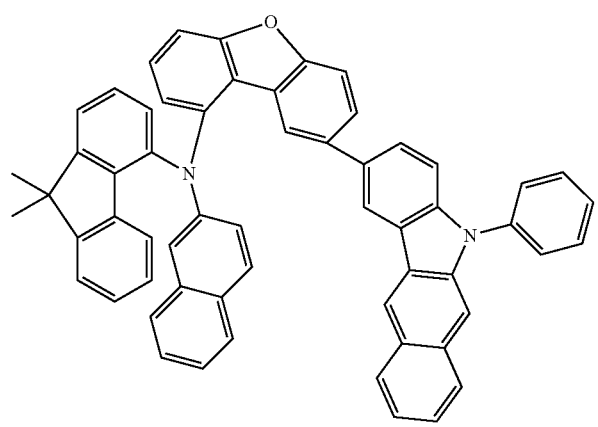 [SMILES: CC1(C)c2ccccc2-c2c(N(c3ccc4ccccc4c3)c3cccc4oc5ccc(-c6ccc7c(c6)c6cc8ccccc8cc6n7-c6ccccc6)cc5c34)cccc21]
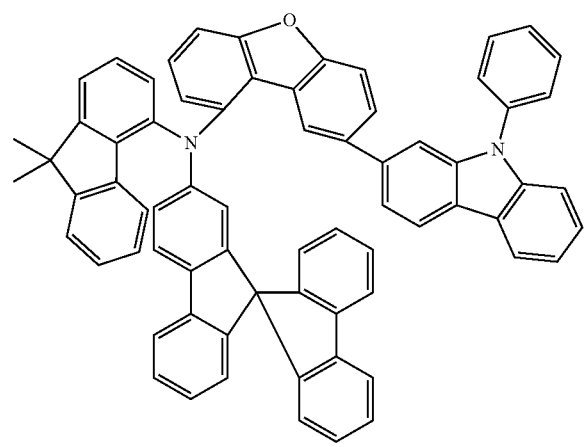 [SMILES: CC1(C)c2ccccc2-c2c(N(c3ccc4c(c3)C3(c5ccccc5-c5ccccc53)c3ccccc3-4)c3cccc4oc5ccc(-c6ccc7c8ccccc8n(-c8ccccc8)c7c6)cc5c34)cccc21]

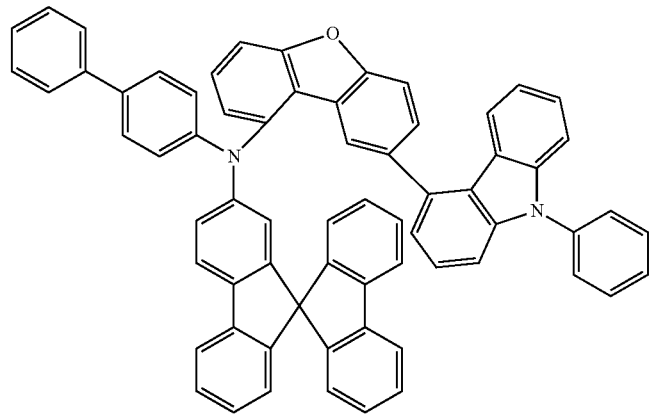 [SMILES: c1ccc(-c2ccc(N(c3ccc4c(c3)C3(c5ccccc5-c5ccccc53)c3ccccc3-4)c3cccc4oc5ccc(-c6cccc7c6c6ccccc6n7-c6ccccc6)cc5c34)cc2)cc1]
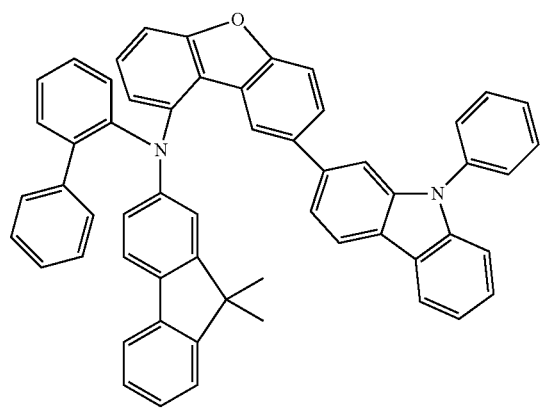 [SMILES: CC1(C)c2ccccc2-c2ccc(N(c3ccccc3-c3ccccc3)c3cccc4oc5ccc(-c6ccc7c8ccccc8n(-c8ccccc8)c7c6)cc5c34)cc21]
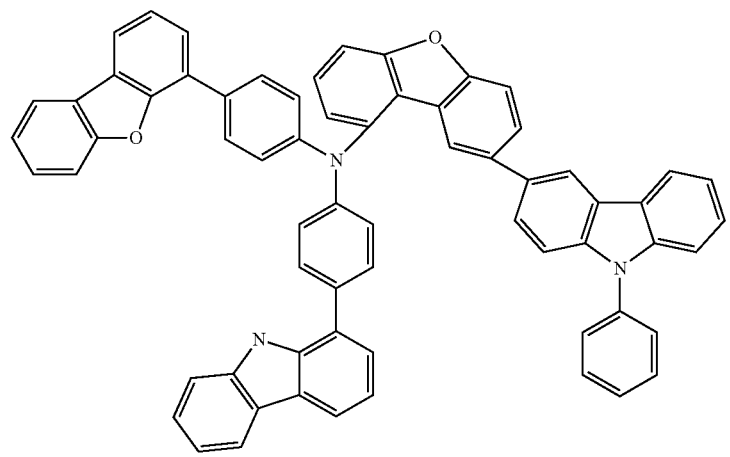 [SMILES: c1ccc(-n2c3ccccc3c3cc(-c4ccc5oc6cccc(N(c7ccc(-c8cccc9c8[nH]c8ccccc89)cc7)c7ccc(-c8cccc9c8oc8ccccc89)cc7)c6c5c4)ccc32)cc1]

-continued
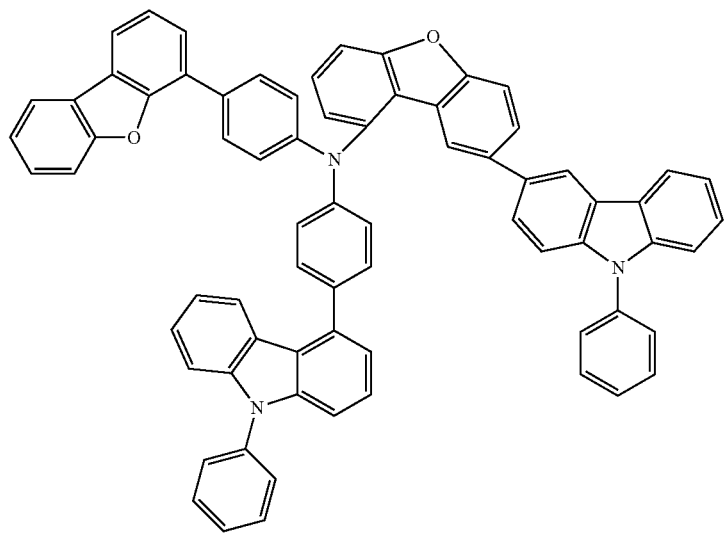 [SMILES: c1ccc(-n2c3ccccc3c3cc(-c4ccc5oc6cccc(N(c7ccc(-c8cccc9c8oc8ccccc89)cc7)c7ccc(-c8cccc9c8c8ccccc8n9-c8ccccc8)cc7)c6c5c4)ccc32)cc1]
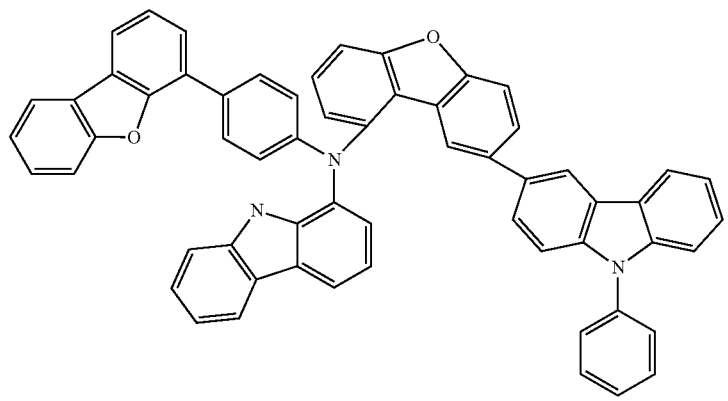 [SMILES: c1ccc(-n2c3ccccc3c3cc(-c4ccc5oc6cccc(N(c7ccc(-c8cccc9c8oc8ccccc89)cc7)c7cccc8c7[nH]c7ccccc78)c6c5c4)ccc32)cc1]
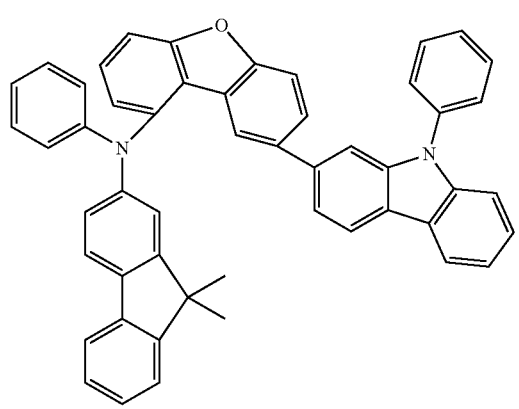 [SMILES: CC1(C)c2ccccc2-c2ccc(N(c3ccccc3)c3cccc4oc5ccc(-c6ccc7c8ccccc8n(-c8ccccc8)c7c6)cc5c34)cc21]

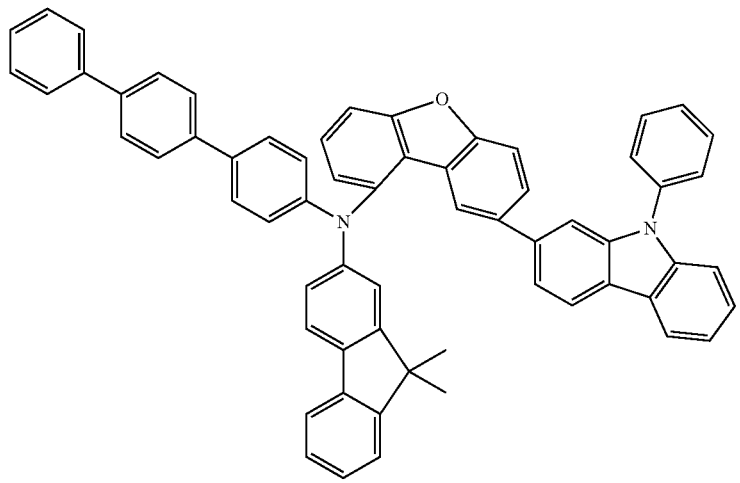 [SMILES: CC1(C)c2ccccc2-c2ccc(N(c3ccc(-c4ccc(-c5ccccc5)cc4)cc3)c3cccc4oc5ccc(-c6ccc7c8ccccc8n(-c8ccccc8)c7c6)cc5c34)cc21]
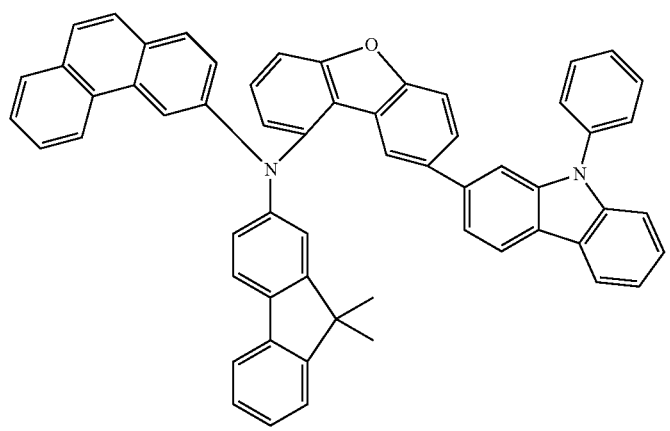 [SMILES: CC1(C)c2ccccc2-c2ccc(N(c3ccc4ccc5ccccc5c4c3)c3cccc4oc5ccc(-c6ccc7c8ccccc8n(-c8ccccc8)c7c6)cc5c34)cc21]
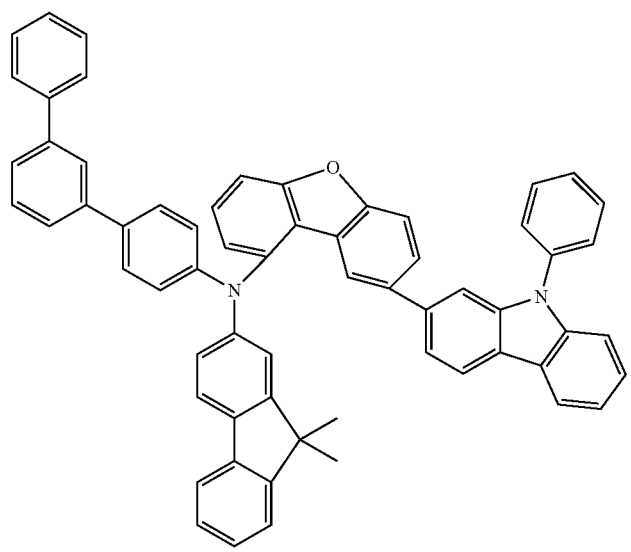 [SMILES: CC1(C)c2ccccc2-c2ccc(N(c3ccc(-c4cccc(-c5ccccc5)c4)cc3)c3cccc4oc5ccc(-c6ccc7c8ccccc8n(-c8ccccc8)c7c6)cc5c34)cc21]

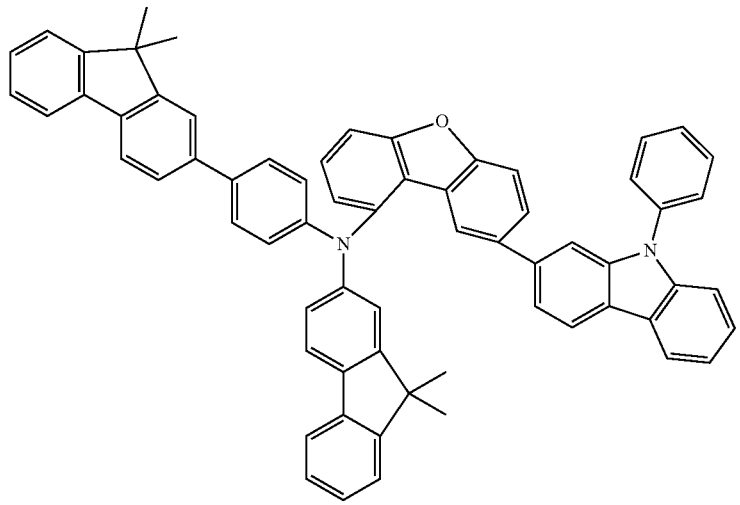 [SMILES: CC1(C)c2ccccc2-c2ccc(-c3ccc(N(c4ccc5c(c4)C(C)(C)c4ccccc4-5)c4cccc5oc6ccc(-c7ccc8c9ccccc9n(-c9ccccc9)c8c7)cc6c45)cc3)cc21]
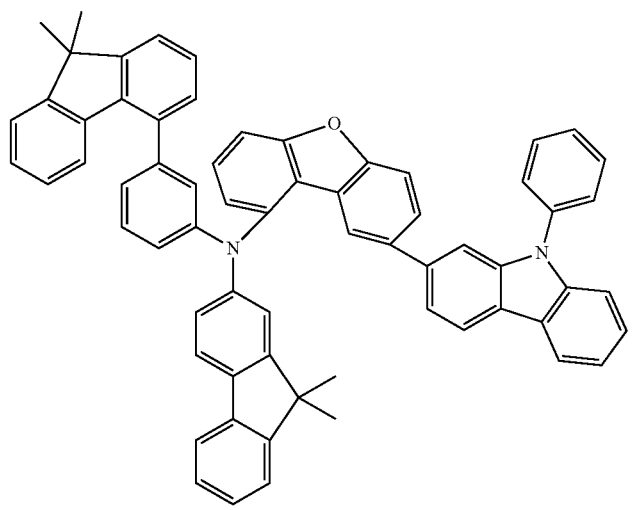 [SMILES: CC1(C)c2ccccc2-c2ccc(N(c3cccc(-c4cccc5c4-c4ccccc4C5(C)C)c3)c3cccc4oc5ccc(-c6ccc7c8ccccc8n(-c8ccccc8)c7c6)cc5c34)cc21]
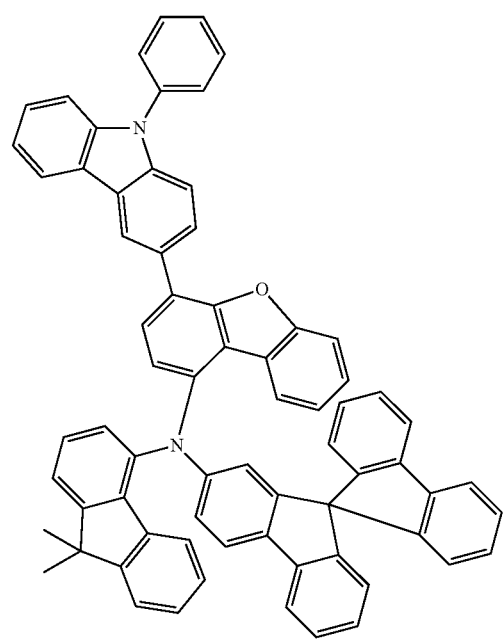 [SMILES: CC1(C)c2ccccc2-c2c(N(c3ccc4c(c3)C3(c5ccccc5-c5ccccc53)c3ccccc3-4)c3ccc(-c4ccc5c(c4)c4ccccc4n5-c4ccccc4)c4oc5ccccc5c34)cccc21]

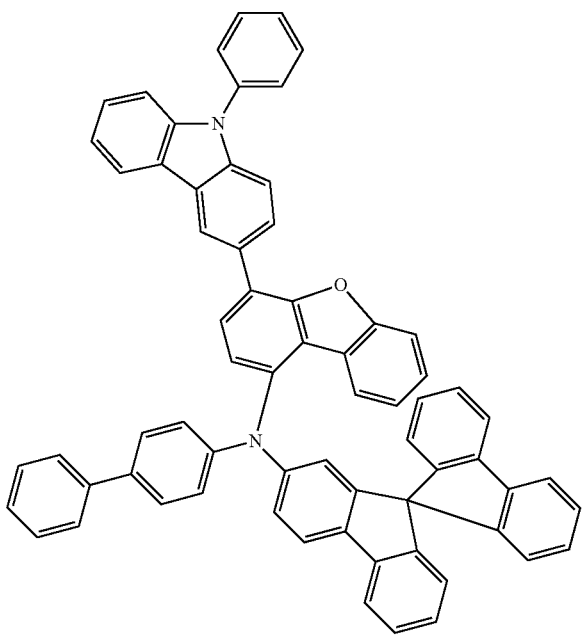 [SMILES: c1ccc(-c2ccc(N(c3ccc4c(c3)C3(c5ccccc5-c5ccccc53)c3ccccc3-4)c3ccc(-c4ccc5c(c4)c4ccccc4n5-c4ccccc4)c4oc5ccccc5c34)cc2)cc1]
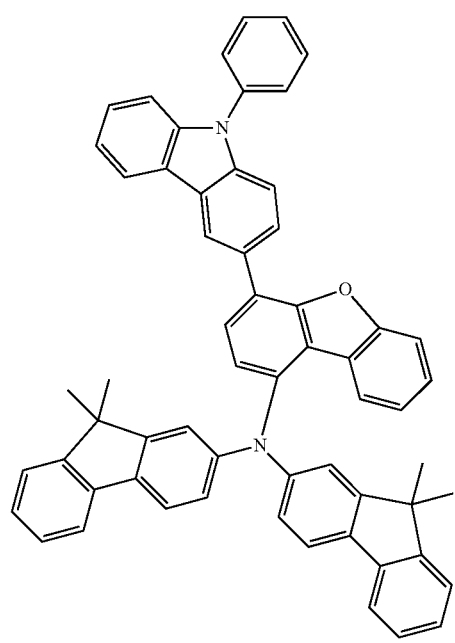 [SMILES: CC1(C)c2ccccc2-c2ccc(N(c3ccc4c(c3)C(C)(C)c3ccccc3-4)c3ccc(-c4ccc5c(c4)c4ccccc4n5-c4ccccc4)c4oc5ccccc5c34)cc21]

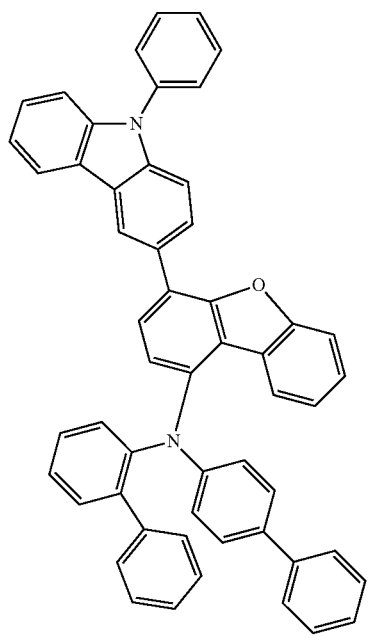 [SMILES: c1ccc(-c2ccc(N(c3ccccc3-c3ccccc3)c3ccc(-c4ccc5c(c4)c4ccccc4n5-c4ccccc4)c4oc5ccccc5c34)cc2)cc1]
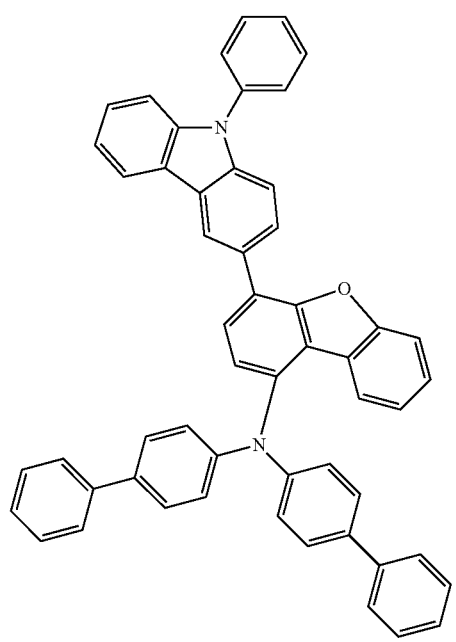 [SMILES: c1ccc(-c2ccc(N(c3ccc(-c4ccccc4)cc3)c3ccc(-c4ccc5c(c4)c4ccccc4n5-c4ccccc4)c4oc5ccccc5c34)cc2)cc1]

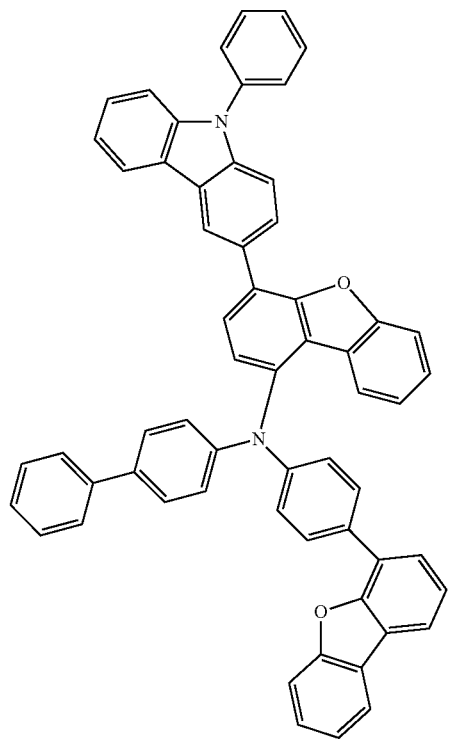 [SMILES: c1ccc(-c2ccc(N(c3ccc(-c4cccc5c4oc4ccccc45)cc3)c3ccc(-c4ccc5c(c4)c4ccccc4n5-c4ccccc4)c4oc5ccccc5c34)cc2)cc1]
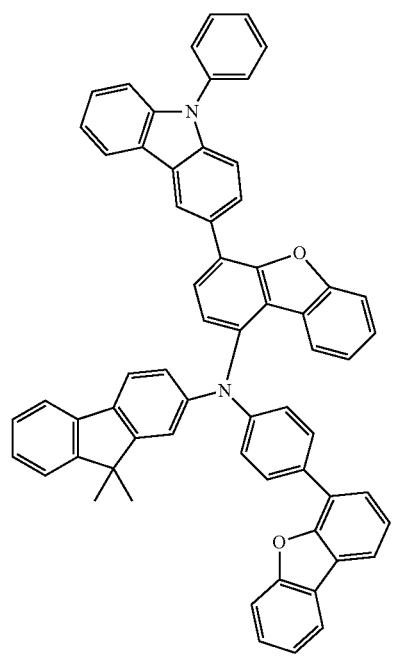 [SMILES: CC1(C)c2ccccc2-c2ccc(N(c3ccc(-c4cccc5c4oc4ccccc45)cc3)c3ccc(-c4ccc5c(c4)c4ccccc4n5-c4ccccc4)c4oc5ccccc5c34)cc21]

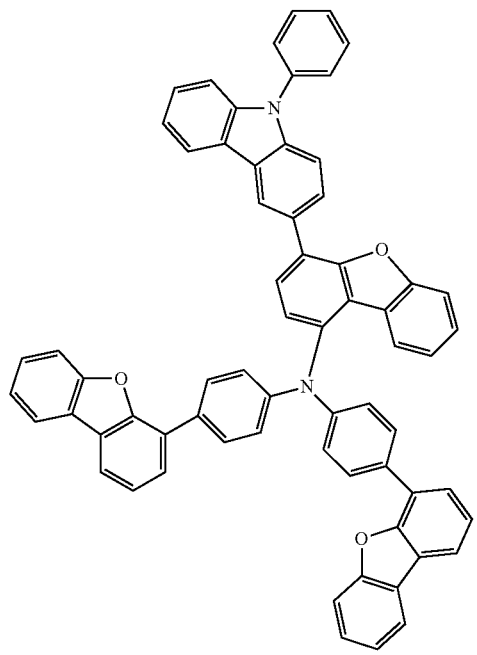 [SMILES: c1ccc(-n2c3ccccc3c3cc(-c4ccc(N(c5ccc(-c6cccc7c6oc6ccccc67)cc5)c5ccc(-c6cccc7c6oc6ccccc67)cc5)c5c4oc4ccccc45)ccc32)cc1]
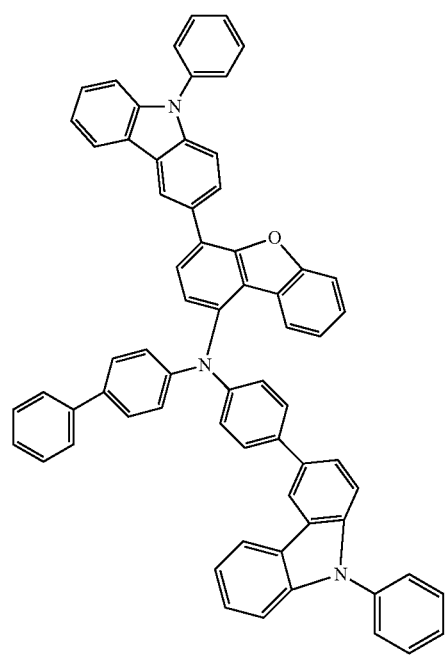 [SMILES: c1ccc(-c2ccc(N(c3ccc(-c4ccc5c(c4)c4ccccc4n5-c4ccccc4)cc3)c3ccc(-c4ccc5c(c4)c4ccccc4n5-c4ccccc4)c4oc5ccccc5c34)cc2)cc1]

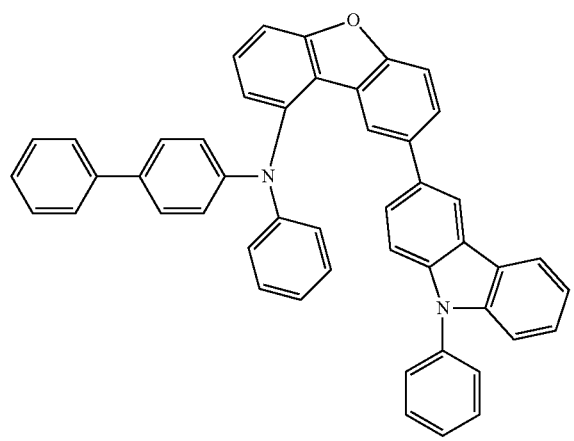 [SMILES: c1ccc(-c2ccc(N(c3ccccc3)c3cccc4oc5ccc(-c6ccc7c(c6)c6ccccc6n7-c6ccccc6)cc5c34)cc2)cc1]
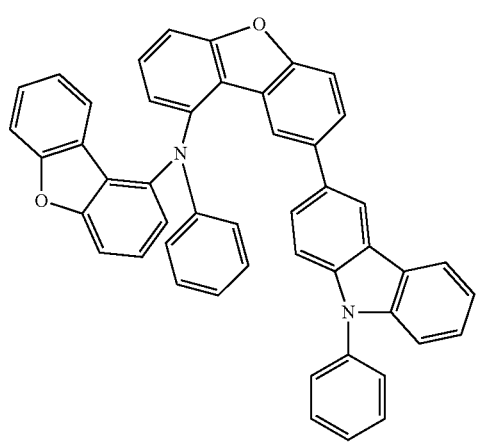 [SMILES: c1ccc(N(c2cccc3oc4ccccc4c23)c2cccc3oc4ccc(-c5ccc6c(c5)c5ccccc5n6-c5ccccc5)cc4c23)cc1]
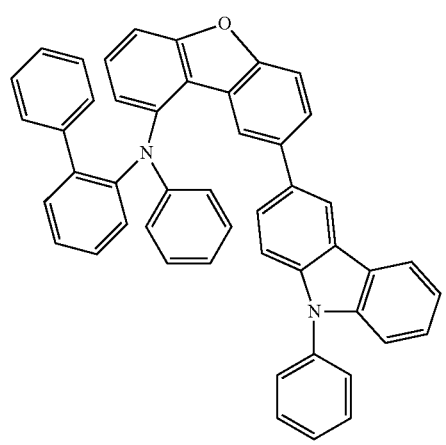 [SMILES: c1ccc(-c2ccccc2N(c2ccccc2)c2cccc3oc4ccc(-c5ccc6c(c5)c5ccccc5n6-c5ccccc5)cc4c23)cc1]

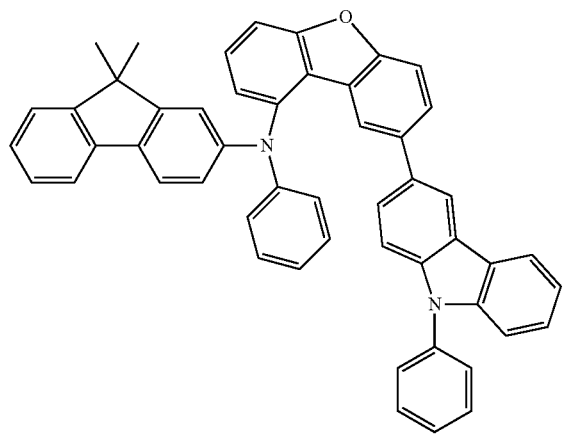 [SMILES: CC1(C)c2ccccc2-c2ccc(N(c3ccccc3)c3cccc4oc5ccc(-c6ccc7c(c6)c6ccccc6n7-c6ccccc6)cc5c34)cc21]
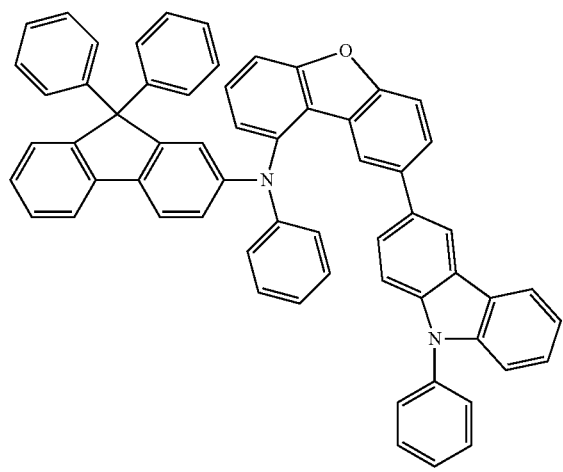 [SMILES: c1ccc(N(c2ccc3c(c2)C(c2ccccc2)(c2ccccc2)c2ccccc2-3)c2cccc3oc4ccc(-c5ccc6c(c5)c5ccccc5n6-c5ccccc5)cc4c23)cc1]
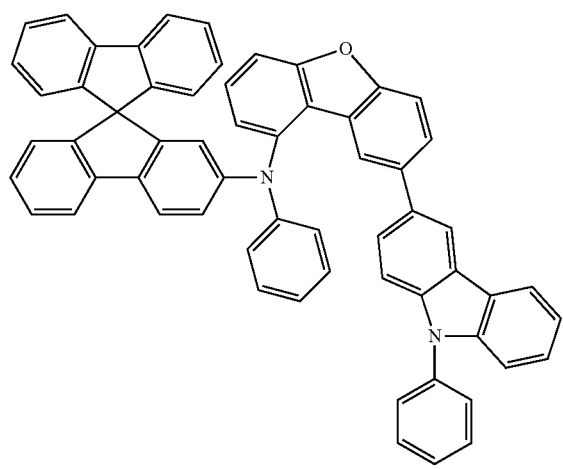 [SMILES: c1ccc(N(c2ccc3c(c2)C2(c4ccccc4-c4ccccc42)c2ccccc2-3)c2cccc3oc4ccc(-c5ccc6c(c5)c5ccccc5n6-c5ccccc5)cc4c23)cc1]

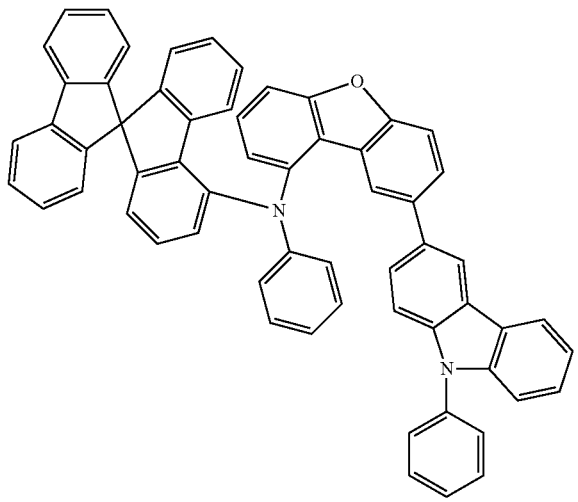 [SMILES: c1ccc(N(c2cccc3c2-c2ccccc2C32c3ccccc3-c3ccccc32)c2cccc3oc4ccc(-c5ccc6c(c5)c5ccccc5n6-c5ccccc5)cc4c23)cc1]
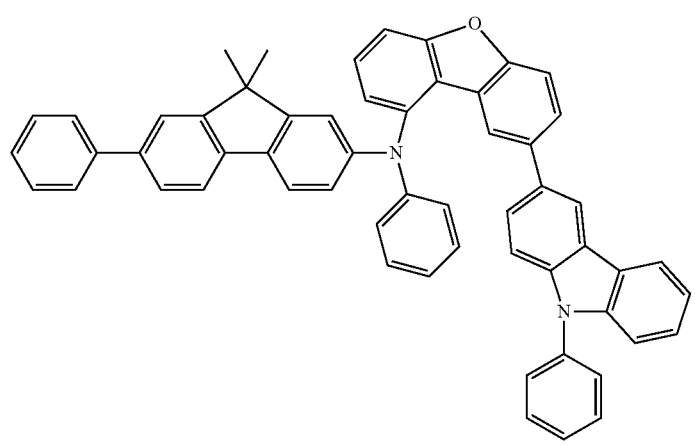 [SMILES: CC1(C)c2cc(-c3ccccc3)ccc2-c2ccc(N(c3ccccc3)c3cccc4oc5ccc(-c6ccc7c(c6)c6ccccc6n7-c6ccccc6)cc5c34)cc21]
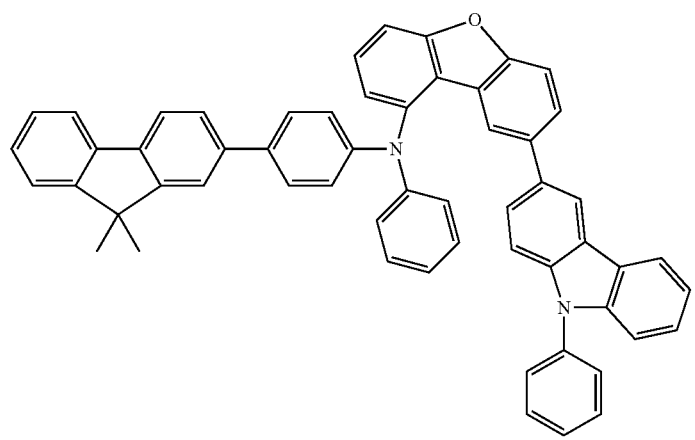 [SMILES: CC1(C)c2ccccc2-c2ccc(-c3ccc(N(c4ccccc4)c4cccc5oc6ccc(-c7ccc8c(c7)c7ccccc7n8-c7ccccc7)cc6c45)cc3)cc21]

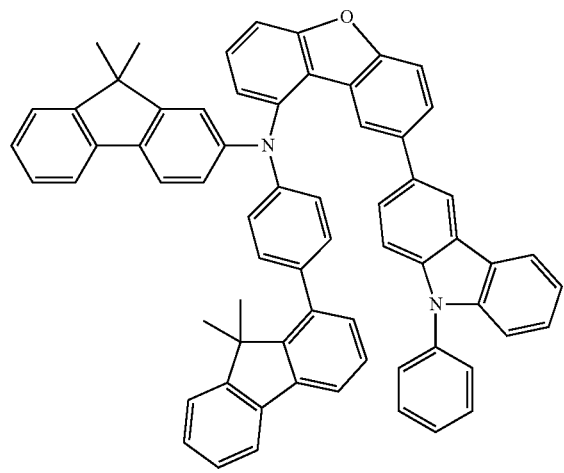 [SMILES: CC1(C)c2ccccc2-c2ccc(N(c3ccc(-c4cccc5c4C(C)(C)c4ccccc4-5)cc3)c3cccc4oc5ccc(-c6ccc7c(c6)c6ccccc6n7-c6ccccc6)cc5c34)cc21]
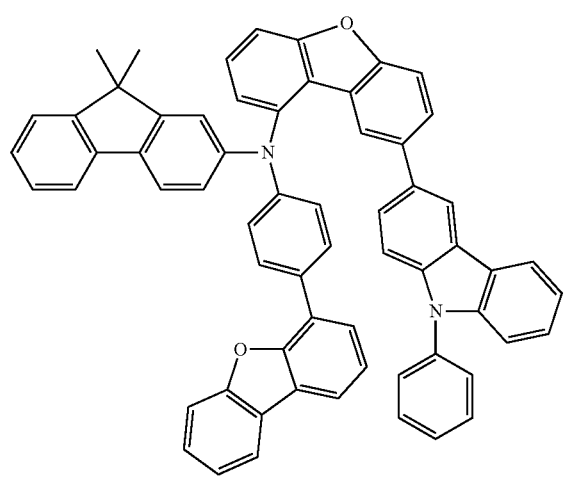 [SMILES: CC1(C)c2ccccc2-c2ccc(N(c3ccc(-c4cccc5c4oc4ccccc45)cc3)c3cccc4oc5ccc(-c6ccc7c(c6)c6ccccc6n7-c6ccccc6)cc5c34)cc21]
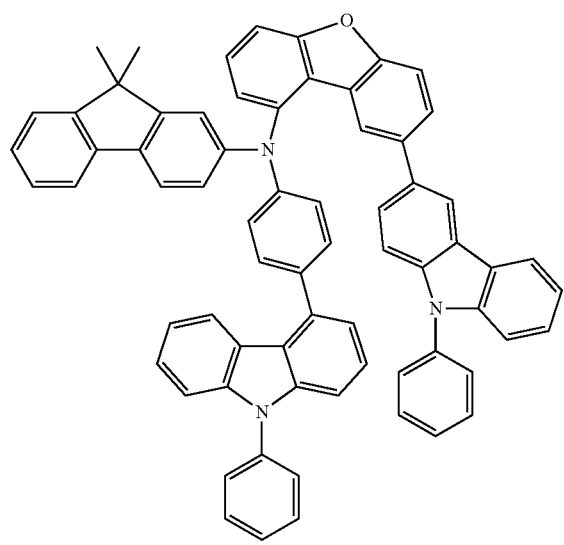 [SMILES: CC1(C)c2ccccc2-c2ccc(N(c3ccc(-c4cccc5c4c4ccccc4n5-c4ccccc4)cc3)c3cccc4oc5ccc(-c6ccc7c(c6)c6ccccc6n7-c6ccccc6)cc5c34)cc21]

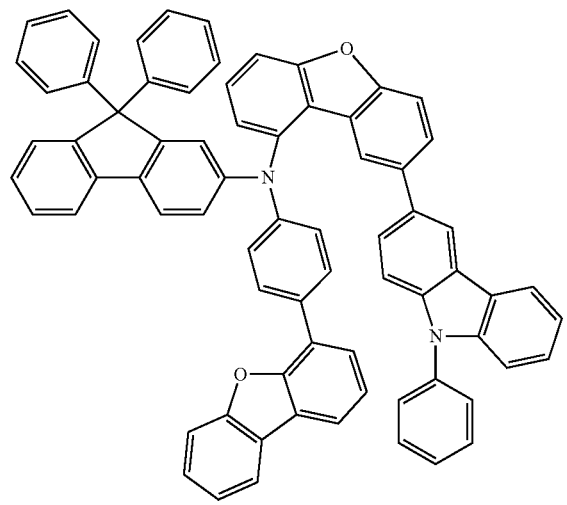 [SMILES: c1ccc(-n2c3ccccc3c3cc(-c4ccc5oc6cccc(N(c7ccc(-c8cccc9c8oc8ccccc89)cc7)c7ccc8c(c7)C(c7ccccc7)(c7ccccc7)c7ccccc7-8)c6c5c4)ccc32)cc1]
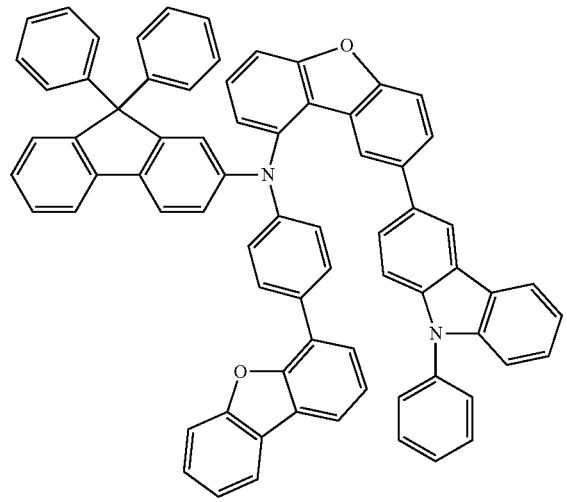 [SMILES: c1ccc(-n2c3ccccc3c3cc(-c4ccc5oc6cccc(N(c7ccc(-c8cccc9c8oc8ccccc89)cc7)c7ccc8c(c7)C(c7ccccc7)(c7ccccc7)c7ccccc7-8)c6c5c4)ccc32)cc1]
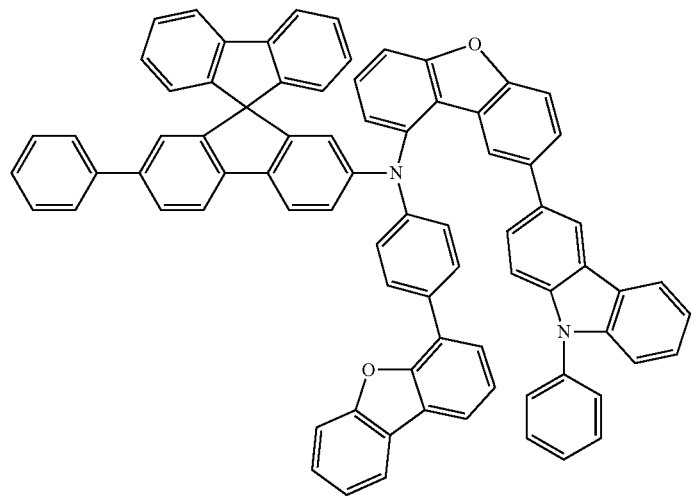 [SMILES: c1ccc(-c2ccc3c(c2)C2(c4ccccc4-c4ccccc42)c2cc(N(c4ccc(-c5cccc6c5oc5ccccc56)cc4)c4cccc5oc6ccc(-c7ccc8c(c7)c7ccccc7n8-c7ccccc7)cc6c45)ccc2-3)cc1]

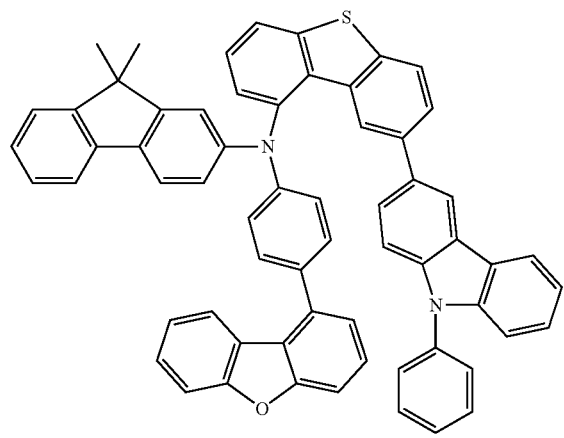 [SMILES: CC1(C)c2ccccc2-c2ccc(N(c3ccc(-c4cccc5oc6ccccc6c45)cc3)c3cccc4sc5ccc(-c6ccc7c(c6)c6ccccc6n7-c6ccccc6)cc5c34)cc21]
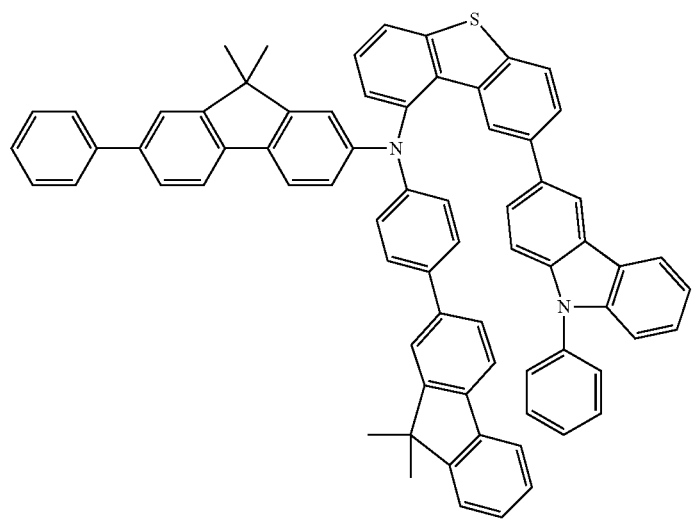 [SMILES: CC1(C)c2ccccc2-c2ccc(-c3ccc(N(c4ccc5c(c4)C(C)(C)c4cc(-c6ccccc6)ccc4-5)c4cccc5sc6ccc(-c7ccc8c(c7)c7ccccc7n8-c7ccccc7)cc6c45)cc3)cc21]
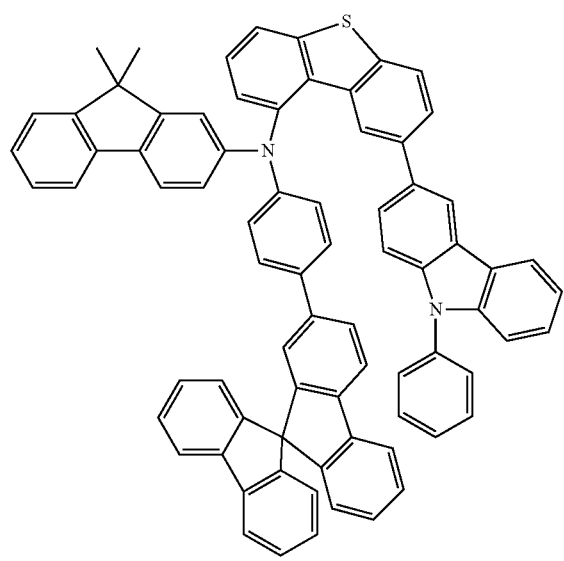 [SMILES: CC1(C)c2ccccc2-c2ccc(N(c3ccc(-c4ccc5c(c4)C4(c6ccccc6-c6ccccc64)c4ccccc4-5)cc3)c3cccc4sc5ccc(-c6ccc7c(c6)c6ccccc6n7-c6ccccc6)cc5c34)cc21]

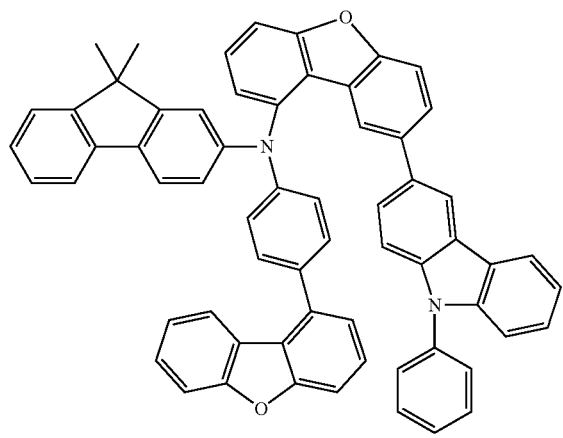 [SMILES: CC1(C)c2ccccc2-c2ccc(N(c3ccc(-c4cccc5oc6ccccc6c45)cc3)c3cccc4oc5ccc(-c6ccc7c(c6)c6ccccc6n7-c6ccccc6)cc5c34)cc21]
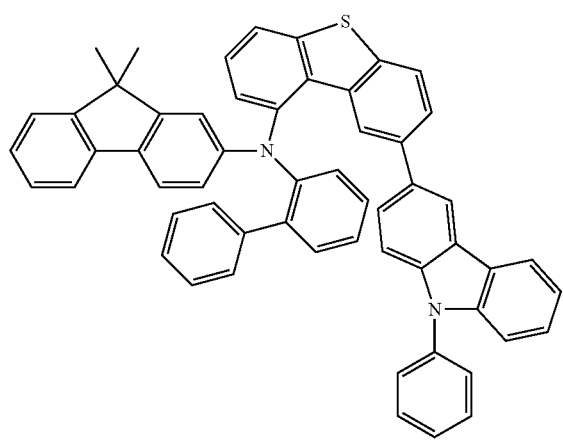 [SMILES: CC1(C)c2ccccc2-c2ccc(N(c3ccccc3-c3ccccc3)c3cccc4sc5ccc(-c6ccc7c(c6)c6ccccc6n7-c6ccccc6)cc5c34)cc21]
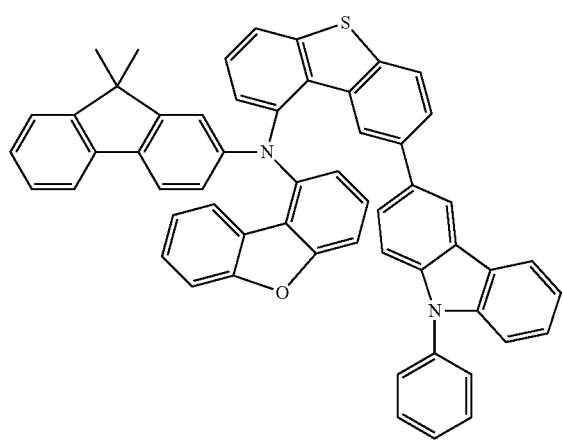 [SMILES: CC1(C)c2ccccc2-c2ccc(N(c3cccc4oc5ccccc5c34)c3cccc4sc5ccc(-c6ccc7c(c6)c6ccccc6n7-c6ccccc6)cc5c34)cc21]

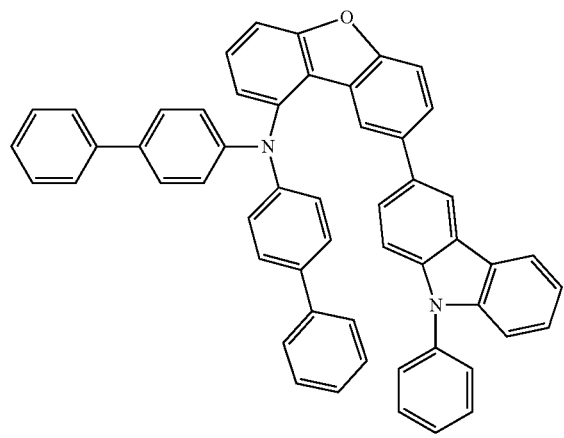 [SMILES: c1ccc(-c2ccc(N(c3ccc(-c4ccccc4)cc3)c3cccc4oc5ccc(-c6ccc7c(c6)c6ccccc6n7-c6ccccc6)cc5c34)cc2)cc1]
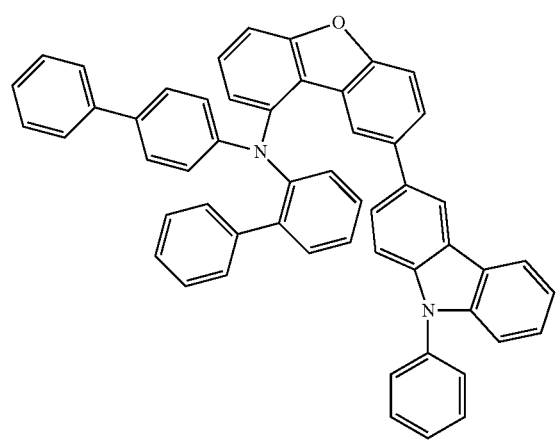 [SMILES: c1ccc(-c2ccc(N(c3ccccc3-c3ccccc3)c3cccc4oc5ccc(-c6ccc7c(c6)c6ccccc6n7-c6ccccc6)cc5c34)cc2)cc1]
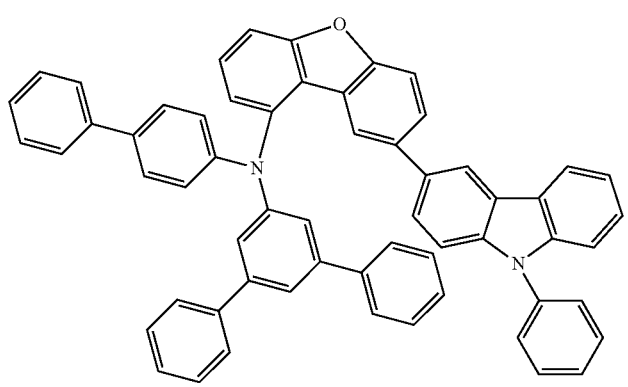 [SMILES: c1ccc(-c2ccc(N(c3cc(-c4ccccc4)cc(-c4ccccc4)c3)c3cccc4oc5ccc(-c6ccc7c(c6)c6ccccc6n7-c6ccccc6)cc5c34)cc2)cc1]

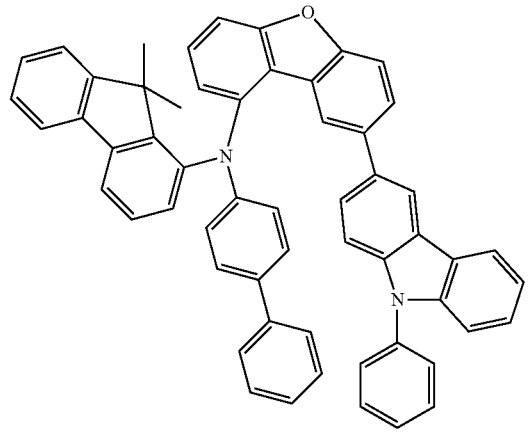 [SMILES: CC1(C)c2ccccc2-c2cccc(N(c3ccc(-c4ccccc4)cc3)c3cccc4oc5ccc(-c6ccc7c(c6)c6ccccc6n7-c6ccccc6)cc5c34)c21]
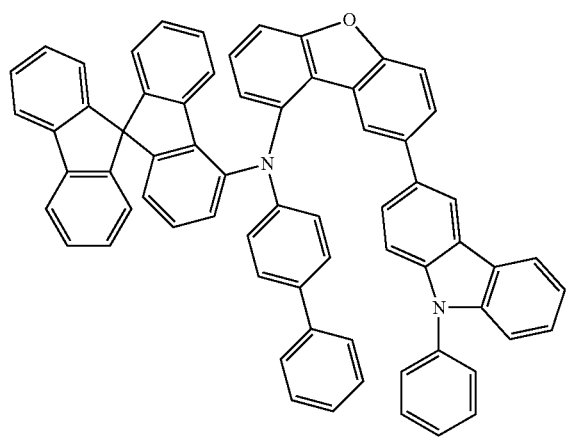 [SMILES: c1ccc(-c2ccc(N(c3cccc4c3-c3ccccc3C43c4ccccc4-c4ccccc43)c3cccc4oc5ccc(-c6ccc7c(c6)c6ccccc6n7-c6ccccc6)cc5c34)cc2)cc1]
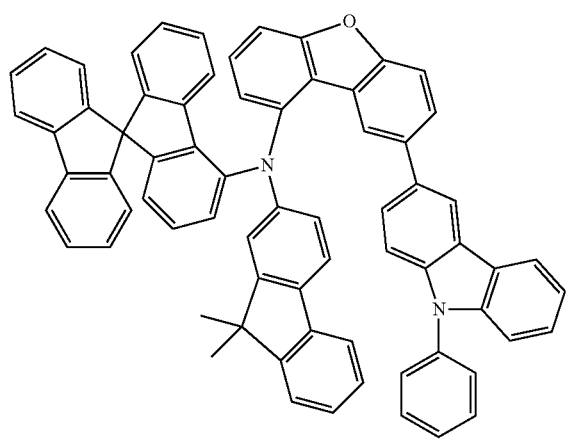 [SMILES: CC1(C)c2ccccc2-c2ccc(N(c3cccc4c3-c3ccccc3C43c4ccccc4-c4ccccc43)c3cccc4oc5ccc(-c6ccc7c(c6)c6ccccc6n7-c6ccccc6)cc5c34)cc21]

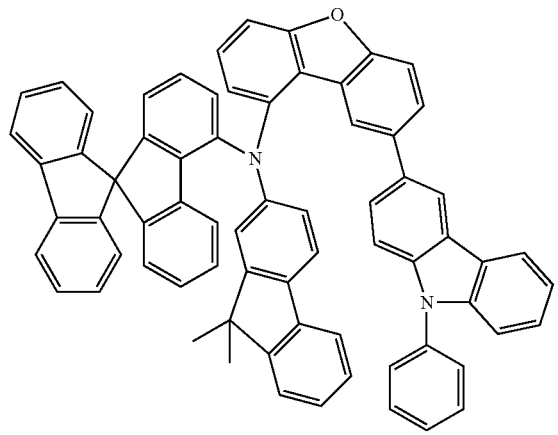 [SMILES: CC1(C)c2ccccc2-c2ccc(N(c3cccc4c3-c3ccccc3C43c4ccccc4-c4ccccc43)c3cccc4oc5ccc(-c6ccc7c(c6)c6ccccc6n7-c6ccccc6)cc5c34)cc21]
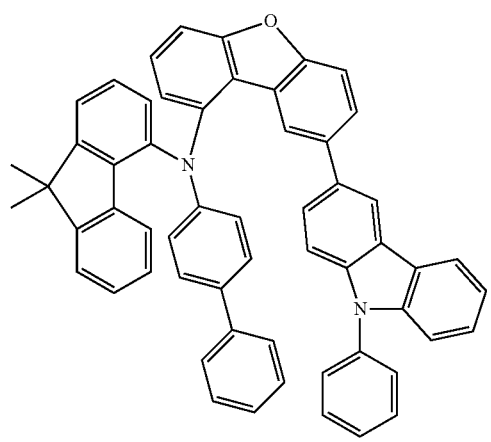 [SMILES: CC1(C)c2ccccc2-c2c(N(c3ccc(-c4ccccc4)cc3)c3cccc4oc5ccc(-c6ccc7c(c6)c6ccccc6n7-c6ccccc6)cc5c34)cccc21]
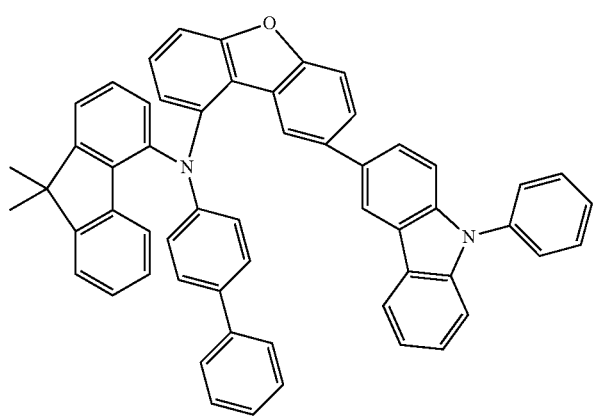 [SMILES: CC1(C)c2ccccc2-c2c(N(c3ccc(-c4ccccc4)cc3)c3cccc4oc5ccc(-c6ccc7c(c6)c6ccccc6n7-c6ccccc6)cc5c34)cccc21]

-continued
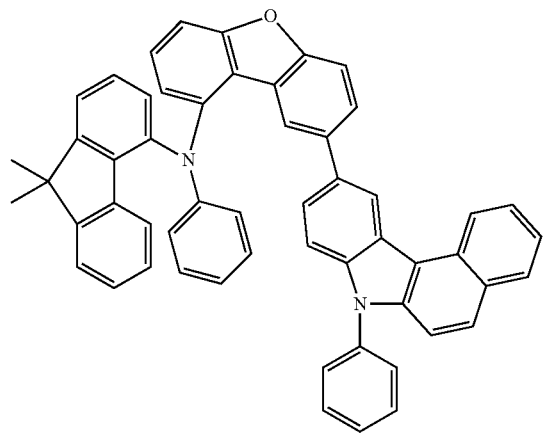 [SMILES: CC1(C)c2ccccc2-c2c(N(c3ccccc3)c3cccc4oc5ccc(-c6ccc7c(c6)c6c8ccccc8ccc6n7-c6ccccc6)cc5c34)cccc21]
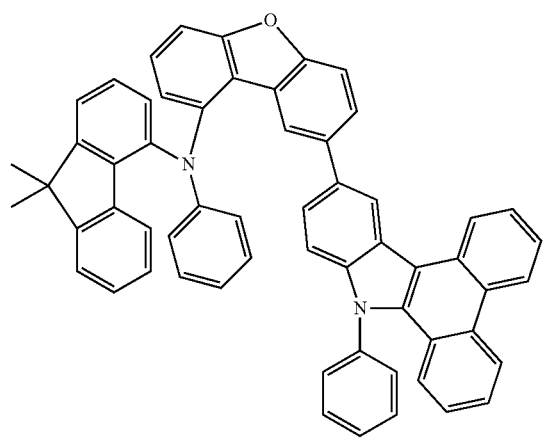 [SMILES: CC1(C)c2ccccc2-c2c(N(c3ccccc3)c3cccc4oc5ccc(-c6ccc7c(c6)c6c8ccccc8c8ccccc8c6n7-c6ccccc6)cc5c34)cccc21]
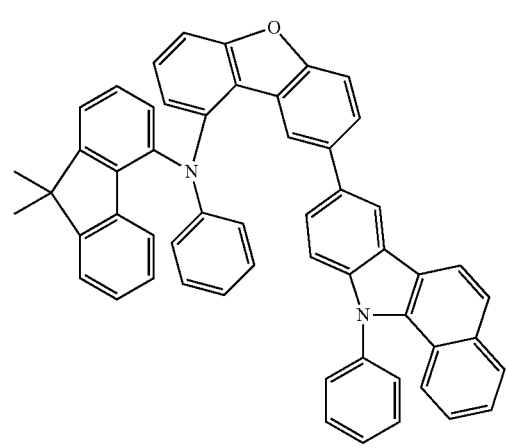 [SMILES: CC1(C)c2ccccc2-c2c(N(c3ccccc3)c3cccc4oc5ccc(-c6ccc7c(c6)c6ccc8ccccc8c6n7-c6ccccc6)cc5c34)cccc21]

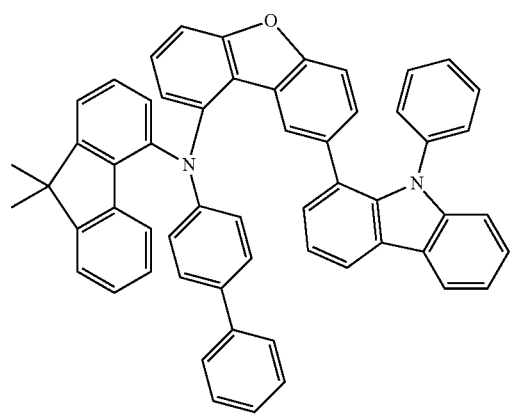 [SMILES: CC1(C)c2ccccc2-c2c(N(c3ccc(-c4ccccc4)cc3)c3cccc4oc5ccc(-c6cccc7c8ccccc8n(-c8ccccc8)c67)cc5c34)cccc21]
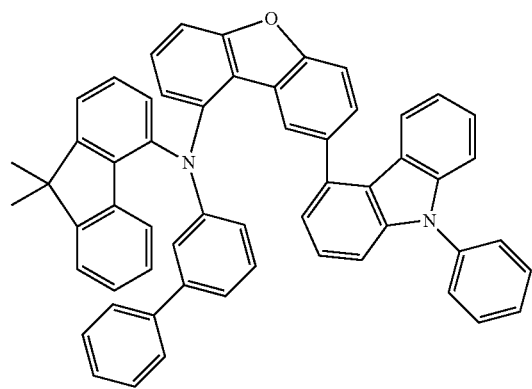 [SMILES: CC1(C)c2ccccc2-c2c(N(c3cccc(-c4ccccc4)c3)c3cccc4oc5ccc(-c6cccc7c6c6ccccc6n7-c6ccccc6)cc5c34)cccc21]
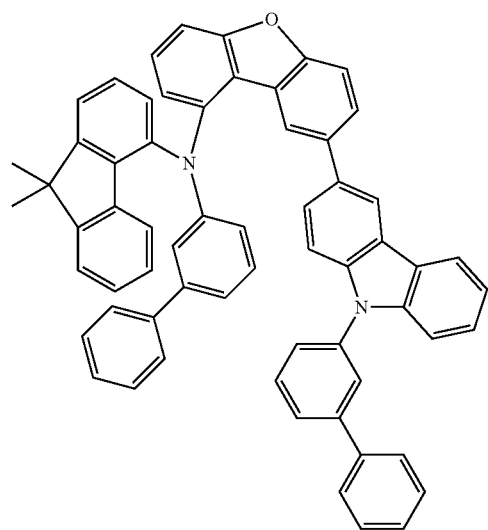 [SMILES: CC1(C)c2ccccc2-c2c(N(c3cccc(-c4ccccc4)c3)c3cccc4oc5ccc(-c6ccc7c(c6)c6ccccc6n7-c6cccc(-c7ccccc7)c6)cc5c34)cccc21]

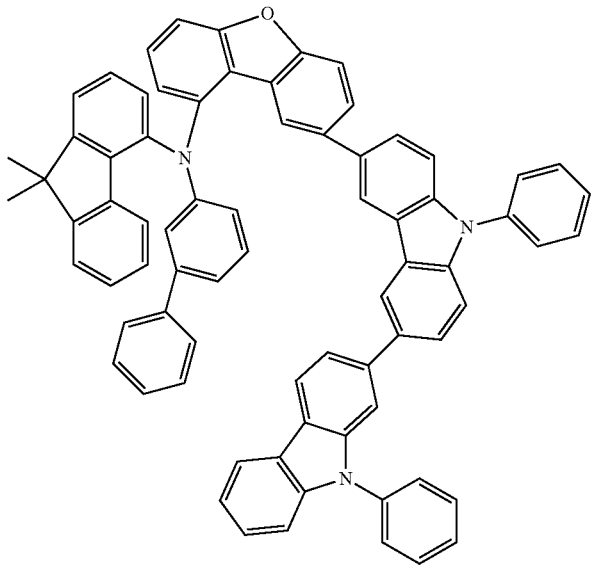 [SMILES: CC1(C)c2ccccc2-c2c(N(c3cccc(-c4ccccc4)c3)c3cccc4oc5ccc(-c6ccc7c(c6)c6cc(-c8ccc9c%10ccccc%10n(-c%10ccccc%10)c9c8)ccc6n7-c6ccccc6)cc5c34)cccc21]
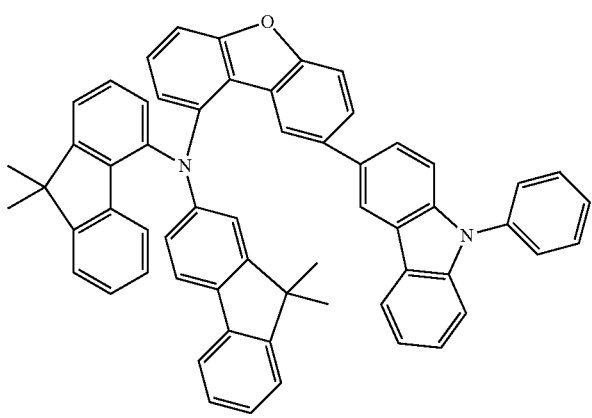 [SMILES: CC1(C)c2ccccc2-c2ccc(N(c3cccc4c3-c3ccccc3C4(C)C)c3cccc4oc5ccc(-c6ccc7c(c6)c6ccccc6n7-c6ccccc6)cc5c34)cc21]
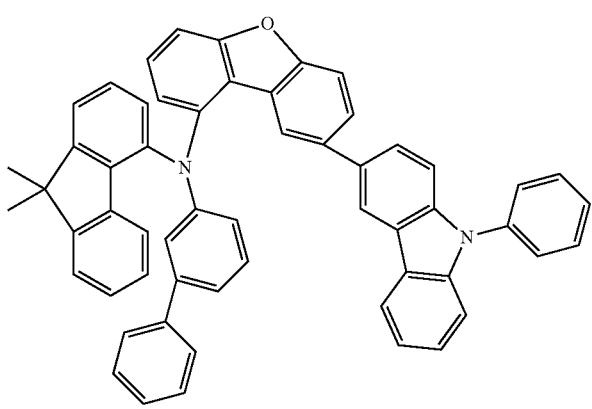 [SMILES: CC1(C)c2ccccc2-c2c(N(c3cccc(-c4ccccc4)c3)c3cccc4oc5ccc(-c6ccc7c(c6)c6ccccc6n7-c6ccccc6)cc5c34)cccc21]

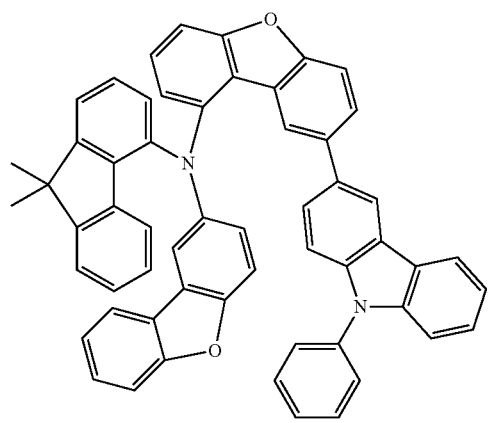 [SMILES: CC1(C)c2ccccc2-c2c(N(c3ccc4oc5ccccc5c4c3)c3cccc4oc5ccc(-c6ccc7c(c6)c6ccccc6n7-c6ccccc6)cc5c34)cccc21]
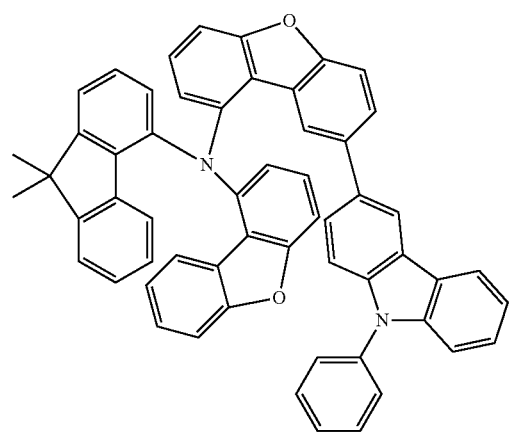 [SMILES: CC1(C)c2ccccc2-c2c(N(c3cccc4oc5ccccc5c34)c3cccc4oc5ccc(-c6ccc7c(c6)c6ccccc6n7-c6ccccc6)cc5c34)cccc21]
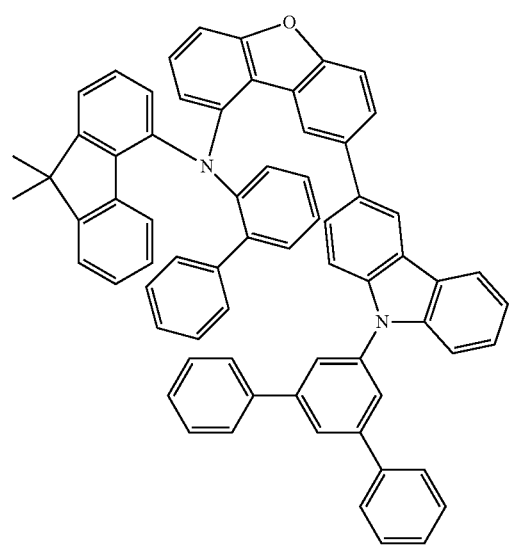 [SMILES: CC1(C)c2ccccc2-c2c(N(c3ccccc3-c3ccccc3)c3cccc4oc5ccc(-c6ccc7c(c6)c6ccccc6n7-c6cc(-c7ccccc7)cc(-c7ccccc7)c6)cc5c34)cccc21]

-continued
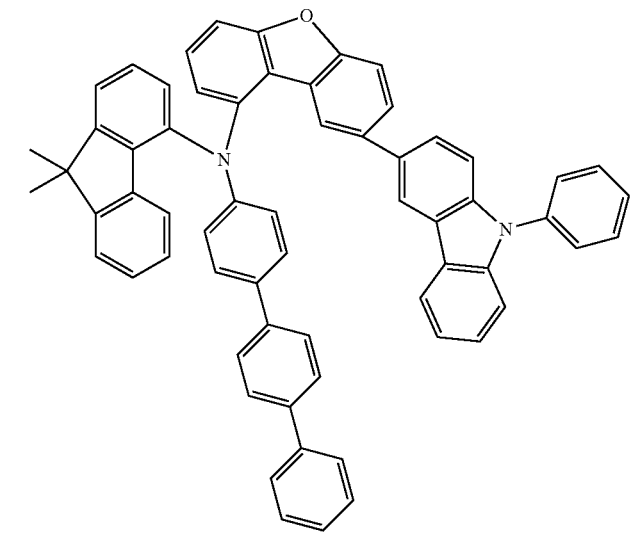 [SMILES: CC1(C)c2ccccc2-c2c(N(c3ccc(-c4ccc(-c5ccccc5)cc4)cc3)c3cccc4oc5ccc(-c6ccc7c(c6)c6ccccc6n7-c6ccccc6)cc5c34)cccc21]
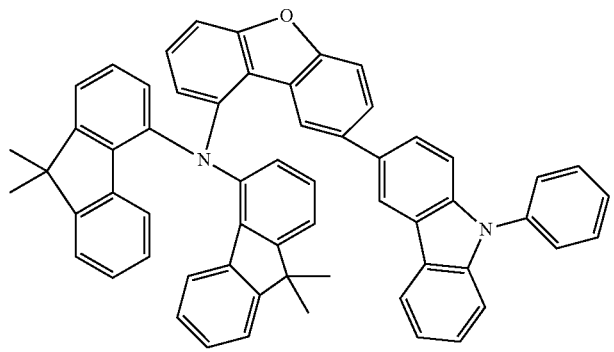 [SMILES: CC1(C)c2ccccc2-c2c(N(c3cccc4c3-c3ccccc3C4(C)C)c3cccc4oc5ccc(-c6ccc7c(c6)c6ccccc6n7-c6ccccc6)cc5c34)cccc21]
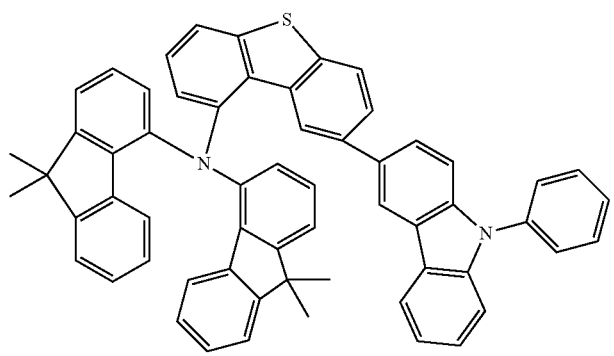 [SMILES: CC1(C)c2ccccc2-c2c(N(c3cccc4c3-c3ccccc3C4(C)C)c3cccc4sc5ccc(-c6ccc7c(c6)c6ccccc6n7-c6ccccc6)cc5c34)cccc21]
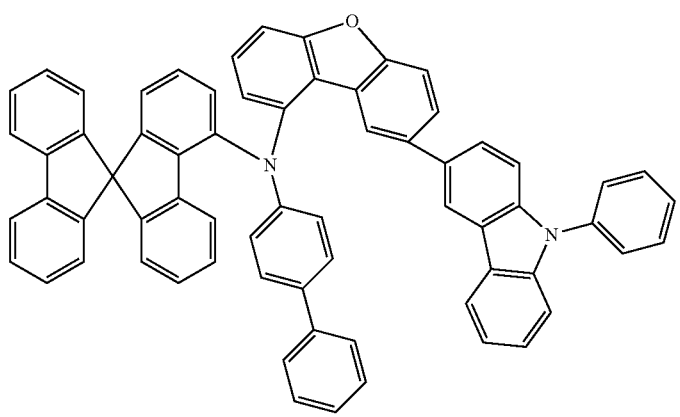 [SMILES: c1ccc(-c2ccc(N(c3cccc4c3-c3ccccc3C43c4ccccc4-c4ccccc43)c3cccc4oc5ccc(-c6ccc7c(c6)c6ccccc6n7-c6ccccc6)cc5c34)cc2)cc1]

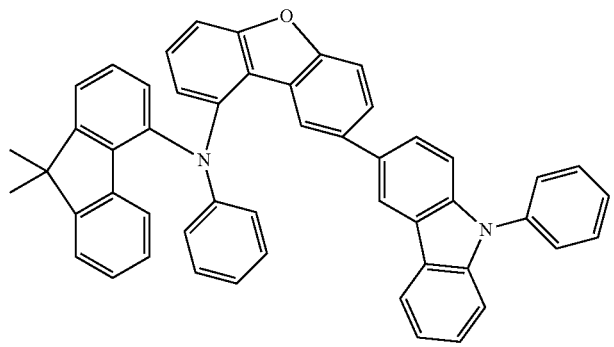 [SMILES: CC1(C)c2ccccc2-c2c(N(c3ccccc3)c3cccc4oc5ccc(-c6ccc7c(c6)c6ccccc6n7-c6ccccc6)cc5c34)cccc21]
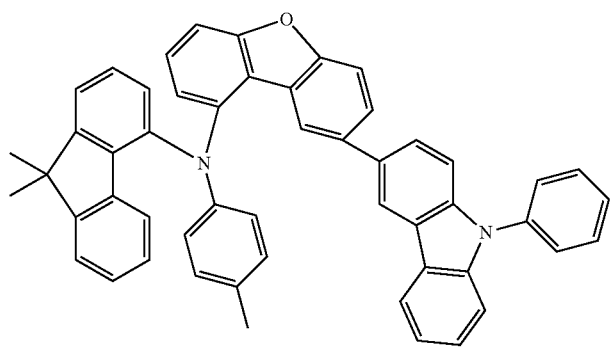 [SMILES: Cc1ccc(N(c2cccc3c2-c2ccccc2C3(C)C)c2cccc3oc4ccc(-c5ccc6c(c5)c5ccccc5n6-c5ccccc5)cc4c23)cc1]
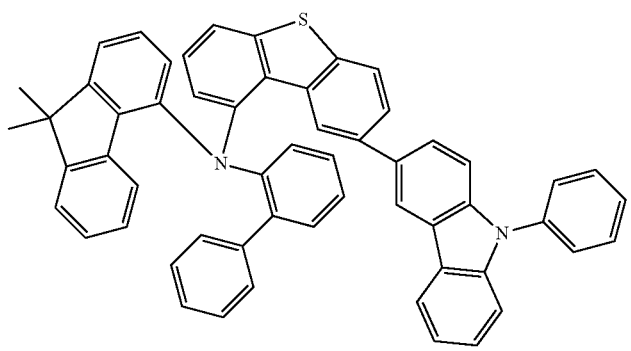 [SMILES: CC1(C)c2ccccc2-c2c(CN(c3ccccc3-c3ccccc3)c3cccc4sc5ccc(-c6ccc7c(c6)c6ccccc6n7-c6ccccc6)cc5c34)cccc21]
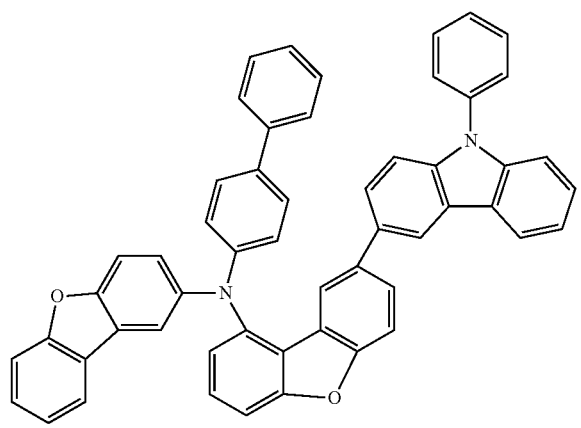 [SMILES: c1ccc(-c2ccc(N(c3ccc4oc5ccccc5c4c3)c3cccc4oc5ccc(-c6ccc7c(c6)c6ccccc6n7-c6ccccc6)cc5c34)cc2)cc1]

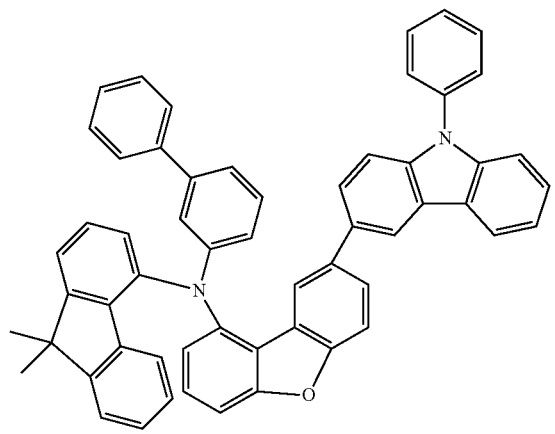 [SMILES: CC1(C)c2ccccc2-c2c(N(c3cccc(-c4ccccc4)c3)c3cccc4oc5ccc(-c6ccc7c(c6)c6ccccc6n7-c6ccccc6)cc5c34)cccc21]
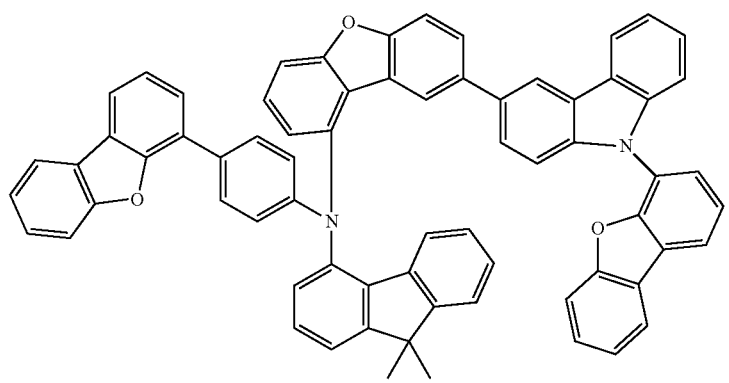 [SMILES: CC1(C)c2ccccc2-c2c(N(c3ccc(-c4cccc5c4oc4ccccc45)cc3)c3cccc4oc5ccc(-c6ccc7c(c6)c6ccccc6n7-c6cccc7c6oc6ccccc67)cc5c34)cccc21]
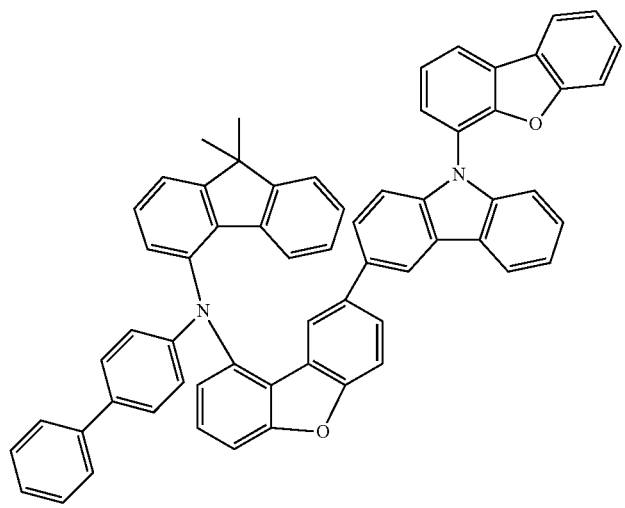 [SMILES: CC1(C)c2ccccc2-c2c(N(c3ccc(-c4ccccc4)cc3)c3cccc4oc5ccc(-c6ccc7c(c6)c6ccccc6n7-c6cccc7c6oc6ccccc67)cc5c34)cccc21]

-continued
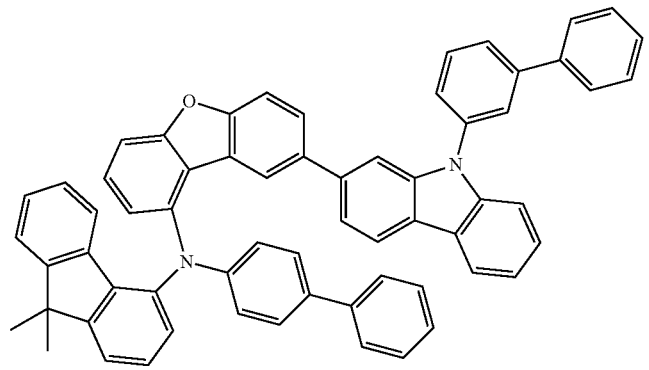 [SMILES: CC1(C)c2ccccc2-c2c(N(c3ccc(-c4ccccc4)cc3)c3cccc4oc5ccc(-c6ccc7c8ccccc8n(-c8cccc(-c9ccccc9)c8)c7c6)cc5c34)cccc21]
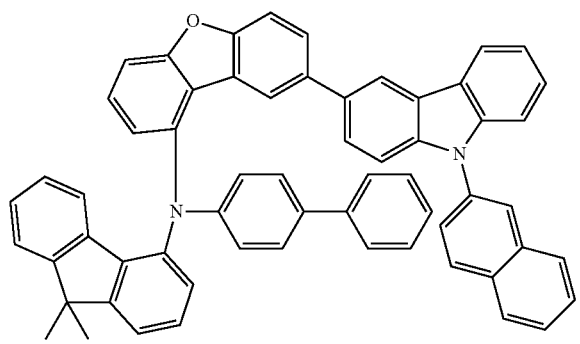 [SMILES: CC1(C)c2ccccc2-c2c(N(c3ccc(-c4ccccc4)cc3)c3cccc4oc5ccc(-c6ccc7c(c6)c6ccccc6n7-c6ccc7ccccc7c6)cc5c34)cccc21]
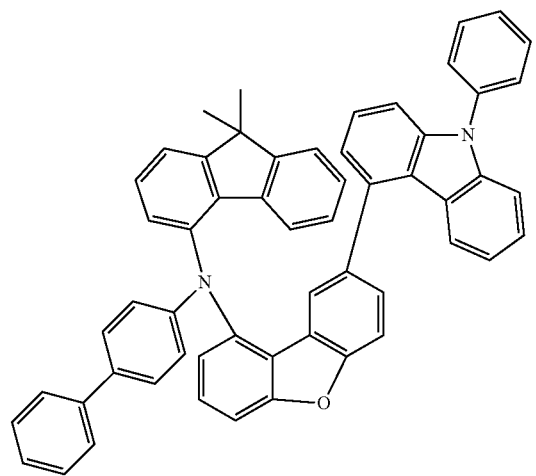 [SMILES: CC1(C)c2ccccc2-c2c(N(c3ccc(-c4ccccc4)cc3)c3cccc4oc5ccc(-c6cccc7c6c6ccccc6n7-c6ccccc6)cc5c34)cccc21]

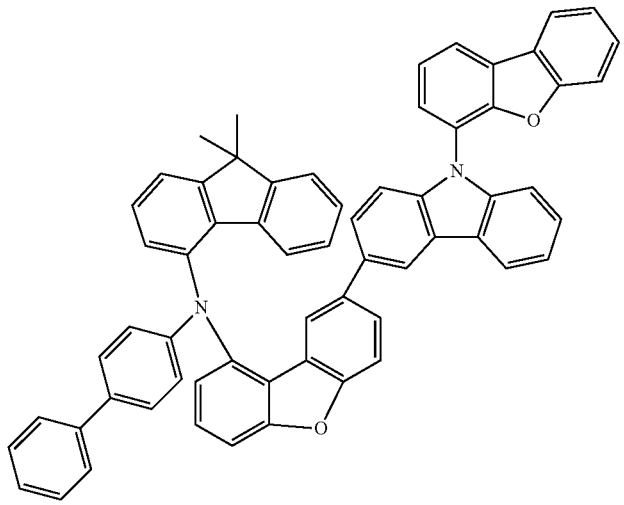 [SMILES: CC1(C)c2ccccc2-c2c(N(c3ccc(-c4ccccc4)cc3)c3cccc4oc5ccc(-c6ccc7c(c6)c6ccccc6n7-c6cccc7c6oc6ccccc67)cc5c34)cccc21]
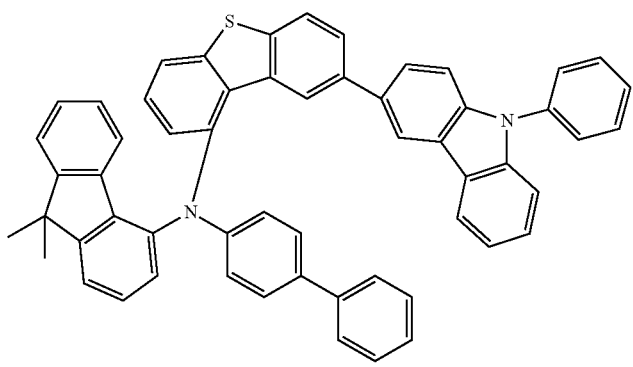 [SMILES: CC1(C)c2ccccc2-c2c(N(c3ccc(-c4ccccc4)cc3)c3cccc4sc5ccc(-c6ccc7c(c6)c6ccccc6n7-c6ccccc6)cc5c34)cccc21]
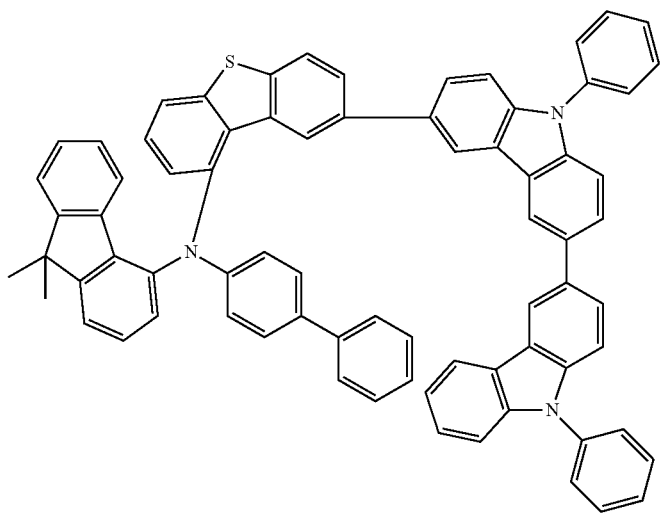 [SMILES: CC1(C)c2ccccc2-c2c(N(c3ccc(-c4ccccc4)cc3)c3cccc4sc5ccc(-c6ccc7c(c6)c6cc(-c8ccc9c(c8)c8ccccc8n9-c8ccccc8)ccc6n7-c6ccccc6)cc5c34)cccc21]

-continued
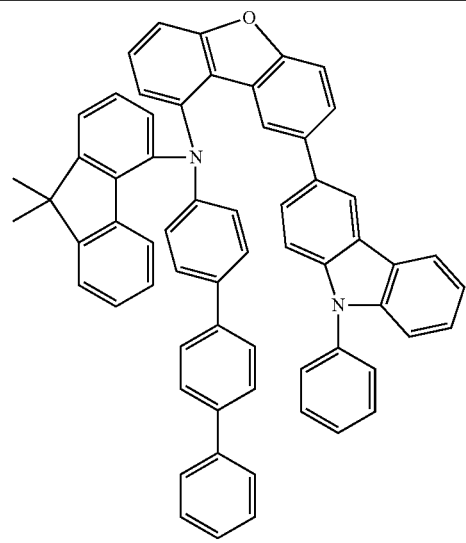
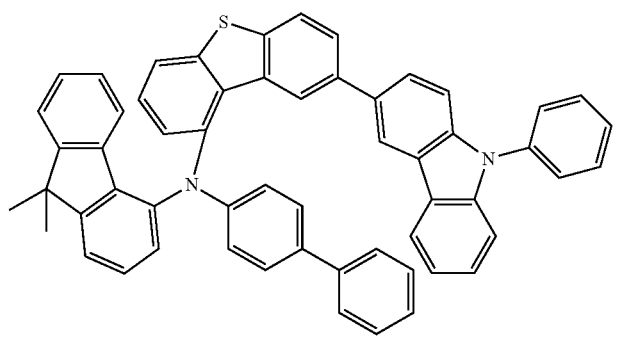 [SMILES: CC1(C)c2ccccc2-c2c(N(c3ccc(-c4ccccc4)cc3)c3cccc4sc5ccc(-c6ccc7c(c6)c6ccccc6n7-c6ccccc6)cc5c34)cccc21]
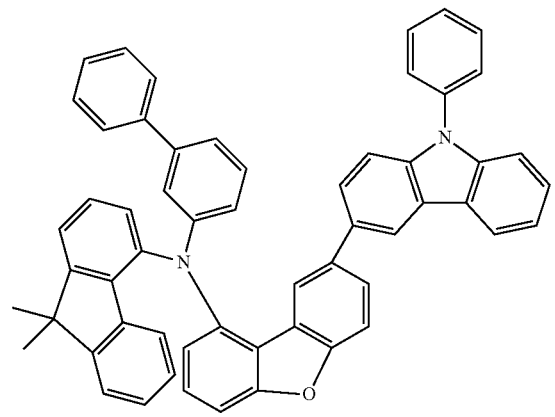 [SMILES: CC1(C)c2ccccc2-c2c(N(c3cccc(-c4ccccc4)c3)c3cccc4oc5ccc(-c6ccc7c(c6)c6ccccc6n7-c6ccccc6)cc5c34)cccc21]
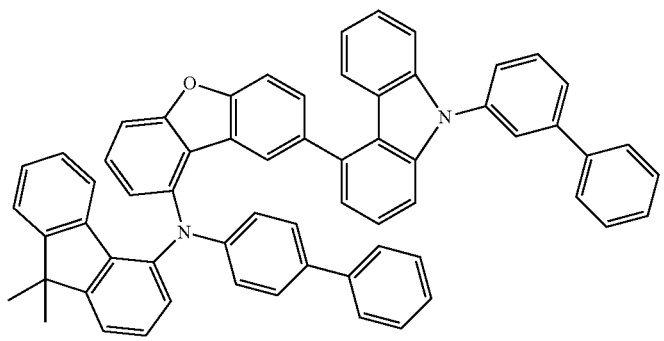 [SMILES: CC1(C)c2ccccc2-c2c(N(c3ccc(-c4ccccc4)cc3)c3cccc4oc5ccc(-c6cccc7c6c6ccccc6n7-c6cccc(-c7ccccc7)c6)cc5c34)cccc21]

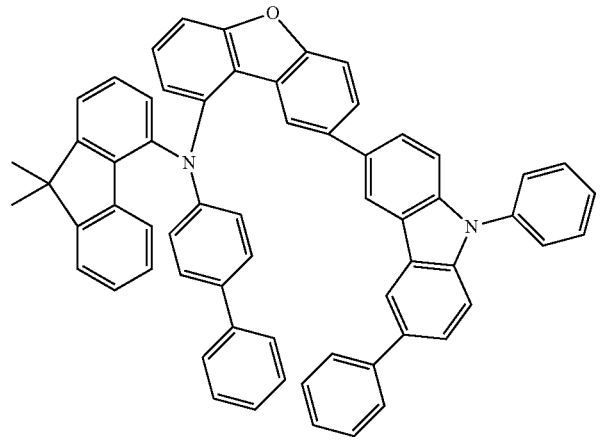 [SMILES: CC1(C)c2ccccc2-c2c(N(c3ccc(-c4ccccc4)cc3)c3cccc4oc5ccc(-c6ccc7c(c6)c6cc(-c8ccccc8)ccc6n7-c6ccccc6)cc5c34)cccc21]
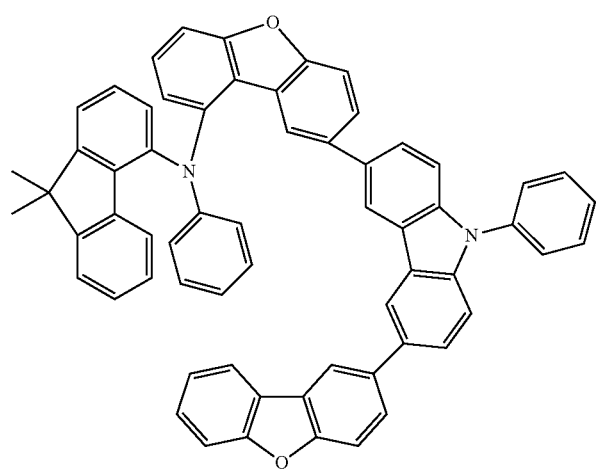 [SMILES: CC1(C)c2ccccc2-c2c(N(c3ccccc3)c3cccc4oc5ccc(-c6ccc7c(c6)c6cc(-c8ccc9oc%10ccccc%10c9c8)ccc6n7-c6ccccc6)cc5c34)cccc21]
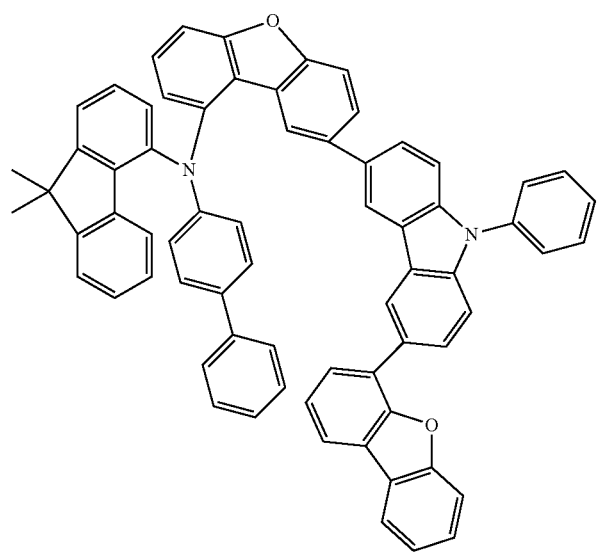 [SMILES: CC1(C)c2ccccc2-c2c(N(c3ccc(-c4ccccc4)cc3)c3cccc4oc5ccc(-c6ccc7c(c6)c6cc(-c8cccc9c8oc8ccccc89)ccc6n7-c6ccccc6)cc5c34)cccc21]

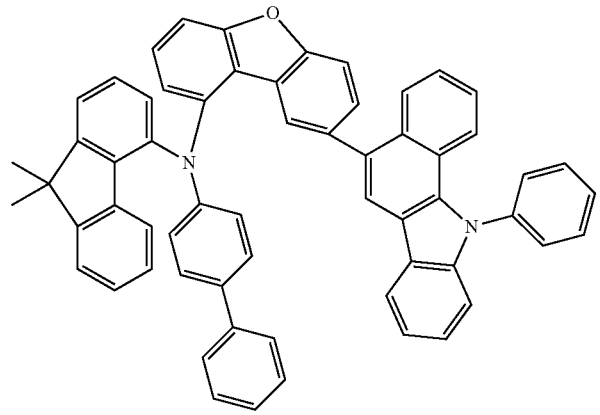 [SMILES: CC1(C)c2ccccc2-c2c(N(c3ccc(-c4ccccc4)cc3)c3cccc4oc5ccc(-c6cc7c8ccccc8n(-c8ccccc8)c7c7ccccc67)cc5c34)cccc21]
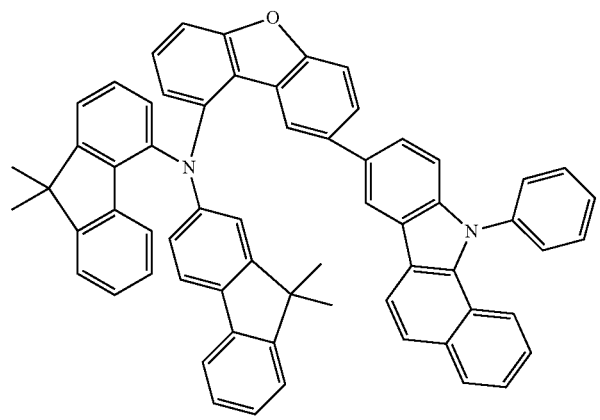 [SMILES: CC1(C)c2ccccc2-c2ccc(N(c3cccc4c3-c3ccccc3C4(C)C)c3cccc4oc5ccc(-c6ccc7c(c6)c6ccc8ccccc8c6n7-c6ccccc6)cc5c34)cc21]
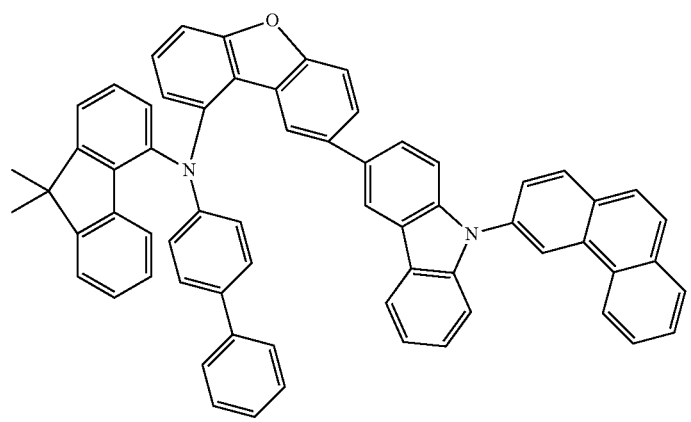 [SMILES: CC1(C)c2ccccc2-c2c(N(c3ccc(-c4ccccc4)cc3)c3cccc4oc5ccc(-c6ccc7c(c6)c6ccccc6n7-c6ccc7ccc8ccccc8c7c6)cc5c34)cccc21]

-continued
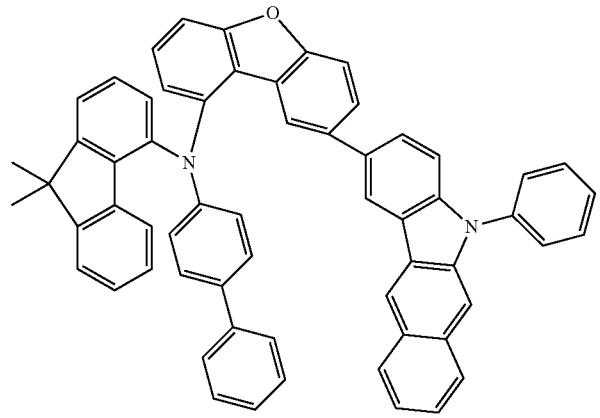 [SMILES: CC1(C)c2ccccc2-c2c(N(c3ccc(-c4ccccc4)cc3)c3cccc4oc5ccc(-c6ccc7c(c6)c6cc8ccccc8cc6n7-c6ccccc6)cc5c34)cccc21]
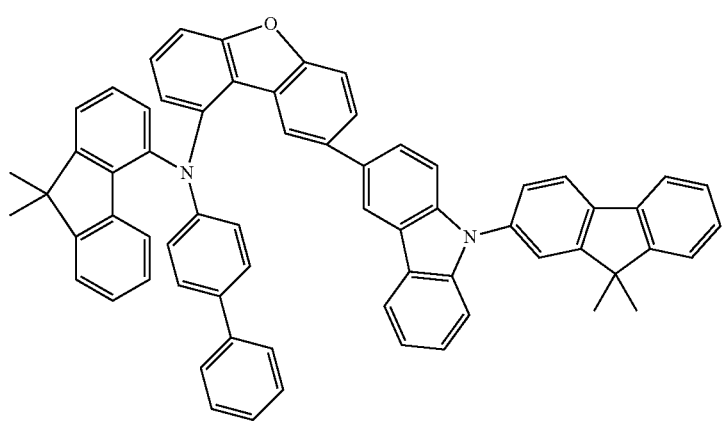 [SMILES: CC1(C)c2ccccc2-c2ccc(-n3c4ccccc4c4cc(-c5ccc6oc7cccc(N(c8ccc(-c9ccccc9)cc8)c8cccc9c8-c8ccccc8C9(C)C)c7c6c5)ccc43)cc21]
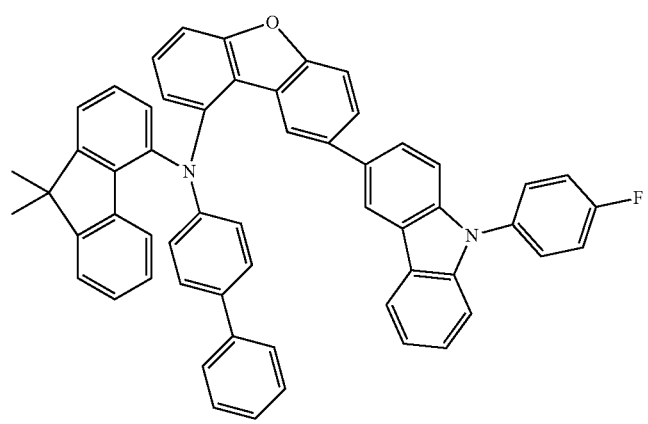 [SMILES: CC1(C)c2ccccc2-c2c(N(c3ccc(-c4ccccc4)cc3)c3cccc4oc5ccc(-c6ccc7c(c6)c6ccccc6n7-c6ccc(F)cc6)cc5c34)cccc21]

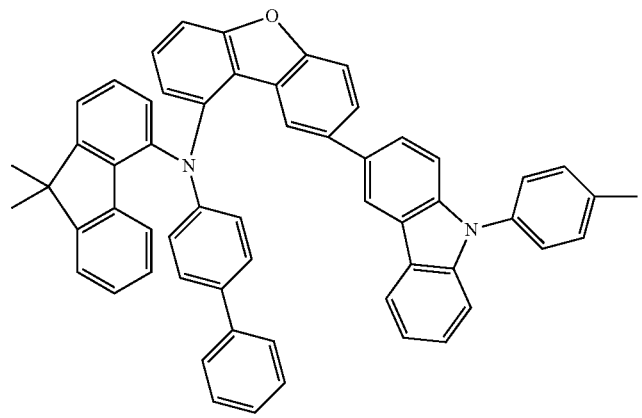
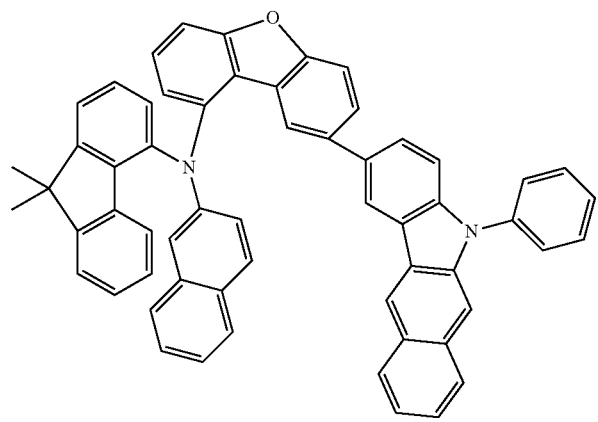 [SMILES: CC1(C)c2ccccc2-c2c(N(c3ccc4ccccc4c3)c3cccc4oc5ccc(-c6ccc7c(c6)c6cc8ccccc8cc6n7-c6ccccc6)cc5c34)cccc21]
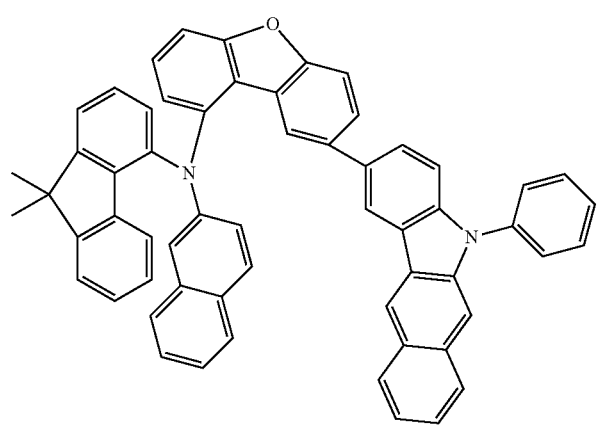 [SMILES: CC1(C)c2ccccc2-c2c(N(c3ccc4ccccc4c3)c3cccc4oc5ccc(-c6ccc7c(c6)c6cc8ccccc8cc6n7-c6ccccc6)cc5c34)cccc21]

-continued
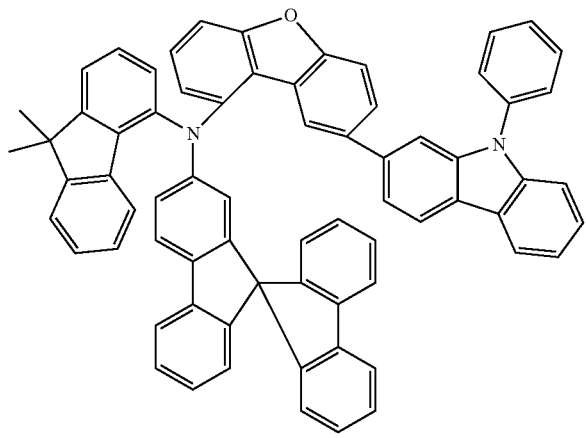 [SMILES: CC1(C)c2ccccc2-c2c(N(c3ccc4c(c3)C3(c5ccccc5-c5ccccc53)c3ccccc3-4)c3cccc4oc5ccc(-c6ccc7c8ccccc8n(-c8ccccc8)c7c6)cc5c34)cccc21]
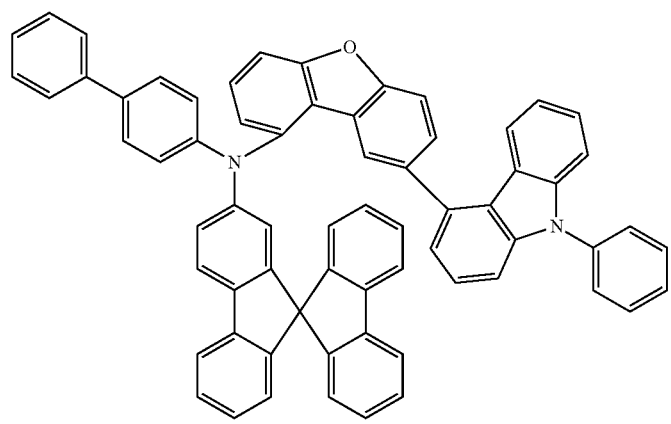 [SMILES: c1ccc(-c2ccc(N(c3ccc4c(c3)C3(c5ccccc5-c5ccccc53)c3ccccc3-4)c3cccc4oc5ccc(-c6cccc7c6c6ccccc6n7-c6ccccc6)cc5c34)cc2)cc1]
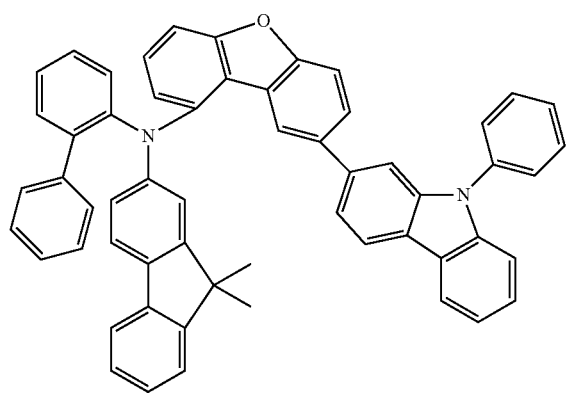 [SMILES: CC1(C)c2ccccc2-c2ccc(N(c3ccccc3-c3ccccc3)c3cccc4oc5ccc(-c6ccc7c8ccccc8n(-c8ccccc8)c7c6)cc5c34)cc21]

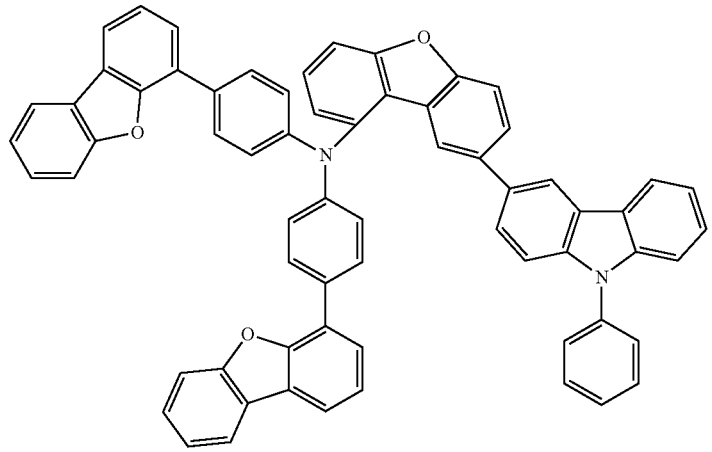 [SMILES: c1ccc(-n2c3ccccc3c3cc(-c4ccc5oc6cccc(N(c7ccc(-c8cccc9c8oc8ccccc89)cc7)c7ccc(-c8cccc9c8oc8ccccc89)cc7)c6c5c4)ccc32)cc1]
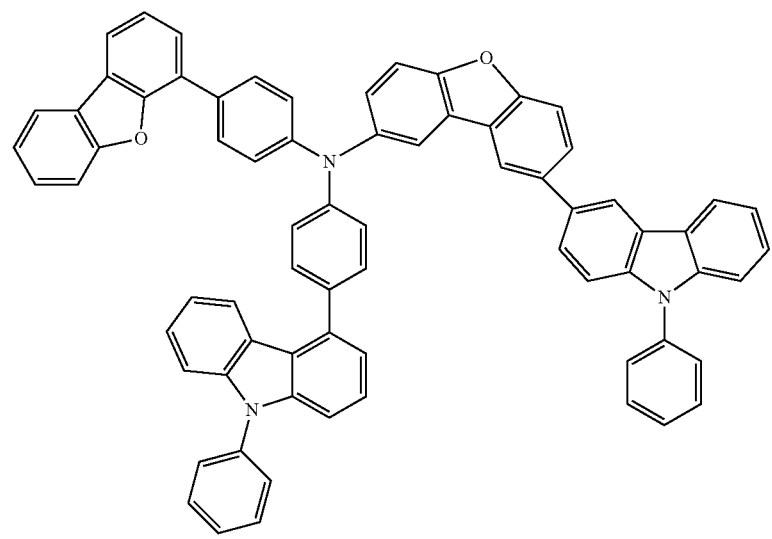 [SMILES: c1ccc(-n2c3ccccc3c3cc(-c4ccc5oc6ccc(N(c7ccc(-c8cccc9c8oc8ccccc89)cc7)c7ccc(-c8cccc9c8c8ccccc8n9-c8ccccc8)cc7)cc6c5c4)ccc32)cc1]
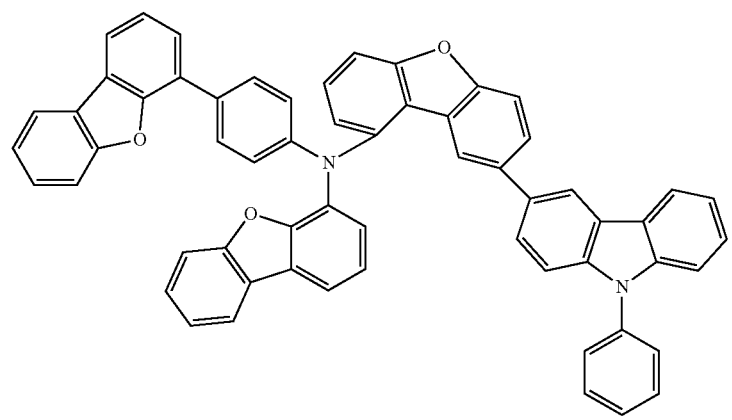 [SMILES: c1ccc(-n2c3ccccc3c3cc(-c4ccc5oc6cccc(N(c7ccc(-c8cccc9c8oc8ccccc89)cc7)c7cccc8c7oc7ccccc78)c6c5c4)ccc32)cc1]

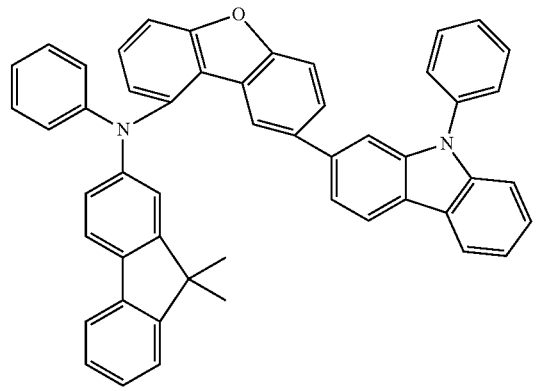 [SMILES: CC1(C)c2ccccc2-c2ccc(N(c3ccccc3)c3cccc4oc5ccc(-c6ccc7c8ccccc8n(-c8ccccc8)c7c6)cc5c34)cc21]
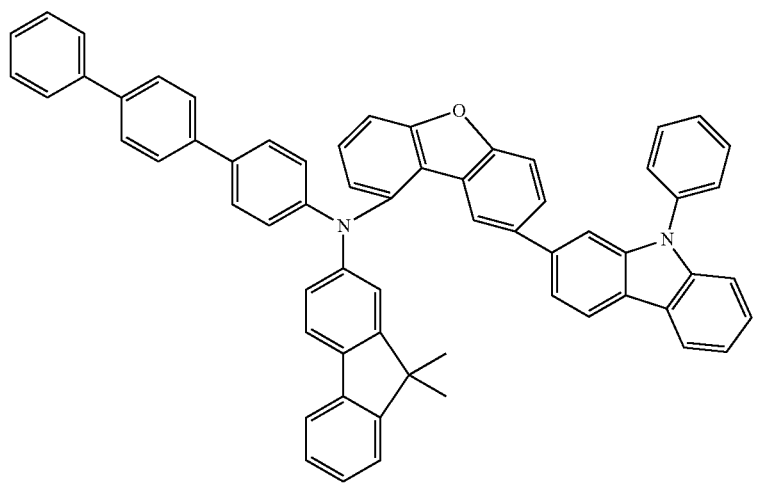 [SMILES: CC1(C)c2ccccc2-c2ccc(N(c3ccc(-c4ccc(-c5ccccc5)cc4)cc3)c3cccc4oc5ccc(-c6ccc7c8ccccc8n(-c8ccccc8)c7c6)cc5c34)cc21]
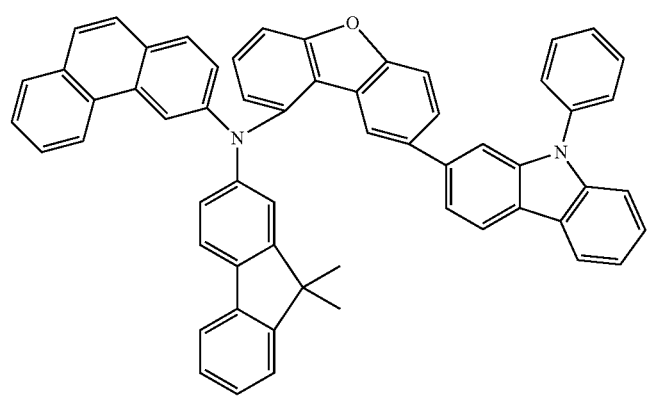 [SMILES: CC1(C)c2ccccc2-c2ccc(N(c3ccc4ccc5ccccc5c4c3)c3cccc4oc5ccc(-c6ccc7c8ccccc8n(-c8ccccc8)c7c6)cc5c34)cc21]

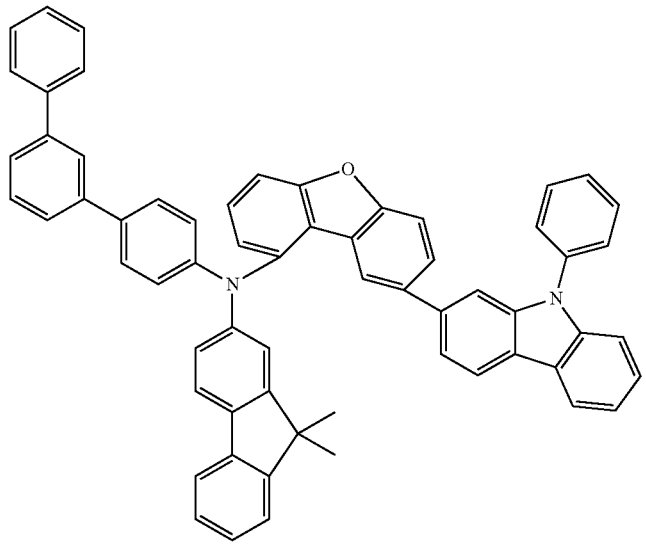 [SMILES: CC1(C)c2ccccc2-c2ccc(N(c3ccc(-c4cccc(-c5ccccc5)c4)cc3)c3cccc4oc5ccc(-c6ccc7c8ccccc8n(-c8ccccc8)c7c6)cc5c34)cc21]
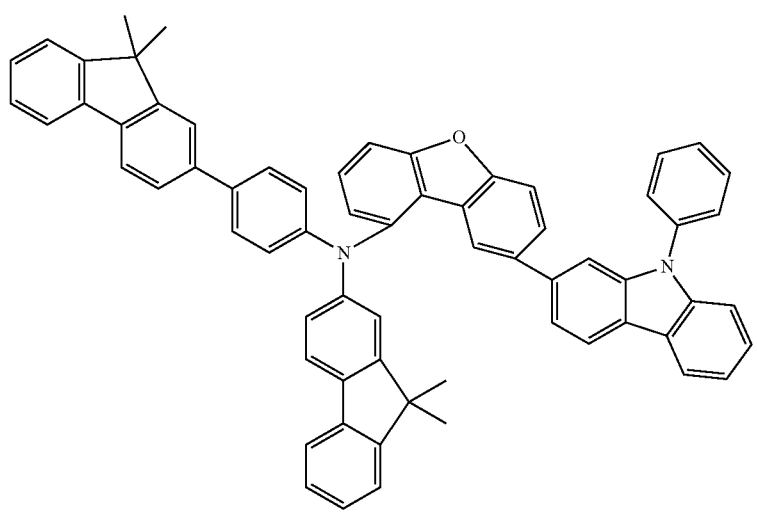 [SMILES: CC1(C)c2ccccc2-c2ccc(-c3ccc(N(c4ccc5c(c4)C(C)(C)c4ccccc4-5)c4cccc5oc6ccc(-c7ccc8c9ccccc9n(-c9ccccc9)c8c7)cc6c45)cc3)cc21]
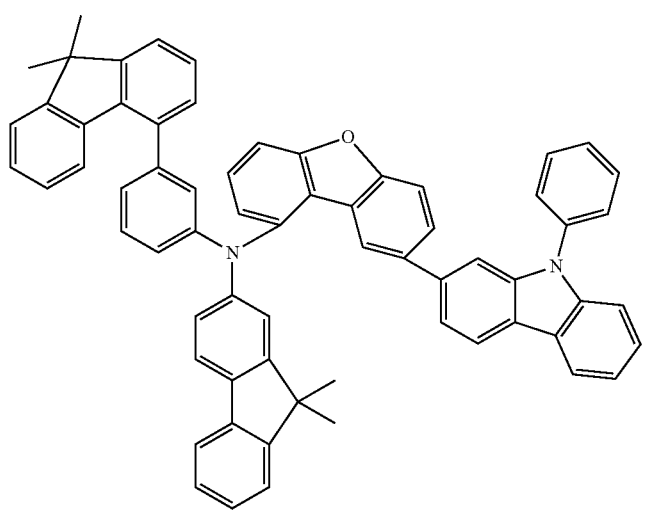 [SMILES: CC1(C)c2ccccc2-c2ccc(N(c3cccc(-c4cccc5c4-c4ccccc4C5(C)C)c3)c3cccc4oc5ccc(-c6ccc7c8ccccc8n(-c8ccccc8)c7c6)cc5c34)cc21]

-continued
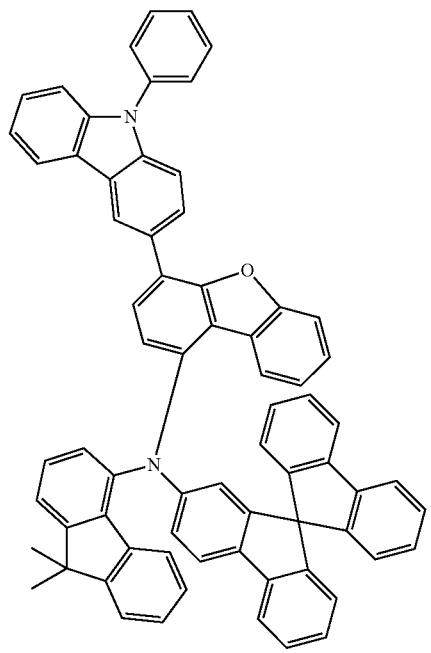 [SMILES: CC1(C)c2ccccc2-c2c(N(c3ccc4c(c3)C3(c5ccccc5-c5ccccc53)c3ccccc3-4)c3ccc(-c4ccc5c(c4)c4ccccc4n5-c4ccccc4)c4oc5ccccc5c34)cccc21]
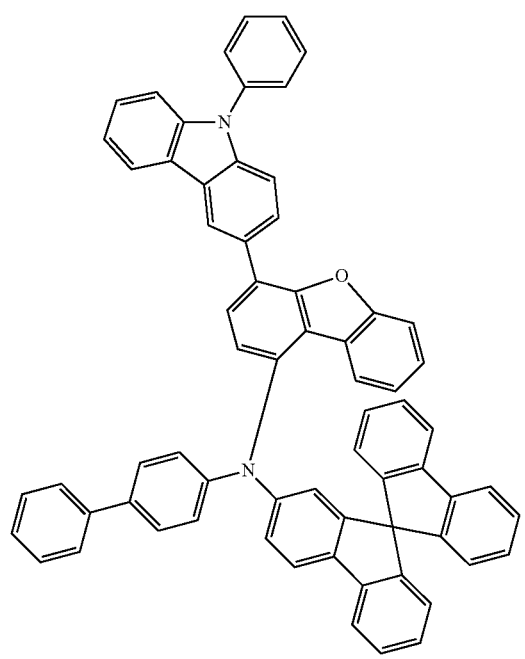 [SMILES: c1ccc(-c2ccc(N(c3ccc4c(c3)C3(c5ccccc5-c5ccccc53)c3ccccc3-4)c3ccc(-c4ccc5c(c4)c4ccccc4n5-c4ccccc4)c4oc5ccccc5c34)cc2)cc1]

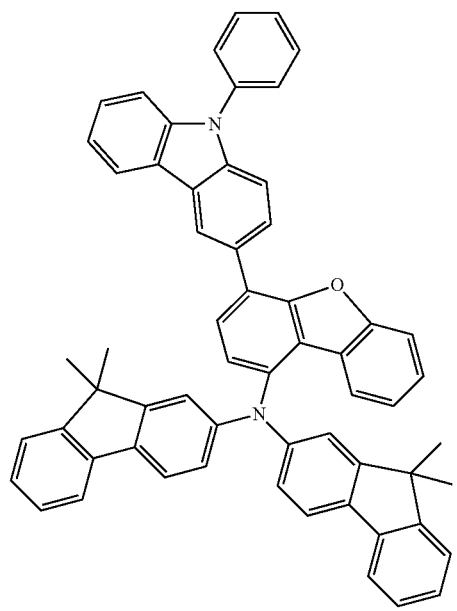 [SMILES: CC1(C)c2ccccc2-c2ccc(N(c3ccc4c(c3)C(C)(C)c3ccccc3-4)c3ccc(-c4ccc5c(c4)c4ccccc4n5-c4ccccc4)c4oc5ccccc5c34)cc21]
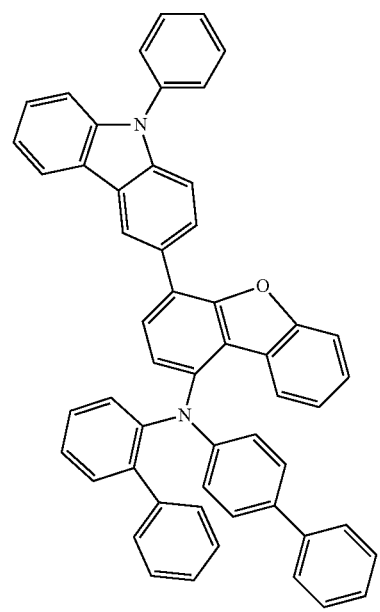 [SMILES: c1ccc(-c2ccc(N(c3ccccc3-c3ccccc3)c3ccc(-c4ccc5c(c4)c4ccccc4n5-c4ccccc4)c4oc5ccccc5c34)cc2)cc1]

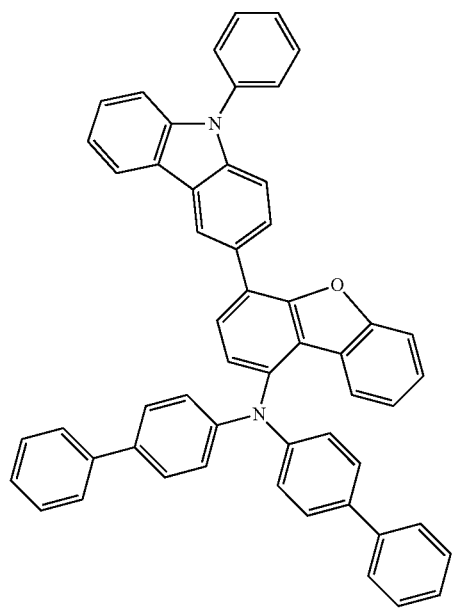 [SMILES: c1ccc(-c2ccc(N(c3ccc(-c4ccccc4)cc3)c3ccc(-c4ccc5c(c4)c4ccccc4n5-c4ccccc4)c4oc5ccccc5c34)cc2)cc1]
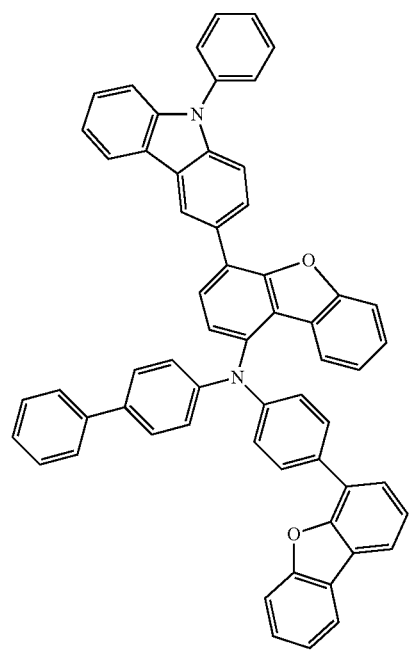 [SMILES: c1ccc(-c2ccc(N(c3ccc(-c4cccc5c4oc4ccccc45)cc3)c3ccc(-c4ccc5c(c4)c4ccccc4n5-c4ccccc4)c4oc5ccccc5c34)cc2)cc1]

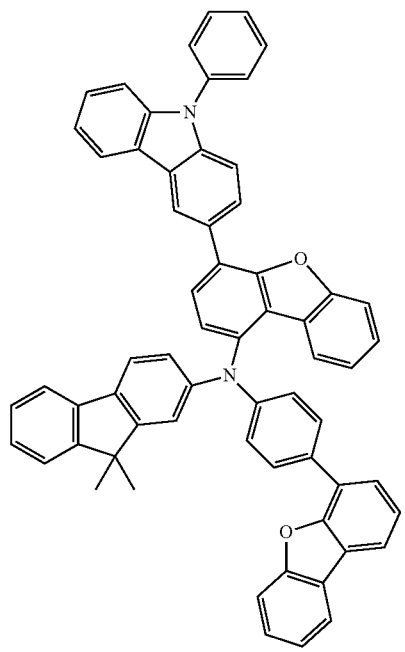 [SMILES: CC1(C)c2ccccc2-c2ccc(N(c3ccc(-c4cccc5c4oc4ccccc45)cc3)c3ccc(-c4ccc5c(c4)c4ccccc4n5-c4ccccc4)c4oc5ccccc5c34)cc21]
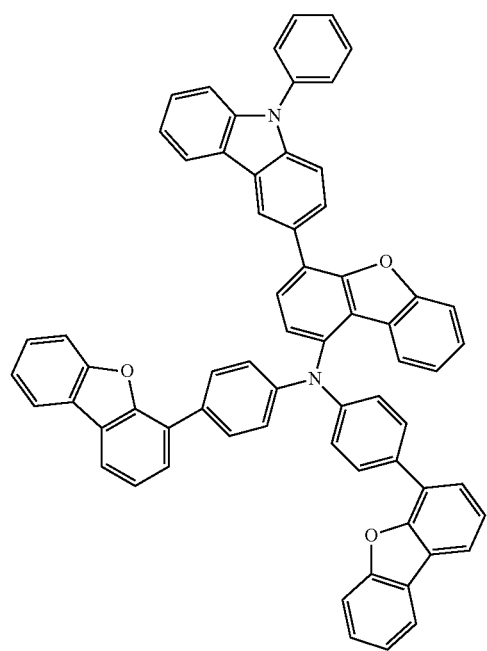 [SMILES: c1ccc(-n2c3ccccc3c3cc(-c4ccc(N(c5ccc(-c6cccc7c6oc6ccccc67)cc5)c5ccc(-c6cccc7c6oc6ccccc67)cc5)c5c4oc4ccccc45)ccc32)cc1]

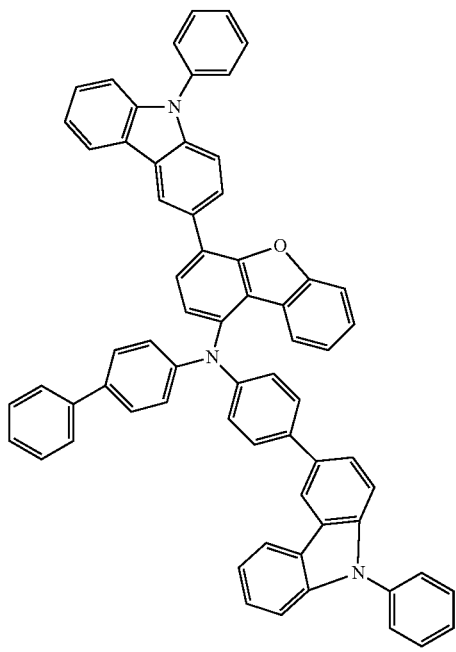 [SMILES: c1ccc(-c2ccc(N(c3ccc(-c4ccc5c(c4)c4ccccc4n5-c4ccccc4)cc3)c3ccc(-c4ccc5c(c4)c4ccccc4n5-c4ccccc4)c4oc5ccccc5c34)cc2)cc1]
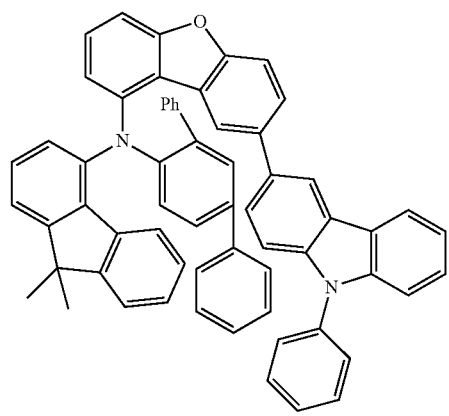 [SMILES: CC1(C)c2ccccc2-c2c(N(c3ccc(-c4ccccc4)cc3-c3ccccc3)c3cccc4oc5ccc(-c6ccc7c(c6)c6ccccc6n7-c6ccccc6)cc5c34)cccc21]
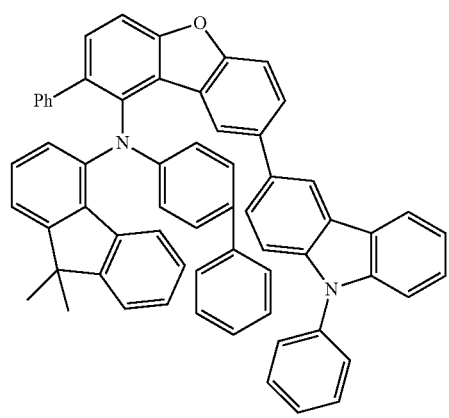 [SMILES: CC1(C)c2ccccc2-c2c(N(c3ccc(-c4ccccc4)cc3)c3c(-c4ccccc4)ccc4oc5ccc(-c6ccc7c(c6)c6ccccc6n7-c6ccccc6)cc5c34)cccc21]

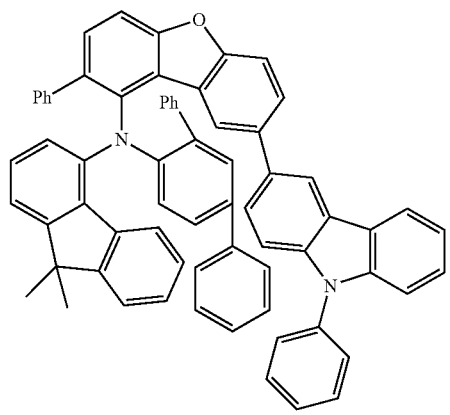 [SMILES: CC1(C)c2ccccc2-c2c(N(c3ccc(-c4ccccc4)cc3-c3ccccc3)c3c(-c4ccccc4)ccc4oc5ccc(-c6ccc7c(c6)c6ccccc6n7-c6ccccc6)cc5c34)cccc21]
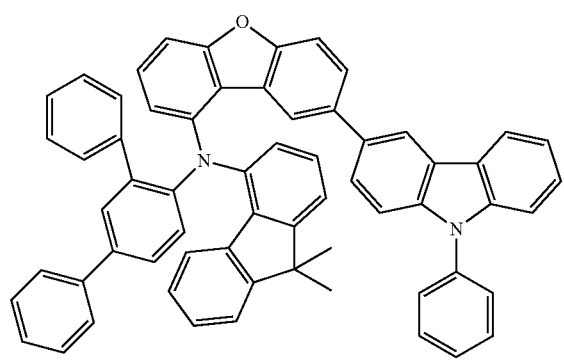 [SMILES: CC1(C)c2ccccc2-c2c(N(c3ccc(-c4ccccc4)cc3-c3ccccc3)c3cccc4oc5ccc(-c6ccc7c(c6)c6ccccc6n7-c6ccccc6)cc5c34)cccc21]
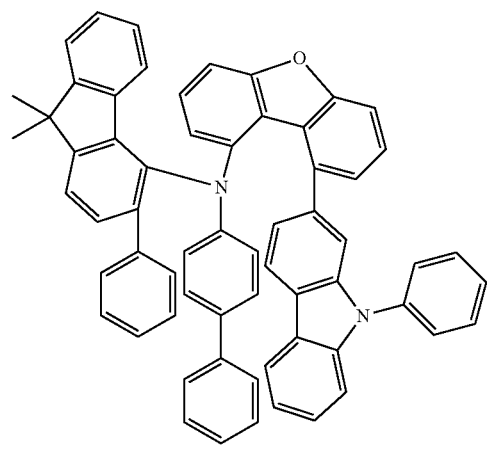 [SMILES: CC1(C)c2ccccc2-c2c1ccc(-c1ccccc1)c2N(c1ccc(-c2ccccc2)cc1)c1cccc2oc3cccc(-c4ccc5c6ccccc6n(-c6ccccc6)c5c4)c3c12]

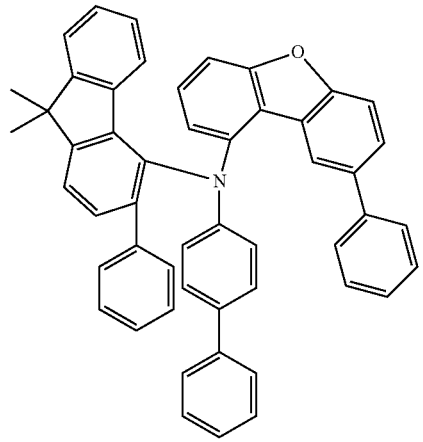 [SMILES: CC1(C)c2ccccc2-c2c1ccc(-c1ccccc1)c2N(c1ccc(-c2ccccc2)cc1)c1cccc2oc3ccc(-c4ccccc4)cc3c12]
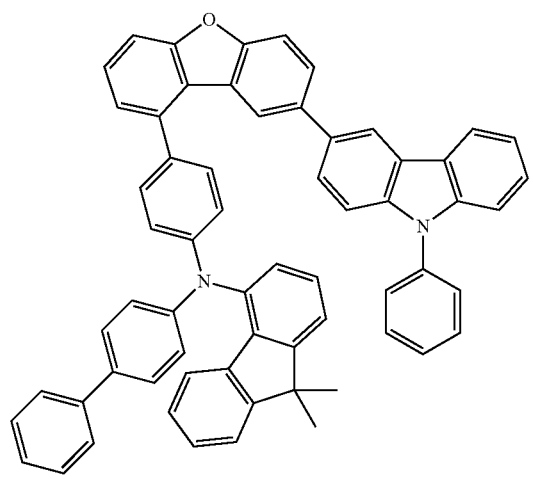 [SMILES: CC1(C)c2ccccc2-c2c(N(c3ccc(-c4ccccc4)cc3)c3ccc(-c4cccc5oc6ccc(-c7ccc8c(c7)c7ccccc7n8-c7ccccc7)cc6c45)cc3)cccc21]
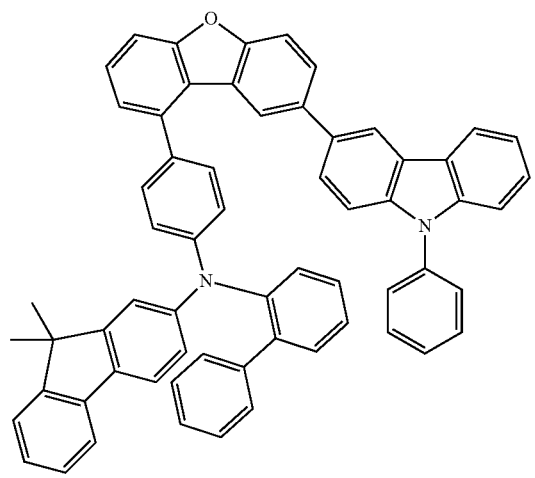 [SMILES: CC1(C)c2ccccc2-c2ccc(N(c3ccc(-c4cccc5oc6ccc(-c7ccc8c(c7)c7ccccc7n8-c7ccccc7)cc6c45)cc3)c3ccccc3-c3ccccc3)cc21]

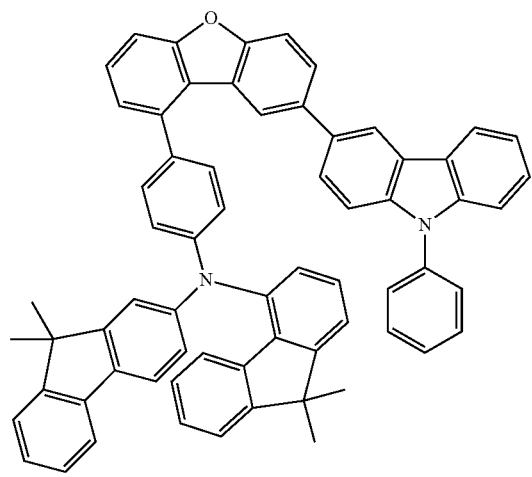 [SMILES: CC1(C)c2ccccc2-c2ccc(N(c3ccc(-c4cccc5oc6ccc(-c7ccc8c(c7)c7ccccc7n8-c7ccccc7)cc6c45)cc3)c3cccc4c3-c3ccccc3C4(C)C)cc21]
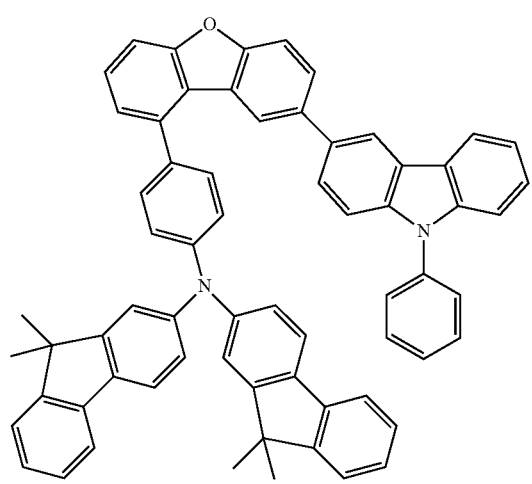 [SMILES: CC1(C)c2ccccc2-c2ccc(N(c3ccc(-c4cccc5oc6ccc(-c7ccc8c(c7)c7ccccc7n8-c7ccccc7)cc6c45)cc3)c3ccc4c(c3)C(C)(C)c3ccccc3-4)cc21]
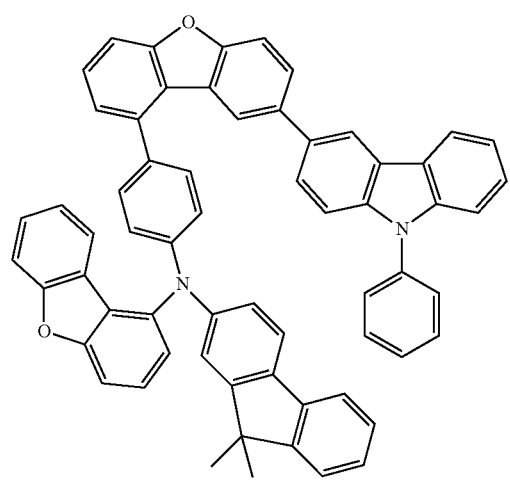 [SMILES: CC1(C)c2ccccc2-c2ccc(N(c3ccc(-c4cccc5oc6ccc(-c7ccc8c(c7)c7ccccc7n8-c7ccccc7)cc6c45)cc3)c3cccc4oc5ccccc5c34)cc21]

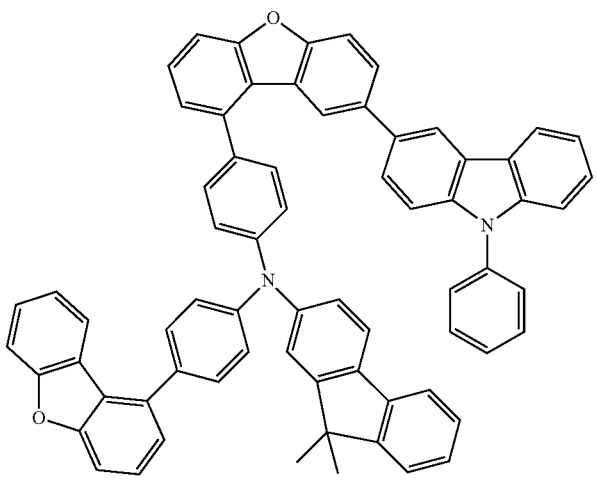 [SMILES: CC1(C)c2ccccc2-c2ccc(N(c3ccc(-c4cccc5oc6ccccc6c45)cc3)c3ccc(-c4cccc5oc6ccc(-c7ccc8c(c7)c7ccccc7n8-c7ccccc7)cc6c45)cc3)cc21]
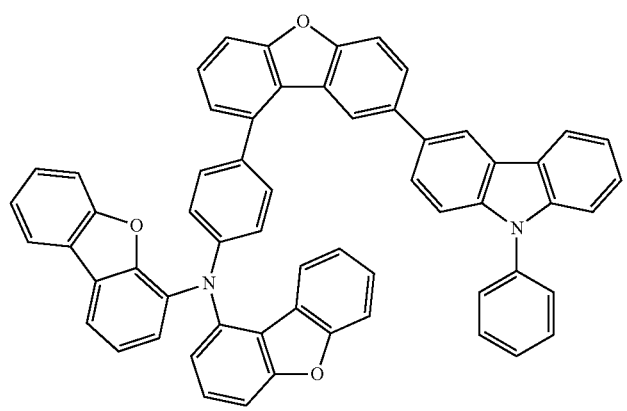 [SMILES: c1ccc(-n2c3ccccc3c3cc(-c4ccc5oc6cccc(-c7ccc(N(c8cccc9c8oc8ccccc89)c8cccc9oc%10ccccc%10c89)cc7)c6c5c4)ccc32)cc1]
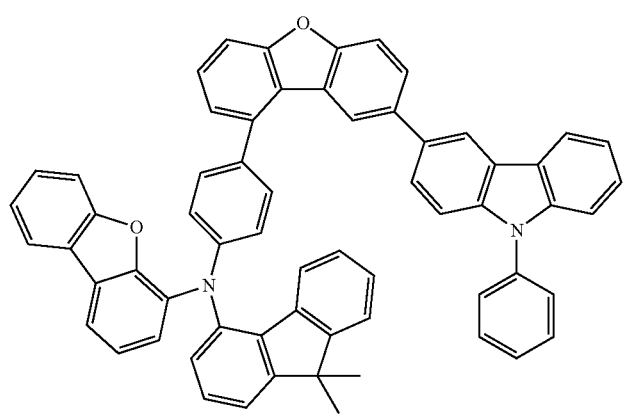 [SMILES: CC1(C)c2ccccc2-c2c(N(c3ccc(-c4cccc5oc6ccc(-c7ccc8c(c7)c7ccccc7n8-c7ccccc7)cc6c45)cc3)c3cccc4c3oc3ccccc34)cccc21]

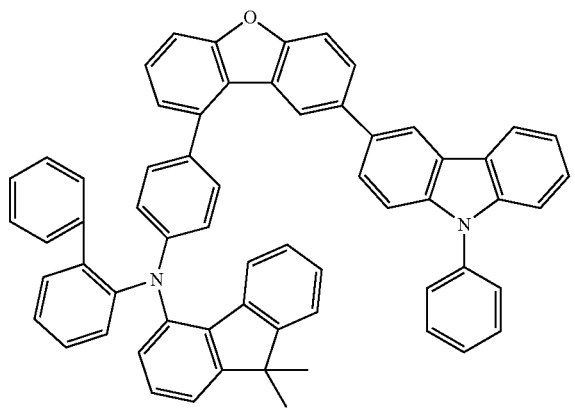 [SMILES: CC1(C)c2ccccc2-c2c(N(c3ccc(-c4cccc5oc6ccc(-c7ccc8c(c7)c7ccccc7n8-c7ccccc7)cc6c45)cc3)c3ccccc3-c3ccccc3)cccc21]
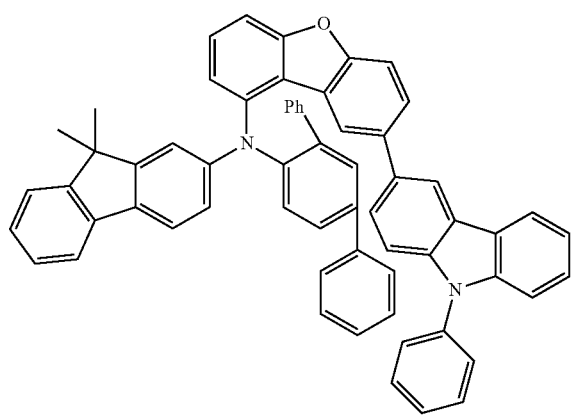 [SMILES: CC1(C)c2ccccc2-c2ccc(N(c3ccc(-c4ccccc4)cc3-c3ccccc3)c3cccc4oc5ccc(-c6ccc7c(c6)c6ccccc6n7-c6ccccc6)cc5c34)cc21]
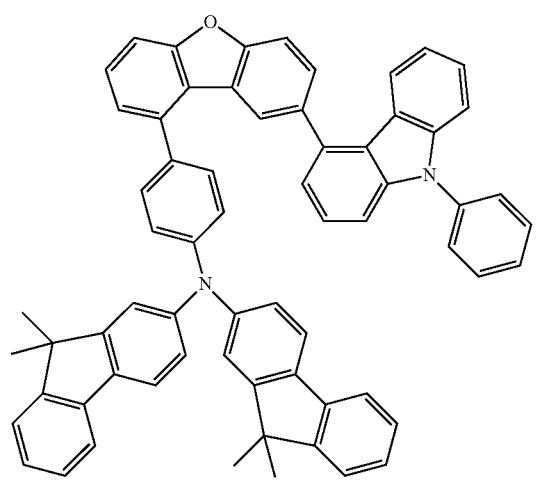 [SMILES: CC1(C)c2ccccc2-c2ccc(N(c3ccc(-c4cccc5oc6ccc(-c7cccc8c7c7ccccc7n8-c7ccccc7)cc6c45)cc3)c3ccc4c(c3)C(C)(C)c3ccccc3-4)cc21]

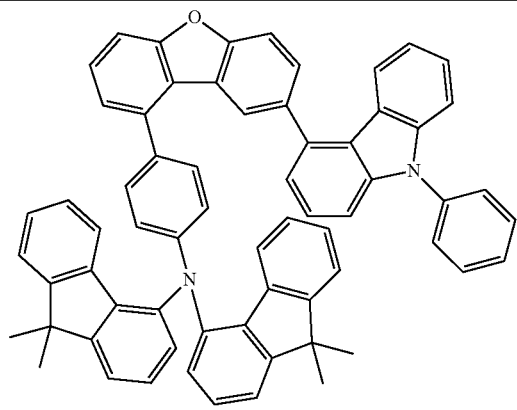
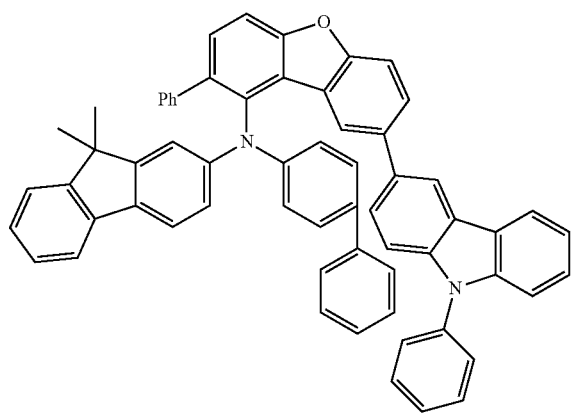 [SMILES: CC1(C)c2ccccc2-c2ccc(N(c3ccc(-c4ccccc4)cc3)c3c(-c4ccccc4)ccc4oc5ccc(-c6ccc7c(c6)c6ccccc6n7-c6ccccc6)cc5c34)cc21]
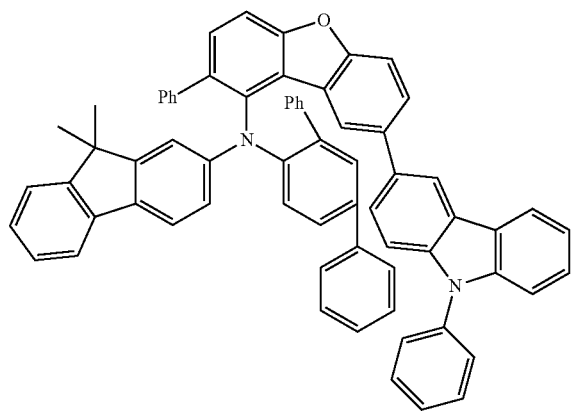 [SMILES: CC1(C)c2ccccc2-c2ccc(N(c3ccc(-c4ccccc4)cc3-c3ccccc3)c3c(-c4ccccc4)ccc4oc5ccc(-c6ccc7c(c6)c6ccccc6n7-c6ccccc6)cc5c34)cc21]
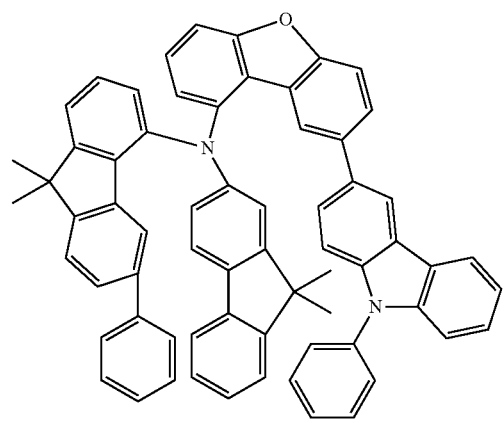 [SMILES: CC1(C)c2ccccc2-c2ccc(N(c3cccc4c3-c3cc(-c5ccccc5)ccc3C4(C)C)c3cccc4oc5ccc(-c6ccc7c(c6)c6ccccc6n7-c6ccccc6)cc5c34)cc21]

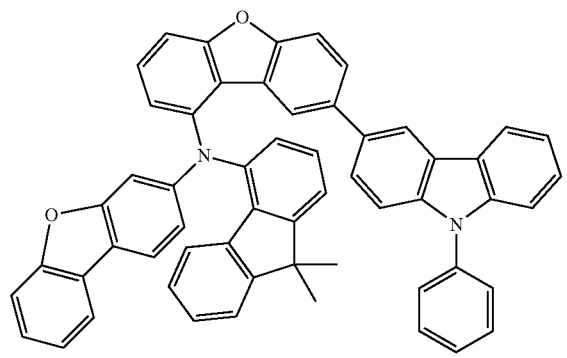 [SMILES: CC1(C)c2ccccc2-c2c(N(c3ccc4c(c3)oc3ccccc34)c3cccc4oc5ccc(-c6ccc7c(c6)c6ccccc6n7-c6ccccc6)cc5c34)cccc21]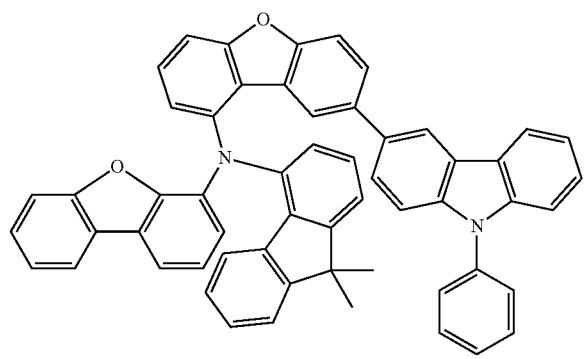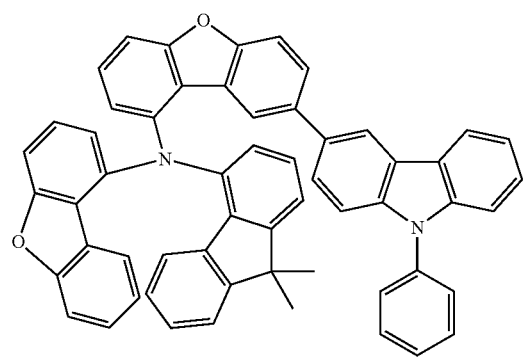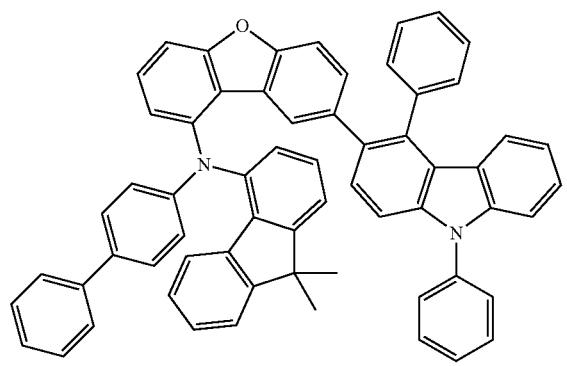 [SMILES: CC1(C)c2ccccc2-c2c(N(c3ccc(-c4ccccc4)cc3)c3cccc4oc5ccc(-c6ccc7c(c6-c6ccccc6)c6ccccc6n7-c6ccccc6)cc5c34)cccc21]

-continued
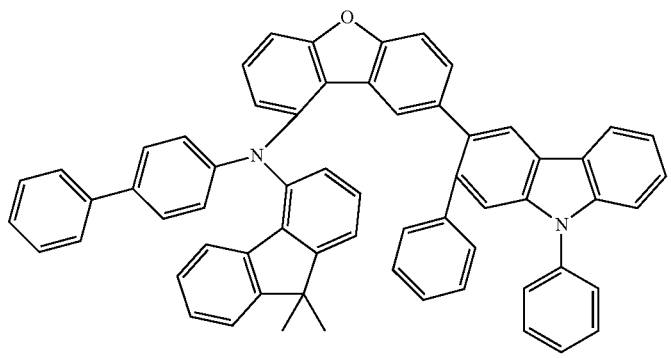 [SMILES: CC1(C)c2ccccc2-c2c(N(c3ccc(-c4ccccc4)cc3)c3cccc4oc5ccc(-c6cc7c8ccccc8n(-c8ccccc8)c7cc6-c6ccccc6)cc5c34)cccc21]
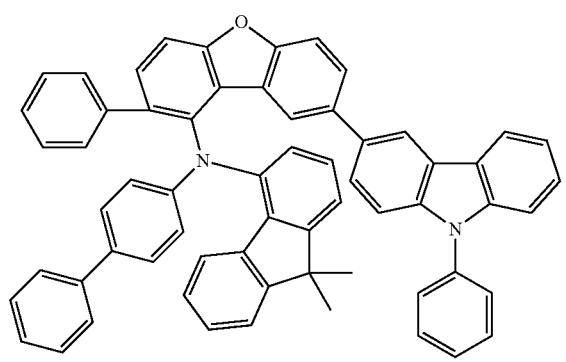
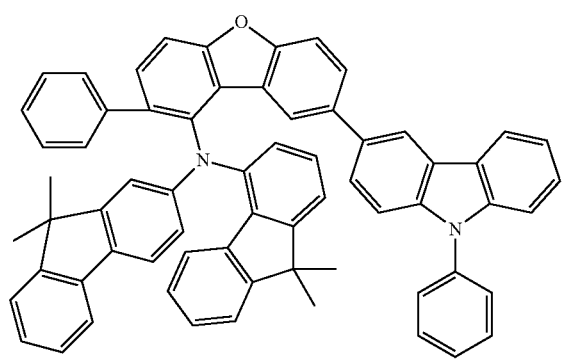 [SMILES: CC1(C)c2ccccc2-c2ccc(N(c3cccc4c3-c3ccccc3C4(C)C)c3c(-c4ccccc4)ccc4oc5ccc(-c6ccc7c(c6)c6ccccc6n7-c6ccccc6)cc5c34)cc21]
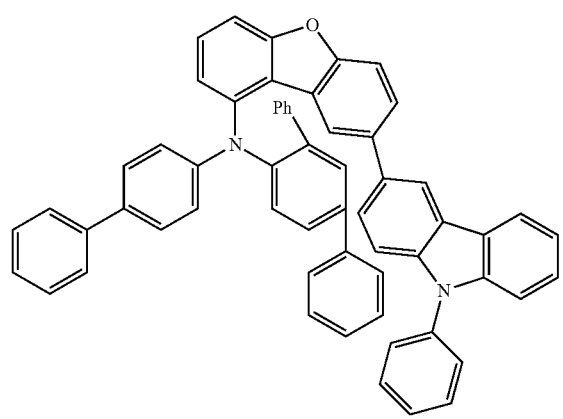 [SMILES: c1ccc(-c2ccc(N(c3ccc(-c4ccccc4)cc3-c3ccccc3)c3cccc4oc5ccc(-c6ccc7c(c6)c6ccccc6n7-c6ccccc6)cc5c34)cc2)cc1]

-continued
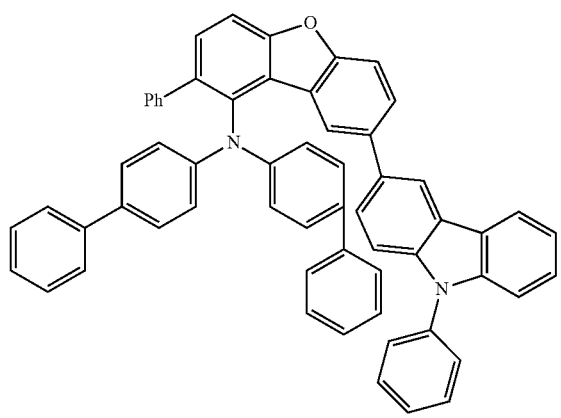 [SMILES: c1ccc(-c2ccc(N(c3ccc(-c4ccccc4)cc3)c3c(-c4ccccc4)ccc4oc5ccc(-c6ccc7c(c6)c6ccccc6n7-c6ccccc6)cc5c34)cc2)cc1]
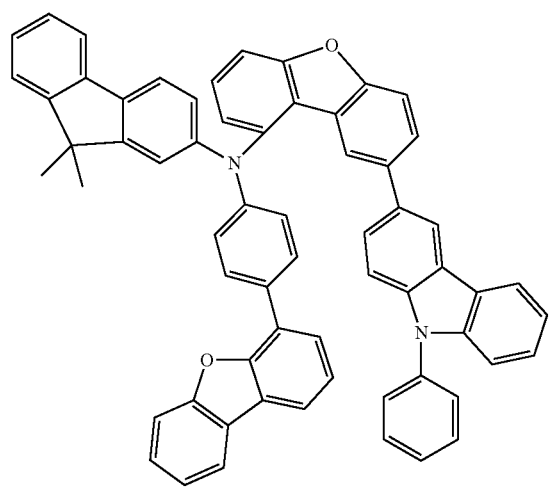 [SMILES: CC1(C)c2ccccc2-c2ccc(N(c3ccc(-c4cccc5c4oc4ccccc45)cc3)c3cccc4oc5ccc(-c6ccc7c(c6)c6ccccc6n7-c6ccccc6)cc5c34)cc21]
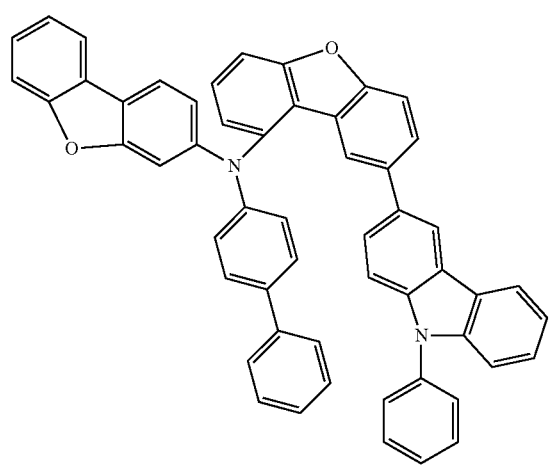 [SMILES: c1ccc(-c2ccc(N(c3ccc4c(c3)oc3ccccc34)c3cccc4oc5ccc(-c6ccc7c(c6)c6ccccc6n7-c6ccccc6)cc5c34)cc2)cc1]

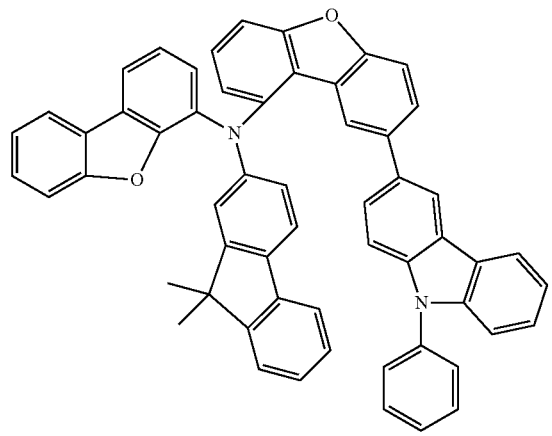 [SMILES: CC1(C)c2ccccc2-c2ccc(N(c3cccc4c3oc3ccccc34)c3cccc4oc5ccc(-c6ccc7c(c6)c6ccccc6n7-c6ccccc6)cc5c34)cc21]
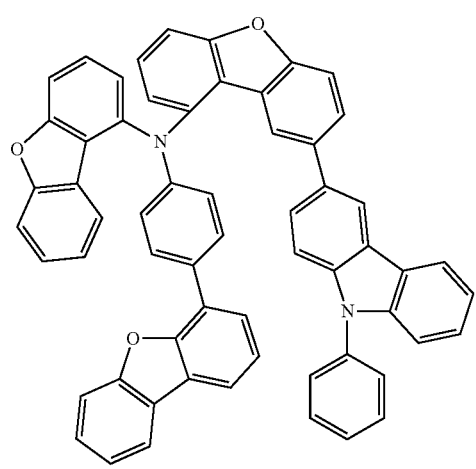 [SMILES: c1ccc(-n2c3ccccc3c3cc(-c4ccc5oc6cccc(N(c7ccc(-c8cccc9c8oc8ccccc89)cc7)c7cccc8oc9ccccc9c78)c6c5c4)ccc32)cc1]
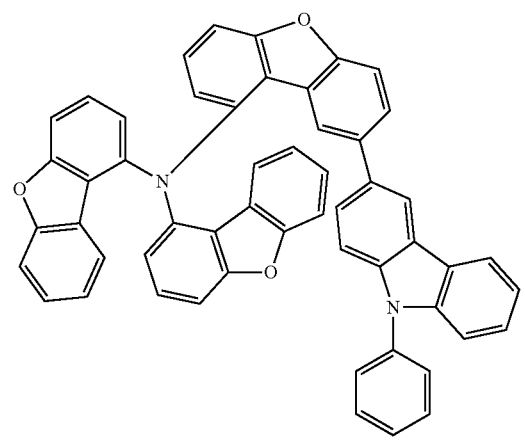 [SMILES: c1ccc(-n2c3ccccc3c3cc(-c4ccc5oc6cccc(N(c7cccc8oc9ccccc9c78)c7cccc8oc9ccccc9c78)c6c5c4)ccc32)cc1]

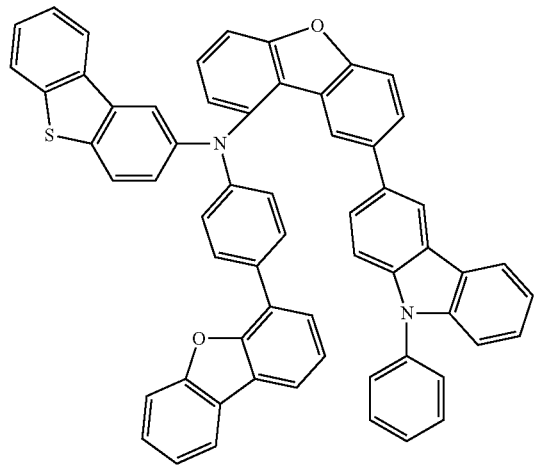 [SMILES: c1ccc(-n2c3ccccc3c3cc(-c4ccc5oc6cccc(N(c7ccc(-c8cccc9c8oc8ccccc89)cc7)c7ccc8sc9ccccc9c8c7)c6c5c4)ccc32)cc1]
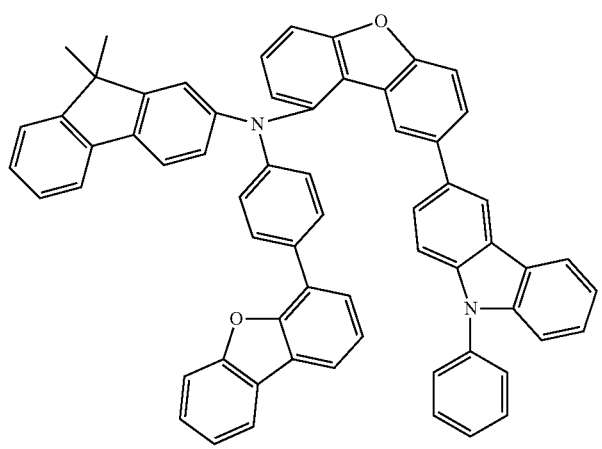 [SMILES: CC1(C)c2ccccc2-c2ccc(N(c3ccc(-c4cccc5c4oc4ccccc45)cc3)c3cccc4oc5ccc(-c6ccc7c(c6)c6ccccc6n7-c6ccccc6)cc5c34)cc21]
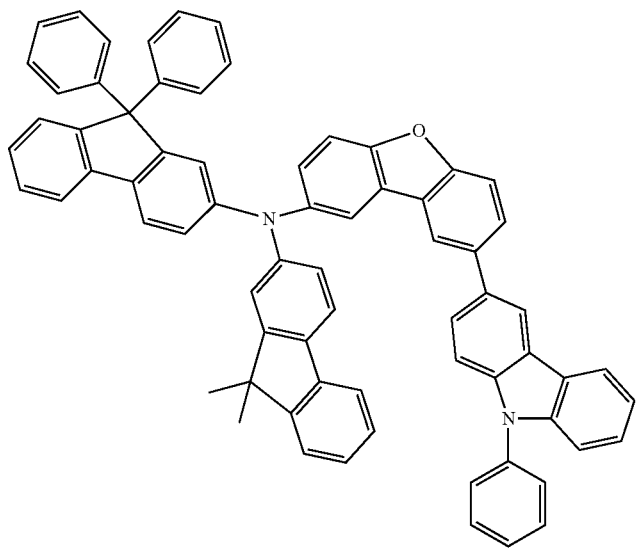 [SMILES: CC1(C)c2ccccc2-c2ccc(N(c3ccc4c(c3)C(c3ccccc3)(c3ccccc3)c3ccccc3-4)c3ccc4oc5ccc(-c6ccc7c(c6)c6ccccc6n7-c6ccccc6)cc5c4c3)cc21]

-continued
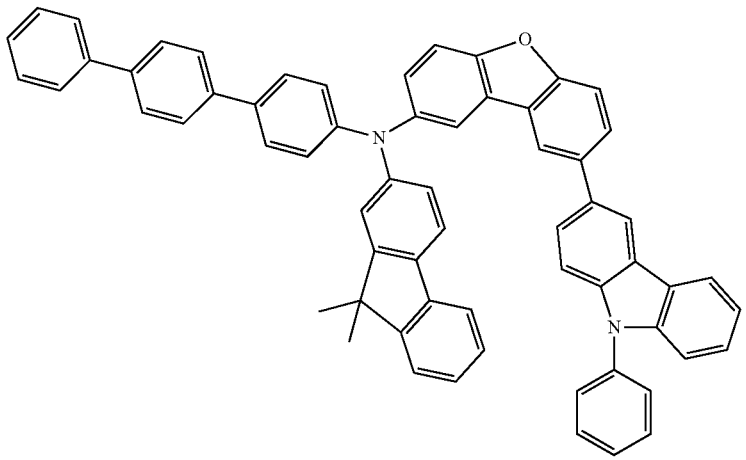 [SMILES: CC1(C)c2ccccc2-c2ccc(N(c3ccc(-c4ccc(-c5ccccc5)cc4)cc3)c3ccc4oc5ccc(-c6ccc7c(c6)c6ccccc6n7-c6ccccc6)cc5c4c3)cc21]
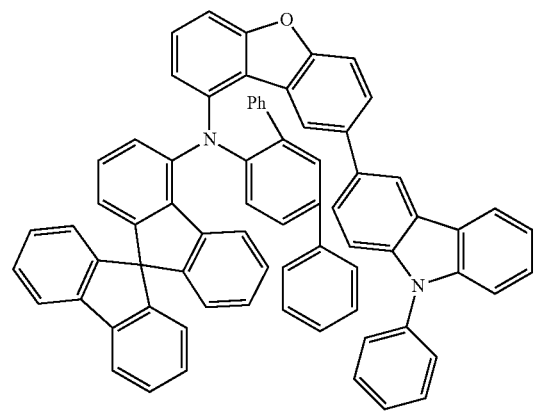 [SMILES: c1ccc(-c2ccc(N(c3cccc4c3-c3ccccc3C43c4ccccc4-c4ccccc43)c3cccc4oc5ccc(-c6ccc7c(c6)c6ccccc6n7-c6ccccc6)cc5c34)c(-c3ccccc3)c2)cc1]
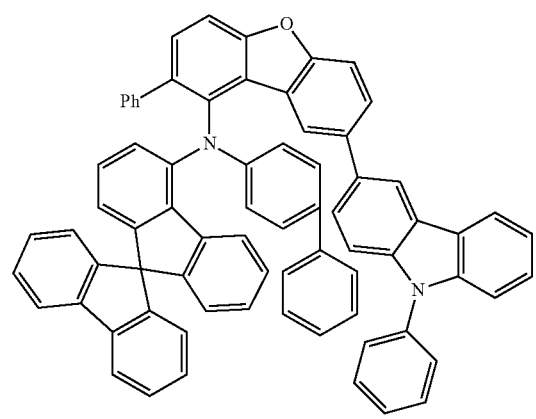 [SMILES: c1ccc(-c2ccc(N(c3cccc4c3-c3ccccc3C43c4ccccc4-c4ccccc43)c3c(-c4ccccc4)ccc4oc5ccc(-c6ccc7c(c6)c6ccccc6n7-c6ccccc6)cc5c34)cc2)cc1]

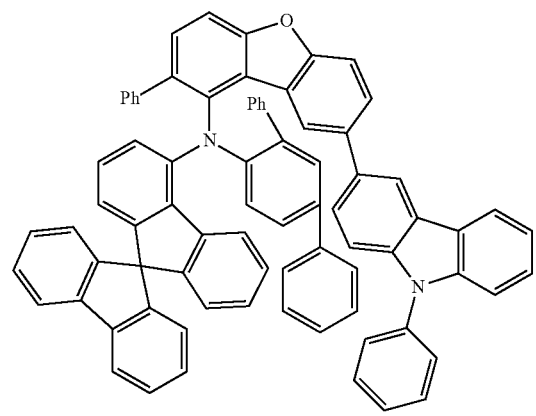 [SMILES: c1ccc(-c2ccc(N(c3cccc4c3-c3ccccc3C43c4ccccc4-c4ccccc43)c3c(-c4ccccc4)ccc4oc5ccc(-c6ccc7c(c6)c6ccccc6n7-c6ccccc6)cc5c34)c(-c3ccccc3)c2)cc1]
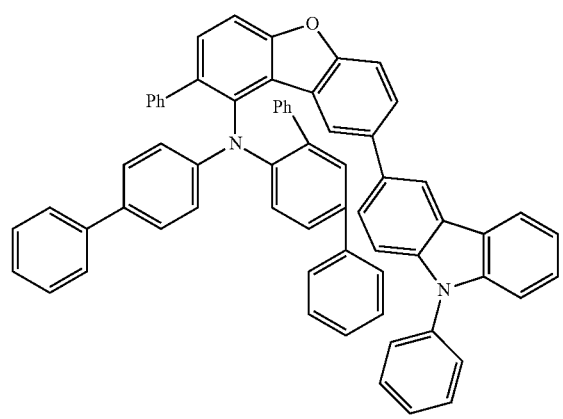 [SMILES: c1ccc(-c2ccc(N(c3ccc(-c4ccccc4)cc3-c3ccccc3)c3c(-c4ccccc4)ccc4oc5ccc(-c6ccc7c(c6)c6ccccc6n7-c6ccccc6)cc5c34)cc2)cc1]
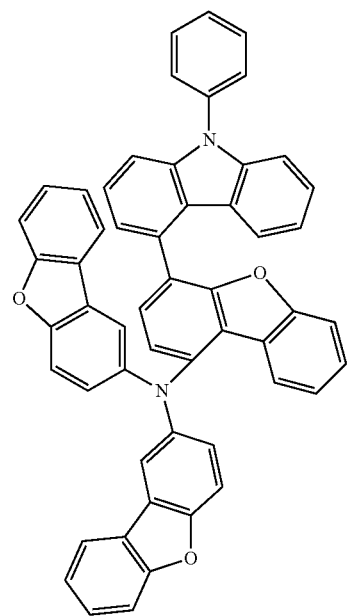 [SMILES: c1ccc(-n2c3ccccc3c3c(-c4ccc(N(c5ccc6oc7ccccc7c6c5)c5ccc6oc7ccccc7c6c5)c5c4oc4ccccc45)cccc32)cc1]

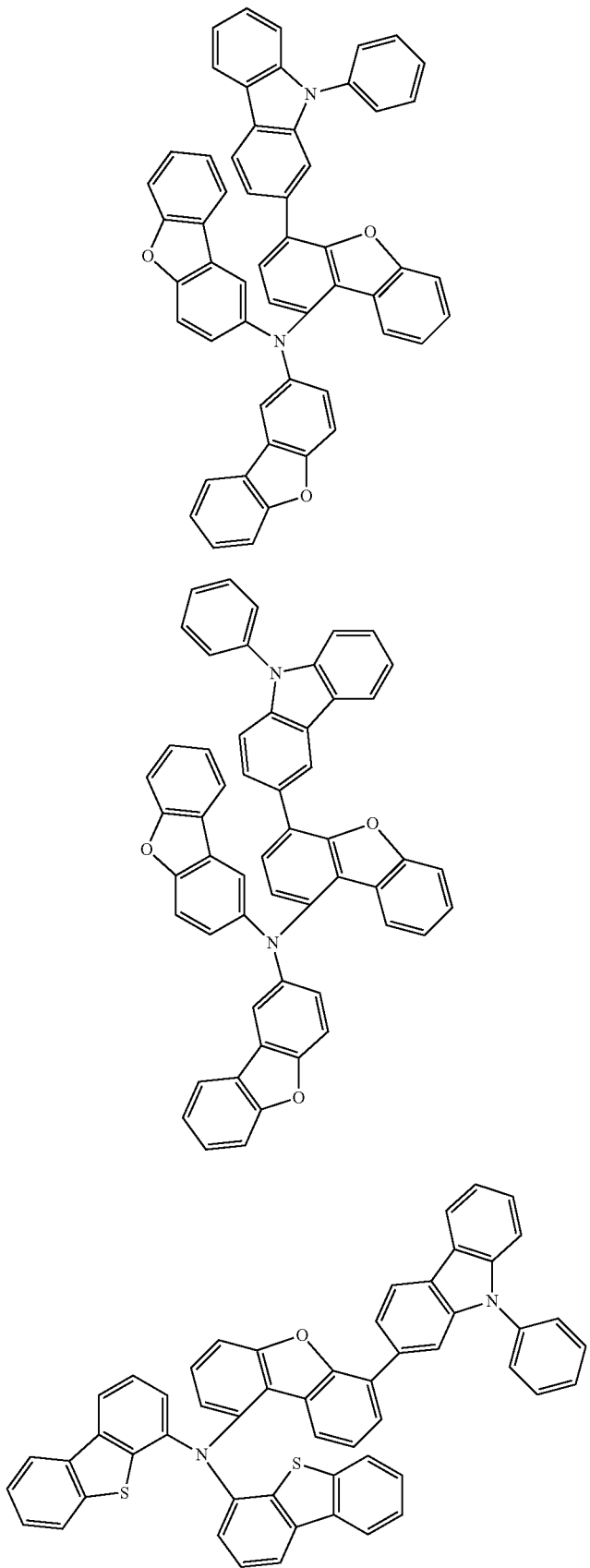

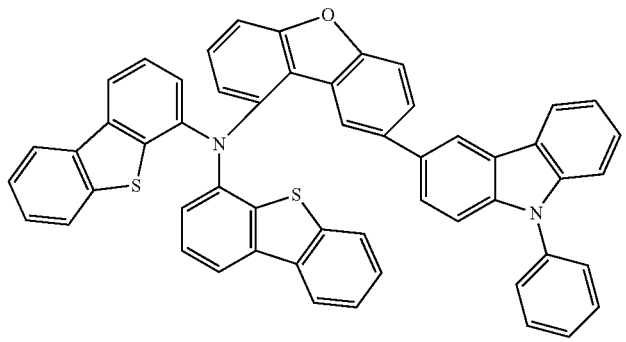 [SMILES: c1ccc(-n2c3ccccc3c3cc(-c4ccc5oc6cccc(N(c7cccc8c7sc7ccccc78)c7cccc8c7sc7ccccc78)c6c5c4)ccc32)cc1]
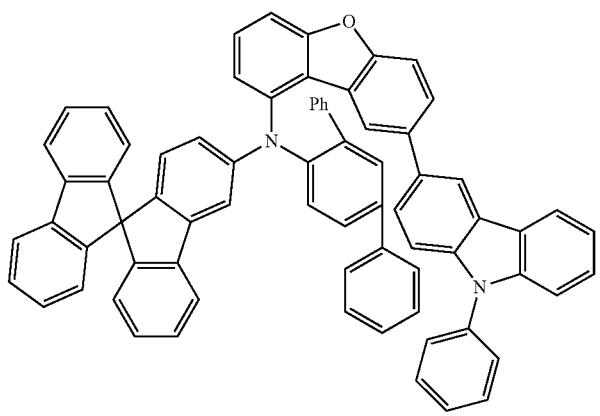 [SMILES: c1ccc(-c2ccc(N(c3ccc4c(c3)-c3ccccc3C43c4ccccc4-c4ccccc43)c3cccc4oc5ccc(-c6ccc7c(c6)c6ccccc6n7-c6ccccc6)cc5c34)c(-c3ccccc3)c2)cc1]
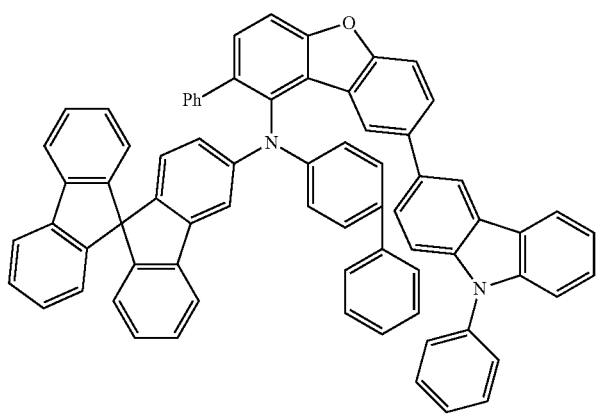 [SMILES: c1ccc(-c2ccc(N(c3ccc4c(c3)-c3ccccc3C43c4ccccc4-c4ccccc43)c3c(-c4ccccc4)ccc4oc5ccc(-c6ccc7c(c6)c6ccccc6n7-c6ccccc6)cc5c34)cc2)cc1]
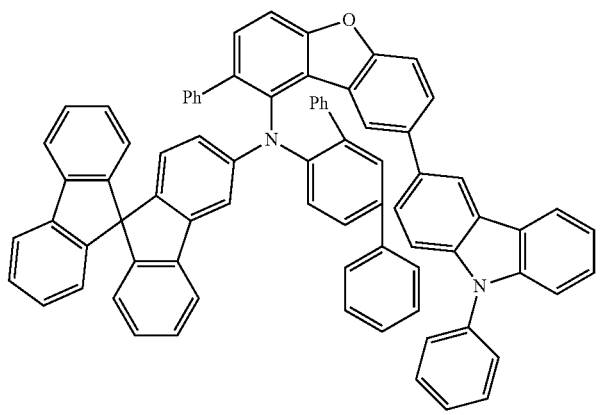 [SMILES: c1ccc(-c2ccc(N(c3ccc4c(c3)-c3ccccc3C43c4ccccc4-c4ccccc43)c3c(-c4ccccc4)ccc4oc5ccc(-c6ccc7c(c6)c6ccccc6n7-c6ccccc6)cc5c34)c(-c3ccccc3)c2)cc1]

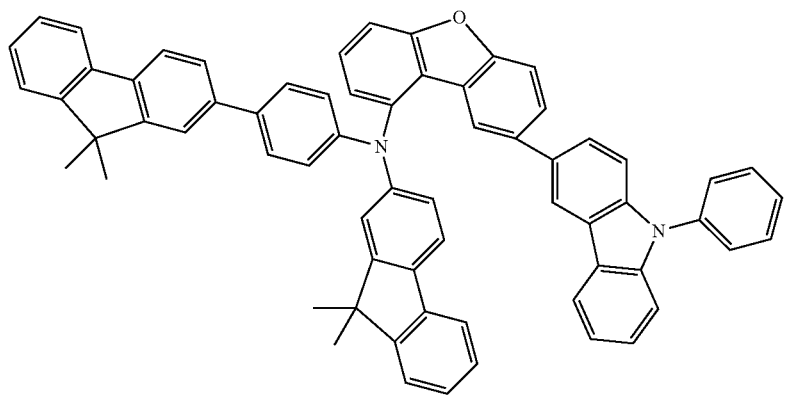 [SMILES: CC1(C)c2ccccc2-c2ccc(-c3ccc(N(c4ccc5c(c4)C(C)(C)c4ccccc4-5)c4cccc5oc6ccc(-c7ccc8c(c7)c7ccccc7n8-c7ccccc7)cc6c45)cc3)cc21]
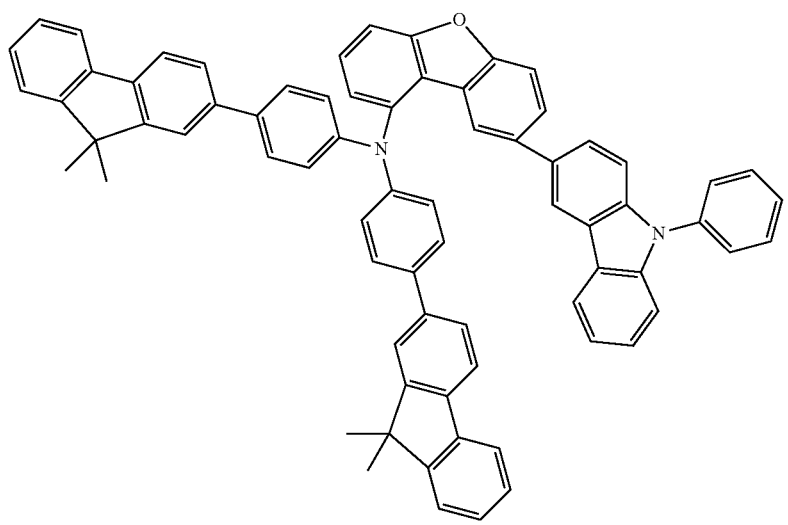 [SMILES: CC1(C)c2ccccc2-c2ccc(-c3ccc(N(c4ccc(-c5ccc6c(c5)C(C)(C)c5ccccc5-6)cc4)c4cccc5oc6ccc(-c7ccc8c(c7)c7ccccc7n8-c7ccccc7)cc6c45)cc3)cc21]
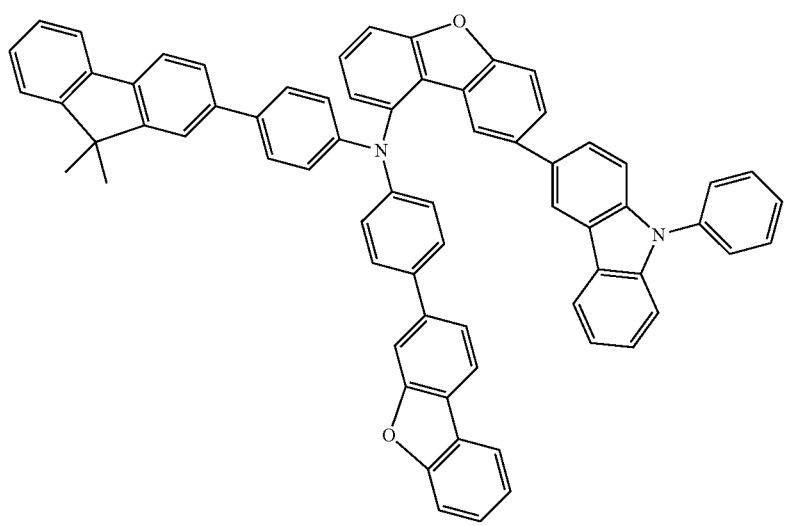 [SMILES: CC1(C)c2ccccc2-c2ccc(-c3ccc(N(c4ccc(-c5ccc6c(c5)oc5ccccc56)cc4)c4cccc5oc6ccc(-c7ccc8c(c7)c7ccccc7n8-c7ccccc7)cc6c45)cc3)cc21]

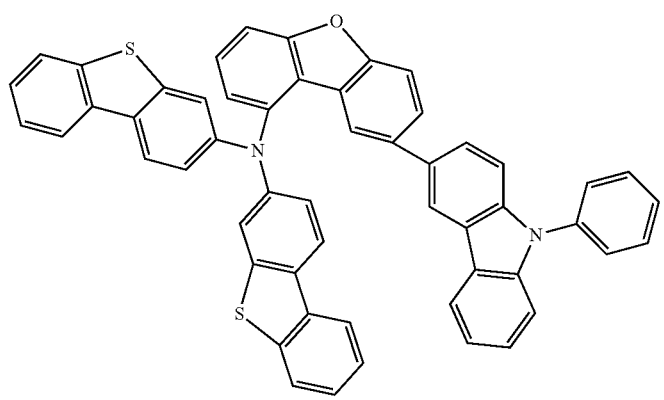 [SMILES: c1ccc(-n2c3ccccc3c3cc(-c4ccc5oc6cccc(N(c7ccc8c(c7)sc7ccccc78)c7ccc8c(c7)sc7ccccc78)c6c5c4)ccc32)cc1]
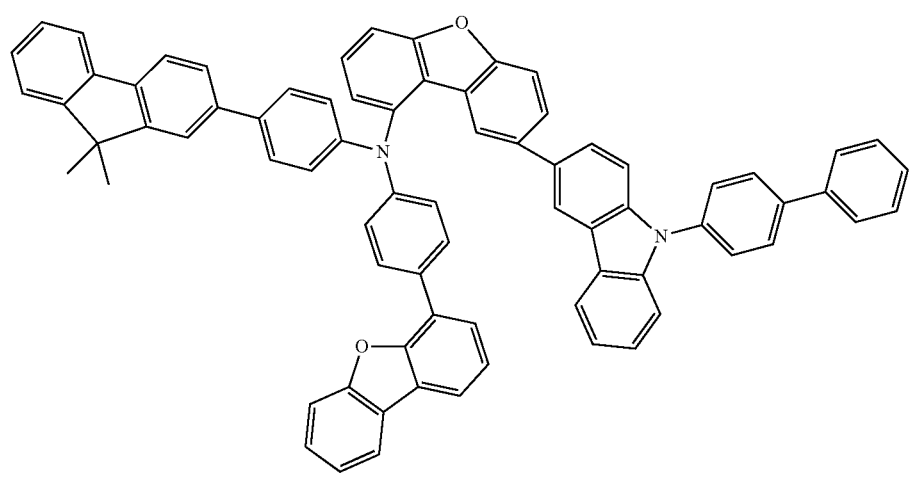 [SMILES: CC1(C)c2ccccc2-c2ccc(-c3ccc(N(c4ccc(-c5cccc6c5oc5ccccc56)cc4)c4cccc5oc6ccc(-c7ccc8c(c7)c7ccccc7n8-c7ccc(-c8ccccc8)cc7)cc6c45)cc3)cc21]
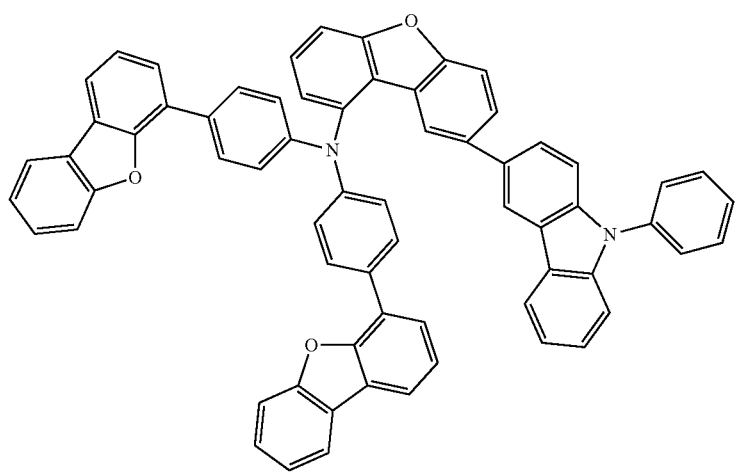 [SMILES: c1ccc(-n2c3ccccc3c3cc(-c4ccc5oc6cccc(N(c7ccc(-c8cccc9c8oc8ccccc89)cc7)c7ccc(-c8cccc9c8oc8ccccc89)cc7)c6c5c4)ccc32)cc1]

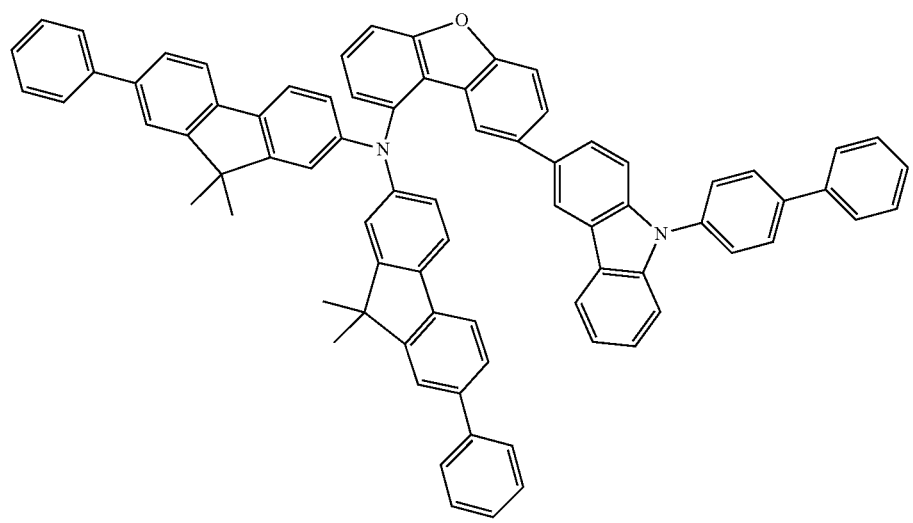 [SMILES: CC1(C)c2cc(-c3ccccc3)ccc2-c2ccc(N(c3ccc4c(c3)C(C)(C)c3cc(-c5ccccc5)ccc3-4)c3cccc4oc5ccc(-c6ccc7c(c6)c6ccccc6n7-c6ccc(-c7ccccc7)cc6)cc5c34)cc21]
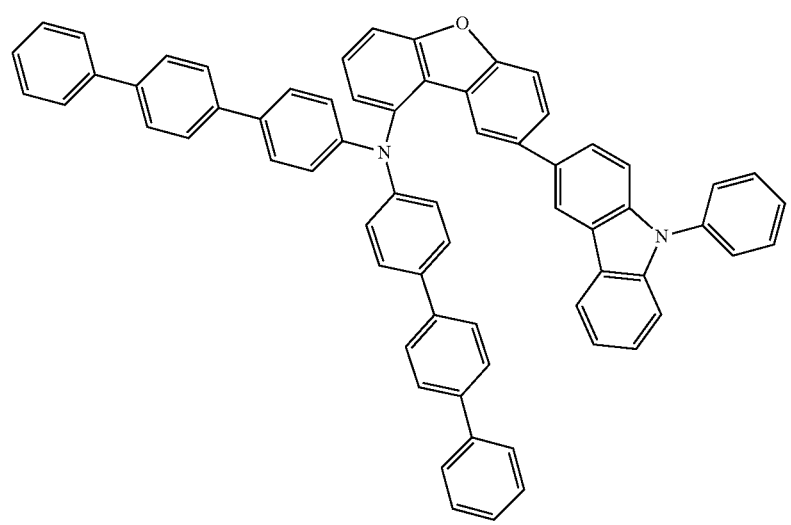 [SMILES: c1ccc(-c2ccc(-c3ccc(N(c4ccc(-c5ccc(-c6ccccc6)cc5)cc4)c4cccc5oc6ccc(-c7ccc8c(c7)c7ccccc7n8-c7ccccc7)cc6c45)cc3)cc2)cc1]
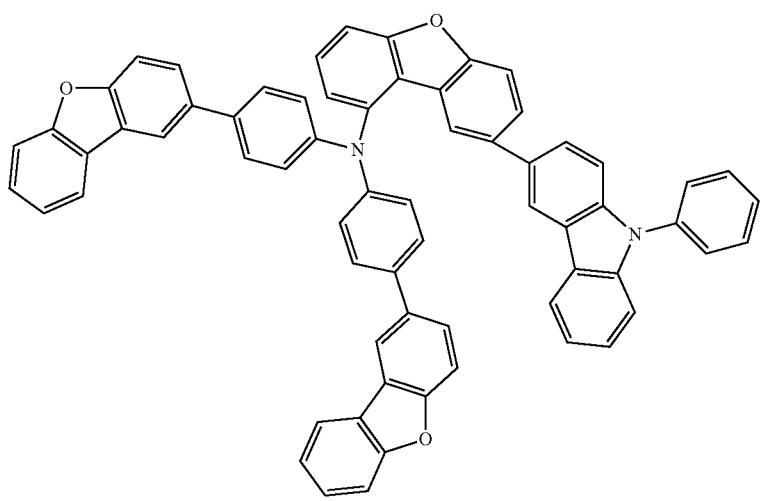 [SMILES: c1ccc(-n2c3ccccc3c3cc(-c4ccc5oc6cccc(N(c7ccc(-c8ccc9oc%10ccccc%10c9c8)cc7)c7ccc(-c8ccc9oc%10ccccc%10c9c8)cc7)c6c5c4)ccc32)cc1]

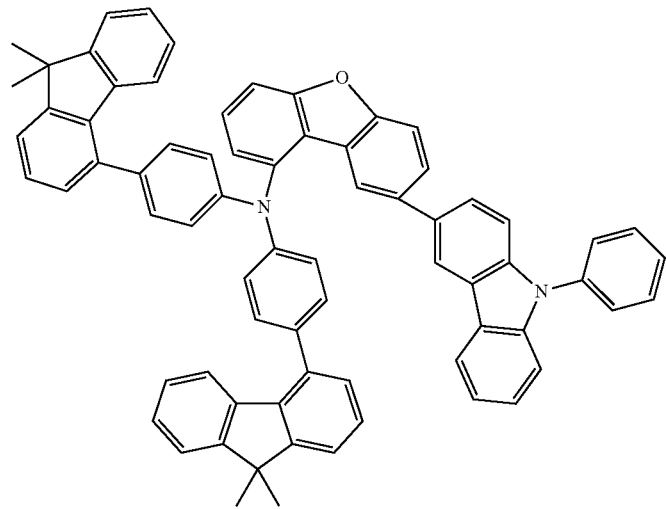 [SMILES: CC1(C)c2ccccc2-c2c(-c3ccc(N(c4ccc(-c5cccc6c5-c5ccccc5C6(C)C)cc4)c4cccc5oc6ccc(-c7ccc8c(c7)c7ccccc7n8-c7ccccc7)cc6c45)cc3)cccc21]
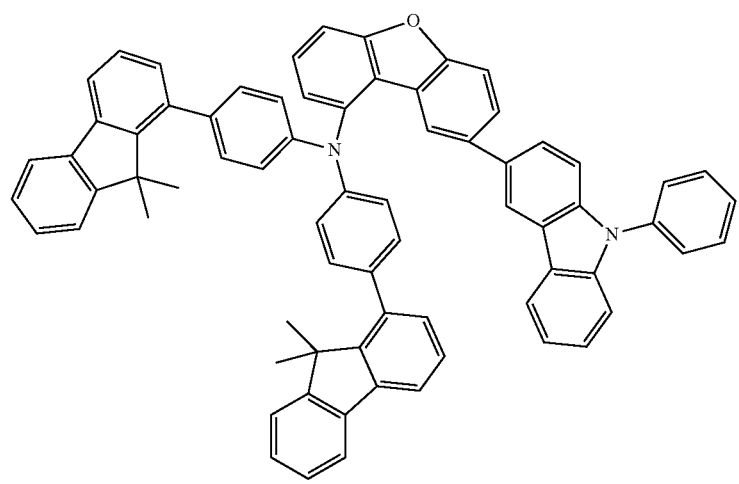 [SMILES: CC1(C)c2ccccc2-c2cccc(-c3ccc(N(c4ccc(-c5cccc6c5C(C)(C)c5ccccc5-6)cc4)c4cccc5oc6ccc(-c7ccc8c(c7)c7ccccc7n8-c7ccccc7)cc6c45)cc3)c21]
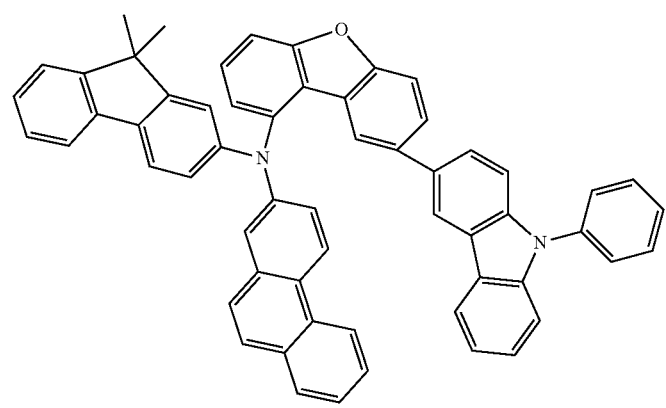 [SMILES: CC1(C)c2ccccc2-c2ccc(N(c3ccc4c(ccc5ccccc54)c3)c3cccc4oc5ccc(-c6ccc7c(c6)c6ccccc6n7-c6ccccc6)cc5c34)cc21]

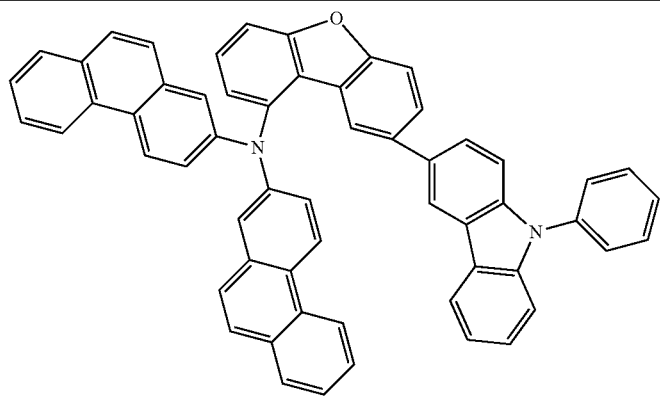
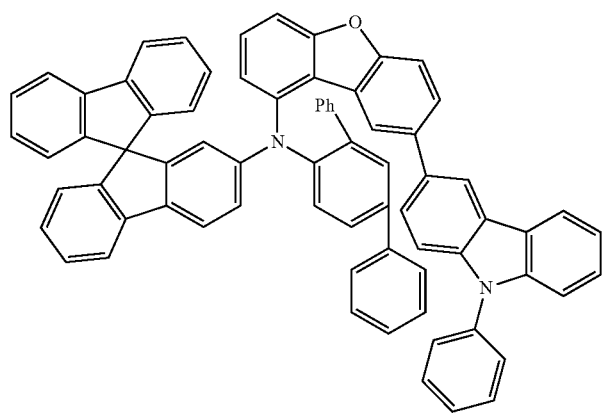 [SMILES: c1ccc(-c2ccc(N(c3ccc4c(c3)C3(c5ccccc5-c5ccccc53)c3ccccc3-4)c3cccc4oc5ccc(-c6ccc7c(c6)c6ccccc6n7-c6ccccc6)cc5c34)c(-c3ccccc3)c2)cc1]
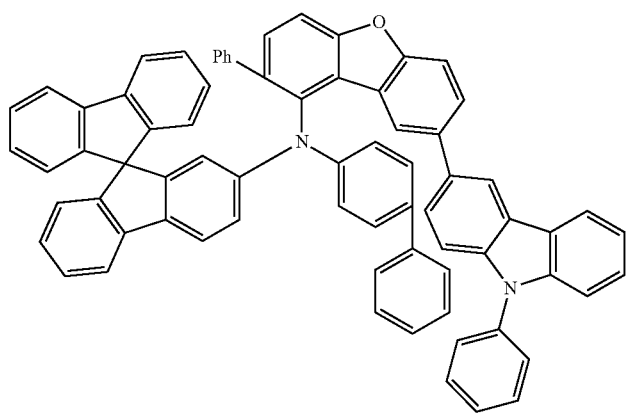 [SMILES: c1ccc(-c2ccc(N(c3ccc4c(c3)C3(c5ccccc5-c5ccccc53)c3ccccc3-4)c3c(-c4ccccc4)ccc4oc5ccc(-c6ccc7c(c6)c6ccccc6n7-c6ccccc6)cc5c34)cc2)cc1]
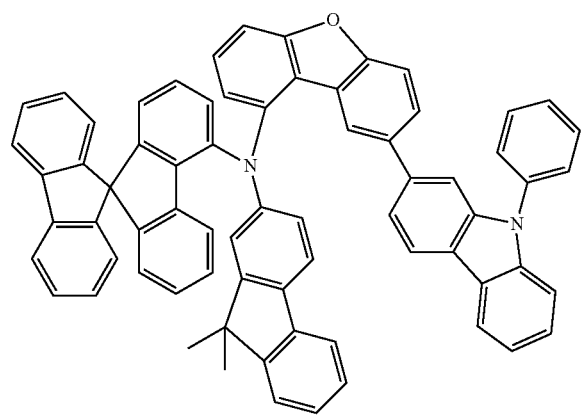 [SMILES: CC1(C)c2ccccc2-c2ccc(N(c3cccc4c3-c3ccccc3C43c4ccccc4-c4ccccc43)c3cccc4oc5ccc(-c6ccc7c8ccccc8n(-c8ccccc8)c7c6)cc5c34)cc21]

-continued
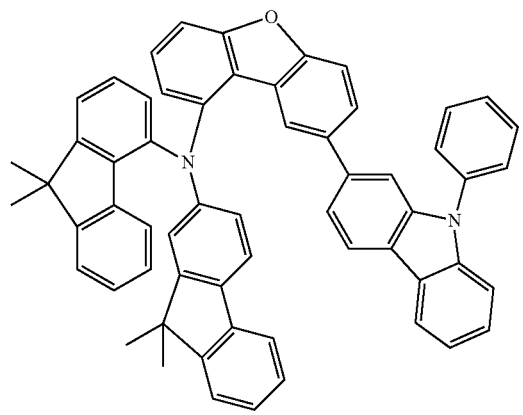 [SMILES: CC1(C)c2ccccc2-c2ccc(N(c3cccc4c3-c3ccccc3C4(C)C)c3cccc4oc5ccc(-c6ccc7c8ccccc8n(-c8ccccc8)c7c6)cc5c34)cc21]
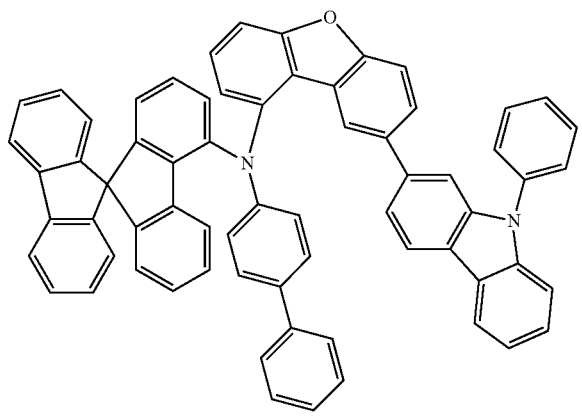 [SMILES: c1ccc(-c2ccc(N(c3cccc4c3-c3ccccc3C43c4ccccc4-c4ccccc43)c3cccc4oc5ccc(-c6ccc7c8ccccc8n(-c8ccccc8)c7c6)cc5c34)cc2)cc1]
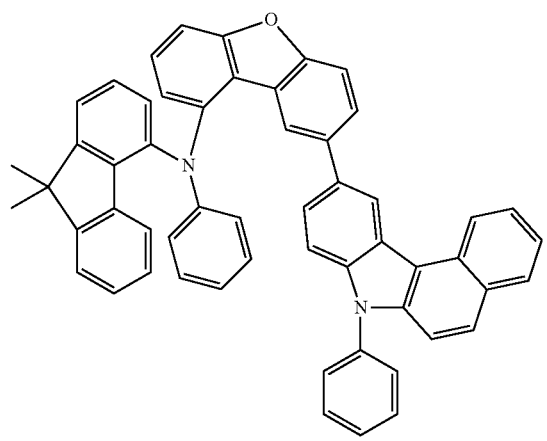 [SMILES: CC1(C)c2ccccc2-c2c(N(c3ccccc3)c3cccc4oc5ccc(-c6ccc7c(c6)c6c8ccccc8ccc6n7-c6ccccc6)cc5c34)cccc21]
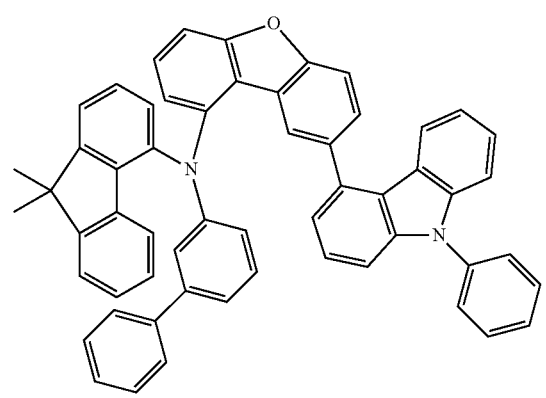 [SMILES: CC1(C)c2ccccc2-c2c(N(c3cccc(-c4ccccc4)c3)c3cccc4oc5ccc(-c6cccc7c6c6ccccc6n7-c6ccccc6)cc5c34)cccc21]

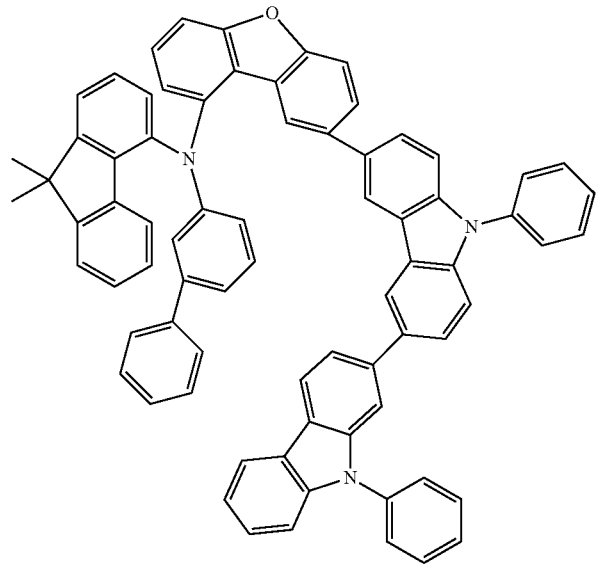 [SMILES: CC1(C)c2ccccc2-c2c(N(c3cccc(-c4ccccc4)c3)c3cccc4oc5ccc(-c6ccc7c(c6)c6cc(-c8ccc9c%10ccccc%10n(-c%10ccccc%10)c9c8)ccc6n7-c6ccccc6)cc5c34)cccc21]
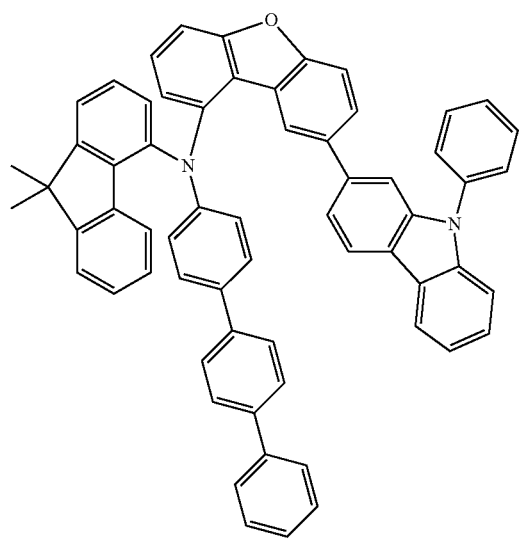 [SMILES: CC1(C)c2ccccc2-c2c(N(c3ccc(-c4ccc(-c5ccccc5)cc4)cc3)c3cccc4oc5ccc(-c6ccc7c8ccccc8n(-c8ccccc8)c7c6)cc5c34)cccc21]
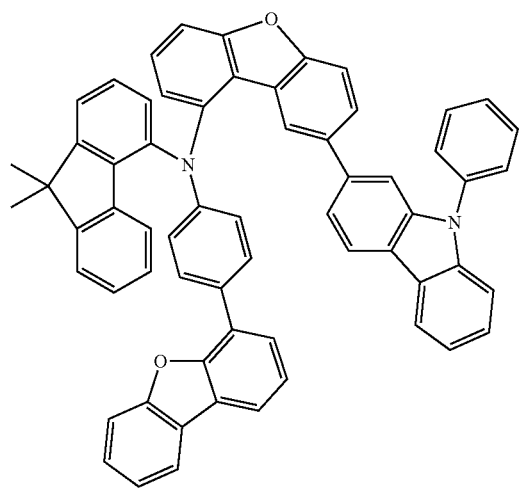 [SMILES: CC1(C)c2ccccc2-c2c(N(c3ccc(-c4cccc5c4oc4ccccc45)cc3)c3cccc4oc5ccc(-c6ccc7c8ccccc8n(-c8ccccc8)c7c6)cc5c34)cccc21]

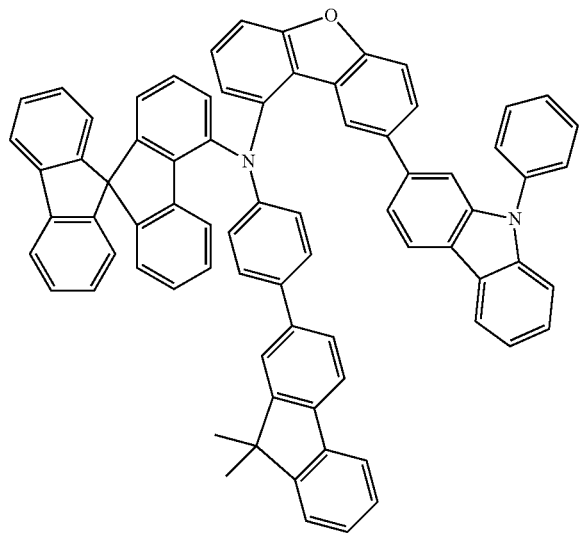 [SMILES: CC1(C)c2ccccc2-c2ccc(-c3ccc(N(c4cccc5c4-c4ccccc4C54c5ccccc5-c5ccccc54)c4cccc5oc6ccc(-c7ccc8c9ccccc9n(-c9ccccc9)c8c7)cc6c45)cc3)cc21]
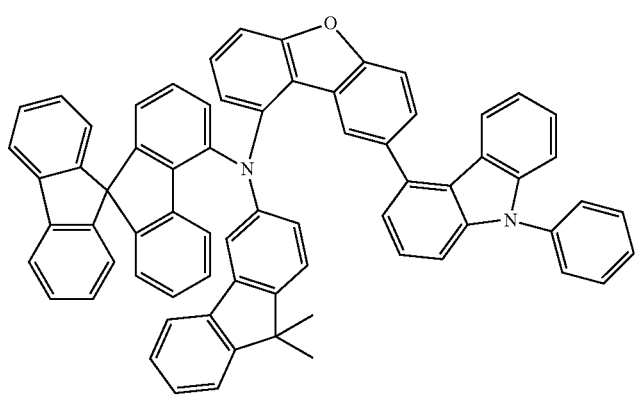 [SMILES: CC1(C)c2ccccc2-c2cc(N(c3cccc4c3-c3ccccc3C43c4ccccc4-c4ccccc43)c3cccc4oc5ccc(-c6cccc7c6c6ccccc6n7-c6ccccc6)cc5c34)ccc21]
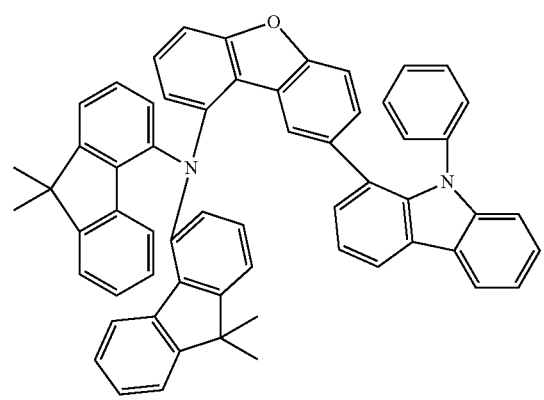 [SMILES: CC1(C)c2ccccc2-c2c(N(c3cccc4c3-c3ccccc3C4(C)C)c3cccc4oc5ccc(-c6cccc7c8ccccc8n(-c8ccccc8)c67)cc5c34)cccc21]

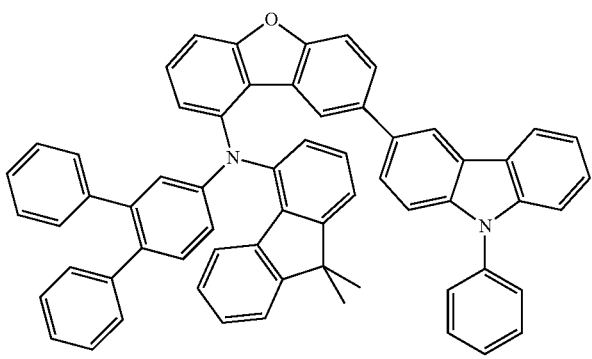 [SMILES: CC1(C)c2ccccc2-c2c(N(c3ccc(-c4ccccc4)c(-c4ccccc4)c3)c3cccc4oc5ccc(-c6ccc7c(c6)c6ccccc6n7-c6ccccc6)cc5c34)cccc21]
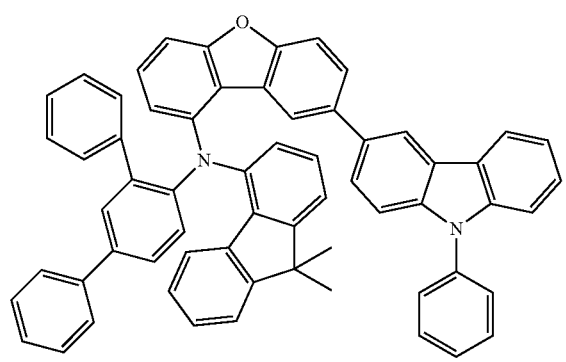 [SMILES: CC1(C)c2ccccc2-c2c(N(c3ccc(-c4ccccc4)cc3-c3ccccc3)c3cccc4oc5ccc(-c6ccc7c(c6)c6ccccc6n7-c6ccccc6)cc5c34)cccc21]
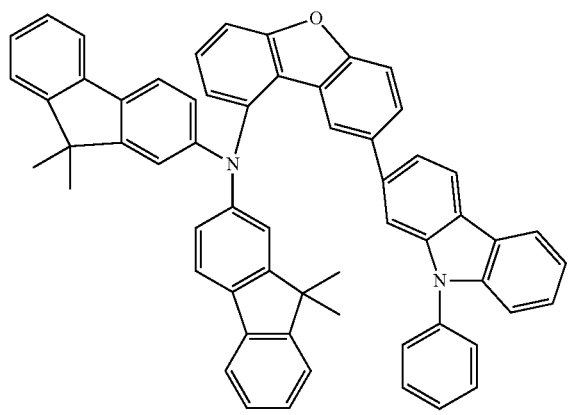 [SMILES: CC1(C)c2ccccc2-c2ccc(N(c3ccc4c(c3)C(C)(C)c3ccccc3-4)c3cccc4oc5ccc(-c6ccc7c8ccccc8n(-c8ccccc8)c7c6)cc5c34)cc21]
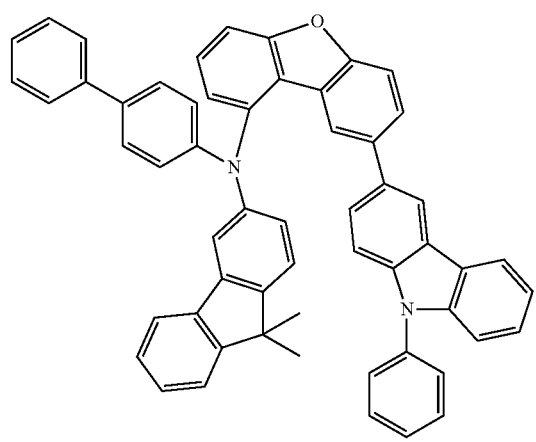 [SMILES: CC1(C)c2ccccc2-c2cc(N(c3ccc(-c4ccccc4)cc3)c3cccc4oc5ccc(-c6ccc7c(c6)c6ccccc6n7-c6ccccc6)cc5c34)ccc21]

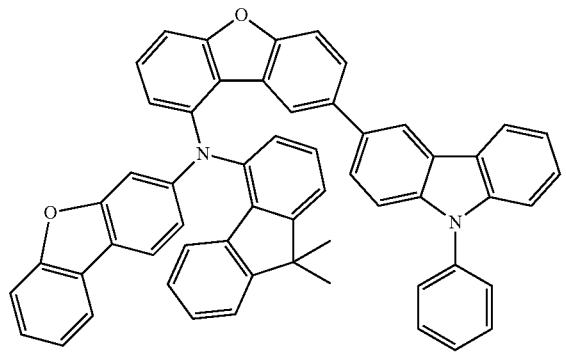 [SMILES: CC1(C)c2ccccc2-c2c(N(c3ccc4c(c3)oc3ccccc34)c3cccc4oc5ccc(-c6ccc7c(c6)c6ccccc6n7-c6ccccc6)cc5c34)cccc21]
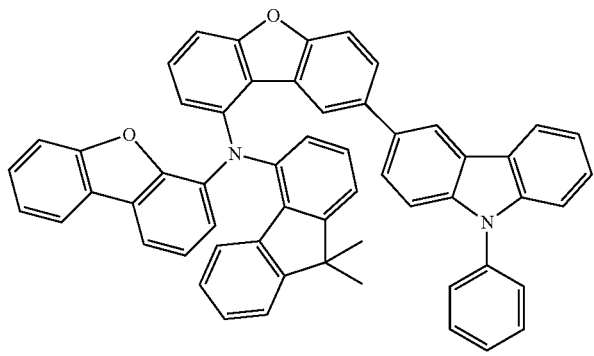 [SMILES: CC1(C)c2ccccc2-c2c(N(c3cccc4c3oc3ccccc34)c3cccc4oc5ccc(-c6ccc7c(c6)c6ccccc6n7-c6ccccc6)cc5c34)cccc21]
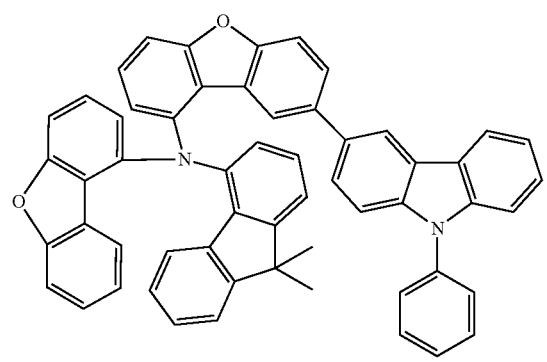 [SMILES: CC1(C)c2ccccc2-c2c(N(c3cccc4oc5ccccc5c34)c3cccc4oc5ccc(-c6ccc7c(c6)c6ccccc6n7-c6ccccc6)cc5c34)cccc21]
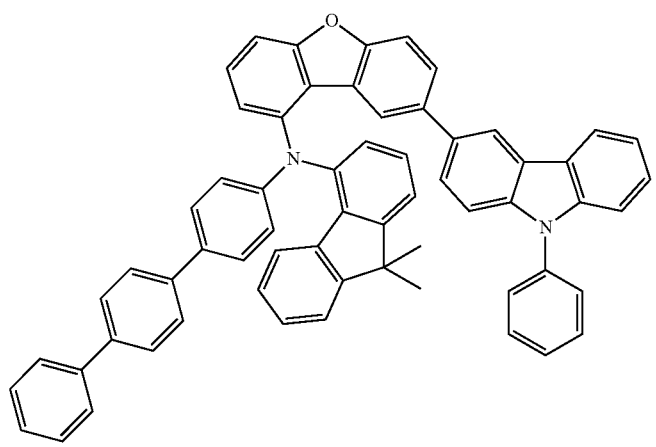 [SMILES: CC1(C)c2ccccc2-c2c(N(c3ccc(-c4ccc(-c5ccccc5)cc4)cc3)c3cccc4oc5ccc(-c6ccc7c(c6)c6ccccc6n7-c6ccccc6)cc5c34)cccc21]

-continued
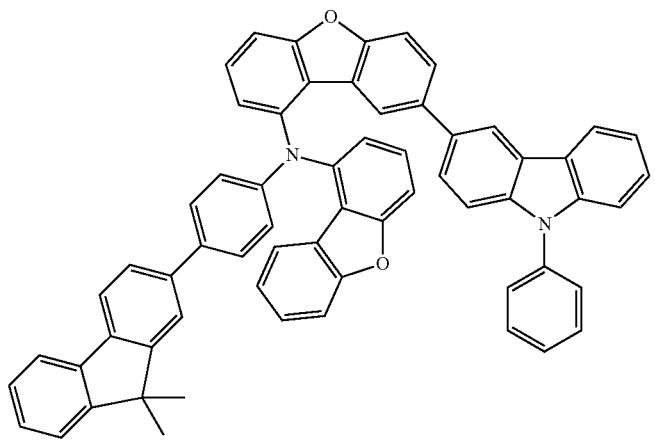 [SMILES: CC1(C)c2ccccc2-c2ccc(-c3ccc(N(c4cccc5oc6ccccc6c45)c4cccc5oc6ccc(-c7ccc8c(c7)c7ccccc7n8-c7ccccc7)cc6c45)cc3)cc21]
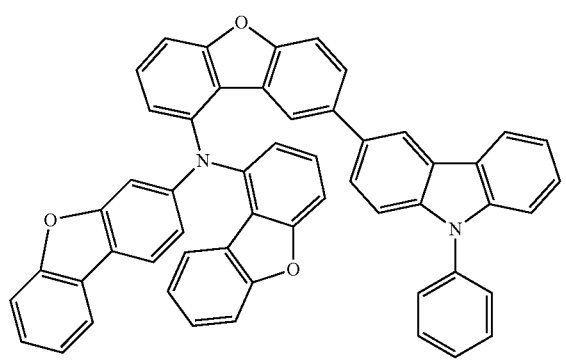 [SMILES: c1ccc(-n2c3ccccc3c3cc(-c4ccc5oc6cccc(N(c7ccc8c(c7)oc7ccccc78)c7cccc8oc9ccccc9c78)c6c5c4)ccc32)cc1]
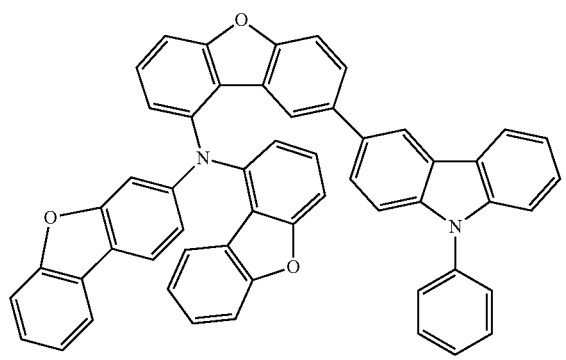 [SMILES: c1ccc(-n2c3ccccc3c3cc(-c4ccc5oc6cccc(N(c7ccc8c(c7)oc7ccccc78)c7cccc8oc9ccccc9c78)c6c5c4)ccc32)cc1]
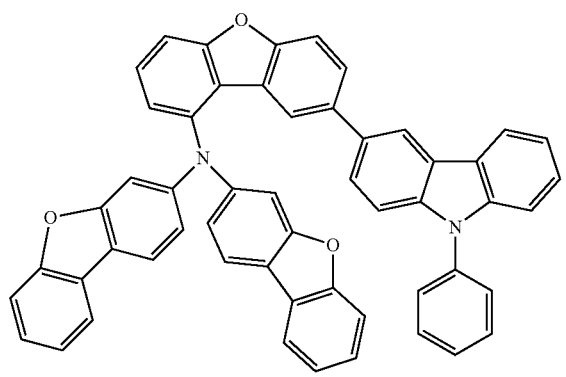 [SMILES: c1ccc(-n2c3ccccc3c3cc(-c4ccc5oc6cccc(N(c7ccc8c(c7)oc7ccccc78)c7ccc8c(c7)oc7ccccc78)c6c5c4)ccc32)cc1]

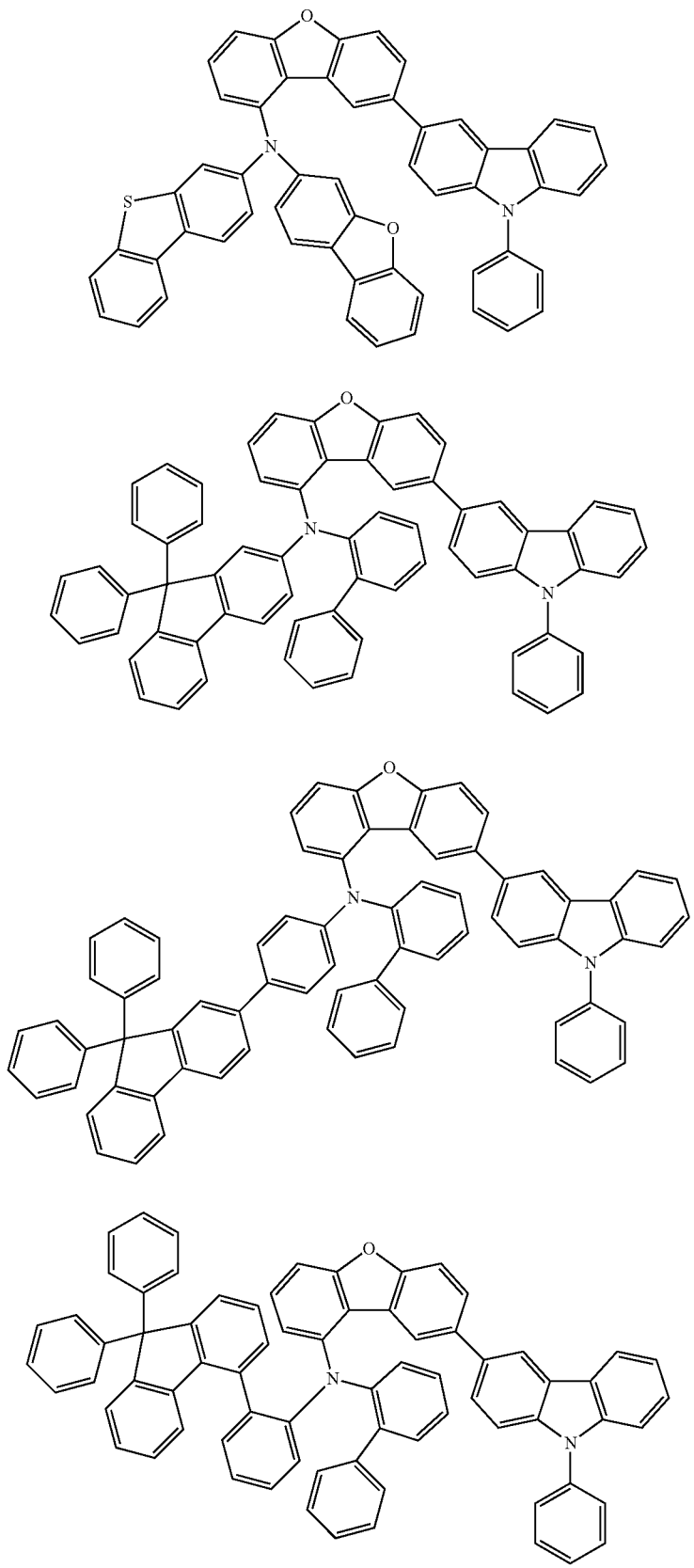

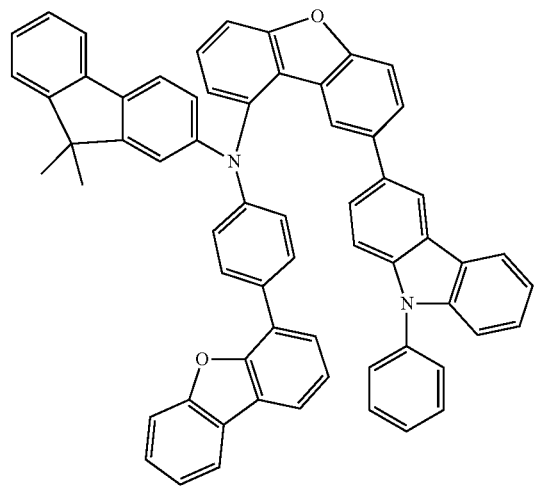 [SMILES: CC1(C)c2ccccc2-c2ccc(N(c3ccc(-c4cccc5c4oc4ccccc45)cc3)c3cccc4oc5ccc(-c6ccc7c(c6)c6ccccc6n7-c6ccccc6)cc5c34)cc21]

-continued
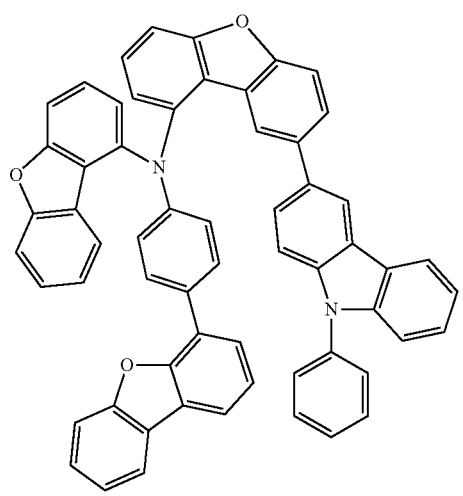 [SMILES: c1ccc(-n2c3ccccc3c3cc(-c4ccc5oc6cccc(N(c7ccc(-c8cccc9c8oc8ccccc89)cc7)c7cccc8oc9ccccc9c78)c6c5c4)ccc32)cc1]
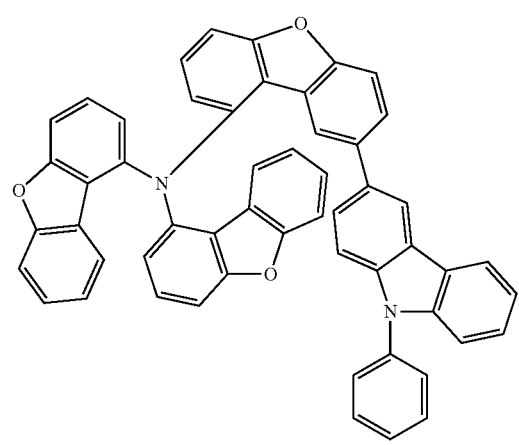 [SMILES: c1ccc(-n2c3ccccc3c3cc(-c4ccc5oc6cccc(N(c7cccc8oc9ccccc9c78)c7cccc8oc9ccccc9c78)c6c5c4)ccc32)cc1]
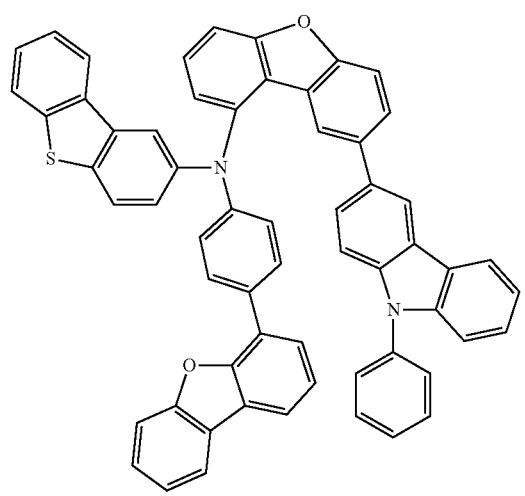 [SMILES: c1ccc(-n2c3ccccc3c3cc(-c4ccc5oc6cccc(N(c7ccc(-c8cccc9c8oc8ccccc89)cc7)c7ccc8sc9ccccc9c8c7)c6c5c4)ccc32)cc1]

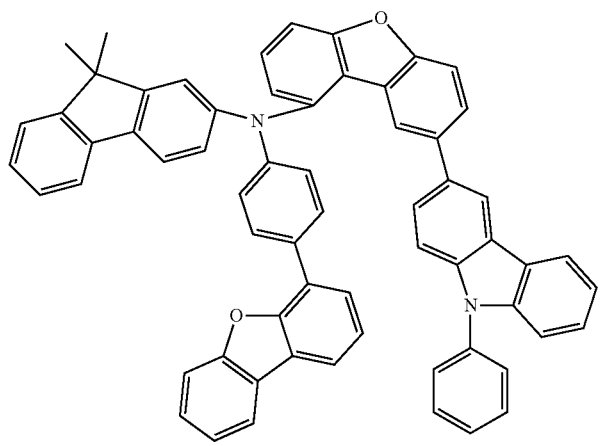 [SMILES: CC1(C)c2ccccc2-c2ccc(N(c3ccc(-c4cccc5c4oc4ccccc45)cc3)c3cccc4oc5ccc(-c6ccc7c(c6)c6ccccc6n7-c6ccccc6)cc5c34)cc21]
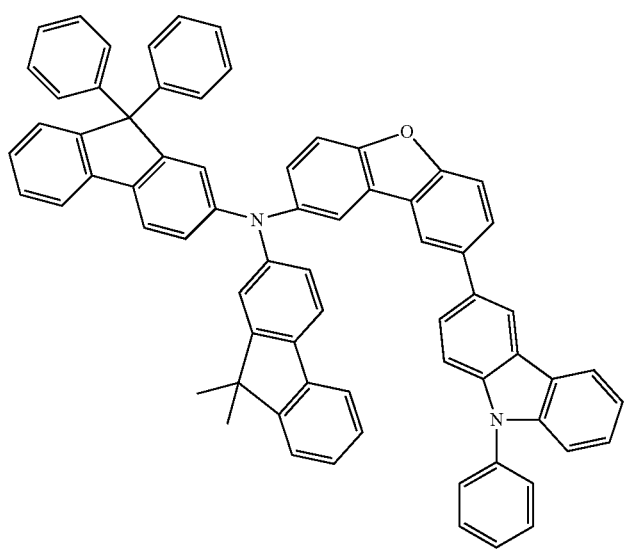 [SMILES: CC1(C)c2ccccc2-c2ccc(N(c3ccc4c(c3)C(c3ccccc3)(c3ccccc3)c3ccccc3-4)c3ccc4oc5ccc(-c6ccc7c(c6)c6ccccc6n7-c6ccccc6)cc5c4c3)cc21]
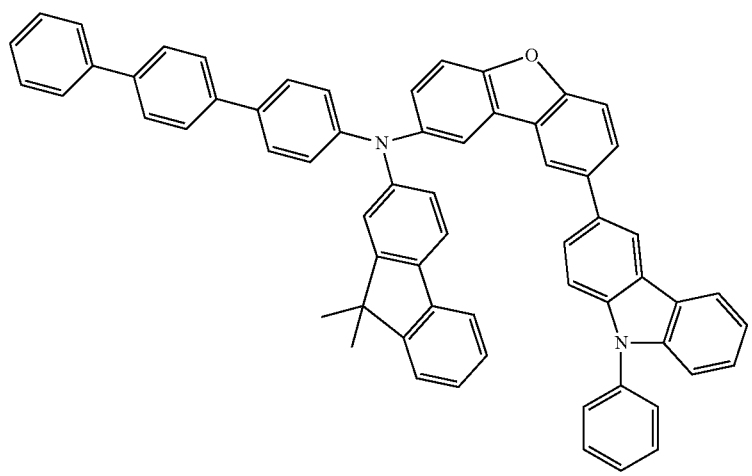 [SMILES: CC1(C)c2ccccc2-c2ccc(N(c3ccc(-c4ccc(-c5ccccc5)cc4)cc3)c3ccc4oc5ccc(-c6ccc7c(c6)c6ccccc6n7-c6ccccc6)cc5c4c3)cc21]

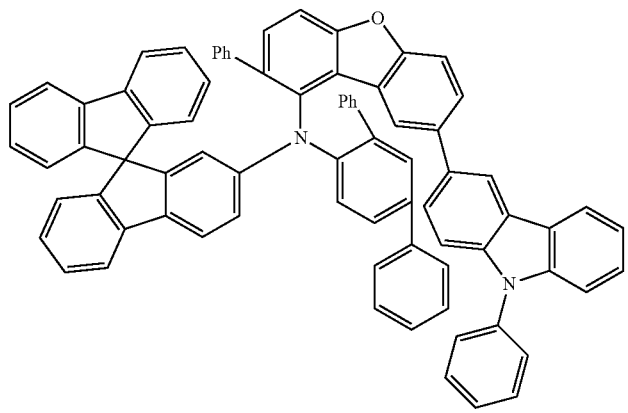 [SMILES: c1ccc(-c2ccc(N(c3ccc4c(c3)C3(c5ccccc5-c5ccccc53)c3ccccc3-4)c3c(-c4ccccc4)ccc4oc5ccc(-c6ccc7c(c6)c6ccccc6n7-c6ccccc6)cc5c34)c(-c3ccccc3)c2)cc1]
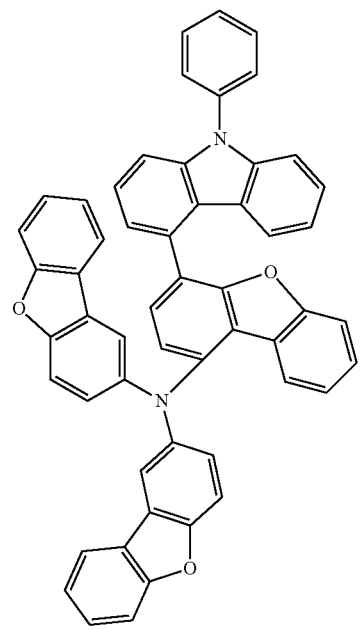 [SMILES: c1ccc(-n2c3ccccc3c3c(-c4ccc(N(c5ccc6oc7ccccc7c6c5)c5ccc6oc7ccccc7c6c5)c5c4oc4ccccc45)cccc32)cc1]
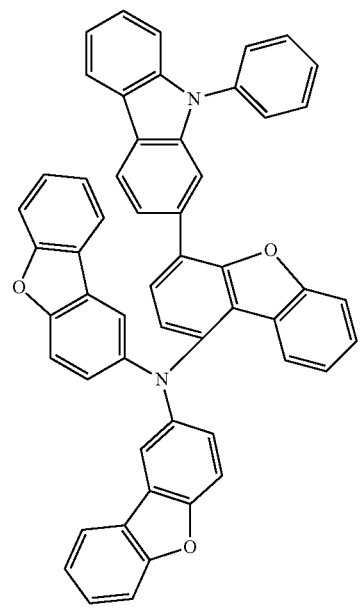 [SMILES: c1ccc(-n2c3ccccc3c3ccc(-c4ccc(N(c5ccc6oc7ccccc7c6c5)c5ccc6oc7ccccc7c6c5)c5c4oc4ccccc45)cc32)cc1]

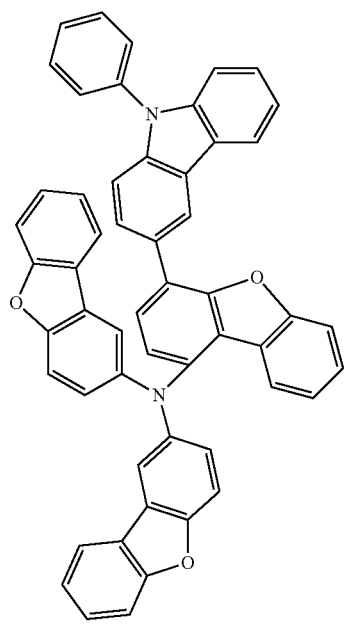 [SMILES: c1ccc(-n2c3ccccc3c3cc(-c4ccc(N(c5ccc6oc7ccccc7c6c5)c5ccc6oc7ccccc7c6c5)c5c4oc4ccccc45)ccc32)cc1]

-continued
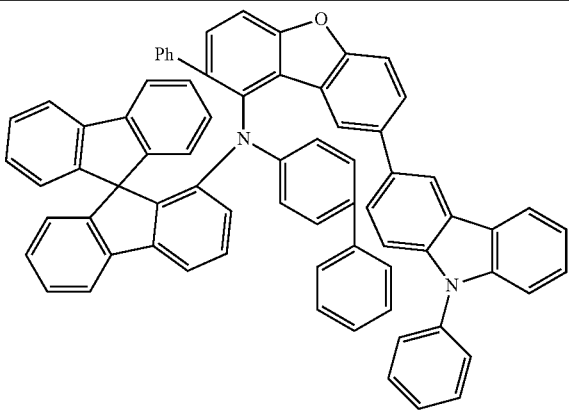
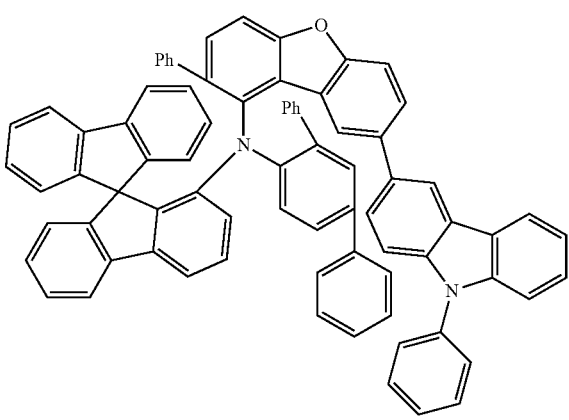 [SMILES: c1ccc(-c2ccc(N(c3cccc4c3C3(c5ccccc5-c5ccccc53)c3ccccc3-4)c3c(-c4ccccc4)ccc4oc5ccc(-c6ccc7c(c6)c6ccccc6n7-c6ccccc6)cc5c34)c(-c3ccccc3)c2)cc1]
The compounds of the invention can be prepared by synthesis steps known to those skilled in the art, for example bromination, Suzuki coupling, Ullmann coupling, Hartwig-Buchwald coupling, etc. A suitable synthesis method is shown in general terms in scheme 1 and scheme 2 below:
Scheme 1
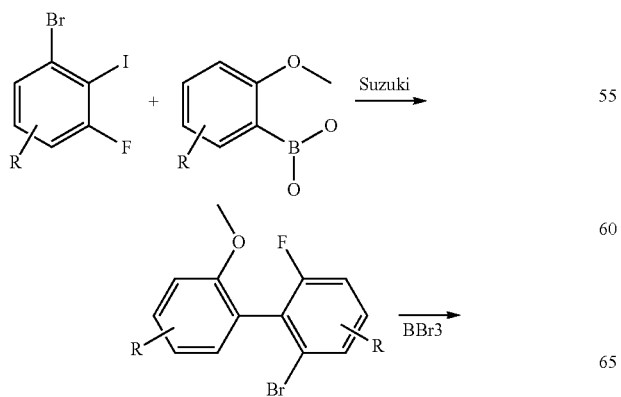
-continued
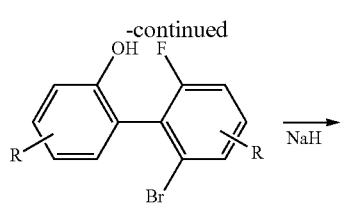
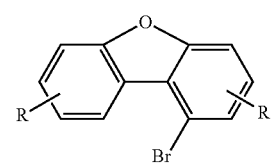

Scheme 2

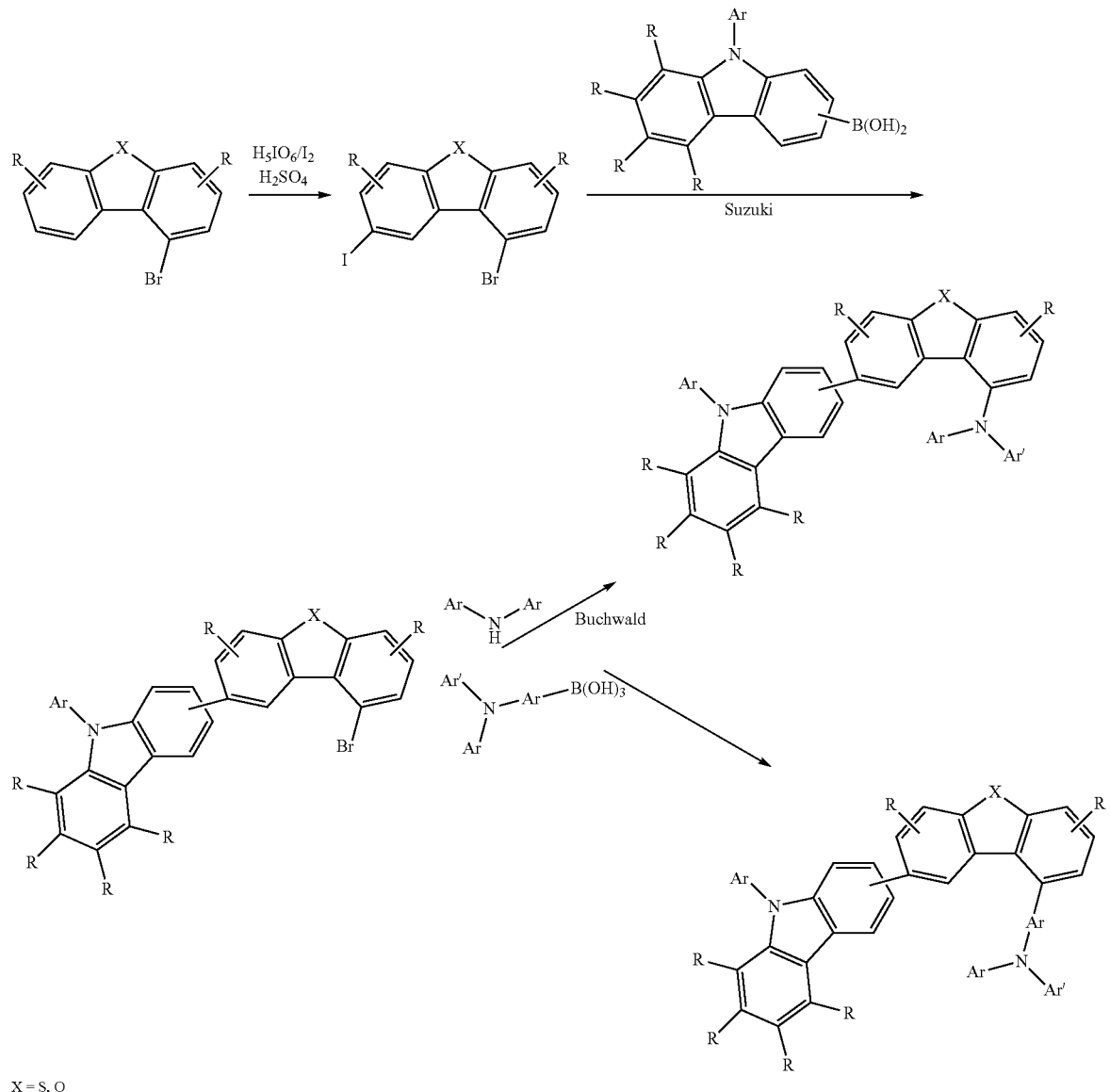

X = S, O

In these schemes, R, in accordance with the formulae (1) or (2), is R, $R^1$ or $R^2$ and Ar, $Ar^1$ are Ar or $Ar^3$.

For the processing of the compounds of the invention from a liquid phase, for example by spin-coating or by printing methods, formulations of the compounds of the invention are required. These formulations may, for example, be solutions, dispersions or emulsions. For this purpose, it may be preferable to use mixtures of two or more solvents. Suitable and preferred solvents are, for example, toluene, anisole, o-, m- or p-xylene, methyl benzoate, mesitylene, tetralin, veratrole, THF, methyl-THF, THP, chlorobenzene, dioxane, phenoxytoluene, especially 3-phenoxytoluene, (−)-fenchone, 1,2,3,5-tetramethylbenzene, 1,2,4,5-tetramethylbenzene, 1-methylnaphthalene, 2-methylbenzothiazole, 2-phenoxyethanol, 2-pyrrolidinone, 3-methylanisole, 4-methylanisole, 3,4-dimethylanisole, 3,5-dimethylanisole, acetophenone, α-terpineol, benzothiazole, butyl benzoate, cumene, cyclohexanol, cyclohexanone, cyclohexylbenzene, decalin, dodecylbenzene, ethyl benzoate, indane, methyl benzoate, NMP, p-cymene, phenetole, 1,4-diisopropylbenzene, dibenzyl ether, diethylene glycol butyl methyl ether, triethylene glycol butyl methyl ether, diethylene glycol dibutyl ether, triethylene glycol dimethyl ether, diethylene glycol monobutyl ether, tripropylene glycol dimethyl ether, tetraethylene glycol dimethyl ether, 2-isopropylnaphthalene, pentylbenzene, hexylbenzene, heptylbenzene, octylbenzene, 1,1-bis(3,4-dimethylphenyl)ethane, hexamethylindane or mixtures of these solvents.

The present invention therefore further provides a formulation comprising a compound of the invention and at least one further compound. The further compound may, for example, be a solvent, especially one of the abovementioned solvents or a mixture of these solvents. The further compound may alternatively be at least one further organic or inorganic compound which is likewise used in the electronic device, for example an emitting compound, especially a phosphorescent dopant, and/or a further matrix material. Suitable emitting compounds and further matrix materials are listed at the back in connection with the organic electroluminescent device. This further compound may alymeric.

The compounds and mixtures of the invention are suitable for use in an electronic device. An electronic device is understood to mean a device containing at least one layer containing at least one organic compound. This component may also comprise inorganic materials or else layers formed entirely from inoterials.

The present invention therefore further provides for the use of the compounds or mixtures of the invention in an electronic device, especially in an organic electrolu device.

The present invention still further provides an electronic device comprising at least one of the above-detailed compounds or mixtures of the invention. In this case, the preferences detailed above for the compound also apply to the electronic devices.

The electronic device is preferably selected from the group consisting of organic electroluminescent devices (OLEDs, PLEDs), organic integrated circuits (O-ICs), organic field-effect transistors (O-FETs), organic thin-film transistors (O-TFTs), organic light-emitting transistors (O-LETs), organic solar cells (O-SCs), organic dye-sensitized solar cells, organic optical detectors, organic photoreceptors, organic field-quench devices (O-FQDs), light-emitting electrochemicalls (LECs), organic laser diodes (O-lasers) and organic plasmon emitting devices, preferably organic electroluminescent devices (OLEDs, PLEDs), especially phosphorescent OLEDs.

The organic electroluminescent device comprises cathode, anode and at least one emitting layer. Apart from these layers, it may also comprise further layers, for example in each case one or more hole injection layers, hole transport layers, hole blocker layers, electron transport layers, electron injection layers, exciton blocker layers, electron blocker layers and/or charge generation layers. It is likewise possible for interlayers having an exciton-blocking function, for example, to be introduced between two emitting layers. However, it should be pointed out that not necessarily every one of these layers need be present. In this case, it is possible for the organic electroluminescent device to contain an emitting layer, or for it to contain a plurality of emitting layers. If a plurality of emission layers are present, these preferably have several emission maxima between 380 nm and 750 nm overall, such that the overall result is white emission; in other words, various emitting compounds which may fluoresce or phosphoresce are used in the emitting layers. Especially preferred are systems having three emitting layers, where the three layers exhibit blue, green and orange or red emission. Also suitable are tandem OLEDs. These may be fluorescent or phosphorescent emission layers or else hybrid systems in which fluorescent and phosphorescent emission layers are combined with one another. A white-emitting electroluminescent device can be used, for example, for lighting applications, but also in combination with a colour filter for full-colour displays.

The compound of the invention according to the above-detailed embodiments may be used in different layers, according to the exact structure. Preference is given to an organic electroluminescent device comprising a compound of formula (1) or formula (2) or as per the preferred embodiments as matrix material for fluorescent or phosphorescent emitters or for emitters that exhibit TADF (thermally activated delayed fluorescence), especially for phosphorescent emitters, and/or in an electron transport layer and/or in an electron-blocking or exciton-blocking layer and/or in a hole transport layer and/or hole injection layer, according to the exact substitution. In this context, the above-detailed preferred embodiments also apply to the use of the materials in organic electronic devices.

In a preferred embodiment of the invention, the compound of formula (1) or formula (2) or according to the preferred embodiments is used as matrix material for a fluorescent or phosphorescent compound, especially for a phosphorescent compound, in an emitting layer. In this case, the organic electroluminescent device may contain an emitting layer, or it may contain a plurality of emitting layers, where at least one emitting layer contains at least one compound of the invention as matrix material.

When the compound of formula (1) or formula (2) or according to the preferred embodiments is used as matrix material for an emitting compound in an emitting layer, it is preferably used in combination with one or more phosphorescent materials (triplet emitters). Phosphorescence in the context of this invention is understood to mean luminescence from an excited state having spin multiplicity >1, especially from an excited triplet state. In the context of this application, all luminescent transition metal complexes and luminescent lanthanide complexes, especially all iridium, platinum and copper complexes, shall be regarded as phosphorescent compounds.

The mixture of the compound of formula (1) or formula (2) or according to the preferred embodiments and the emitting compound contains between 99% and 1% by volume, preferably between 98% and 10% by volume, more preferably between 97% and 60% by volume and especially between 95% and 80% by volume of the compound of formula (1) or formula (2) or according to the preferred embodiments, based on the overall mixture of emitter and matrix material. Correspondingly, the mixture contains between 1% and 99% by volume, preferably between 2% and 90% by volume, more preferably between 3% and 40% by volume and especially between 5% and 20% by volume of the emitter, based on the overall mixture of emitter and matrix material. If the compounds are processed from solution, preference is given to using the corresponding amounts in % by weight rather than the above-specified amounts in % by volume.

Suitable phosphorescent compounds (=triplet emitters) are especially compounds which, when suitably excited, emit light, preferably in the visible region, and also contain at least one atom of atomic number greater than 20, preferably greater than 38 and less than 84, more preferably greater than 56 and less than 80, especially a metal having this atomic number, Preferred phosphorescence emitters used are compounds containing copper, molybdenum, tungsten, rhenium, ruthenium, osmium, rhodium, iridium, palladium, platinum, silver, gold or europium, especially compounds containing iridium or platinum. In the context of the present invention, all luminescent compounds containing the abovementioned metals are regarded as phosphorescent compounds.

Examples of the above-described emitters can be found in applications WO 00/70655, WO 2001/41512, WO 2002/02714, WO 2002/15645, EP 1191613, EP 1191612, EP 1191614, WO 05/033244, WO 05/019373, US 2005/0258742, WO 2009/146770, WO 2010/015307, WO 2010/031485, WO 2010/054731, WO 2010/054728, WO 2010/086089, WO 2010/099852, WO 2010/102709, WO 2011/032626, WO 2011/066898, WO 2011/157339, WO 2012/

007086, WO 2014/008982, WO 2014/023377, WO 2014/094961, WO 2014/094960, WO 2015/036074, WO 2015/104045, WO 2015/117718, WO 2016/015815 and WO 2016/124304. In general, all phosphorescent complexes as used for phosphorescent OLEDs according to the prior art and as known to those skilled in the art in the field of organic electroluminescence are suitable, and the person skilled in the art will be able to use further phosphorescent complexes without exercising inventive skill.

A further preferred embodiment of the present invention is the use of the compound of formula (1) or formula (2) or according to the preferred embodiments as matrix material for a phosphorescent emitter in combination with a further matrix material. In a preferred embodiment of the invention, the further matrix material is a hole-transporting compound. In a further preferred embodiment of the invention, the further matrix material is an electron-transporting compound. In yet a further preferred embodiment, the further matrix material is a compound having a large band gap which is not involved to a significant degree, if at all, in the hole and electron transport in the layer.

Suitable matrix materials which can be used in combination with the compounds of formula (1) or formula (2) or according to the preferred embodiments are aromatic ketones, aromatic phosphine oxides or aromatic sulphoxides or sulphones, for example according to WO 2004/013080, WO 2004/093207, WO 2006/005627 or WO 2010/006680, triarylamines, especially monoamines, for example according to WO 20141015935, carbazole derivatives, e.g. GBP (N,N-biscarbazolylbiphenyl) or the carbazole derivatives disclosed in WO 2005/039246, US 2005/0069729, JP 2004/288381, EP 1205527 or WO 2008/086851, indolocarbazole derivatives, for example according to WO 2007/063754 or WO 2008/056746, indenocarbazole derivatives, for example according to WO 2010/136109 and WO 2011/000455, azacarbazole derivatives, for example according to EP 1617710, EP 1617711, EP 1731584, JP 2005/347160, bipolar matrix materials, for example according to WO 2007/137725, silanes, for example according to WO 2005/111172, azaboroles or boronic esters, for example according to WO 2006/117052, triazine derivatives, for example according to WO 2010/015306, WO 2007/063754 or WO 2008/056746, zinc complexes, for example according to EP 652273 or WO 2009/062578, diazasilole or tetraazasilole derivatives, for example according to WO 2010/054729, diazaphosphole derivatives, for example according to WO 2010/054730, bridged carbazole derivatives, for example according to US 2009/0136779, WO 2010/050778, WO 2011/042107, WO 2011/088877 or WO 2012/143080, triphenylene derivatives, for example according to WO 2012/048781, lactams, for example according to WO 2011/116865, WO 2011/137951 or WO 2013/064206, or 4-spirocarbazole derivatives, for example according to WO 2014/094963 or WO 2015/192939. It is likewise possible for a further phosphorescent emitter which emits at a shorter wavelength than the actual emitter to be present as co-host in the mixture.

Preferred co-host materials are triarylamine derivatives, especially monoamines, indenocarbazole derivatives, 4-spirocarbazole derivatives, lactams and carbazole derivatives.

In a further embodiment of the invention, the organic electroluminescent device of the invention does not contain any separate hole injection layer and/or hole transport layer and/or hole blocker layer and/or electron transport layer, meaning that the emitting layer directly adjoins the hole injection layer or the anode, and/or the emitting layer directly adjoins the electron transport layer or the electron injection layer or the cathode, as described, for example, in WO 2005/053051. It is additionally possible to use a metal complex identical or similar to the metal complex in the emitting layer as hole transport or hole injection material directly adjoining the emitting layer, as described, for example, in WO 2009/030981.

In addition, it is possible to use the compounds of the invention in a hole transport or electron blocker layer.

In the further layers of the organic electroluminescent device of the invention, it is possible to use any materials as typically used according to the prior art. The person skilled in the art is therefore able, without exercising inventive skill, to use any materials known for organic electroluminescent devices in combination with the inventive compounds of formula (1) or formula (2) or according to the preferred embodiments.

Additionally preferred is an organic electroluminescent device, characterized in that one or more layers are coated by a sublimation process. In this case, the materials are applied by vapour deposition in vacuum sublimation systems at an initial pressure of less than $10^{-5}$ mbar, preferably less than $10^{-6}$ mbar. It is also possible that the initial pressure is even lower or higher, for example less than $10^{-7}$ mbar.

Preference is likewise given to an organic electroluminescent device, characterized in that one or more layers are coated by the OVPD (organic vapour phase deposition) method or with the aid of a carrier gas sublimation. In this case, the materials are applied at a pressure between $10^{-5}$ mbar and 1 bar. A special case of this method is the OVJP (organic vapour jet printing) method, in which the materials are applied directly by a nozzle and thus structured.

Preference is additionally given to an organic electroluminescent device, characterized in that one or more layers are produced from solution, for example by spin-coating, or by any printing method, for example inkjet printing, LM (light-induced thermal imaging, thermal transfer printing), screen printing, flexographic printing, offset printing or nozzle printing. For this purpose, soluble compounds are needed, which are obtained, for example, through suitable substitution.

The compounds of the invention have improved oxidation stability, especially in solution, especially compared to diamines that are customarily used. This is important especially for printing processes. The compounds of the invention also feature high thermal stability, and so they can be evaporated without decomposition under high vacuum. The thermal stability also increases the operative lifetime of the compounds.

In addition, hybrid methods are possible, in which, for example, one or more layers are applied from solution and one or more further layers are applied by vapour deposition. For example, it is possible to apply the emitting layer from solution and to apply the electron transport layer by vapour deposition.

These methods are known in general terms to those skilled in the art and can be applied by those skilled in the art without exercising inventive skill to organic electroluminescent devices comprising the compounds of the invention.

The compounds of the invention generally have very good properties on use in organic electroluminescent devices. Especially in the case of use of the compounds of the invention in organic electroluminescent devices, the lifetime is significantly better compared to similar compounds according to the prior art. At the same time, the further properties of the organic electroluminescent device, especially the efficiency and voltage, are likewise better or at least comparable.

The invention is now illustrated in detail by the examples which follow, without any intention of restricting it thereby.

EXAMPLES

The syntheses which follow, unless stated otherwise, are conducted under a protective gas atmosphere in dried solvents. The solvents and reagents can be purchased, for example, from Sigma-ALDRICH or ABCR. For the compounds known from the literature, the corresponding CAS numbers are also reported in each case.

Synthesis Examples a) 4-Bromo-9-methyl-9-phenyl-9H-fluorene

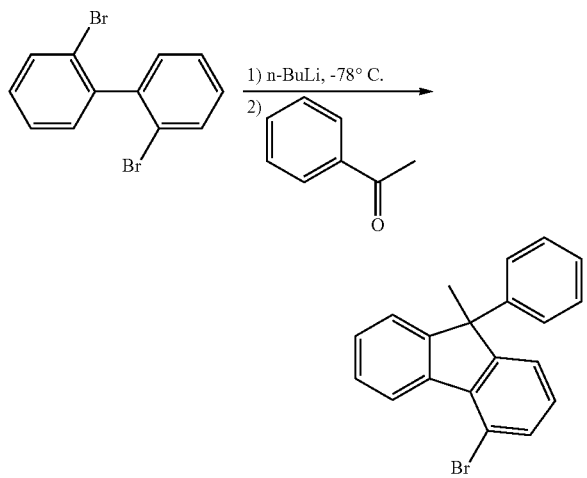

30 g (94 mmol) of 2,2'-dibromobiphenyl are dissolved in a baked-out flask in 200 ml of dried THF. The reaction mixture is cooled to −78° C. At this temperature, 37.7 ml of a 2.5 M solution of n-butyllithium in hexane (94 mmol) are slowly added dropwise (over about 1 h). The mixture is stirred at −70° C. for a further 1 h. Subsequently, 11.1 ml of acetophenone (94 mmol) are dissolved in 100 ml of THF and added dropwise at −70° C. After the addition has ended, the reaction mixture is warmed gradually to room temperature, quenched with NH$_4$Cl and then concentrated on a rotary evaporator. 300 ml of acetic acid are added cautiously to the concentrated solution and then 50 ml of fuming HCl are added. The mixture is heated to 75° C. for 6 h. During this time, a white solid precipitates out. The mixture is cooled to room temperature, and the precipitated solid is filtered off with suction and washed with methanol. The residue is dried at 40° C. under reduced pressure. Yield: 25.3 g (75 mmol) (80% of theory).

a) 4-Bromo-9,9-diphenyl-9H-fluorene

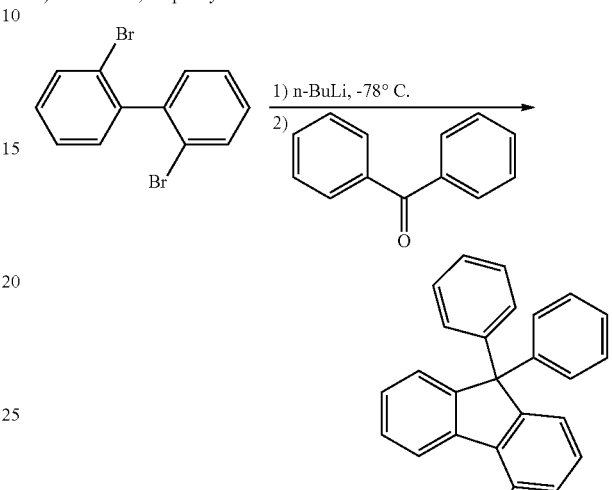

37 g (152 mmol) of 2,2'-dibromobiphenyl are dissolved in a baked-out flask in 300 ml of dried THF. The reaction mixture is cooled to −78° C. At this temperature, 75 ml of a 15% solution of n-butyllithium in hexane (119 mmol) are slowly added dropwise (over about 1 h). The mixture is stirred at −70° C. for a further 1 h. Subsequently, 21.8 g of benzophenone (119 mmol) are dissolved in 100 ml of THF and added dropwise at −70° C. After the addition has ended, the reaction mixture is warmed gradually to room temperature, quenched with NH$_4$Cl and then concentrated on a rotary evaporator. 510 ml of acetic acid are added cautiously to the concentrated solution and then 100 ml of fuming HCl are added. The mixture is heated to 75° C. for 4 h. During this time, a white solid precipitates out. The mixture is cooled to room temperature, and the precipitated solid is filtered off with suction and washed with methanol. The residue is dried at 40° C. under reduced pressure. Yield: 33.2 g (83 mmol) (70% of theory).

The following compounds are prepared in an analogous manner:

| | Reactant 1 | Reactant 2 | Product | Yield |
|---|---|---|---|---|
| b1 | ![biphenyl dibromide] | ![cyclohexanone] | ![spiro product] | 78% |

The following compounds are prepared in an analogous manner:

| | Reactant 1 | Reactant 2 | Product | Yield |
|---|---|---|---|---|
| b2 | 2,2'-dibromobiphenyl | acetone | 9,9-dimethyl-4-bromofluorene | 70% |
| b3 | 2,2'-dibromobiphenyl | bis(4-methylphenyl)methanone | 9,9-bis(4-methylphenyl)-4-bromofluorene | 82% | c) 6-Bromo-2-fluoro-2'-methoxybiphenyl

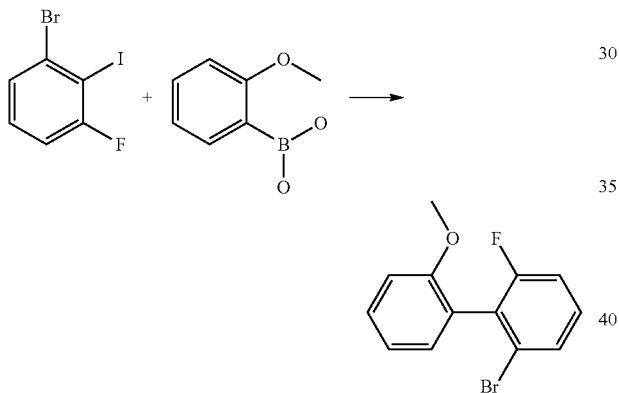

200 g (664 mmol) of 1-bromo-3-fluoro-2-iodobenzene, 101 g (664 mmol) of 2-methoxyphenylboronic acid and 137.5 g (997 mmol) of sodium tetraborate are dissolved in 1000 ml of THF and 600 ml of water, and degassed. 9.3 g (13.3 mmol) of bis(triphenylphosphine)palladium(II) chloride and 1 g (20 mmol) of hydrazinium hydroxide are added. The reaction mixture is then stirred under a protective gas atmosphere at 70° C. for 48 h. The cooled solution is supplemented with toluene, washed repeatedly with water, dried and concentrated. The product is purified via column chromatography on silica gel with toluene/heptane (1:2). Yield: 155 g (553 mmol), 83% of theory.

The following compounds are prepared in an analogous manner:

| | Reactant 1 | Reactant 2 | Product | Yield |
|---|---|---|---|---|
| c1 | [1000576-09-9] | 2-methoxyphenylboronic acid | | 77% |

The following compounds are prepared in an analogous manner:

| | Reactant 1 | Reactant 2 | Product | Yield |
|---|---|---|---|---|
| c2 | 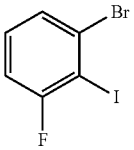 | 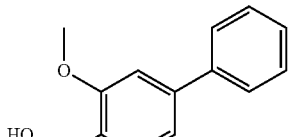 [1379680-54-2] | 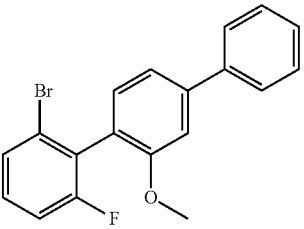 [SMILES: COc1cc(-c2ccccc2)ccc1-c1c(F)cccc1Br] | 74% |
| c3 | 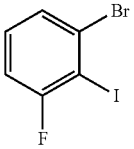 | 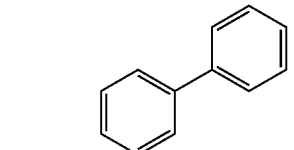 [1199350-14-5] | 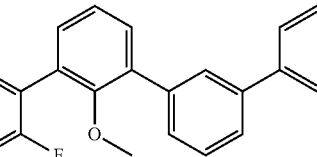 | 76% |
| c4 | 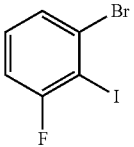 | 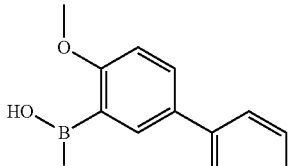 [1114496-44-4] | 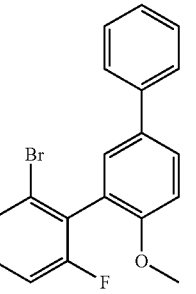 | 71% | c) 6′-Bromo-2′-fluorobiphenyl-2-ol

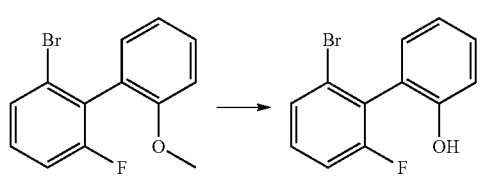

112 g (418 mmol) of 6-bromo-2-fluoro-2′-methoxybiphenyl are dissolved in 2 l of dichloromethane and cooled to 5° C. 41.01 ml (431 mmol) of boron tribromide are added dropwise to this solution within 90 min, and stirring of the mixture continues overnight. The mixture is subsequently admixed gradually with water, and the organic phase is washed three times with water, dried over $Na_2SO_4$, concentrated by rotary evaporation and purified by chromatography. Yield: 104 g (397 mmol), 98% of theory.

| | The following compounds are prepared in an analogous manner: | | |
|---|---|---|---|
| | Reactant 1 | Product | Yield |
| d1 | | | 92% |
| d2 | | | 90% |
| d3 | | | 93% |
| d4 | | | 94% | e) 1-Bromodibenzofuran

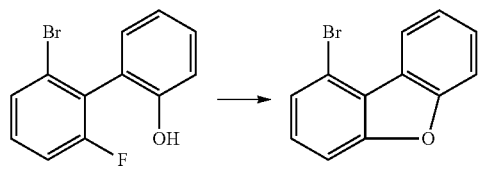

111 g (416 mmol) of 6-bromo-2'-fluorobiphenyl-2-ol are dissolved in 2 l of DMF (max. 0.003% H$_2$O) SeccoSolv® and cooled to 5° C. 20 g (449 mmol) of sodium hydride (60% suspension in paraffin oil) are added to this solution in portions, once the addition has ended the mixture is stirred for 20 min, and then the mixture is heated to 100° C. for 45 min. After cooling, 500 ml of ethanol are added gradually to the mixture, which is concentrated by rotary evaporation and purified by chromatography. Yield: 90 g (367 mmol), 88.5% of theory.

| | The following compounds are prepared in an analogous manner: | | |
|---|---|---|---|
| | Reactant 1 | Product | Yield |
| e1 | | | 81% |

-continued

| | Reactant 1 | Product | Yield |
|---|---|---|---|
| e2 | | | 78% |
| e3 | | | 73% |
| e4 | | | 79% | f) 4-(3-Chlorophenyl)-9,9-spirobifluorene

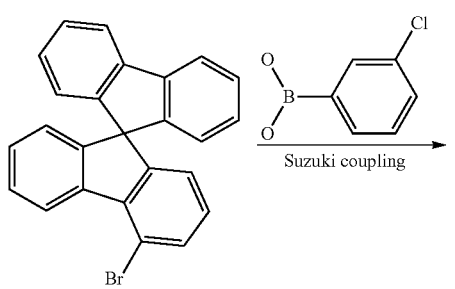

Suzuki coupling

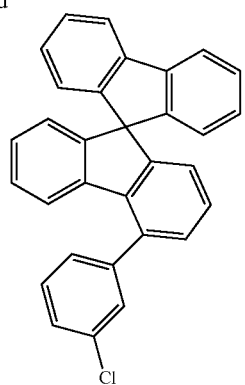

217 g (139 mmol) of 4-chlorobenzeneboronic acid, 50 g (126 mmol) of 4-bromo-9,9-spirobifluorene and 208 ml of an aqueous 2 M $K_2CO_3$ solution (416 mmol) are suspended in 300 ml of tetrahydrofuran. To this suspension are added 1.45 g (1.26 mmol) of tetrakis(triphenylphosphine)palladium(0). The reaction mixture is heated under reflux for 16 h. After cooling, the organic phase is removed, filtered through silica gel, washed three times with 300 ml of water and then concentrated to dryness. After the crude product has been filtered through silica gel with heptane/ethyl acetate (20:1), 48 g (89%) of 4-(3-chlorophenyl)-9,9-spirobifluorene are obtained.

| The following compounds are prepared in an analogous manner: | | | |
|---|---|---|---|
| Reactant 1 | Reactant 2 | Product | Yield |
| f3 | | | 88% |
| f2 | | | 85% |
| f3 | | | 89% | g) Biphenyl-4-yldibenzofuran-1-ylamine

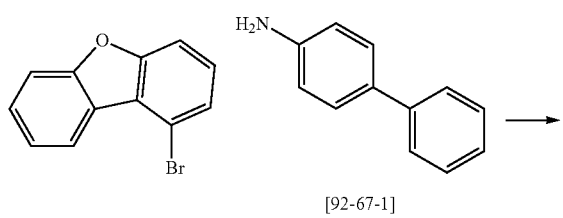

[92-67-1]

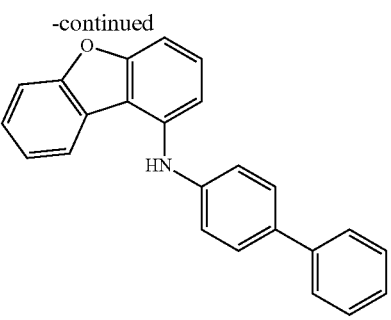

-continued 30.0 g (177 mmol, 1.0 eq) of 4-aminobiphenyl are initially charged together with 43.7 g (177 mmol, 1.0 eq) of 1-bromodibenzofuran and 23.4 g (212 mmol, 1.20 eq) of sodium tert-pentoxide [14593-46-5] in 600 ml of absolute toluene and degassed for 30 minutes. Subsequently, 398 mg (1.77 mmol, 0.01 eq) of palladium(II) acetate [3375-31-3] and 1.46 g (3.56 mmol, 0.02 eq) of 2-dicyclohexylphosphino-2',6'-dimethoxybiphenyl SPHOS [657408-07-6] are added and the mixture is heated under reflux overnight. After the reaction has ended, the mixture is cooled down to room temperature and extracted with 500 ml of water. Subsequently, the aqueous phase is washed three times with toluene, the combined organic phases are dried over sodium sulphate and the solvent is removed on a rotary evaporator. The brown residue is taken up in about 200 ml of toluene and filtered through silica gel. For further purification, a recrystallization from toluene/heptane is conducted. Yield: 44 g (133 mmol), 76% of theory.

| | The following compounds are prepared in an analogous manner: | |
|---|---|---|
| | Reactant 1 | Reactant 2 |
| g1 | 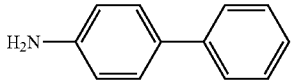 [92-67-1] | 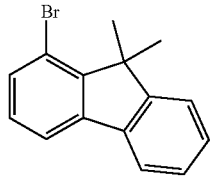 [89827-45-2] |
| g2 | 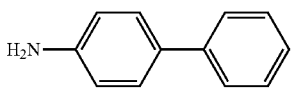 [92-67-1] | 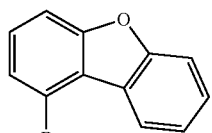 [50548-45-3] |
| g3 | 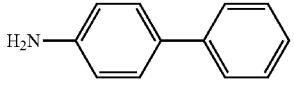 [92-67-1] | 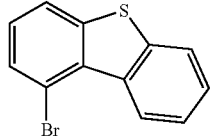 [65642-94-6] |
| g4 | 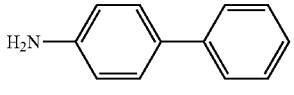 [92-67-1] | 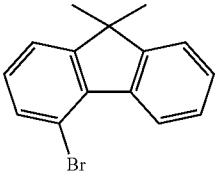 [942615-32-9] |
| g5 | 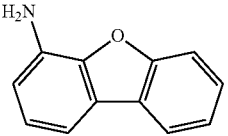 [50548-43-1] | 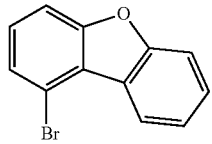 [50548-45-3] |
| g6 | 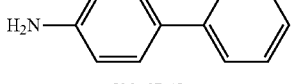 [92-67-1] | 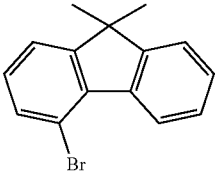 [942615-32-9] |
| g7 | 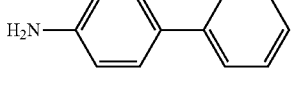 [92-67-1] | 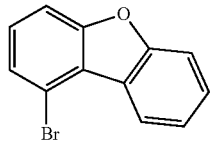 [50548-45-3] |

-continued
The following compounds are prepared in an analogous manner:
g8 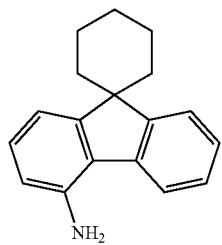
[18998-24-8]
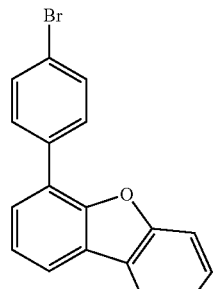
[1225053-54-2]
g9 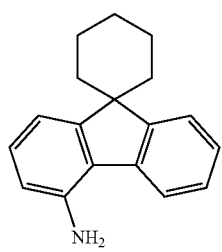
[18998-24-8]
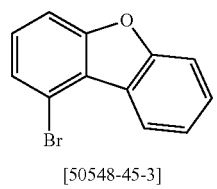 [SMILES: Brc1cccc2oc3ccccc3c12]
[50548-45-3]
g10 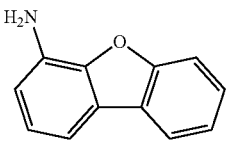
[50548-43-1]
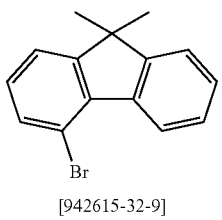 [SMILES: CC1(C)c2ccccc2-c2c(Br)cccc21]
[942615-32-9]
g11 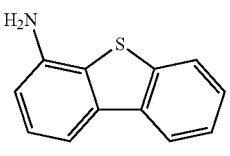
[72433-66-0]
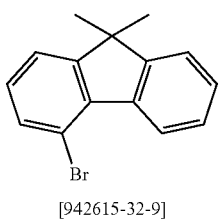 [SMILES: CC1(C)c2ccccc2-c2c(Br)cccc21]
[942615-32-9]
g12 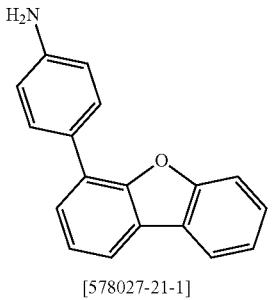 [SMILES: Nc1ccc(-c2cccc3c2oc2ccccc23)cc1]
[578027-21-1]
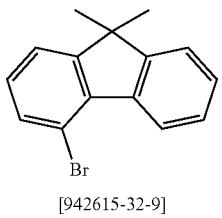 [SMILES: CC1(C)c2ccccc2-c2c(Br)cccc21]
[942615-32-9]

| | | | |
|---|---|---|---|
| \multicolumn{4}{c}{The following compounds are prepared in an analogous manner:} |
| g13 | 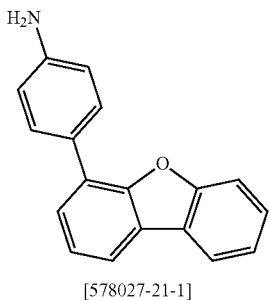 [SMILES: Nc1ccc(-c2cccc3c2oc2ccccc23)cc1] [578027-21-1] | | 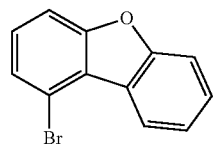 [50548-45-3] |
| g14 | 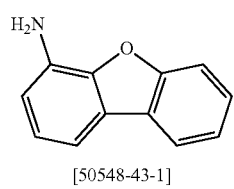 [SMILES: Nc1cccc2c1oc1ccccc12] [50548-43-1] | | 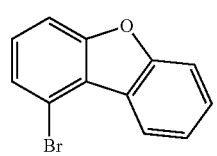 [50548-45-3] |
| g15 | 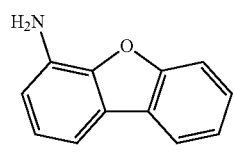 [50548-43-1] | | 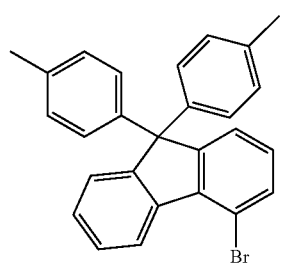 |
| g16 | 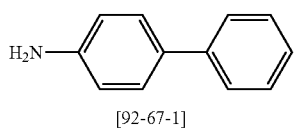 [SMILES: Nc1ccc(-c2ccccc2)cc1] [92-67-1] | | 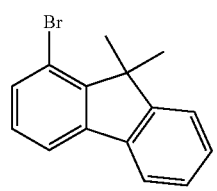 [89827-45-2] |
| g17 | 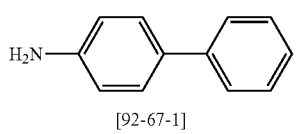 [SMILES: Nc1ccc(-c2ccccc2)cc1] [92-67-1] | | 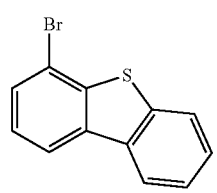 [97511-05-2] |
| g18 | 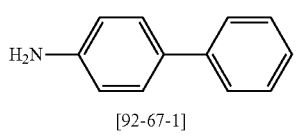 [92-67-1] | | 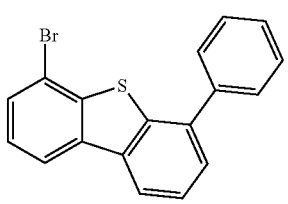 [1415844-67-5] |

| | The following compounds are prepared in an analogous manner: |
|---|---|
| g19 | 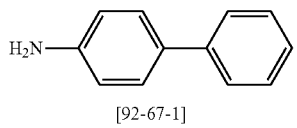 [SMILES: Nc1ccc(-c2ccccc2)cc1] [92-67-1]     [1225053-54-2] |
| g20 | 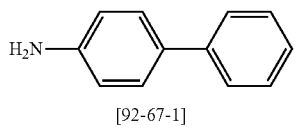 [SMILES: Nc1ccc(-c2ccccc2)cc1] [92-67-1]     [86-76-0] |
| g21 | 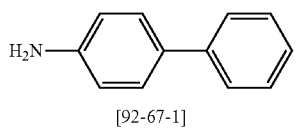 [SMILES: Nc1ccc(-c2ccccc2)cc1] [92-67-1]     [1450933-18-2] |
| g22 | 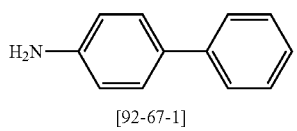 [92-67-1]     [1161009-88-6] |
| g23 | 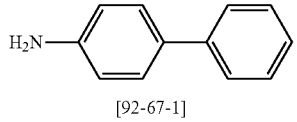 [SMILES: Nc1ccc(-c2ccccc2)cc1] [92-67-1]     [1421789-08-3] |

| | | |
|---|---|---|
| The following compounds are prepared in an analogous manner: | | |
| g24 | 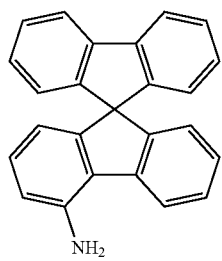 [1579281-06-3] | 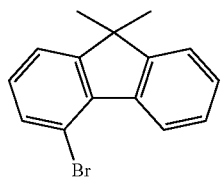 [942615-32-9] |
| g25 | 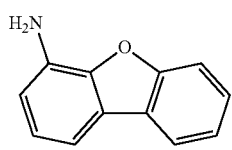 [50548-43-1] | 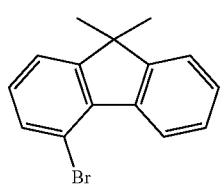 [942615-32-9] |
| g26 | 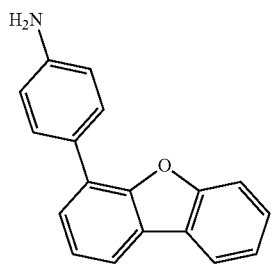 [578027-21-1] | 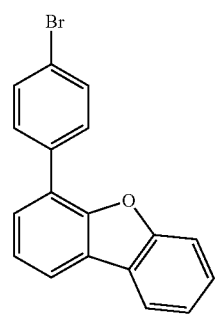 [1225053-54-2] |
| g27 | 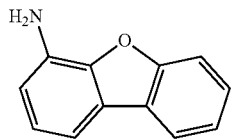 [50548-43-1] | 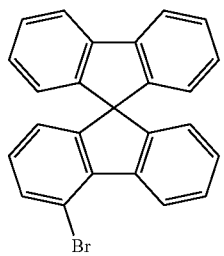 [1161009-88-6] |
| g28 | 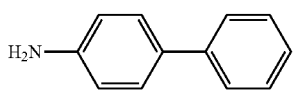 | 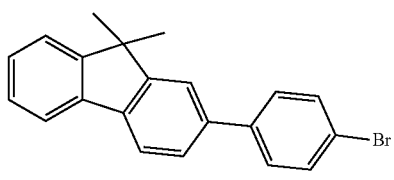 [574750-94-0] |

The following compounds are prepared in an analogous manner:
| | | |
|---|---|---|
| g29 | 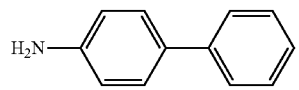 [SMILES: Nc1ccc(-c2ccccc2)cc1] | 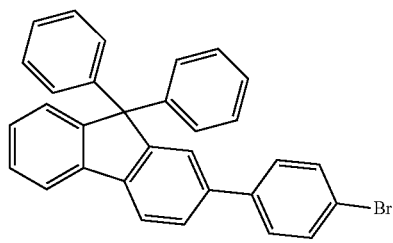<br>[736928-23-7] |
| g30 | 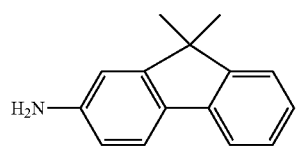<br>[108714-73-4] | 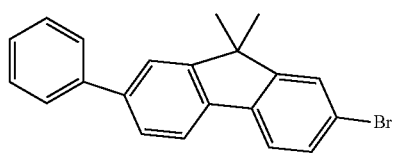<br>[1047992-04-0] |
| g31 | 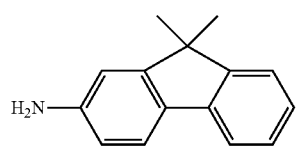<br>[108714-73-4] | 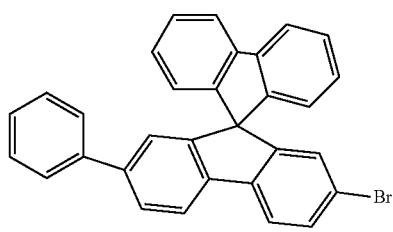<br>[1361305-36-3] |
| g32 | 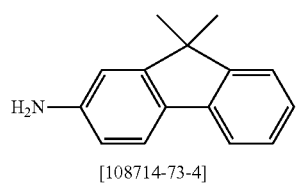 [SMILES: CC1(C)c2ccccc2-c2ccc(N)cc21]<br>[108714-73-4] | 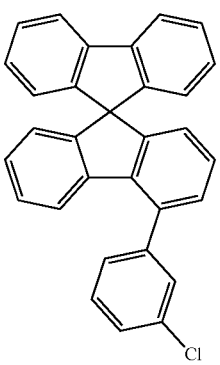 [SMILES: Clc1cccc(-c2cccc3c2-c2ccccc2C32c3ccccc3-c3ccccc32)c1] |
| g33 | 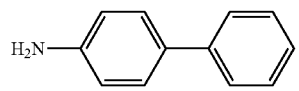 [SMILES: Nc1ccc(-c2ccccc2)cc1] | 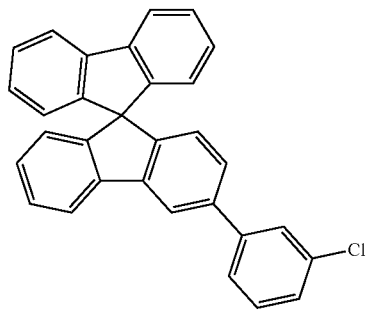 [SMILES: Clc1cccc(-c2ccc3c(c2)-c2ccccc2C32c3ccccc3-c3ccccc32)c1] |

| | | |
|---|---|---|
| The following compounds are prepared in an analogous manner: | | |
| g34 | 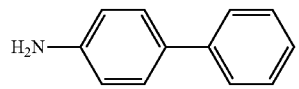 [SMILES: Nc1ccc(-c2ccccc2)cc1] | 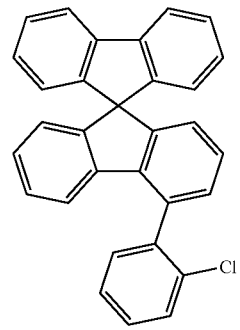 [SMILES: Clc1ccccc1-c1cccc2c1-c1ccccc1C21c2ccccc2-c2ccccc21] |
| g35 | 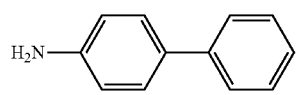 | 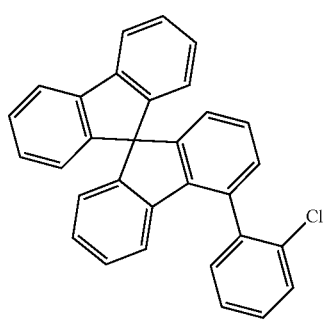 [SMILES: Clc1ccccc1-c1cccc2c1-c1ccccc1C21c2ccccc2-c2ccccc21] |
| g36 | 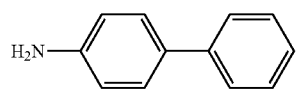 [SMILES: Nc1ccc(-c2ccccc2)cc1] | 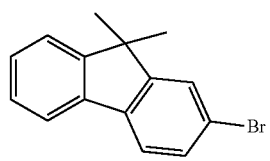 |
| g37 | 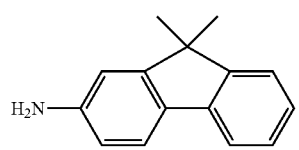
[108714-73-4] | 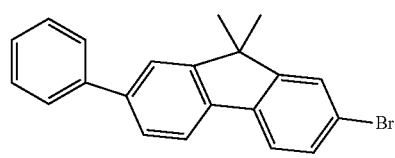
[1047992-04-0] |
| g26 | 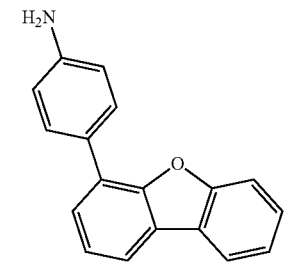
[578027-21-1] | 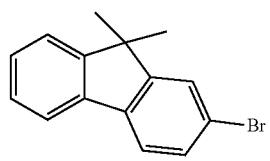 |
| g27 | 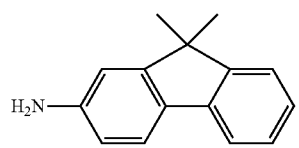
[108714-73-4] | 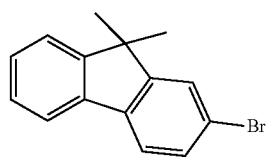 [SMILES: CC1(C)c2ccccc2-c2ccc(Br)cc21] |

-continued
The following compounds are prepared in an analogous manner:
| | | | |
|---|---|---|---|
| g28 | 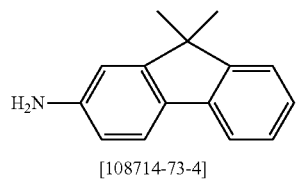 [108714-73-4] | 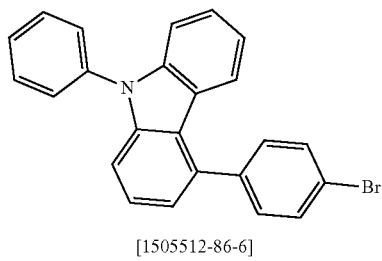 [SMILES: Brc1ccc(-c2cccc3c2c2ccccc2n3-c2ccccc2)cc1] [1505512-86-6] | |
| g29 | 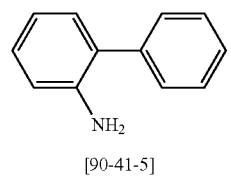 [90-41-5] | 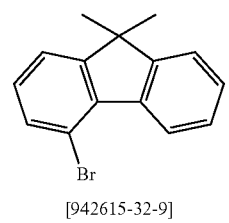 [SMILES: CC1(C)c2ccccc2-c2c(Br)cccc21] [942615-32-9] | |
| g30 | 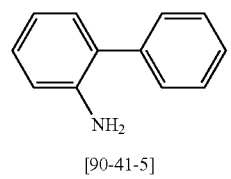 [90-41-5] | 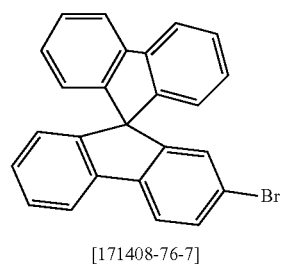 [SMILES: Brc1ccc2c(c1)C1(c3ccccc3-c3ccccc31)c1ccccc1-2] [171408-76-7] | |
| g31 | 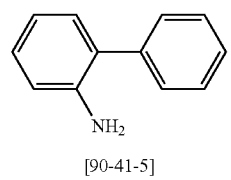 [SMILES: Nc1ccccc1-c1ccccc1] [90-41-5] | 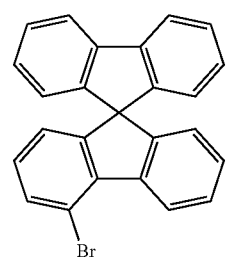 [1161009-88-6] | |
| | Product 3 | Yield [%] |
|---|---|---|
| g1 | 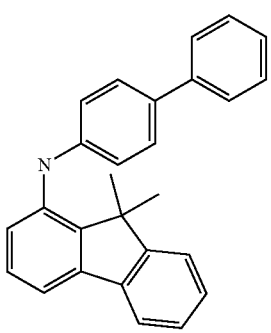 [SMILES: CC1(C)c2ccccc2-c2cccc(Nc3ccc(-c4ccccc4)cc3)c21] | 45 |

| | The following compounds are prepared in an analogous manner: | |
|---|---|---|
| g2 | 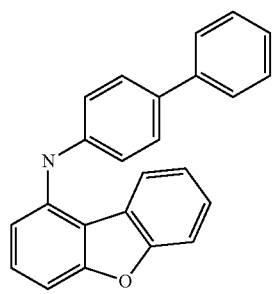 [SMILES: c1ccc(-c2ccc(Nc3cccc4oc5ccccc5c34)cc2)cc1] | 61 |
| g3 | 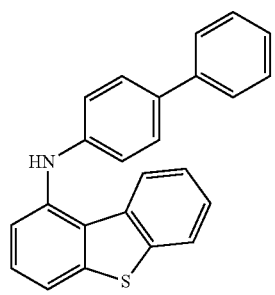 [SMILES: c1ccc(-c2ccc(Nc3cccc4sc5ccccc5c34)cc2)cc1] | 68 |
| g4 | 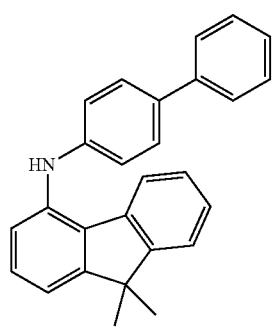 [SMILES: CC1(C)c2ccccc2-c2c(Nc3ccc(-c4ccccc4)cc3)cccc21] | 34 |
| g5 | 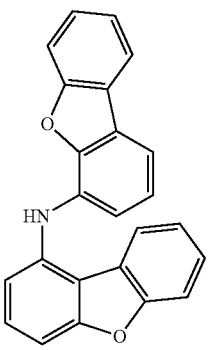 [SMILES: c1ccc2c(c1)oc1c(Nc3cccc4oc5ccccc5c34)cccc12] | 73 |
| g6 | 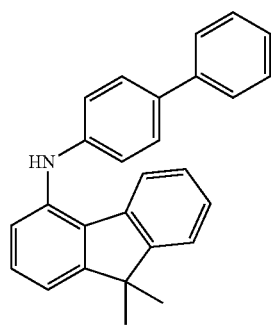 [SMILES: CC1(C)c2ccccc2-c2c(Nc3ccc(-c4ccccc4)cc3)cccc21] | 51 |

| | | |
|---|---|---|
| The following compounds are prepared in an analogous manner: | | |
| g7 | 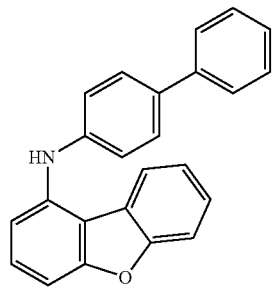 [SMILES: c1ccc(-c2ccc(Nc3cccc4oc5ccccc5c34)cc2)cc1] | 65 |
| g8 | 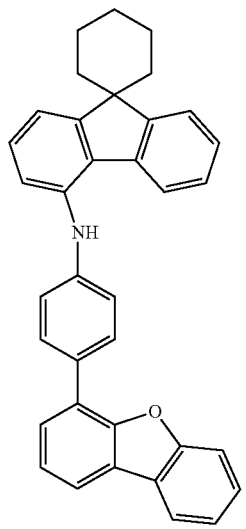 [SMILES: c1ccc2c(c1)-c1c(Nc3ccc(-c4cccc5c4oc4ccccc45)cc3)cccc1C21CCCCC1] | 62 |
| g9 | 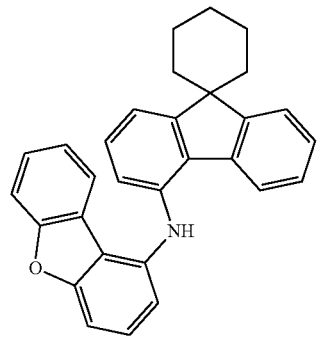 [SMILES: c1ccc2c(c1)-c1c(Nc3cccc4oc5ccccc5c34)cccc1C21CCCCC1] | 43 |
| g10 | 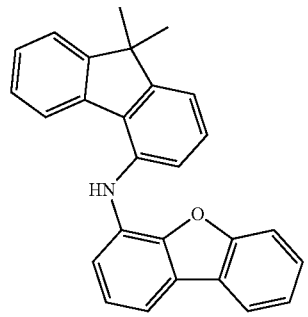 [SMILES: CC1(C)c2ccccc2-c2c(Nc3cccc4c3oc3ccccc34)cccc21] | 34 |

| | | |
|---|---|---|
| The following compounds are prepared in an analogous manner: | | |
| g11 | 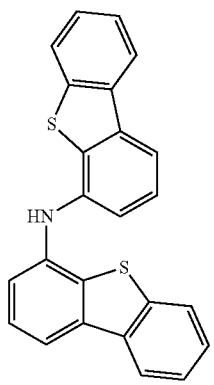 [SMILES: c1ccc2c(c1)sc1c(Nc3cccc4c3sc3ccccc34)cccc12] | 55 |
| g12 | 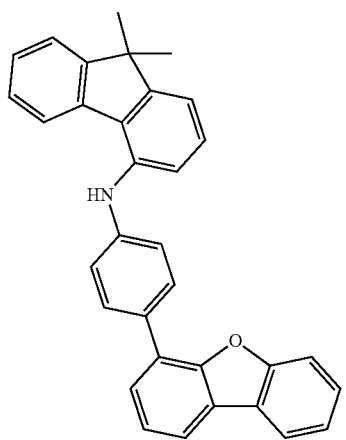 [SMILES: CC1(C)c2ccccc2-c2c(Nc3ccc(-c4cccc5c4oc4ccccc45)cc3)cccc21] | 62 |
| g13 | 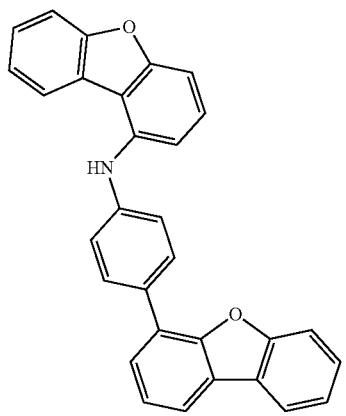 [SMILES: c1ccc2c(c1)oc1c(-c3ccc(Nc4cccc5oc6ccccc6c45)cc3)cccc12] | 70 |
| g14 | 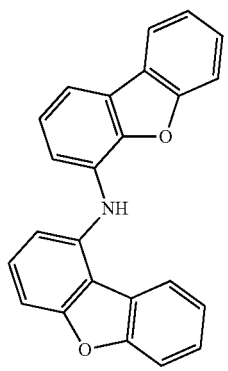 [SMILES: c1ccc2c(c1)oc1c(Nc3cccc4oc5ccccc5c34)cccc12] | 77 |

| | | |
|---|---|---|
| -continued | | |
| The following compounds are prepared in an analogous manner: | | |
| g15 | 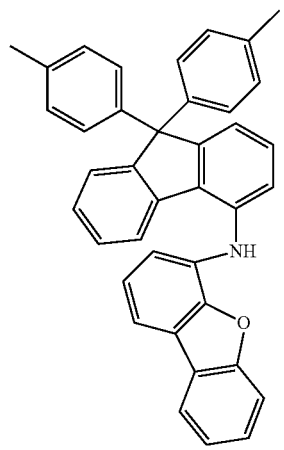 | 75 |
| g16 | 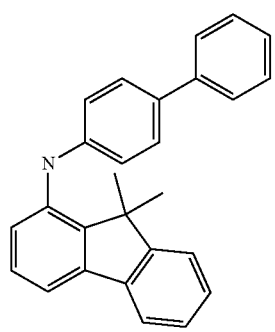 [SMILES: CC1(C)c2ccccc2-c2cccc(Nc3ccc(-c4ccccc4)cc3)c21] | 45 |
| g17 | 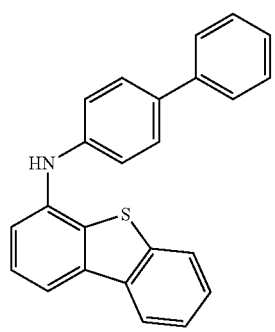 [SMILES: c1ccc(-c2ccc(Nc3cccc4c3sc3ccccc34)cc2)cc1] | 68 |
| g18 | 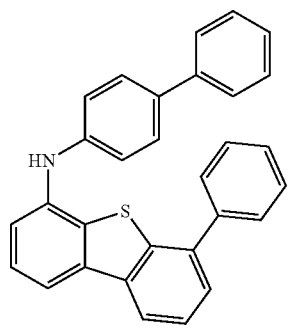 [SMILES: c1ccc(-c2ccc(Nc3cccc4c3sc3c(-c5ccccc5)cccc34)cc2)cc1] | 34 |

-continued
The following compounds are prepared in an analogous manner:
g19 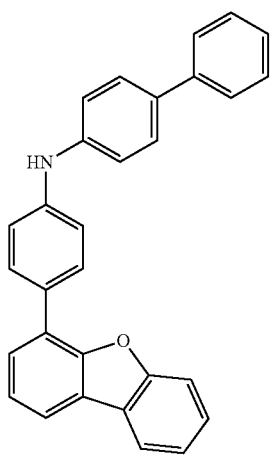 [SMILES: c1ccc(-c2ccc(Nc3ccc(-c4cccc5c4oc4ccccc45)cc3)cc2)cc1] 78
g20 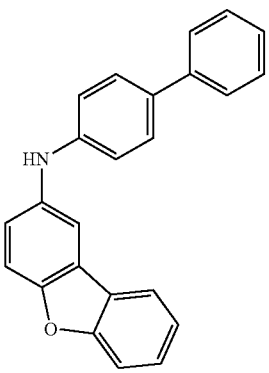 [SMILES: c1ccc(-c2ccc(Nc3ccc4oc5ccccc5c4c3)cc2)cc1] 51
g21 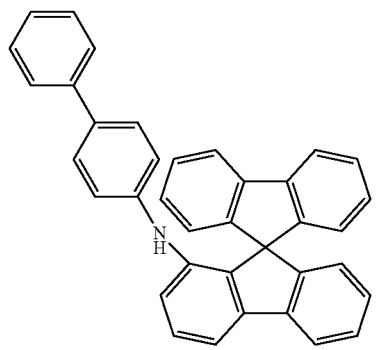 [SMILES: c1ccc(-c2ccc(Nc3cccc4c3C3(c5ccccc5-c5ccccc53)c3ccccc3-4)cc2)cc1] 23
g22 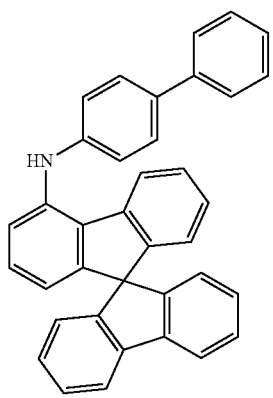 [SMILES: c1ccc(-c2ccc(Nc3cccc4c3-c3ccccc3C43c4ccccc4-c4ccccc43)cc2)cc1] 55

327 328
-continued
The following compounds are prepared in an analogous manner:
| g23 | 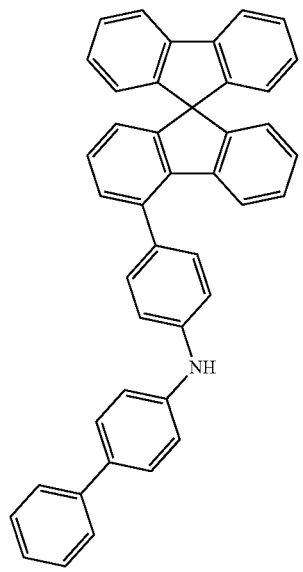 [SMILES: c1ccc(-c2ccc(Nc3ccc(-c4cccc5c4-c4ccccc4C54c5ccccc5-c5ccccc54)cc3)cc2)cc1] | 68 |
| g24 | 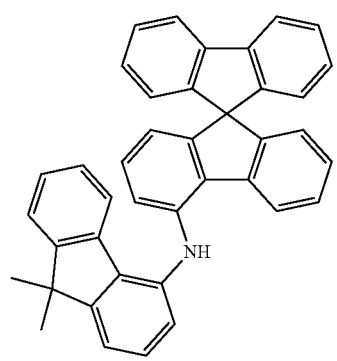 [SMILES: CC1(C)c2ccccc2-c2c(Nc3cccc4c3-c3ccccc3C43c4ccccc4-c4ccccc43)cccc21] | 29 |
| g25 | 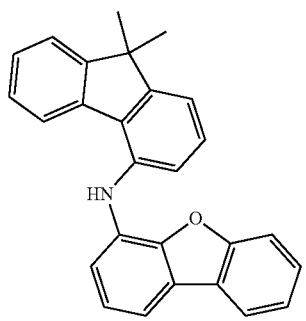 [SMILES: CC1(C)c2ccccc2-c2c(Nc3cccc4c3oc3ccccc34)cccc21] | 34 |

-continued
The following compounds are prepared in an analogous manner:
| | | |
|---|---|---|
| g26 | 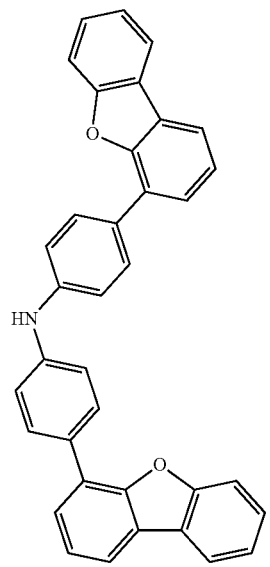 [SMILES: c1ccc2c(c1)oc1c(-c3ccc(Nc4ccc(-c5cccc6c5oc5ccccc56)cc4)cc3)cccc12] | 72 |
| g27 | 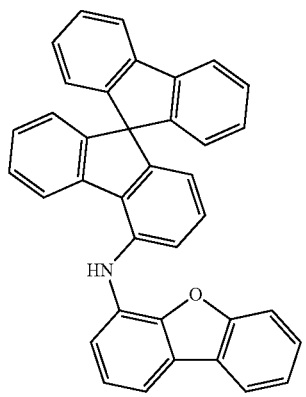 [SMILES: c1ccc2c(c1)-c1ccccc1C21c2ccccc2-c2c(Nc3cccc4c3oc3ccccc34)cccc21] | 45 |
| g28 | 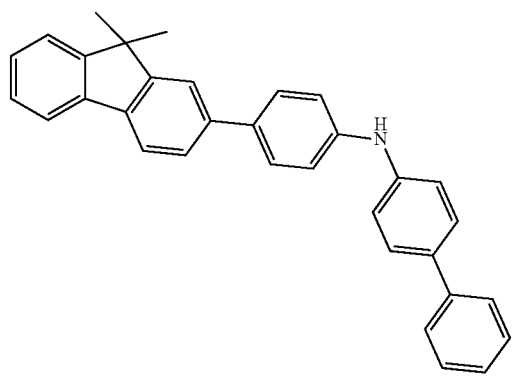 [SMILES: CC1(C)c2ccccc2-c2ccc(-c3ccc(Nc4ccc(-c5ccccc5)cc4)cc3)cc21] | 56 |

-continued
The following compounds are prepared in an analogous manner:
| g29 | 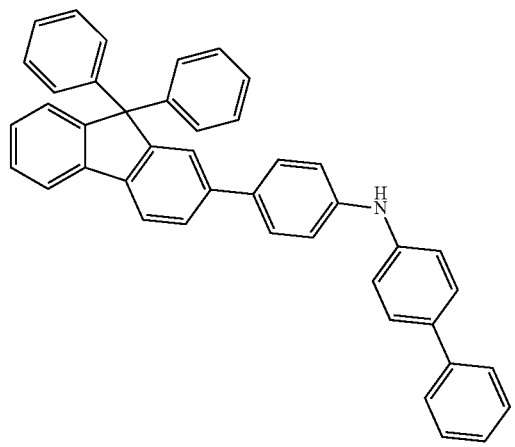 [SMILES: c1ccc(-c2ccc(Nc3ccc(-c4ccc5c(c4)C(c4ccccc4)(c4ccccc4)c4ccccc4-5)cc3)cc2)cc1] | 63 |
| g30 | 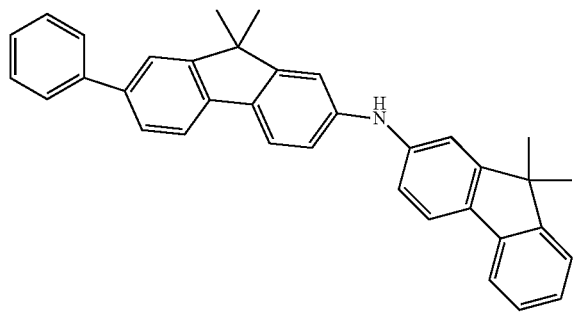 [SMILES: CC1(C)c2ccccc2-c2ccc(Nc3ccc4c(c3)C(C)(C)c3cc(-c5ccccc5)ccc3-4)cc21] | 60 |
| g31 | 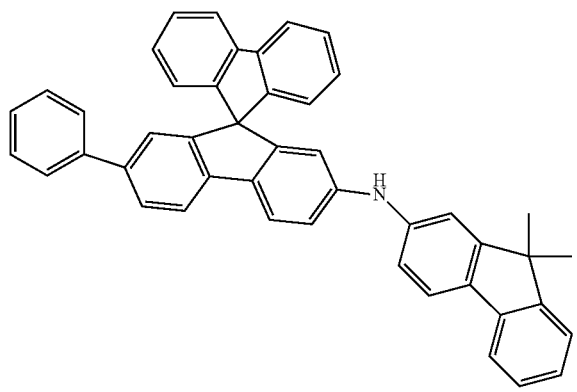 [SMILES: CC1(C)c2ccccc2-c2ccc(Nc3ccc4c(c3)C3(c5ccccc5-c5ccccc53)c3cc(-c5ccccc5)ccc3-4)cc21] | 69 |

-continued
The following compounds are prepared in an analogous manner:
| | | |
|---|---|---|
| g32 | 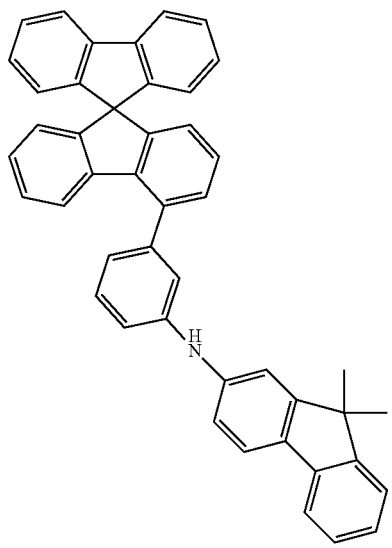 [SMILES: CC1(C)c2ccccc2-c2ccc(Nc3cccc(-c4cccc5c4-c4ccccc4C54c5ccccc5-c5ccccc54)c3)cc21] | 66 |
| g33 | 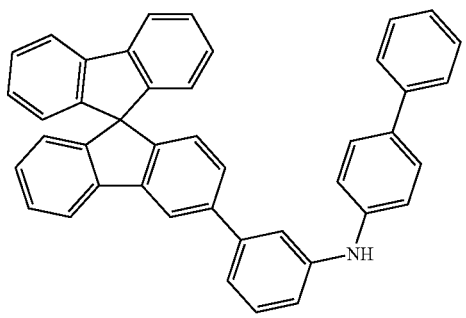 [SMILES: c1ccc(-c2ccc(Nc3cccc(-c4ccc5c(c4)-c4ccccc4C54c5ccccc5-c5ccccc54)c3)cc2)cc1] | 68 |
| g34 | 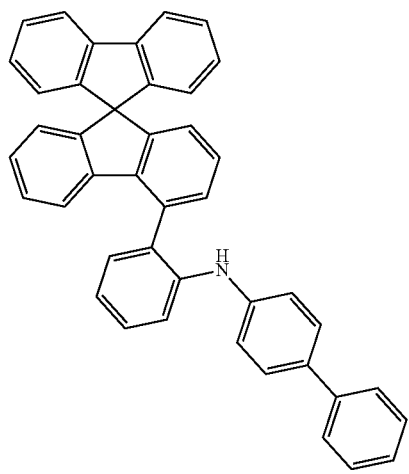 [SMILES: c1ccc(-c2ccc(Nc3ccccc3-c3cccc4c3-c3ccccc3C43c4ccccc4-c4ccccc43)cc2)cc1] | 71 |

The following compounds are prepared in an analogous manner:
| | | |
|---|---|---|
| g35 | 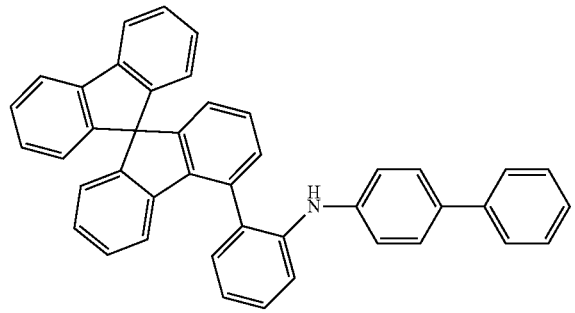 [SMILES: c1ccc(-c2ccc(Nc3ccccc3-c3cccc4c3-c3ccccc3C43c4ccccc4-c4ccccc43)cc2)cc1] | 72 |
| g36 | 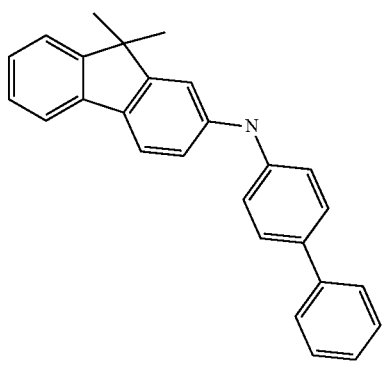 [SMILES: CC1(C)c2ccccc2-c2ccc(Nc3ccc(-c4ccccc4)cc3)cc21] | 77% |
| g37 | 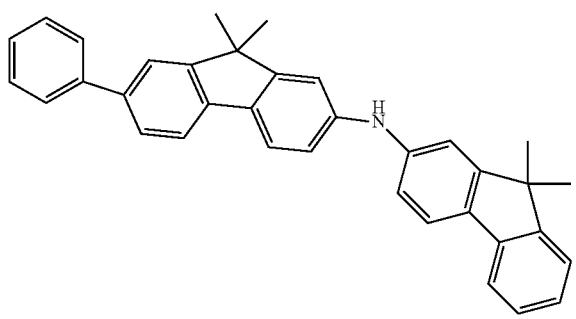 [SMILES: CC1(C)c2ccccc2-c2ccc(Nc3ccc4c(c3)C(C)(C)c3cc(-c5ccccc5)ccc3-4)cc21] | 61 |
| g26 | 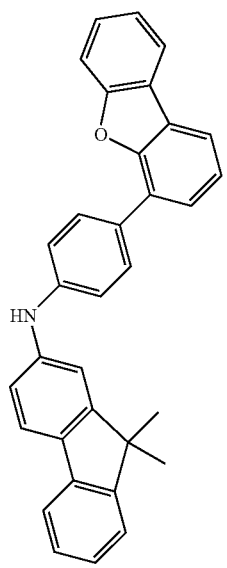 [SMILES: CC1(C)c2ccccc2-c2ccc(Nc3ccc(-c4cccc5c4oc4ccccc45)cc3)cc21] | 74 |

-continued
The following compounds are prepared in an analogous manner:
| g27 | 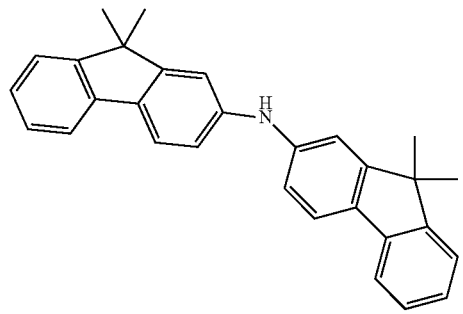 [SMILES: CC1(C)c2ccccc2-c2ccc(Nc3ccc4c(c3)C(C)(C)c3ccccc3-4)cc21] | 66 |
| g28 | 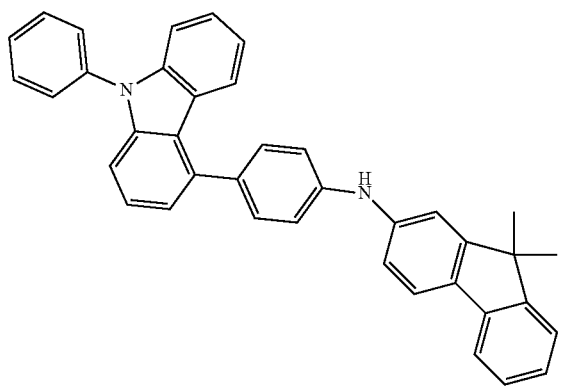 [SMILES: CC1(C)c2ccccc2-c2ccc(Nc3ccc(-c4cccc5c4c4ccccc4n5-c4ccccc4)cc3)cc21] | 60 |
| g29 | 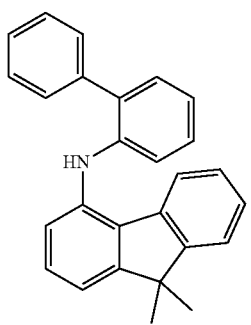 [SMILES: CC1(C)c2ccccc2-c2c(Nc3ccccc3-c3ccccc3)cccc21] | 64 |
| g30 | 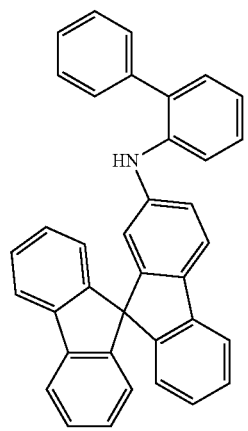 [SMILES: c1ccc(-c2ccccc2Nc2ccc3c(c2)C2(c4ccccc4-c4ccccc42)c2ccccc2-3)cc1] | 60 |

The following compounds are prepared in an analogous manner:

| | |
|---|---|
| g31 | 66 |

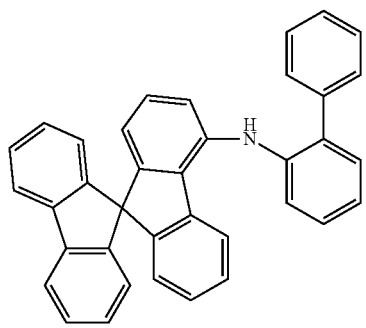 [SMILES: c1ccc(-c2ccccc2Nc2cccc3c2-c2ccccc2C32c3ccccc3-c3ccccc32)cc1]

h) Biphenyl-4-yl(4-bromophenyl)(9,9-dimethyl-9H-fluoren-4-yl)amine

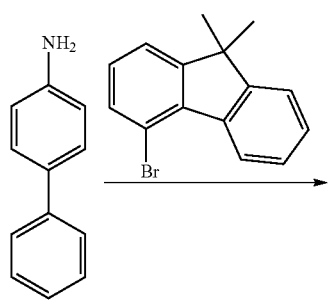

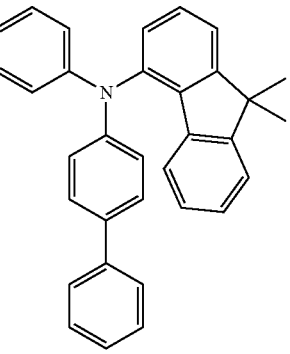

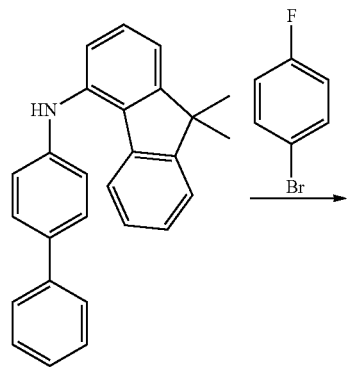

A 1 l four-neck flask is initially charged with 51.3 g (142 mmol, 1.00 eq) of the biphenylamine, and also 75.6 g (426 mmol, 3.00 eq) of 1-bromo-4-fluorobenzene [460-00-4] and 92.5 g (284 mmol, 2.00 eq) of caesium carbonate [534-17-8], and 500 ml of dimethylacetamide were added. The reaction mixture is stirred at 150° C. for three days. After the reaction has ended, the mixture is cooled down to room temperature and the solids are filtered off through Celite. The mother liquor is concentrated and the precipitated solids are filtered and then extracted by stirring with hot methanol. After drying, 43.5 g (135 mmol, 95%) of the colorless product are obtained.

The following compounds are prepared in an analogous manner:

| Reactant 3 | Product 5 | Yield [%] |
|---|---|---|
| h1 | | 78 |

| | Reactant 3 | Product 5 | Yield [%] |
|---|---|---|---|
| h2 | 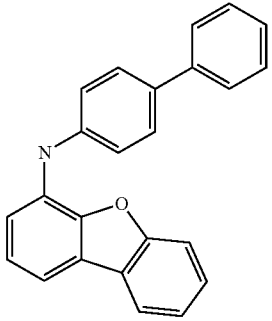 [SMILES: c1ccc(-c2ccc(Nc3cccc4c3oc3ccccc34)cc2)cc1] | 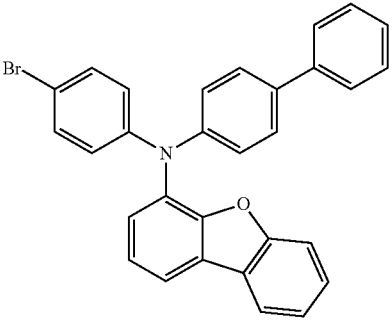 [SMILES: Brc1ccc(N(c2ccc(-c3ccccc3)cc2)c2cccc3c2oc2ccccc23)cc1] | 81 |
| h3 | 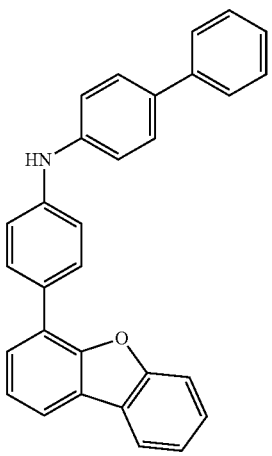 [SMILES: c1ccc(-c2ccc(Nc3ccc(-c4cccc5c4oc4ccccc45)cc3)cc2)cc1] | 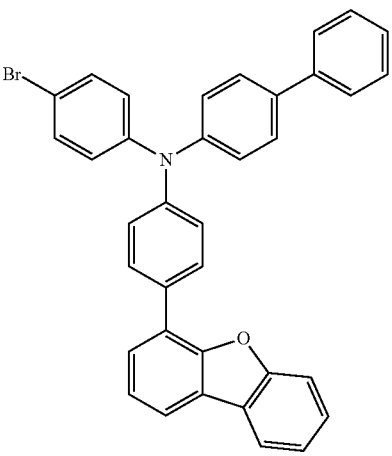 [SMILES: Brc1ccc(N(c2ccc(-c3ccccc3)cc2)c2ccc(-c3cccc4c3oc3ccccc34)cc2)cc1] | 71 |
| h4 | 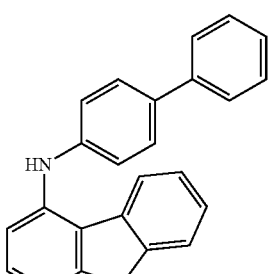 | 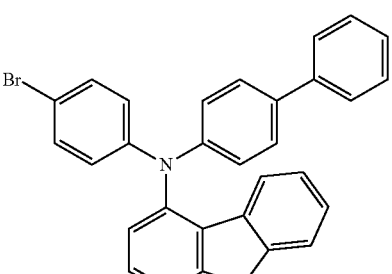 | 65 |
| h5 | 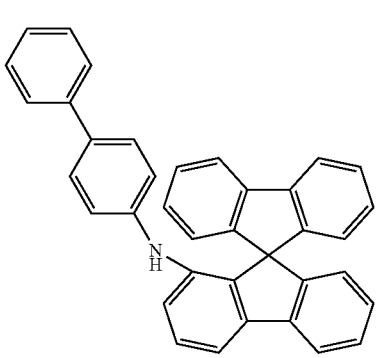 [SMILES: c1ccc(-c2ccc(Nc3cccc4c3C3(c5ccccc5-c5ccccc53)c3ccccc3-4)cc2)cc1] | 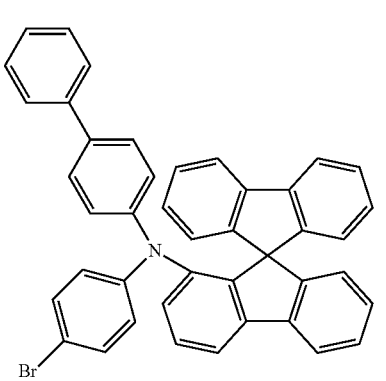 [SMILES: Brc1ccc(N(c2ccc(-c3ccccc3)cc2)c2cccc3c2C2(c4ccccc4-c4ccccc42)c2ccccc2-3)cc1] | 26 |

|  | Reactant 3 | Product 5 | Yield [%] |
|---|---|---|---|
| h6 | 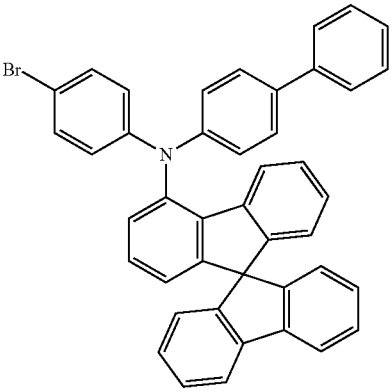 [SMILES: Brc1ccc(N(c2ccc(-c3ccccc3)cc2)c2cccc3c2-c2ccccc2C32c3ccccc3-c3ccccc32)cc1] | | 84 |
| h7 | | | 68 |
| h8 | 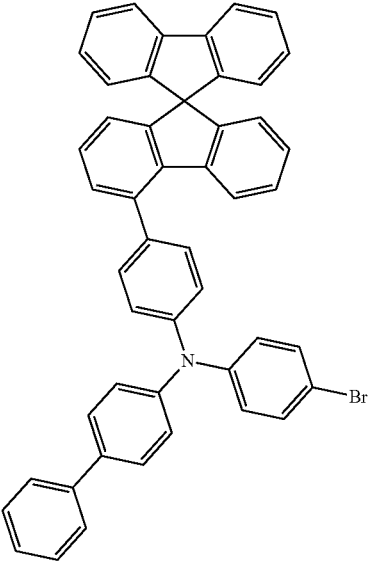 [SMILES: Brc1ccc(N(c2ccc(-c3ccccc3)cc2)c2ccc(-c3cccc4c3-c3ccccc3C43c4ccccc4-c4ccccc43)cc2)cc1] | 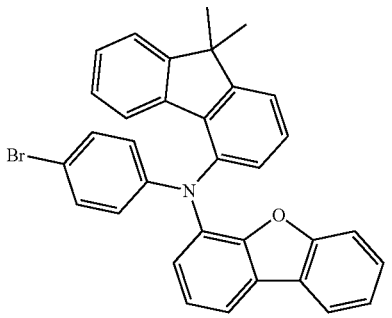 [SMILES: CC1(C)c2ccccc2-c2c(N(c3ccc(Br)cc3)c3cccc4c3oc3ccccc34)cccc21] | 67 |

| | Reactant 3 | Product 5 | Yield [%] |
|---|---|---|---|
| h9 | 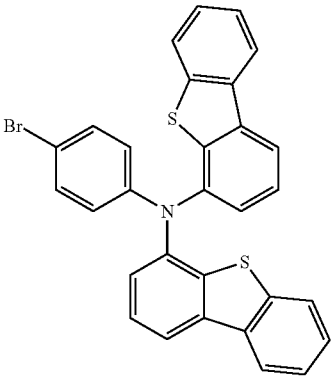 [SMILES: Brc1ccc(N(c2cccc3c2sc2ccccc23)c2cccc3c2sc2ccccc23)cc1] | 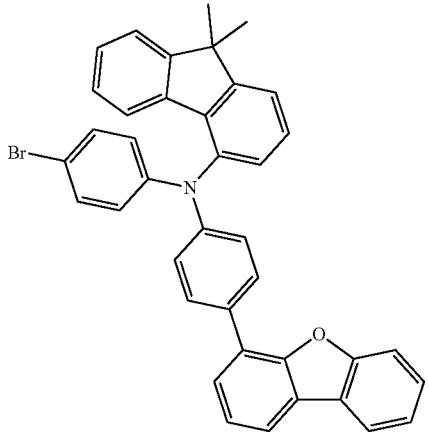 [SMILES: CC1(C)c2ccccc2-c2c(N(c3ccc(Br)cc3)c3ccc(-c4cccc5c4oc4ccccc45)cc3)cccc21] | 56 |
| h10 | | | 44 |
| h11 | 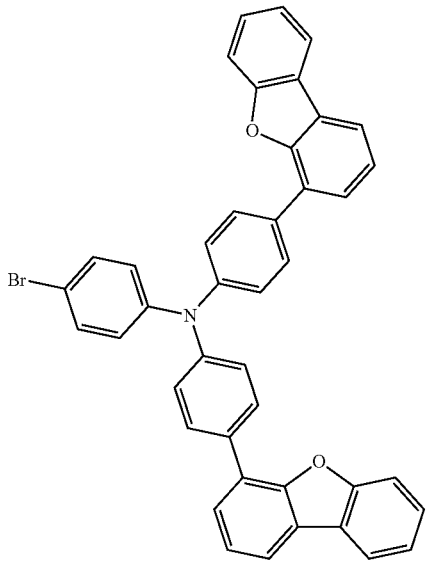 [SMILES: Brc1ccc(N(c2ccc(-c3cccc4c3oc3ccccc34)cc2)c2ccc(-c3cccc4c3oc3ccccc34)cc2)cc1] | | 25 |

-continued

| Reactant 3 | Product 5 | Yield [%] |
|---|---|---|
| h12 | | 59 |
| h13 [102113-98-4] | | 74 |
| h14 | | 70 | j) 1-Bromo-8-iododibenzofuran

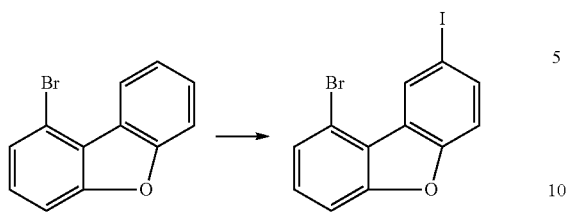

20 g (80 mmol) of dibenzofuran-1-boronic acid, 2.06 g (40.1 mmol) of iodine, 3.13 g (17.8 mmol) of iodic acid, 80 ml of acetic acid, 5 ml of sulphuric acid, 5 ml of water and 2 ml of chloroform are stirred at 65° C. for 3 h. After cooling, the mixture is admixed with water, and the precipitated solids are filtered off with suction and washed three times with water. The residue is recrystallized from toluene and from dichloromethane/heptane. The yield is 25.6 g (68 mmol), corresponding to 85% of theory.

The following compound is prepared in an analogous manner:

| | Reactant 1 | Product | Yield |
|---|---|---|---|
| j1 | Br-dibenzothiophene [65642-94-6] | Br-I-dibenzothiophene | 81% | i) 3-(9-Bromodibenzofuran-2-yl)-9-phenyl-9H-carbazole

58 g (156 mmol) of 1-bromo-8-iododibenzofuran, 50 g (172 mmol) of N-phenylcarbazole-3-boronic acid and 36 g (340 mmol) of sodium carbonate are suspended in 1000 ml of ethylene glycol dimethyl ether and 280 ml of water. 1.8 g (1.5 mmol) of tetrakis(triphenylphosphine)palladium(0) are added to this suspension, and the reaction mixture is heated under reflux for 16 h. After cooling, the organic phase is removed, filtered through silica gel, washed three times with 200 ml of water and then concentrated to dryness. The yield is 48 g (89 mmol), corresponding to 64% of theory.

The following compounds are prepared in an analogous manner:

| | Reactant 1 | Reactant 2 | Product | Yield [%] |
|---|---|---|---|---|
| i1 | Br-dibenzofuran-I | deuterated N-phenylcarbazole-Bpin [1807978-29-5] | deuterated product | 67 |

-continued
| Reactant 1 | Reactant 2 | Product | Yield [%] |
|---|---|---|---|
| i2 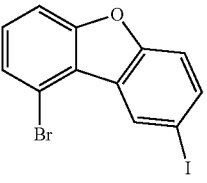 [SMILES: Brc1cccc2oc3ccc(I)cc3c12] | 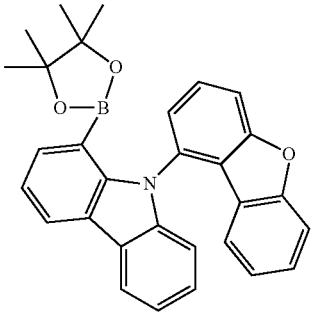 [1807910-31-1] | 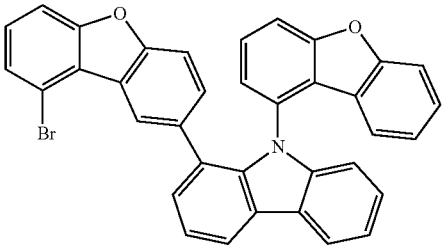 [SMILES: Brc1cccc2oc3ccc(-c4cccc5c6ccccc6n(-c6cccc7oc8ccccc8c67)c45)cc3c12] | 65 |
| i3 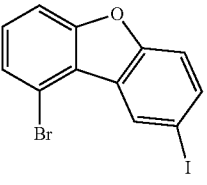 [SMILES: Brc1cccc2oc3ccc(I)cc3c12] | 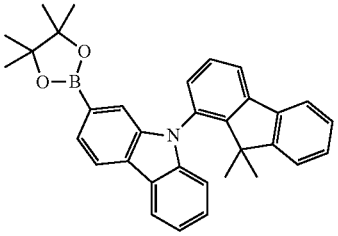 [1807910-29-7] | 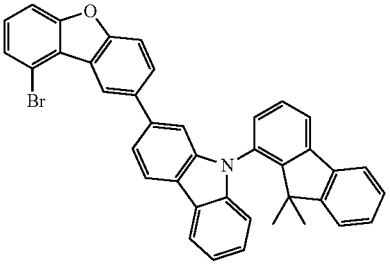 [SMILES: CC1(C)c2ccccc2-c2cccc(-n3c4ccccc4c4ccc(-c5ccc6oc7cccc(Br)c7c6c5)cc43)c21] | 60 |
| i4 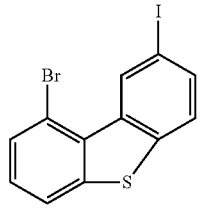 [SMILES: Brc1cccc2sc3ccc(I)cc3c12] | 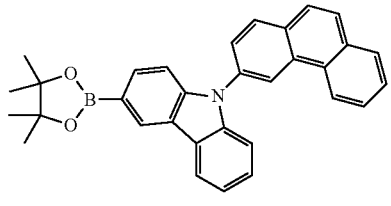 [1801609-54-0] | 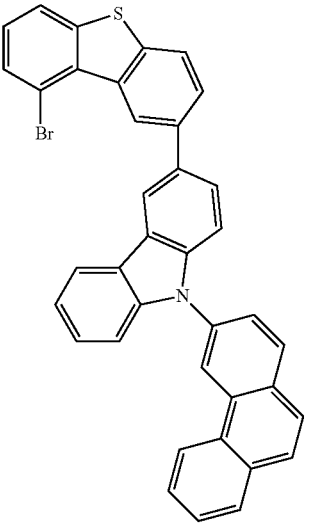 [SMILES: Brc1cccc2sc3ccc(-c4ccc5c(c4)c4ccccc4n5-c4ccc5ccc6ccccc6c5c4)cc3c12] | 63 |
| i5 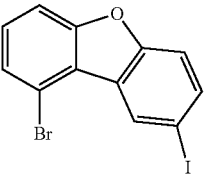 [SMILES: Brc1cccc2oc3ccc(I)cc3c12] | 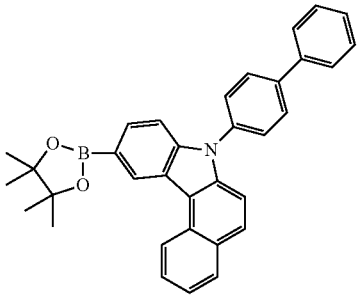 1493716-02-1] | 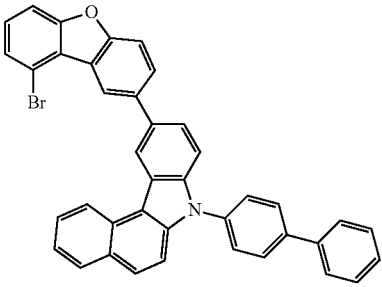 [SMILES: Brc1cccc2oc3ccc(-c4ccc5c(c4)c4c6ccccc6ccc4n5-c4ccc(-c5ccccc5)cc4)cc3c12] | 61 |

-continued
| | Reactant 1 | Reactant 2 | Product | Yield [%] |
|---|---|---|---|---|
| i6 | 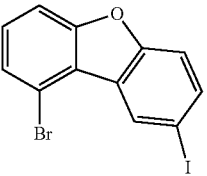 [SMILES: Brc1cccc2oc3ccc(I)cc3c12] | 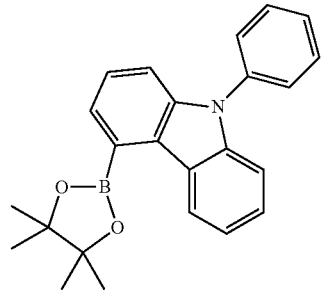<br>[1547492-13-6] | 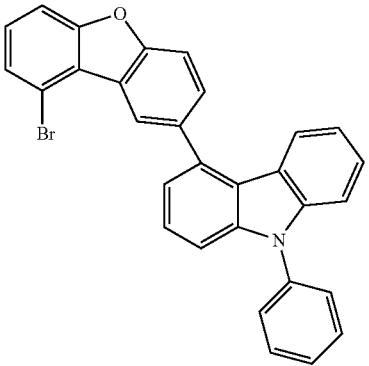 [SMILES: Brc1cccc2oc3ccc(-c4cccc5c4c4ccccc4n5-c4ccccc4)cc3c12] | 60 |
| i7 | 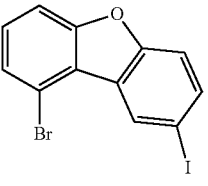 [SMILES: Brc1cccc2oc3ccc(I)cc3c12] | 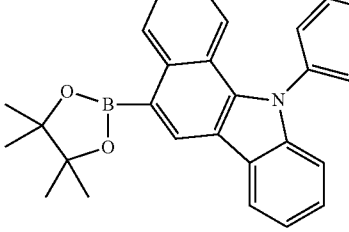<br>[1493715-37-9] | 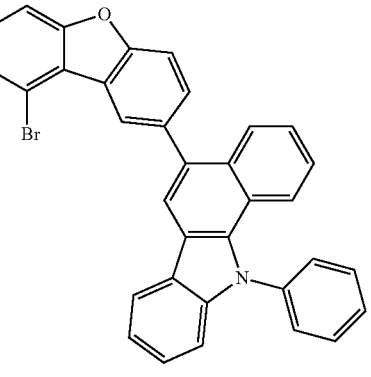 | 56 |
| i8 | 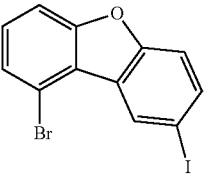 [SMILES: Brc1cccc2oc3ccc(I)cc3c12] | 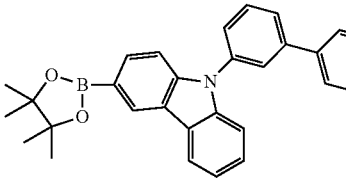<br>[1416814-68-0] | 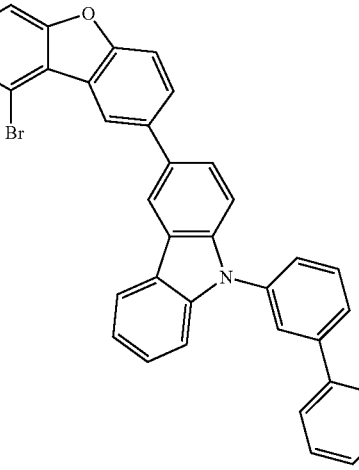 | 68 |
| i9 | 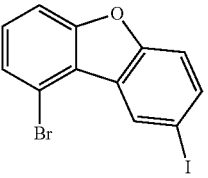 [SMILES: Brc1cccc2oc3ccc(I)cc3c12] | 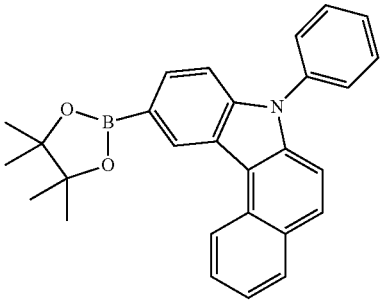<br>[1246562-39-9] | 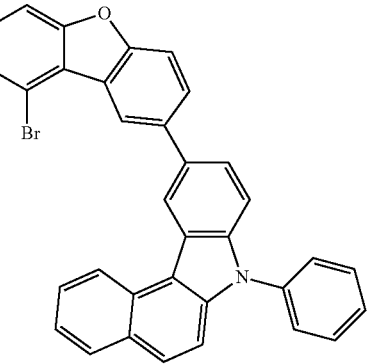 | 67 |

-continued
| Reactant 1 | Reactant 2 | Product | Yield [%] |
|---|---|---|---|
| i10 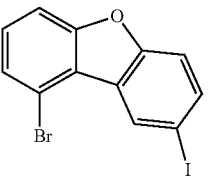 [SMILES: Brc1cccc2oc3ccc(I)cc3c12] | 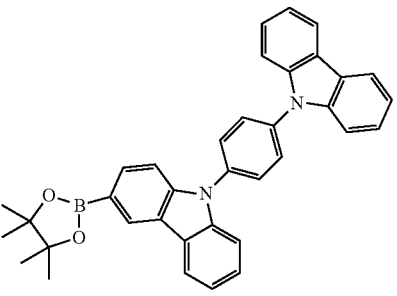 [1240963-83-0] | 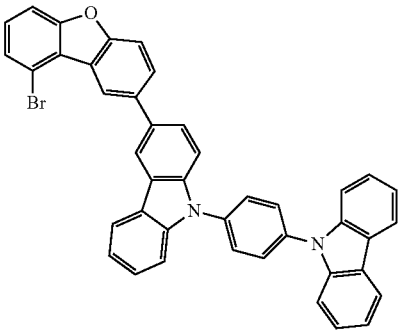 [SMILES: Brc1cccc2oc3ccc(-c4ccc5c(c4)c4ccccc4n5-c4ccc(-n5c6ccccc6c6ccccc65)cc4)cc3c12] | 66 |
| i11 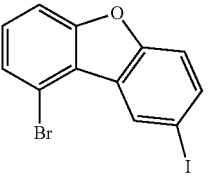 [SMILES: Brc1cccc2oc3ccc(I)cc3c12] | 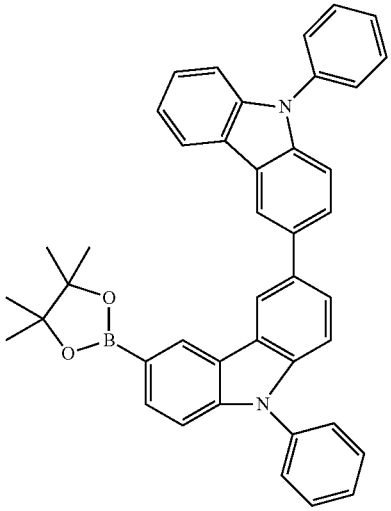 [1572537-61-1] | 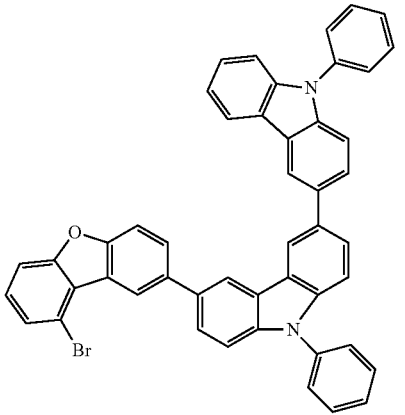 [SMILES: Brc1cccc2oc3ccc(-c4ccc5c(c4)c4cc(-c6ccc7c(c6)c6ccccc6n7-c6ccccc6)ccc4n5-c4ccccc4)cc3c12] | 60 |
| i12 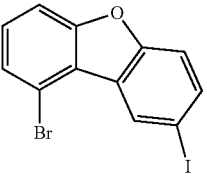 [SMILES: Brc1cccc2oc3ccc(I)cc3c12] | 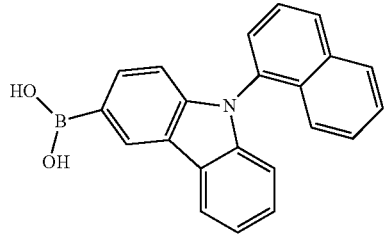 [1133057-97-2] | 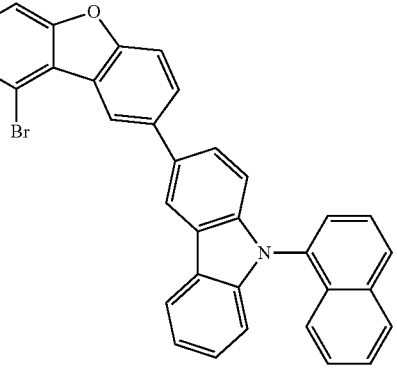 | 63 |

| | | | Yield [%] |
|---|---|---|---|
| Reactant 1 | Reactant 2 | Product | |
| i13 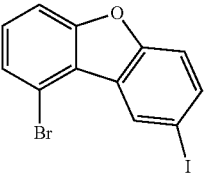 [SMILES: Brc1cccc2oc3ccc(I)cc3c12] | 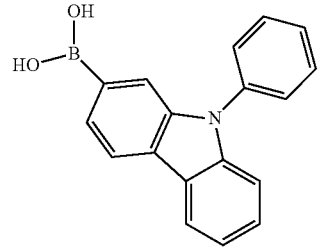<br>[1001911-62-2] | 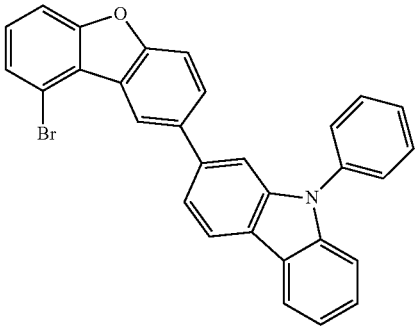 [SMILES: Brc1cccc2oc3ccc(-c4ccc5c6ccccc6n(-c6ccccc6)c5c4)cc3c12] | 62 |
| i14 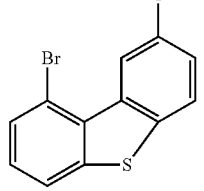 | 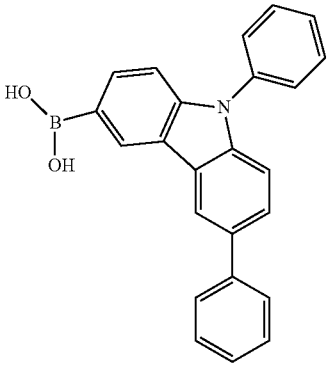<br>[1133058-06-6] | 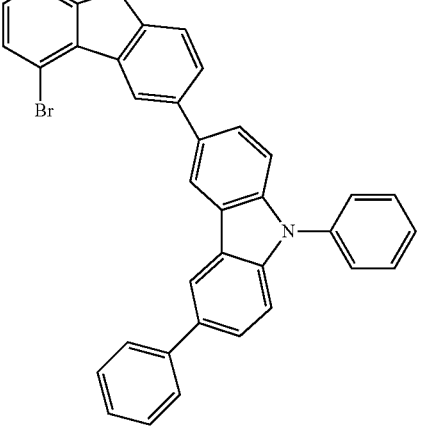 | 59 |
| i15 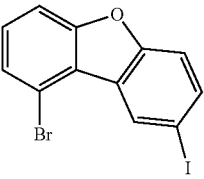 [SMILES: Brc1cccc2oc3ccc(I)cc3c12] | 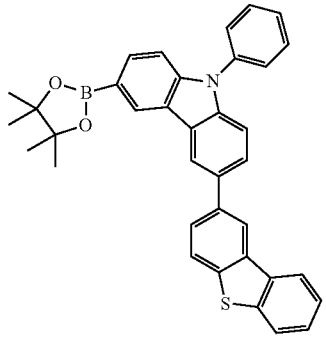<br>[1582801-74-8] | 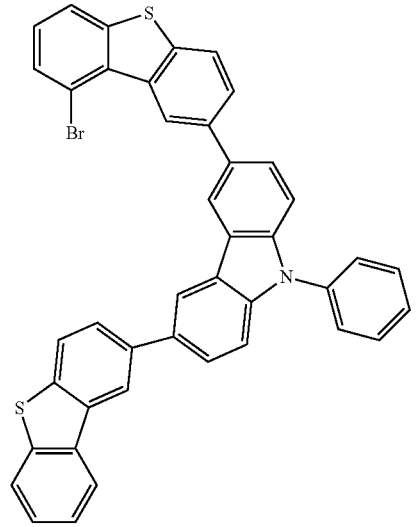 | 65 |

-continued

| | Reactant 1 | Reactant 2 | Product | Yield [%] |
|---|---|---|---|---|
| i16 | 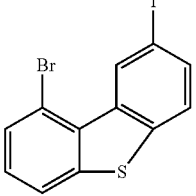 | 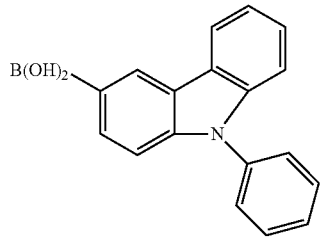 854952-58-2 | 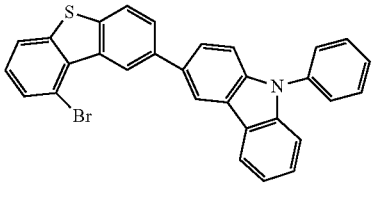 [SMILES: Brc1cccc2sc3ccc(-c4ccc5c(c4)c4ccccc4n5-c4ccccc4)cc3c12] | 57 | k) Biphenyl-4-yl-(9,9-dimethyl-9H-fluoren-4-yl)-[8-(9-phenyl-9H-carbazol-3-yl)dibenzofuran-1-yl]amine

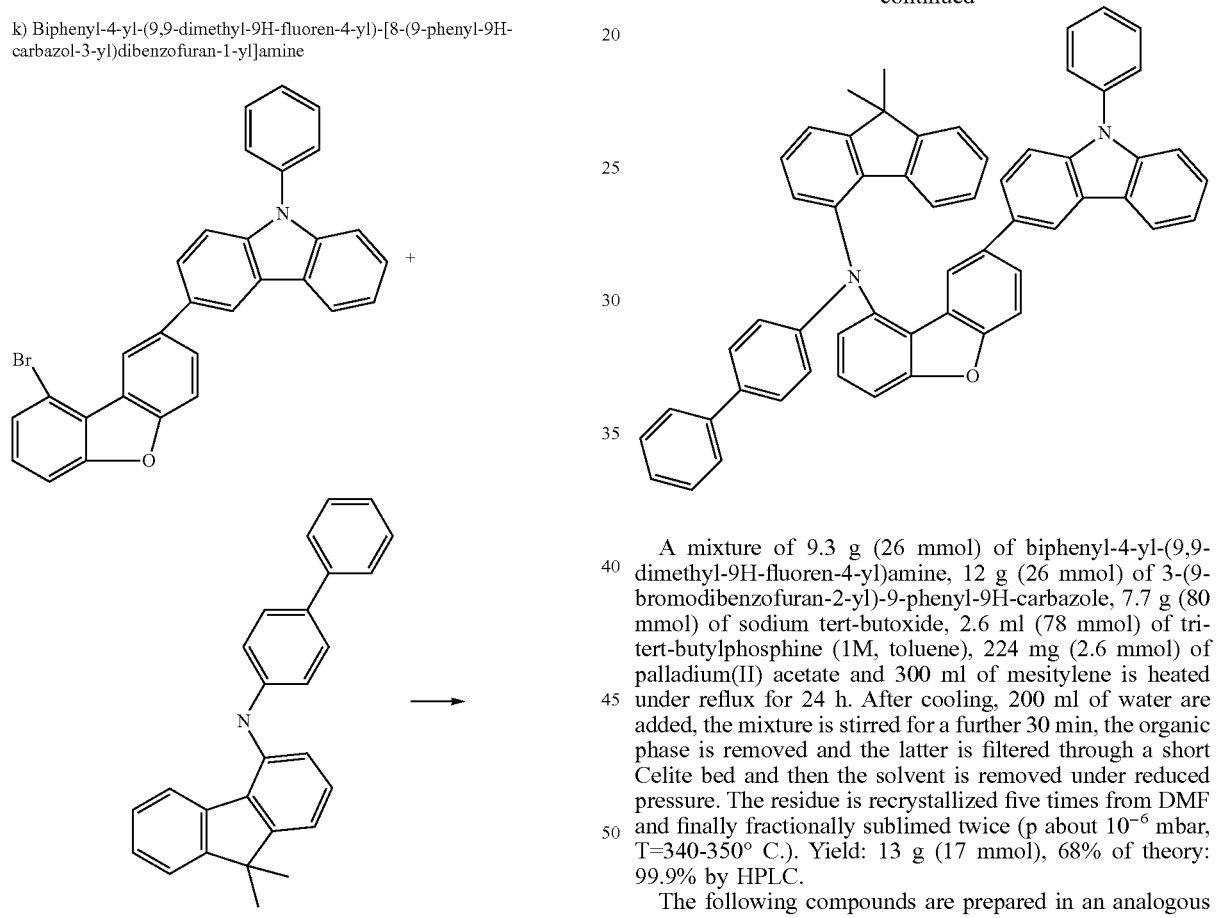

A mixture of 9.3 g (26 mmol) of biphenyl-4-yl-(9,9-dimethyl-9H-fluoren-4-yl)amine, 12 g (26 mmol) of 3-(9-bromodibenzofuran-2-yl)-9-phenyl-9H-carbazole, 7.7 g (80 mmol) of sodium tert-butoxide, 2.6 ml (78 mmol) of tri-tert-butylphosphine (1M, toluene), 224 mg (2.6 mmol) of palladium(II) acetate and 300 ml of mesitylene is heated under reflux for 24 h. After cooling, 200 ml of water are added, the mixture is stirred for a further 30 min, the organic phase is removed and the latter is filtered through a short Celite bed and then the solvent is removed under reduced pressure. The residue is recrystallized five times from DMF and finally fractionally sublimed twice (p about $10^{-6}$ mbar, T=340-350° C.). Yield: 13 g (17 mmol), 68% of theory: 99.9% by HPLC.

The following compounds are prepared in an analogous manner:

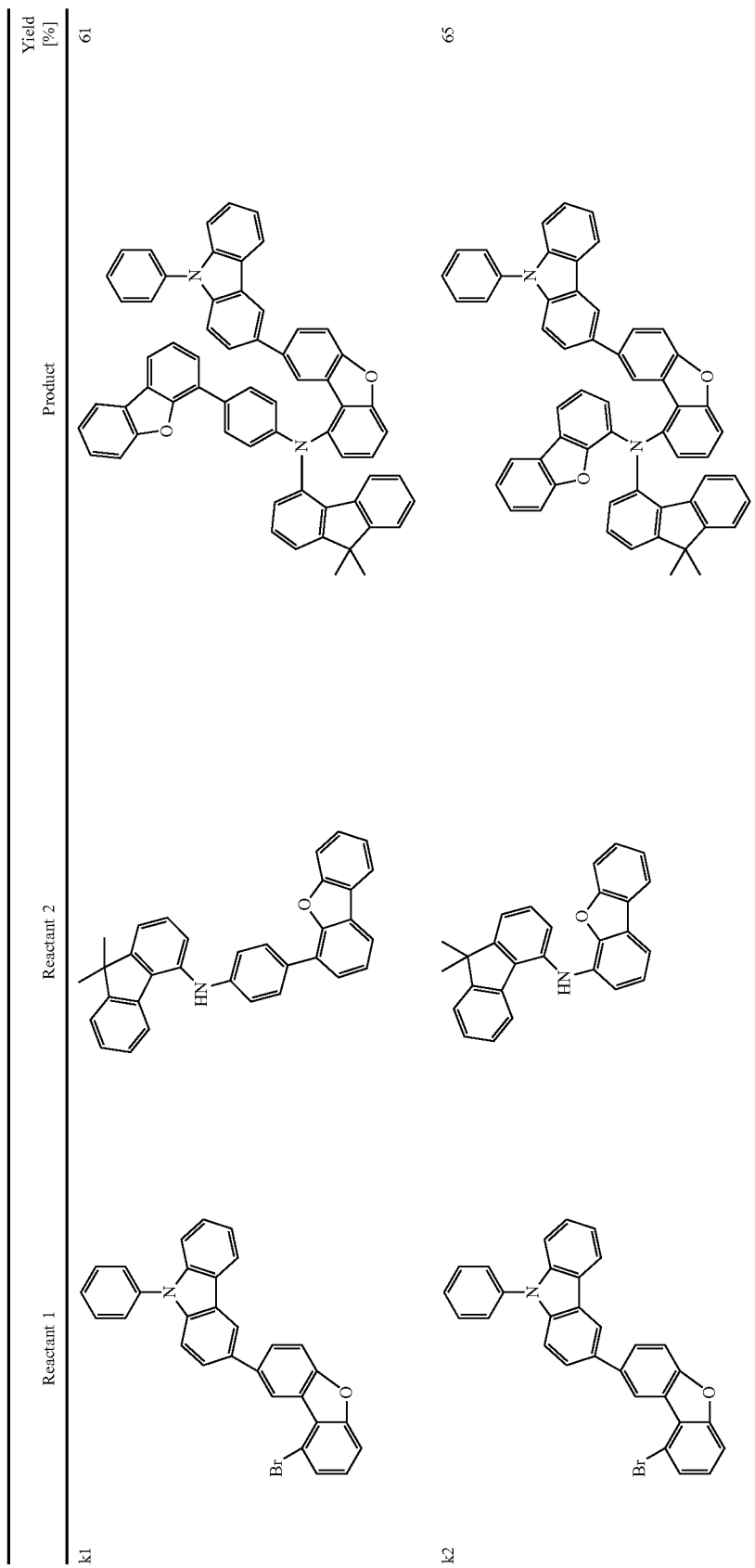

-continued
| | Reactant 1 | Reactant 2 | Product | Yield [%] |
|---|---|---|---|---|
| k3 | 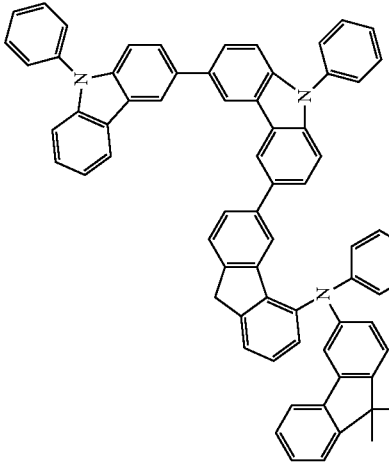 | 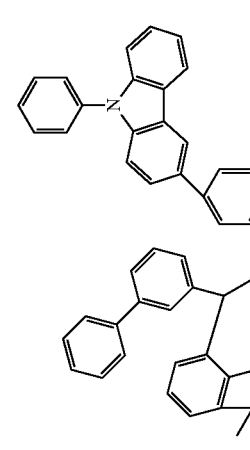  [1776969-70-0] | 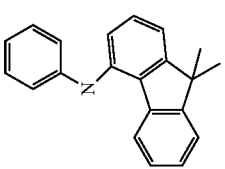 | 57 |
| k4 | 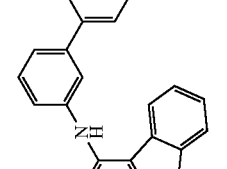 | 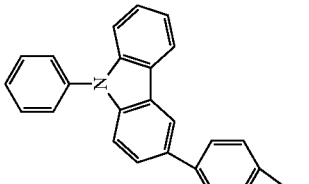  1454679-22-1 | 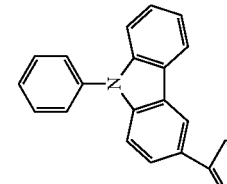 | 72 |

| | Reactant 1 | Reactant 2 | Product | Yield [%] |
|---|---|---|---|---|
| k5 | | | | 63 |
| k6 | | | | 62 |
| k7 | | | | 54 |

| | Reactant 1 | Reactant 2 | Product | Yield [%] |
|---|---|---|---|---|
| k8 | | [1776969-70-0] | | 51 |
| k9 | | | | 53 |

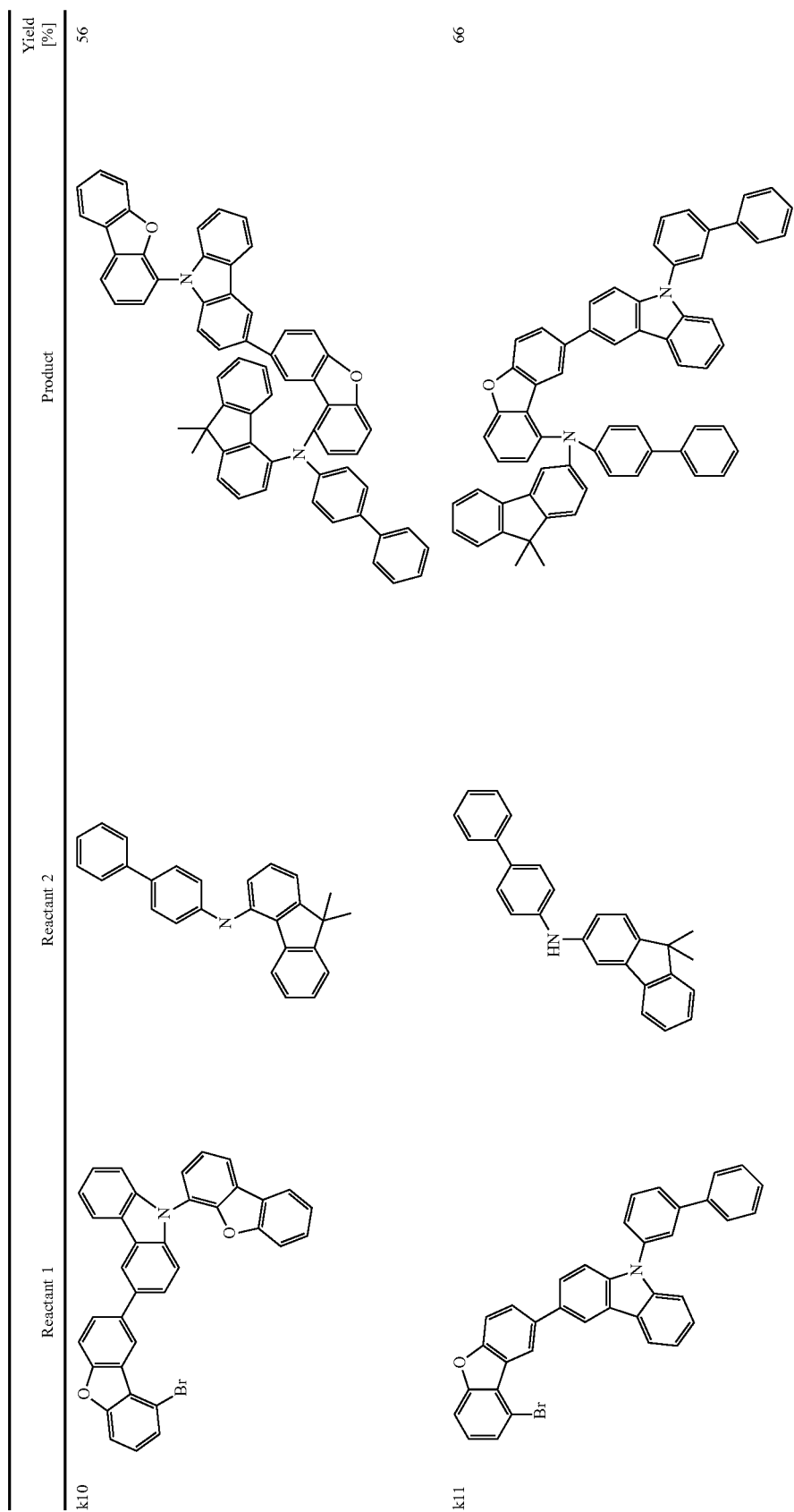

-continued
| | Reactant 1 | Reactant 2 | Product | Yield [%] |
|---|---|---|---|---|
| k12 | | | | 57 |
| k13 | | | | 61 |
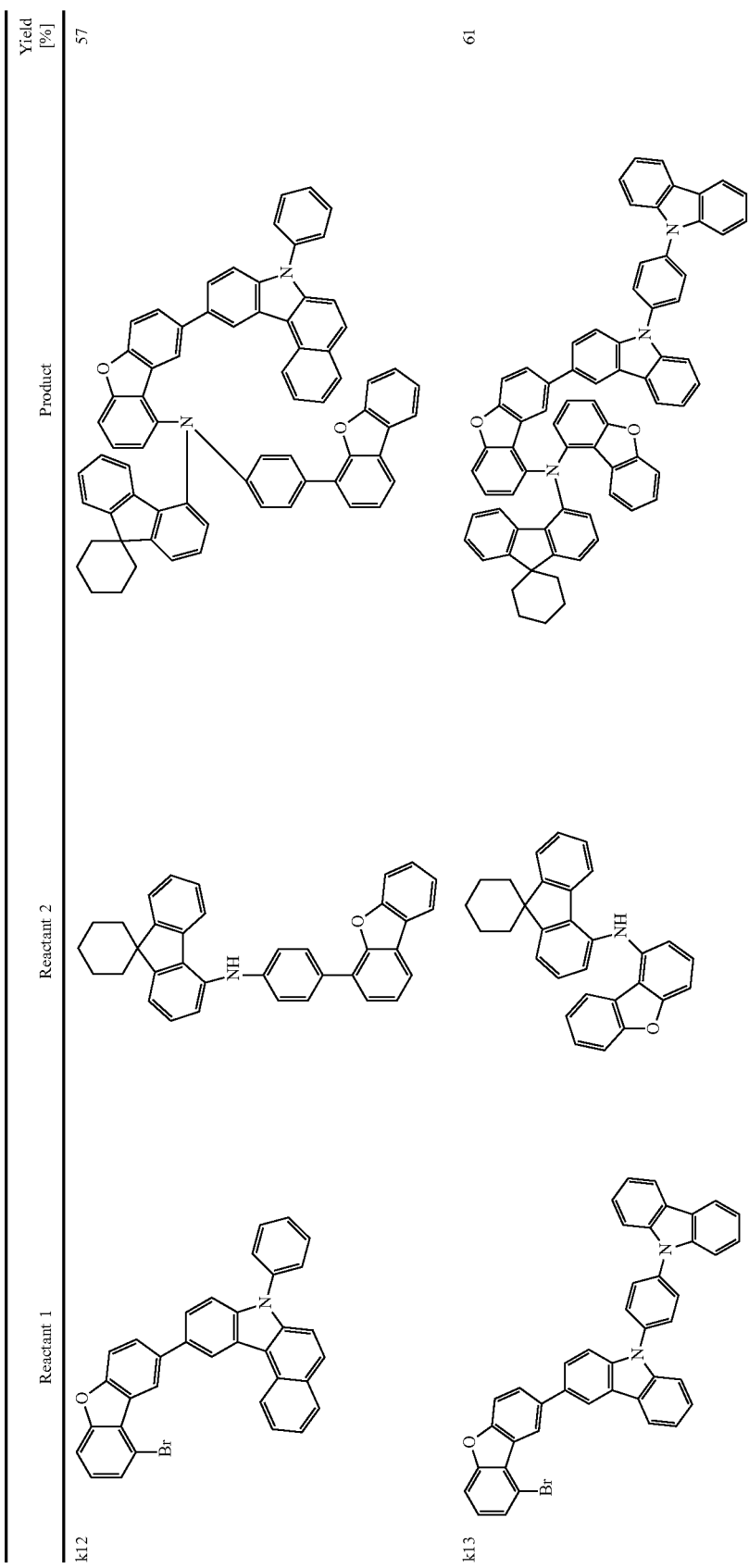

| | Reactant 1 | Reactant 2 | Product | Yield [%] |
|---|---|---|---|---|
| k14 | | | | 52 |
| k15 | | | | 54 |

-continued

| | Reactant 1 | Reactant 2 | Product | Yield [%] |
|---|---|---|---|---|
| k16 | | | | 57 |
| k17 | | | | 61 |
| k18 | | | | 60 |

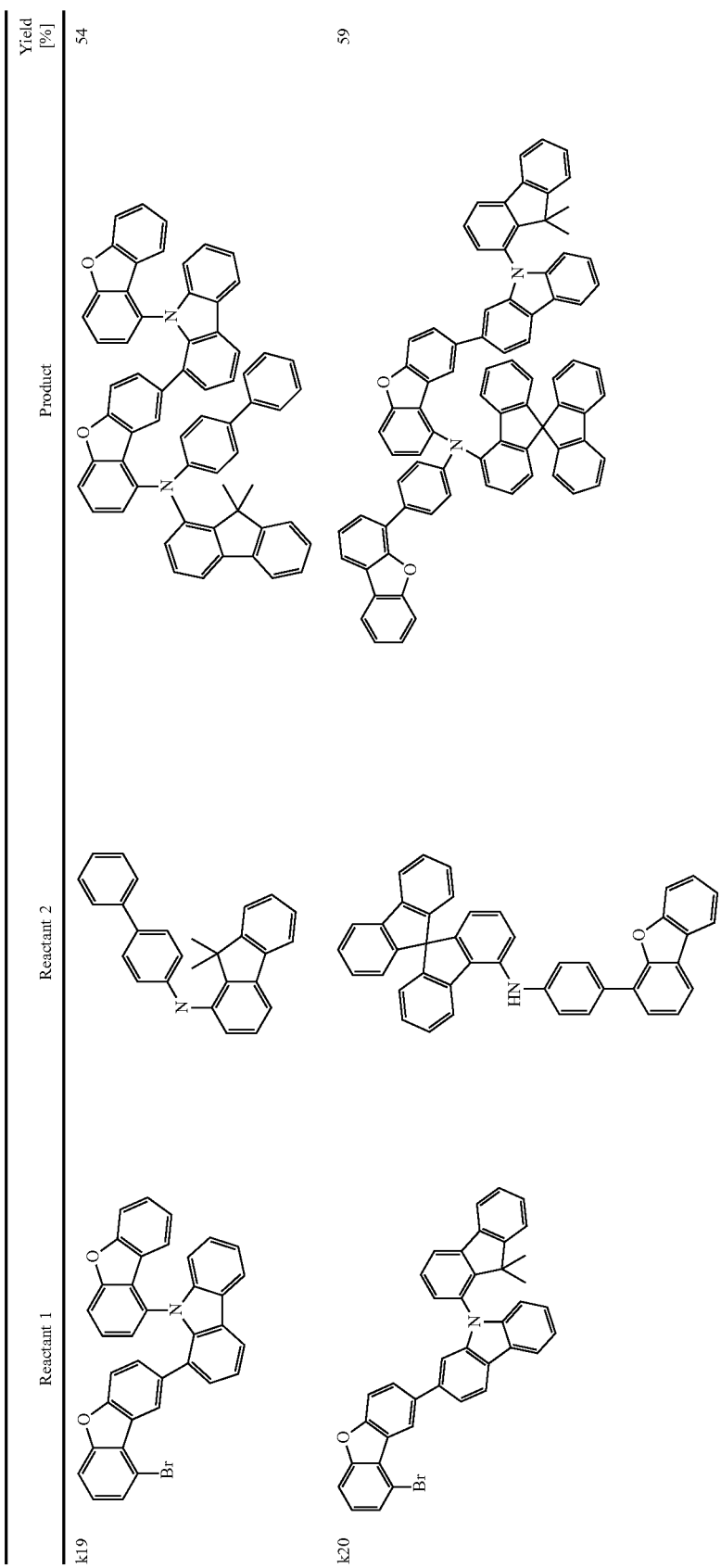

-continued

| | Reactant 1 | Reactant 2 | Product | Yield [%] |
|---|---|---|---|---|
| k21 | | [1579281-06-3] | | 62 |
| k22 | | | | 61 |

| | Reactant 1 | Reactant 2 | Product | Yield [%] |
|---|---|---|---|---|
| k23 | 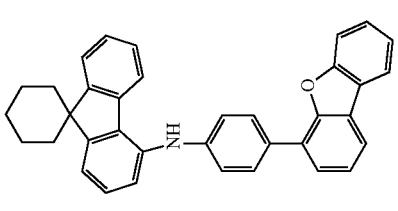 | 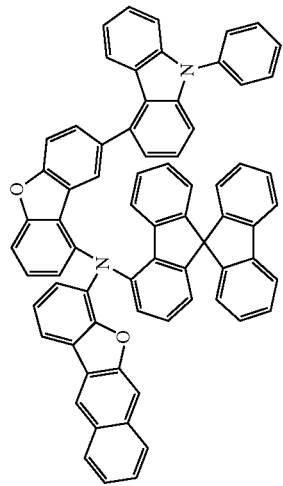 | 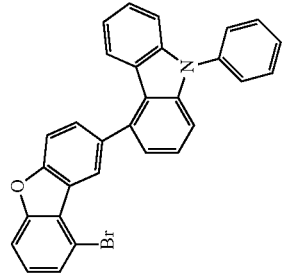 | 53 |
| k24 | 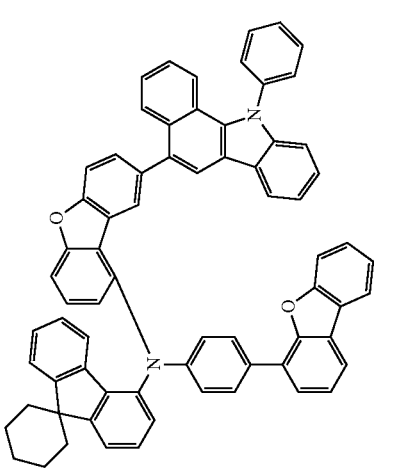 | 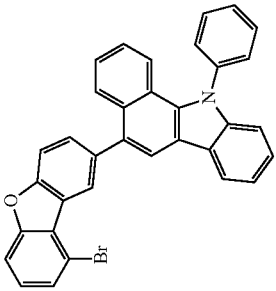 | 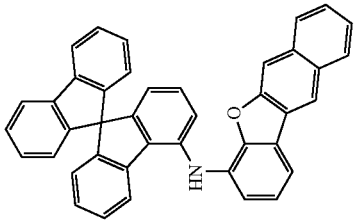 | 50 |

| | Reactant 1 | Reactant 2 | Product | Yield [%] |
|---|---|---|---|---|
| k25 | | | | 61 |
| k26 | | | | 65 |
| k27 | | | | 67 |

| | Reactant 1 | Reactant 2 | Product | Yield [%] |
|---|---|---|---|---|
| k28 | 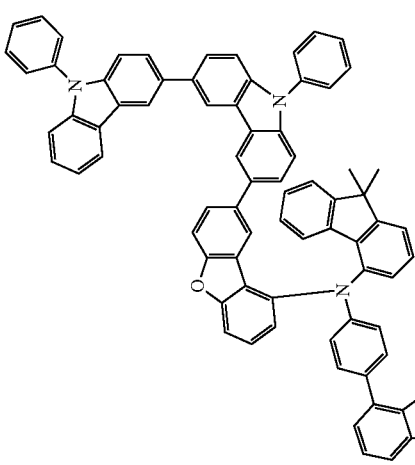 | 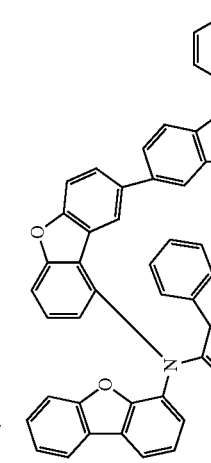 | 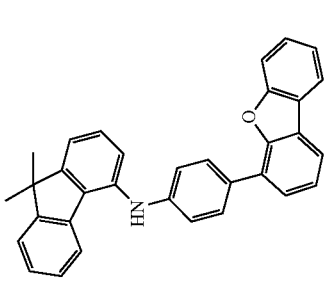 | 52 |
| k29 | 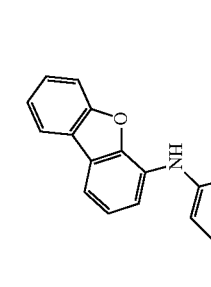 | 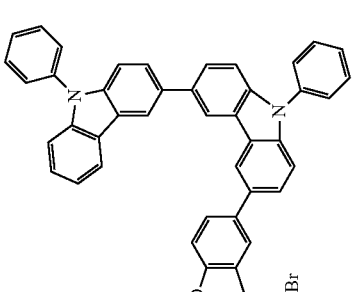 | 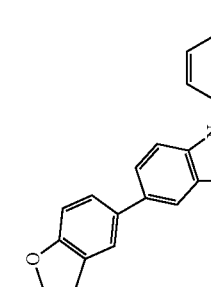 | 68 |

| | Reactant 1 | Reactant 2 | Product | Yield [%] |
|---|---|---|---|---|
| k30 | | | | 71 |
| k31 | | | | 65 |

| | Reactant 1 | Reactant 2 | Product | Yield [%] |
|---|---|---|---|---|
| k32 | 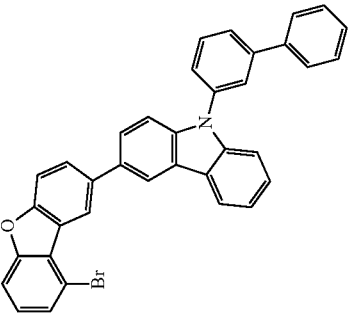 | 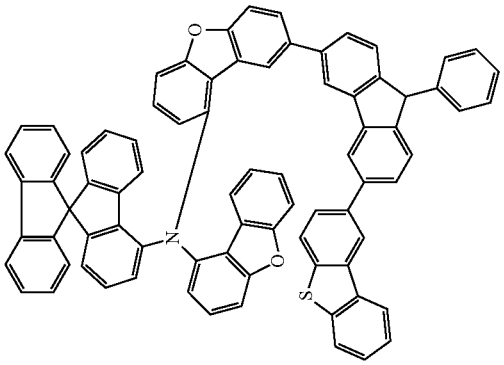 [1579281-06-3] | 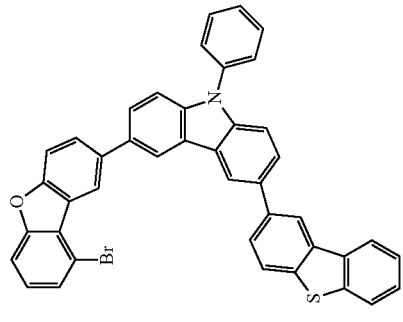 | 64 |
| k33 | 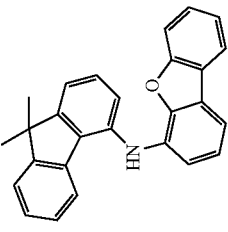 | 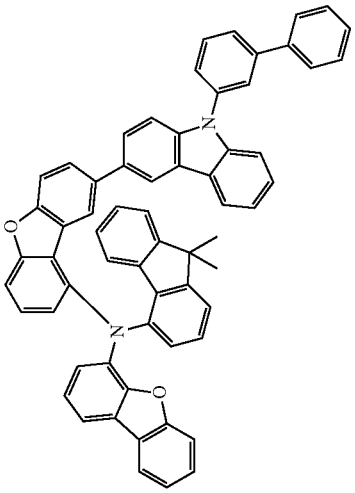 | 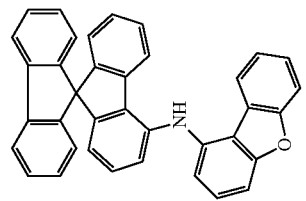 | 61 |

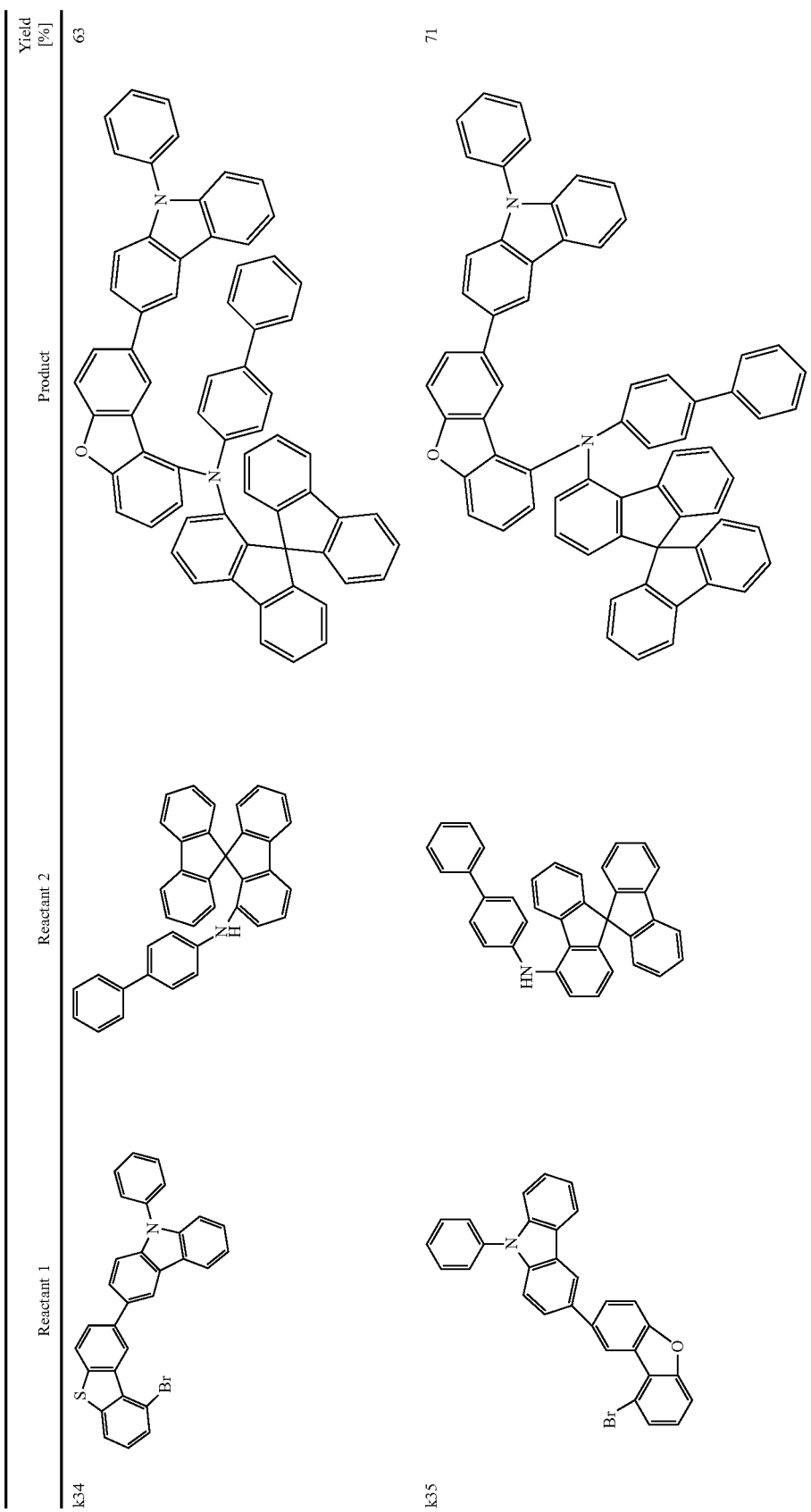

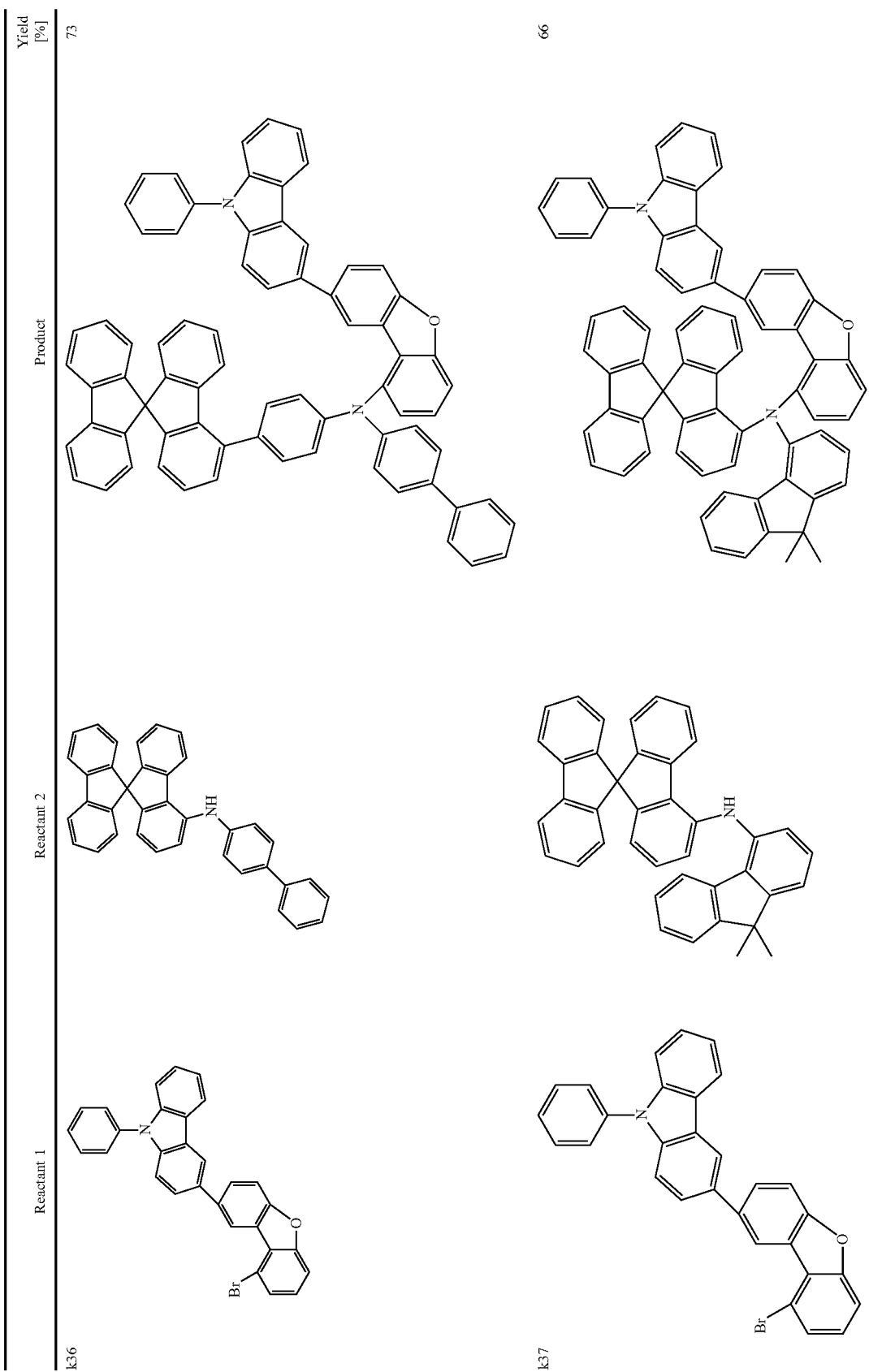

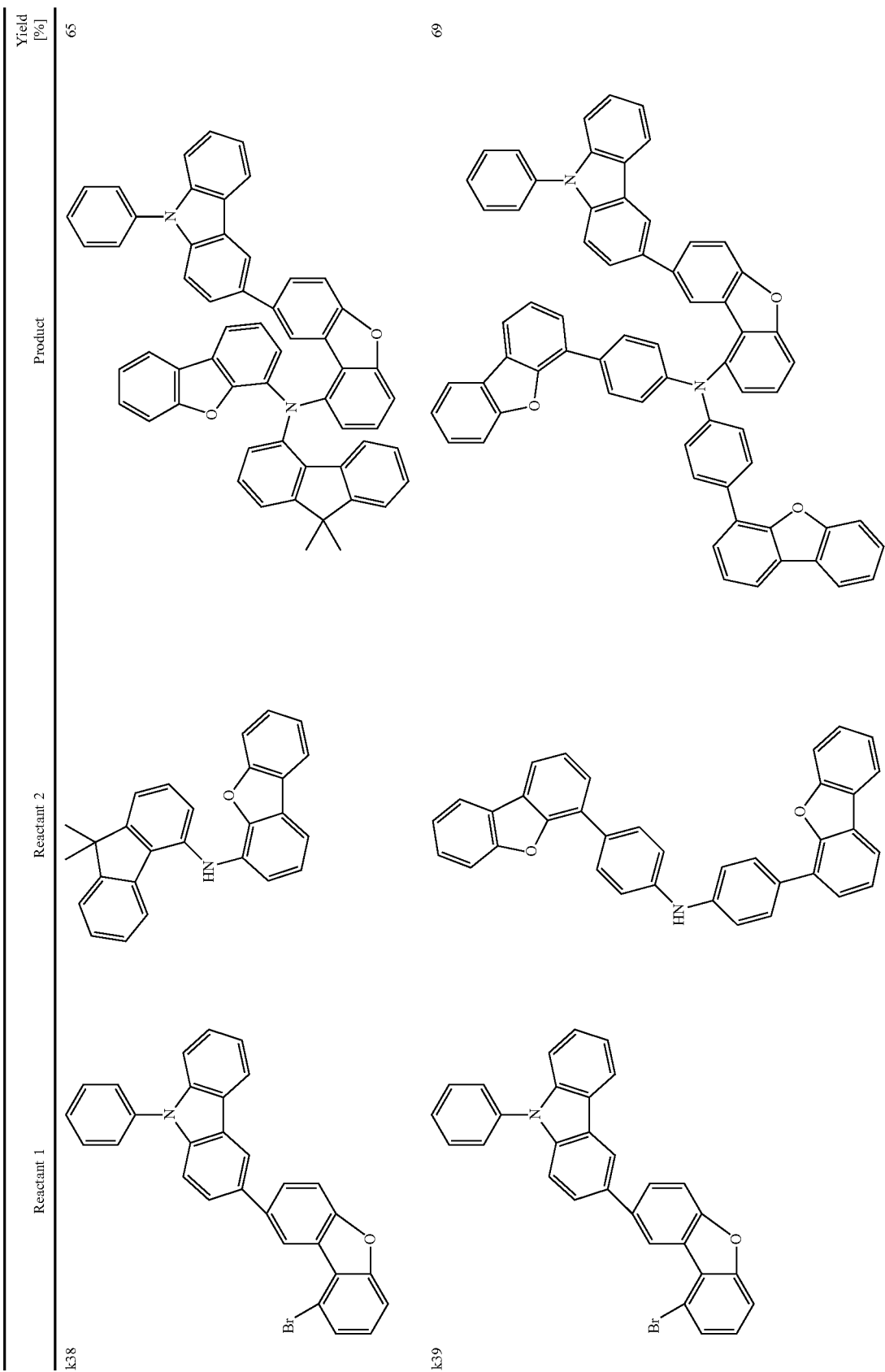

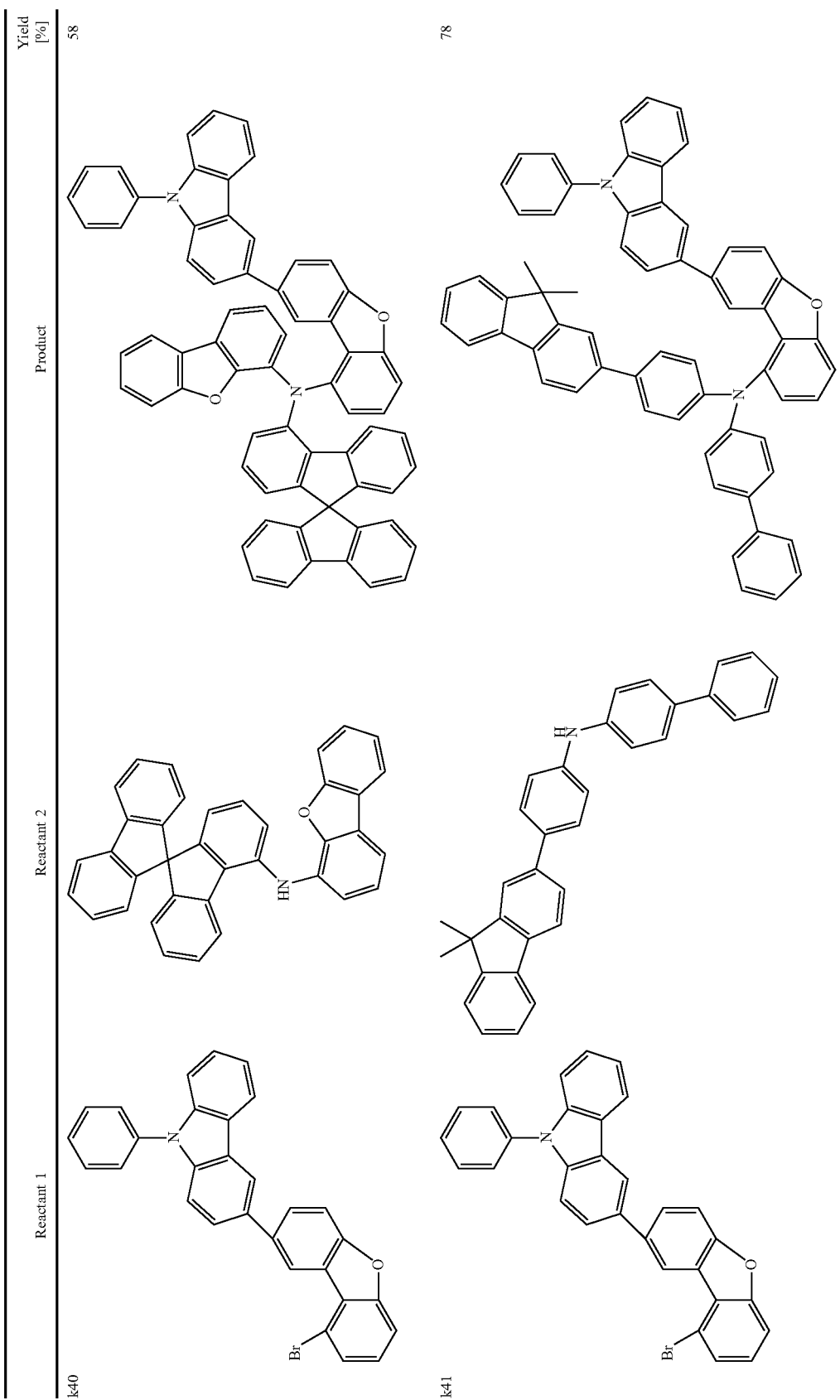

| | Reactant 1 | Reactant 2 | Product | Yield [%] |
|---|---|---|---|---|
| k42 | 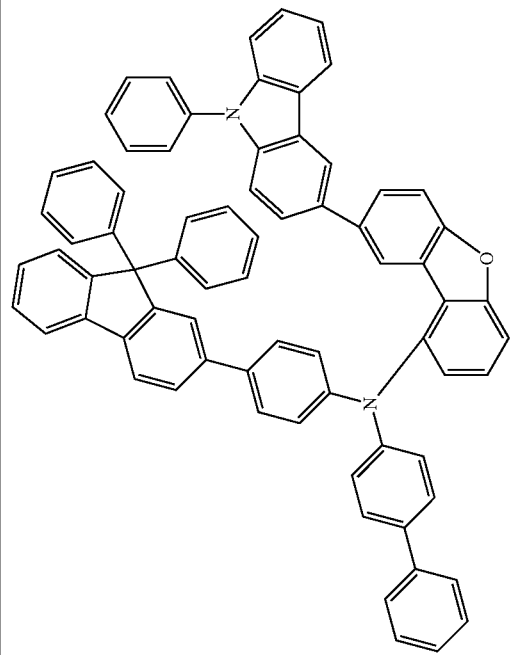 | 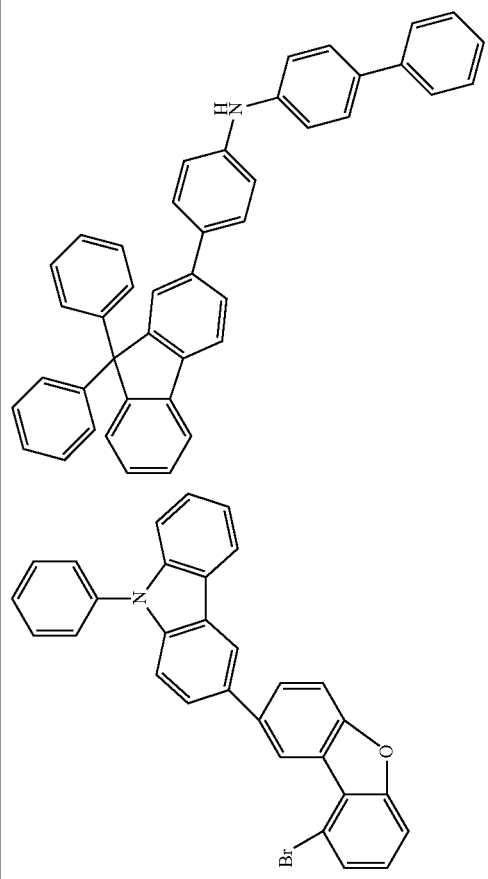 | 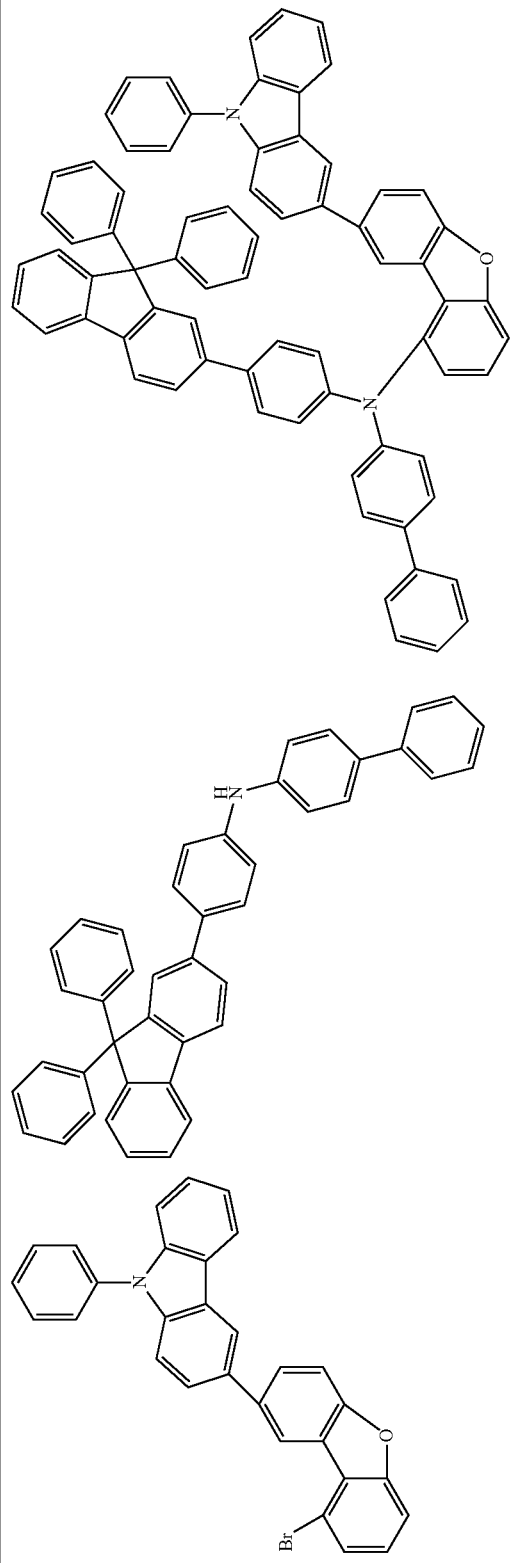 | 77 |

| | Reactant 1 | Reactant 2 | Product | Yield [%] |
|---|---|---|---|---|
| k43 | 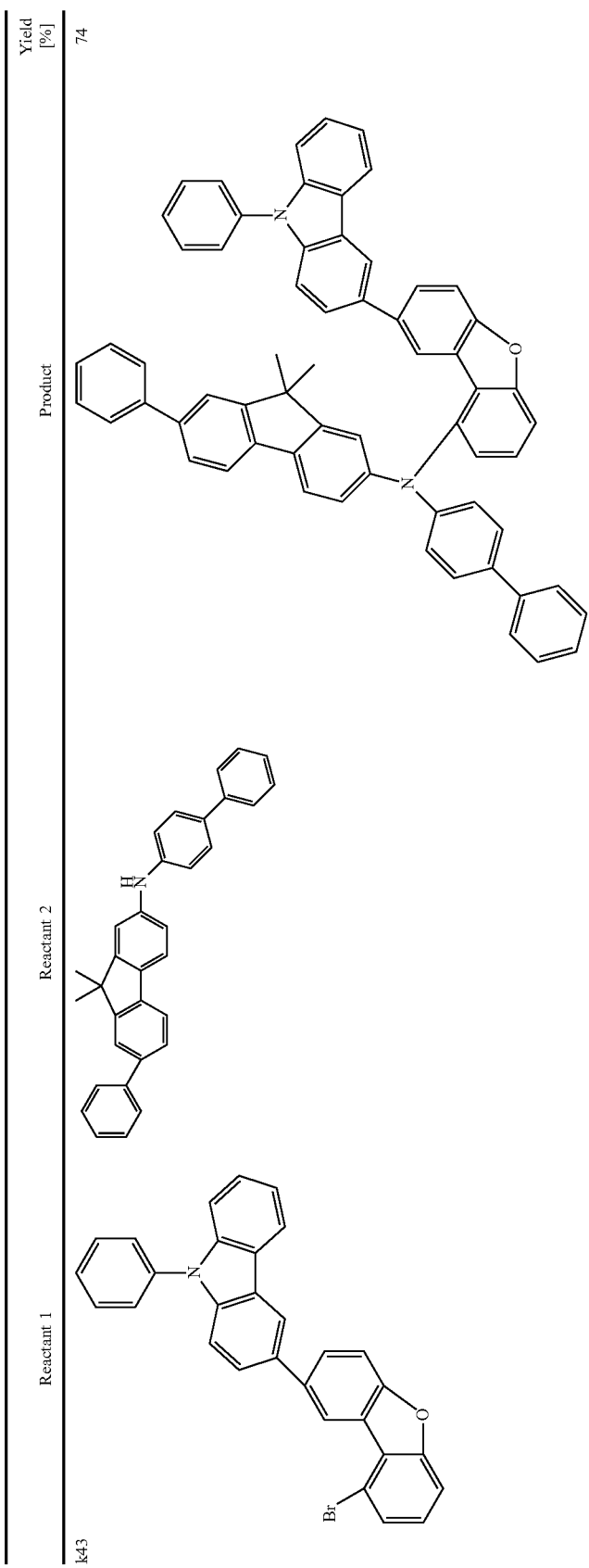 | | | 74 |

-continued
| Reactant 1 | Reactant 2 | Product | Yield [%] |
|---|---|---|---|
| k44 | 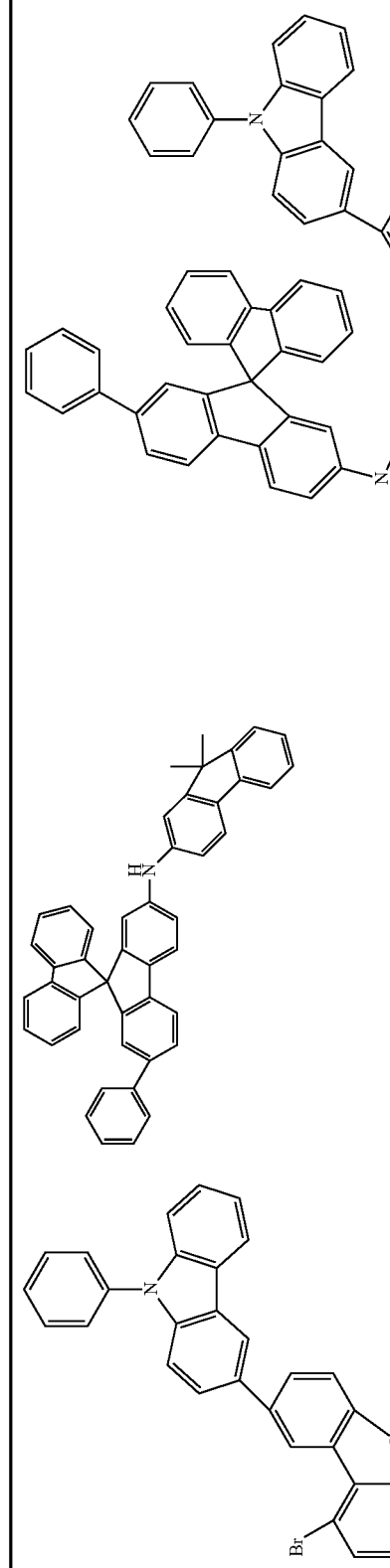 | 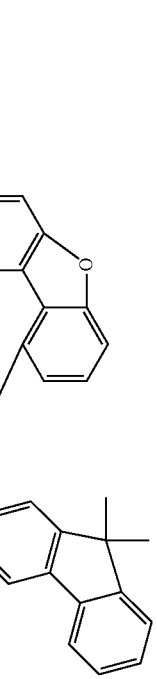 | 70 |

| | Reactant 1 | Reactant 2 | Product | Yield [%] |
|---|---|---|---|---|
| k45 | | | | 63 |
| k46 | | | | 72 |

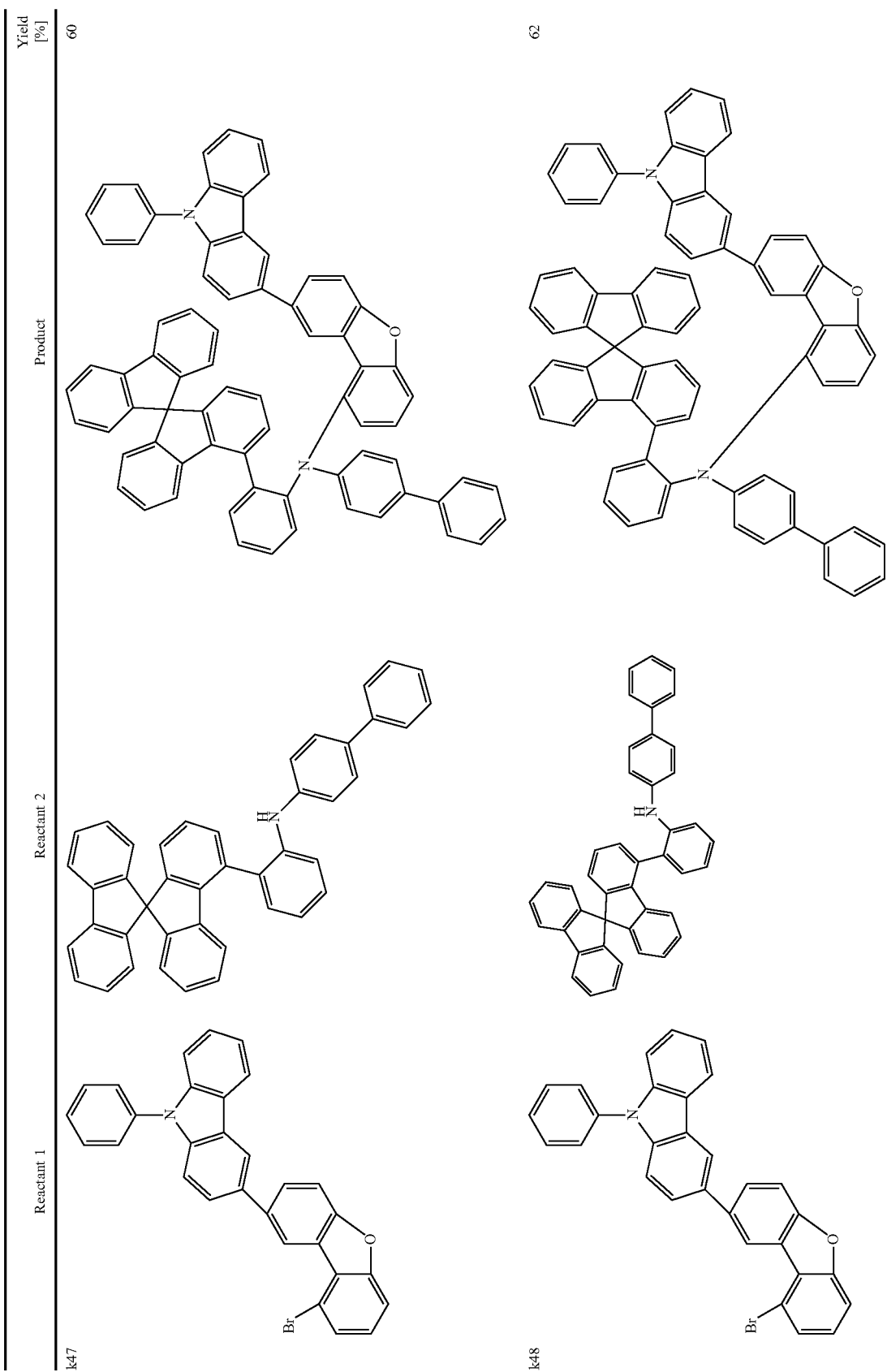

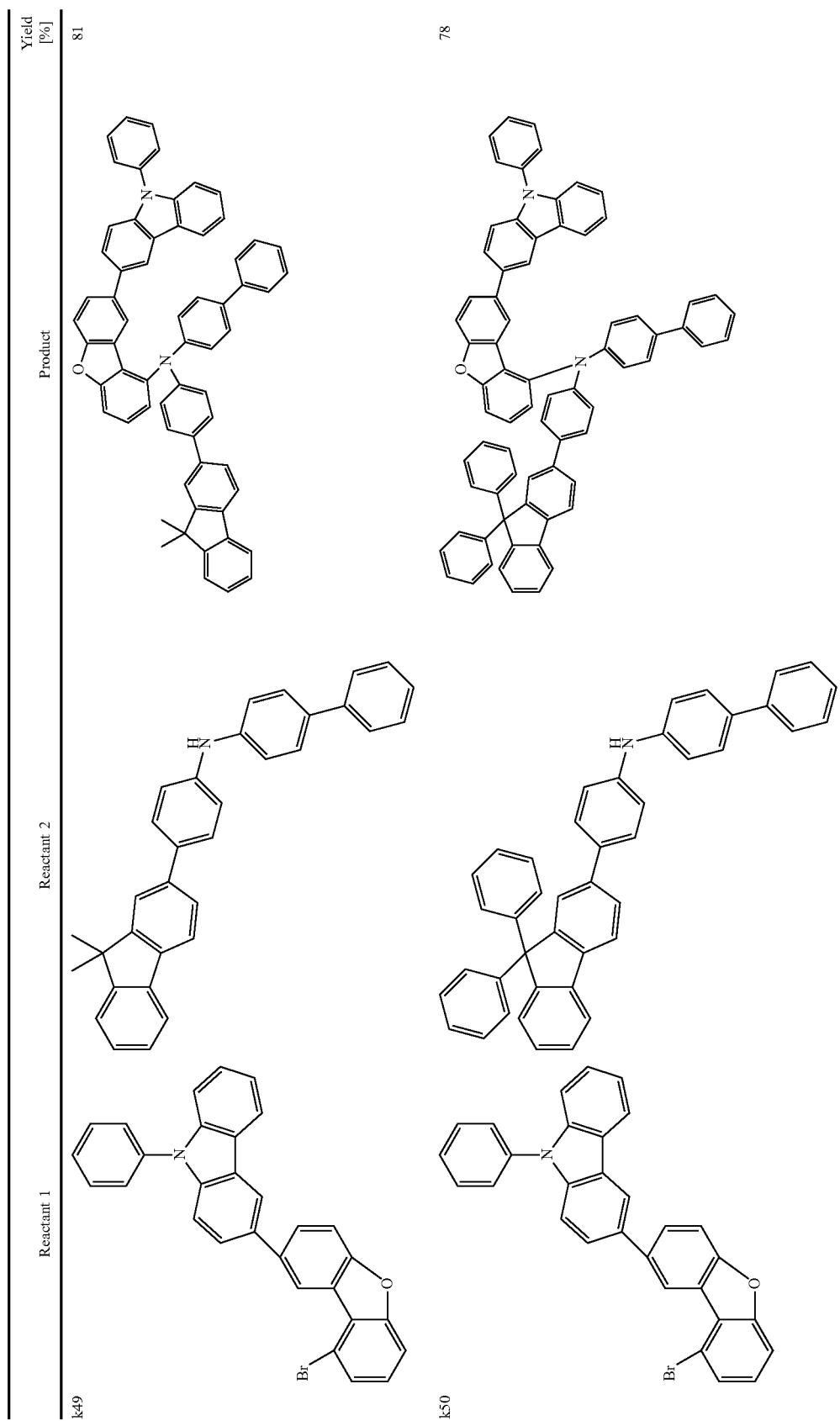

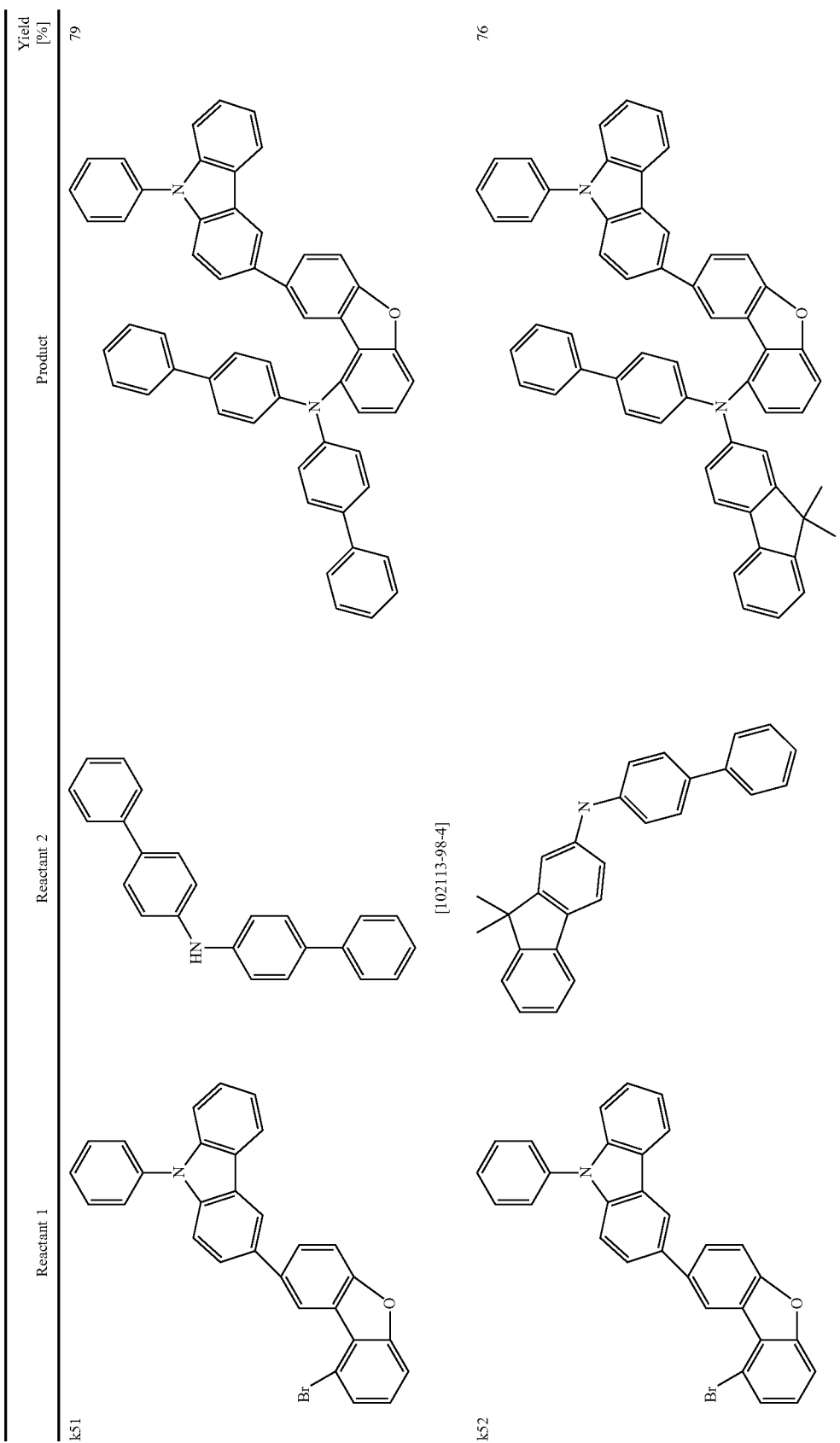

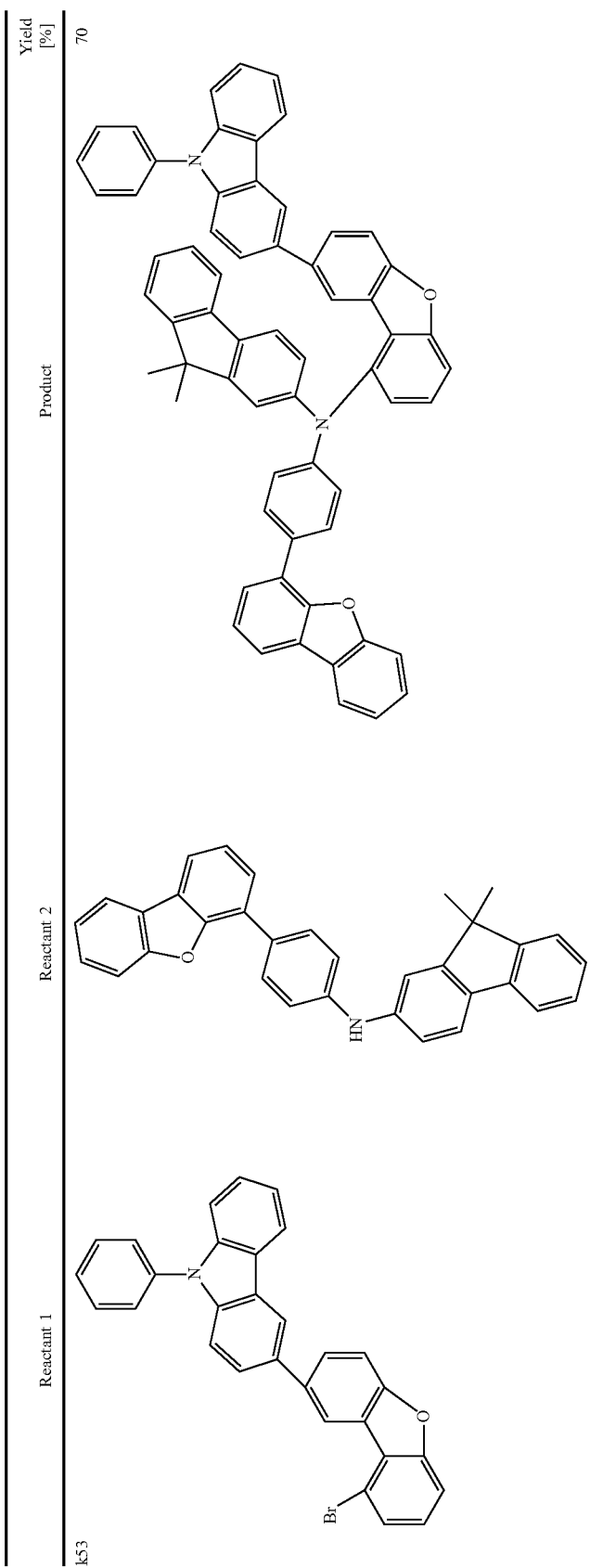
| | Reactant 1 | Reactant 2 | Product | Yield [%] |
|---|---|---|---|---|
| k53 | | | | 70 |

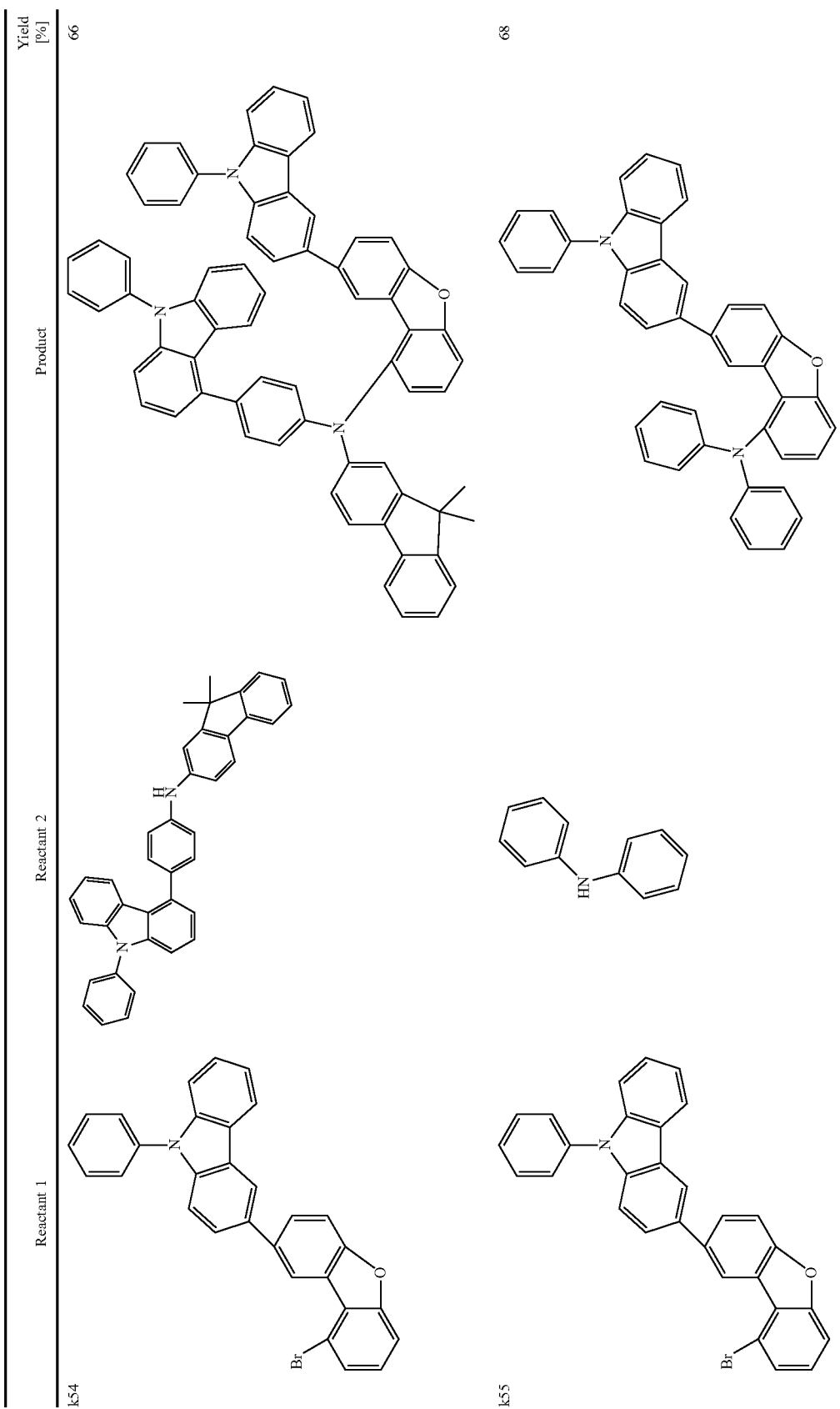

| | Reactant 1 | Reactant 2 | Product | Yield [%] |
|---|---|---|---|---|
| k56 | | | | 62 |
| k57 | | | | 59 |

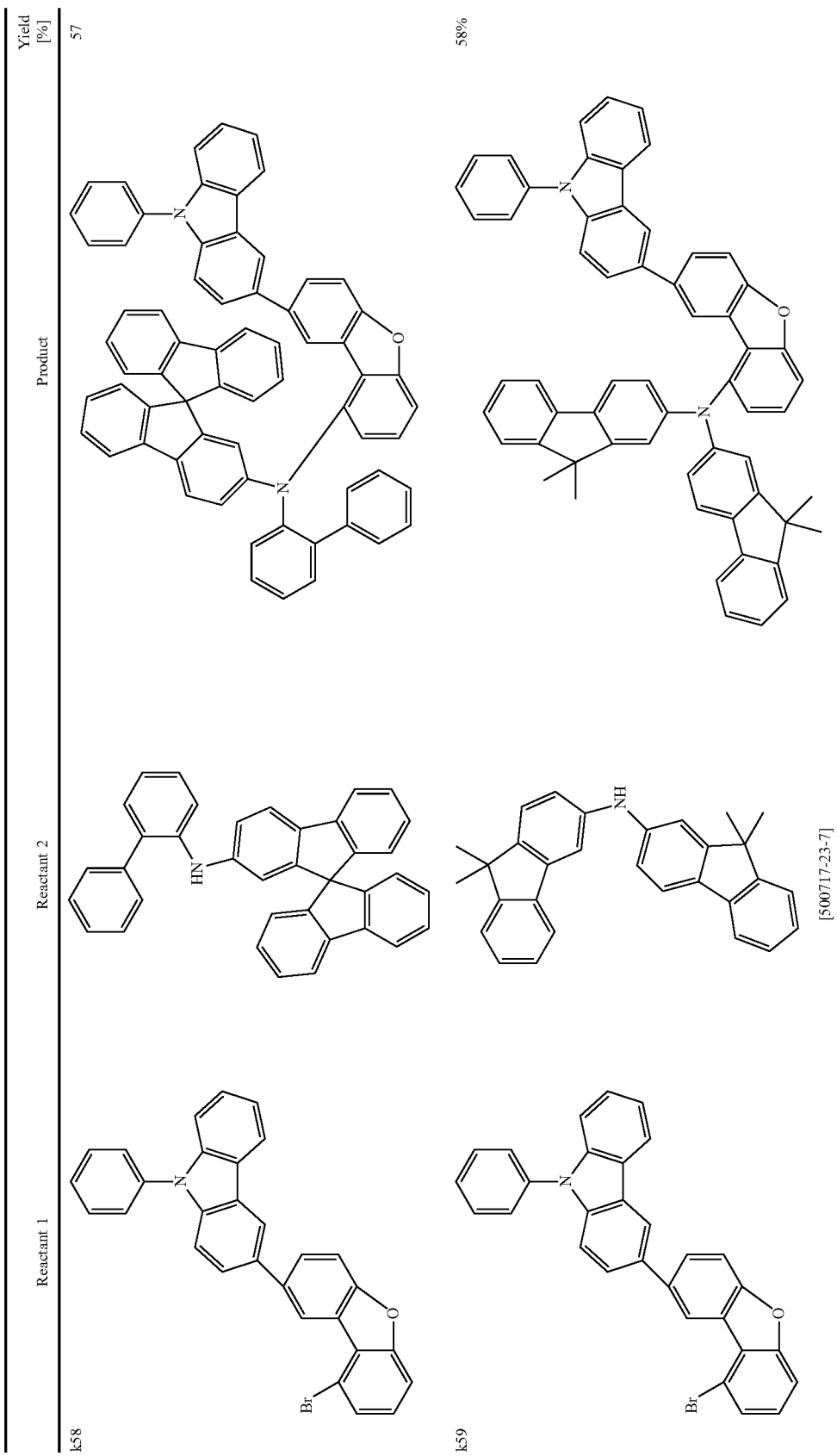

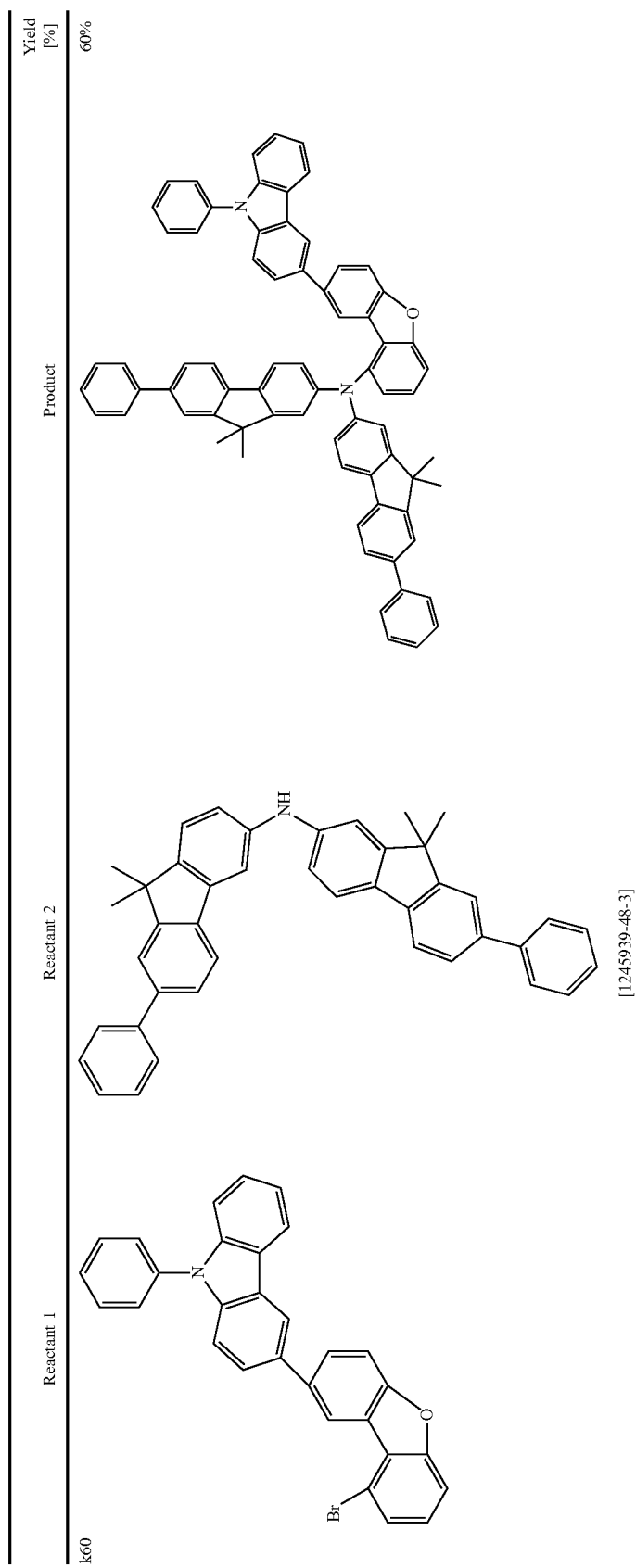

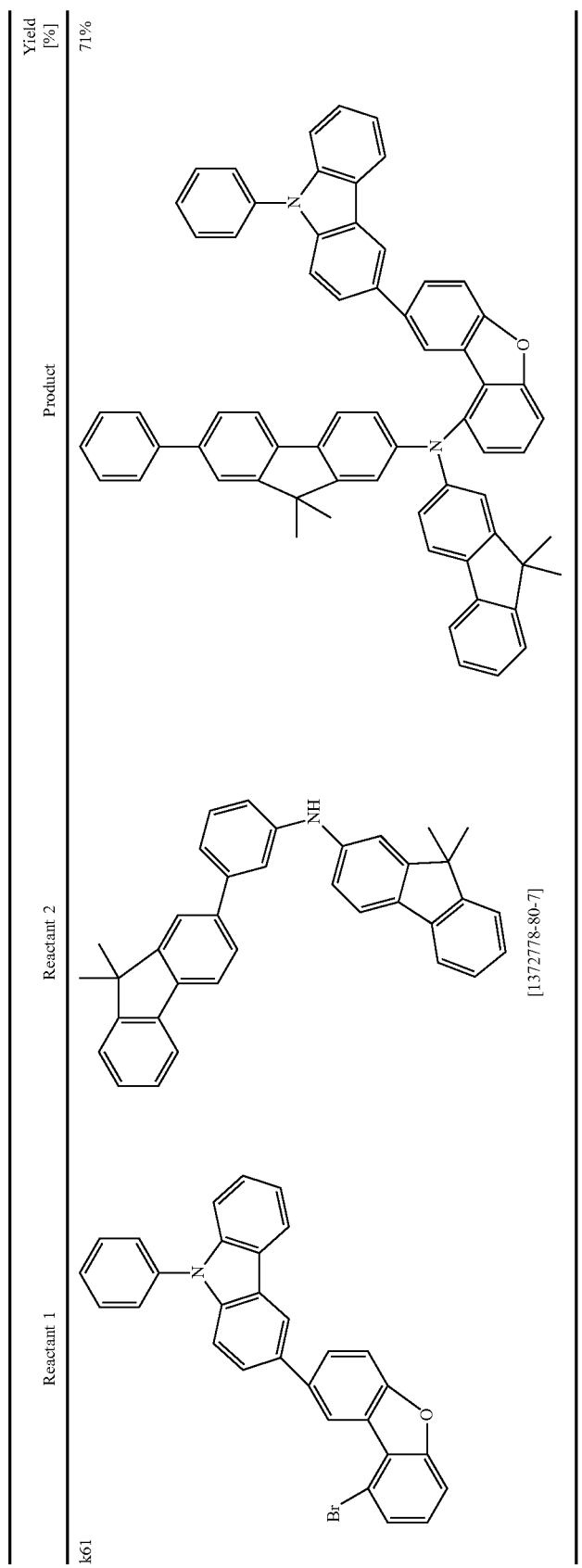

1) 8-(9-Phenyl-9H-carbazol-3-yl)dibenzofuran-1-boronic acid

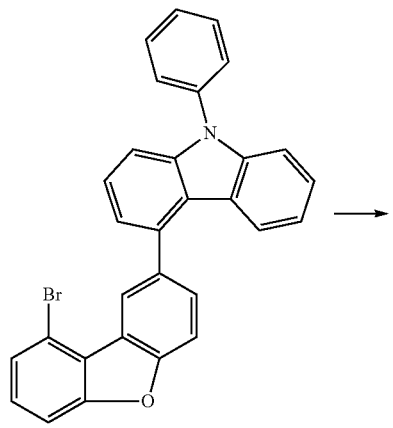

→

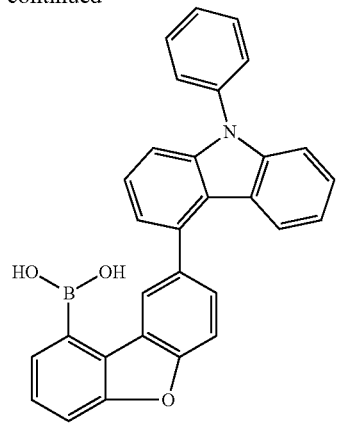

20 g (182 mmol) of 3-(9-bromodibenzofuran-2-yl)-9-phenyl-9H-carbazole are dissolved in 400 ml of dry THF and cooled to −78° C. At this temperature, 77 ml (190 mmol, 2.5 M in hexane) of n-butyllithium are added within about 5 min. and then the mixture is stirred at −78° C. for a further 2.5 h. At this temperature, 38 g (365 mmol) of trimethyl borate are added very rapidly and the reaction is allowed to come gradually to room temperature (about 18 h). The reaction solution is washed with water and the precipitated solids and the organic phase are subjected to azeotropic drying with toluene. The crude product is extracted by stirring from toluene/methylene chloride at about 40° C. and filtered off with suction. After cooling, 200 ml of water are added, the mixture is stirred for a further 30 min, the organic phase is removed and the latter is filtered through a short Celite bed and then the solvent is removed under reduced pressure. The residue is recrystallized five times from DMF and finally fractionally sublimed twice (p about $10^{-6}$ mbar, T=380-340° C.). Yield: 16.7 g (690 mmol), 90% of theory.

The following compounds are prepared in an analogous manner:

| | Reactant 1 | Product | Yield [%] |
|---|---|---|---|
| l1 | | | 84 | m) Biphenyl-4-yl(9,9-dimethyl-9H-fluoren-1-yl){4-[8-(9-phenyl-9H-carbazol-3-yl)dibenzofuran-1-yl]phenyl}amine
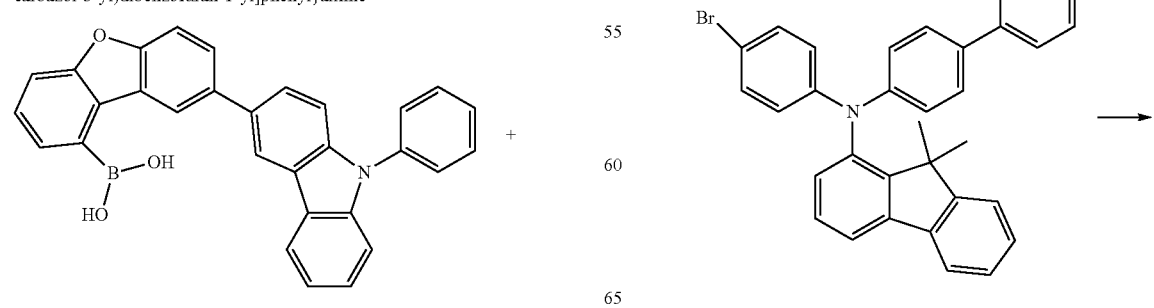

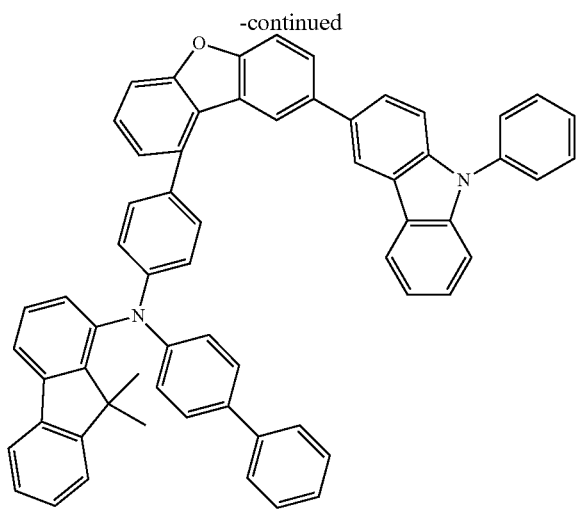

49.8 g (110.0 mmol) of 8-(9-phenyl-9H-carbazol-3-yl)dibenzofuran-1-boronic acid, 56 g (110.0 mmol) of biphenyl-4-yl(4-bromophenyl)(9,9-dimethyl-9H-fluoren-1-yl)-amine and 26 g (210.0 mmol) of sodium carbonate are suspended in 500 ml of ethylene glycol dimethyl ether and 500 ml of water. Added to this suspension are 913 mg (3.0 mmol) of tri-o-tolylphosphine and then 112 mg (0.5 mmol) of palladium(II) acetate, and the reaction mixture is heated under reflux for 16 h. After cooling, the organic phase is removed, filtered through silica gel, washed three times with 200 ml of water and then concentrated to dryness. The product is purified via column chromatography on silica gel with toluene/heptane (1:2) and finally sublimed under high vacuum (p=5×10$^{-7}$ mbar) (99.9% purity). The yield is 87 g (86 mmol), corresponding to 83% of theory.

The following compounds are prepared in an analogous manner:

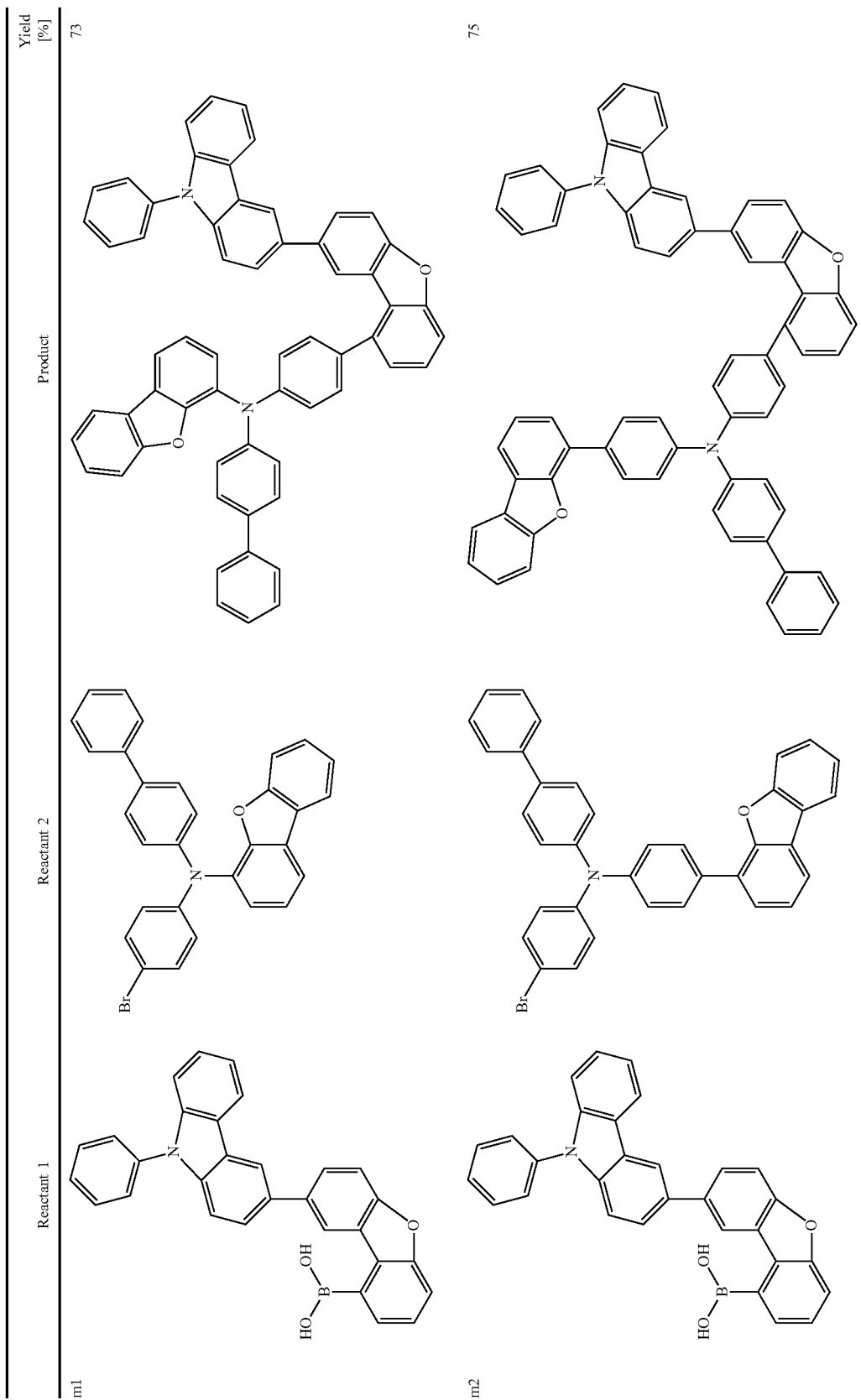

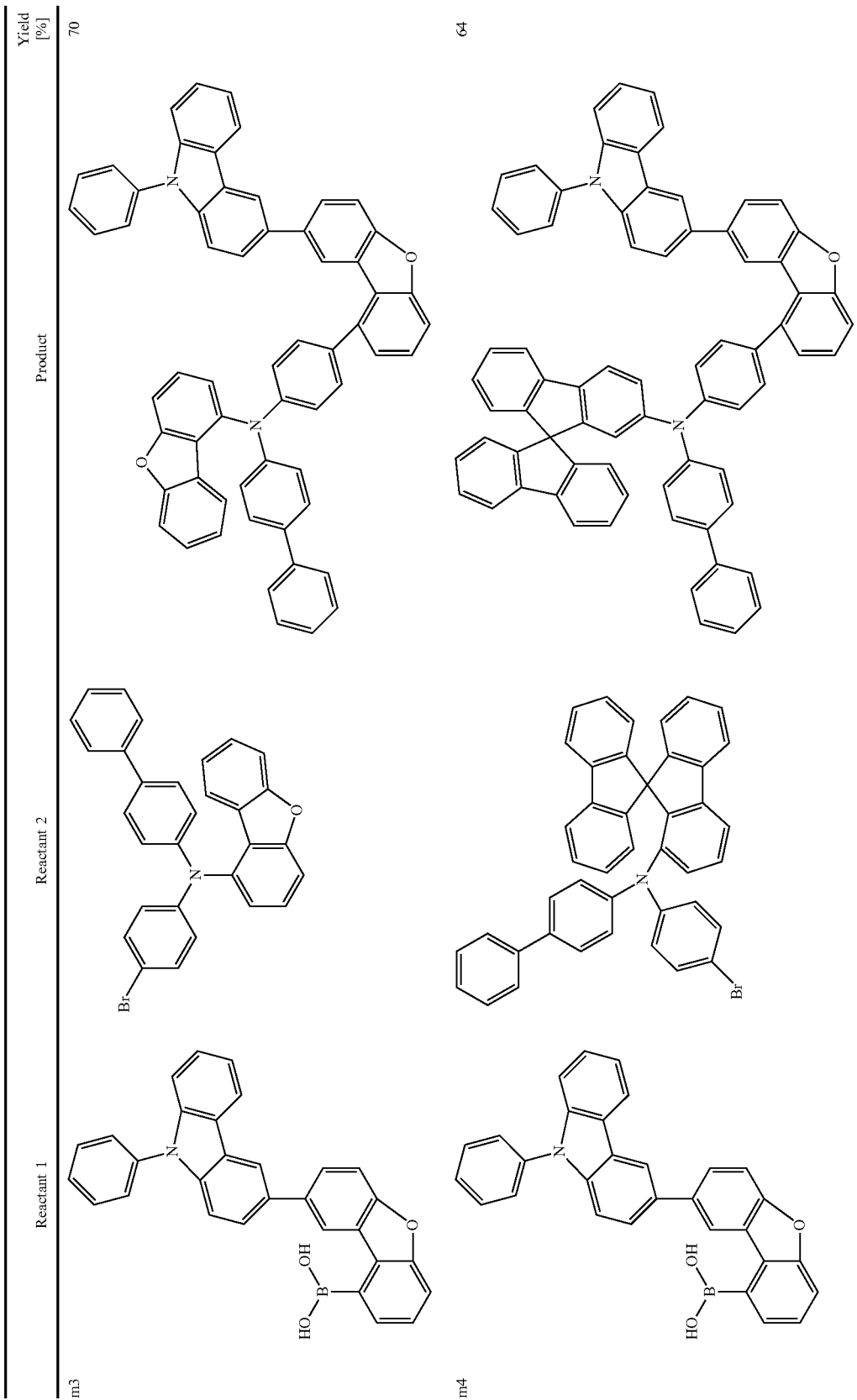

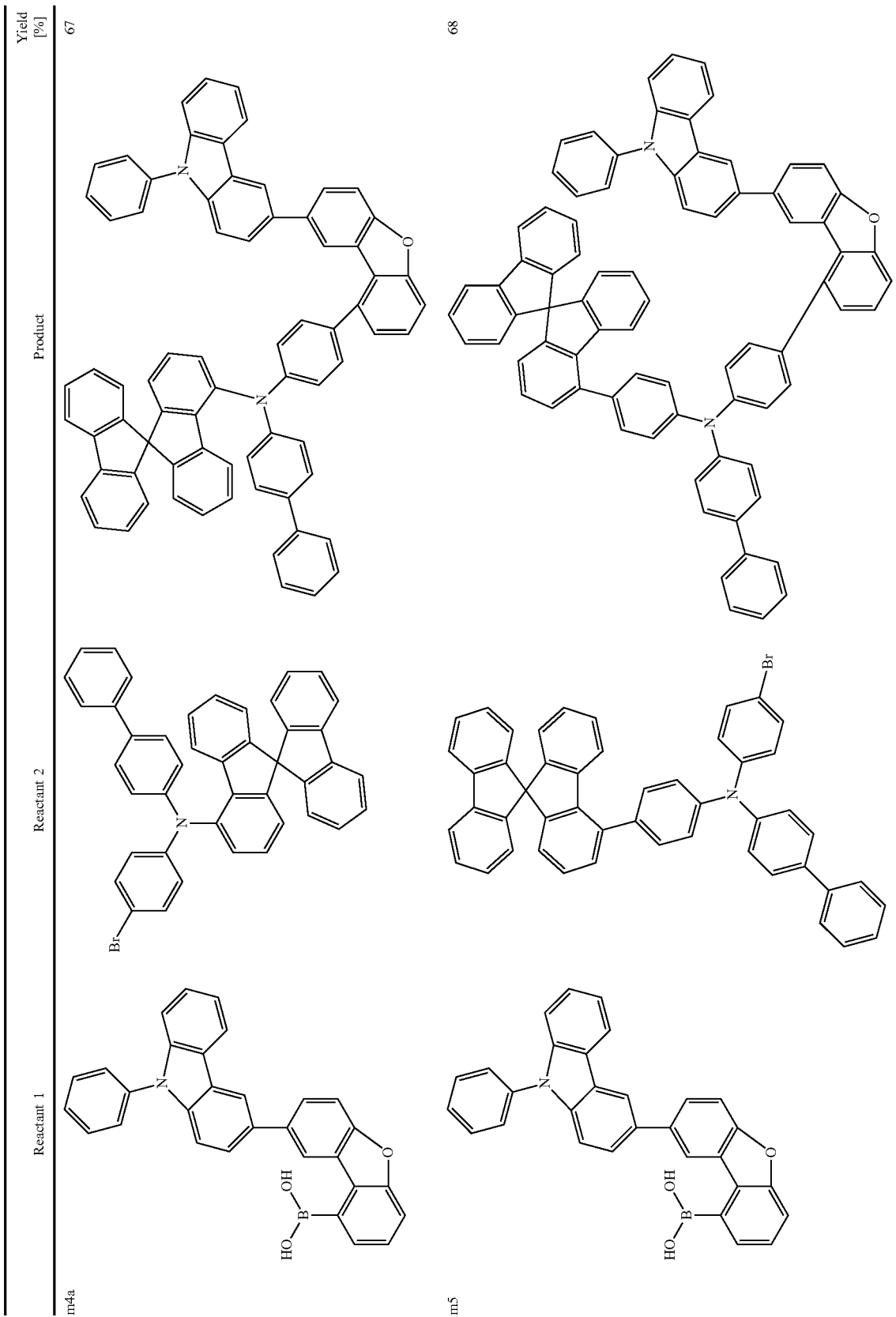

-continued

| Reactant 1 | Reactant 2 | Product | Yield [%] |
|---|---|---|---|
| m6 | | | 73 |
| m7 | | | 66 |

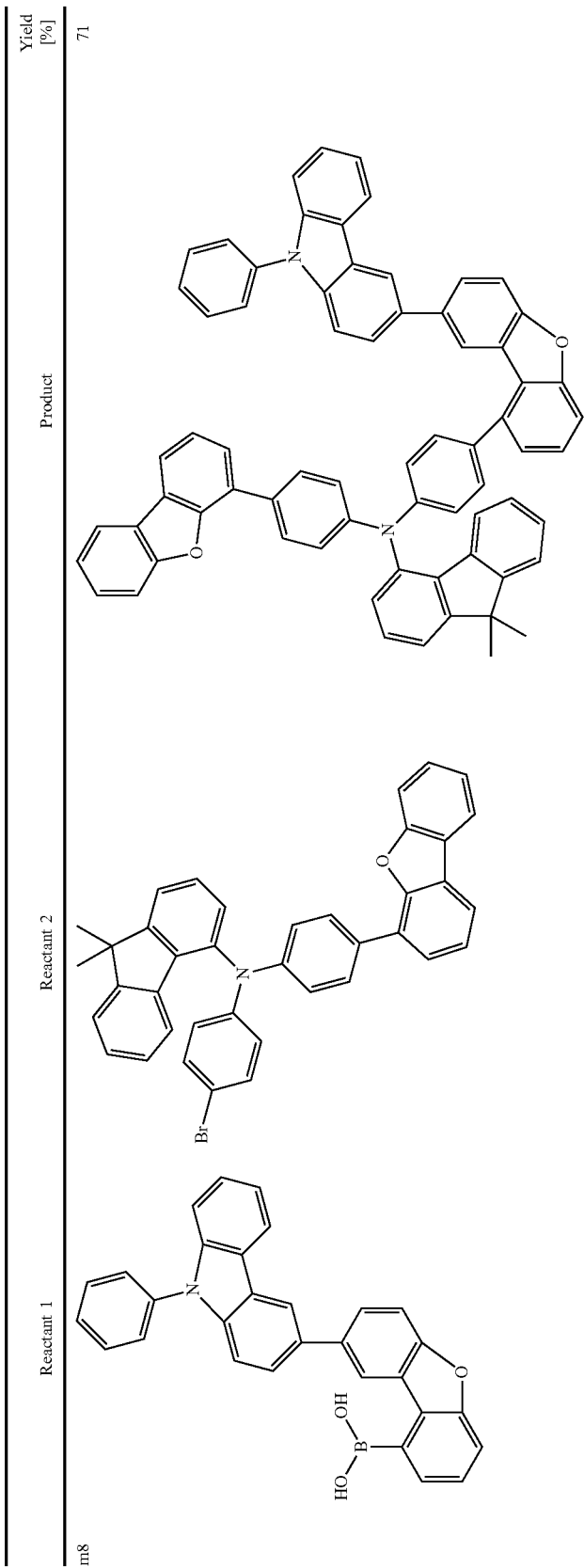

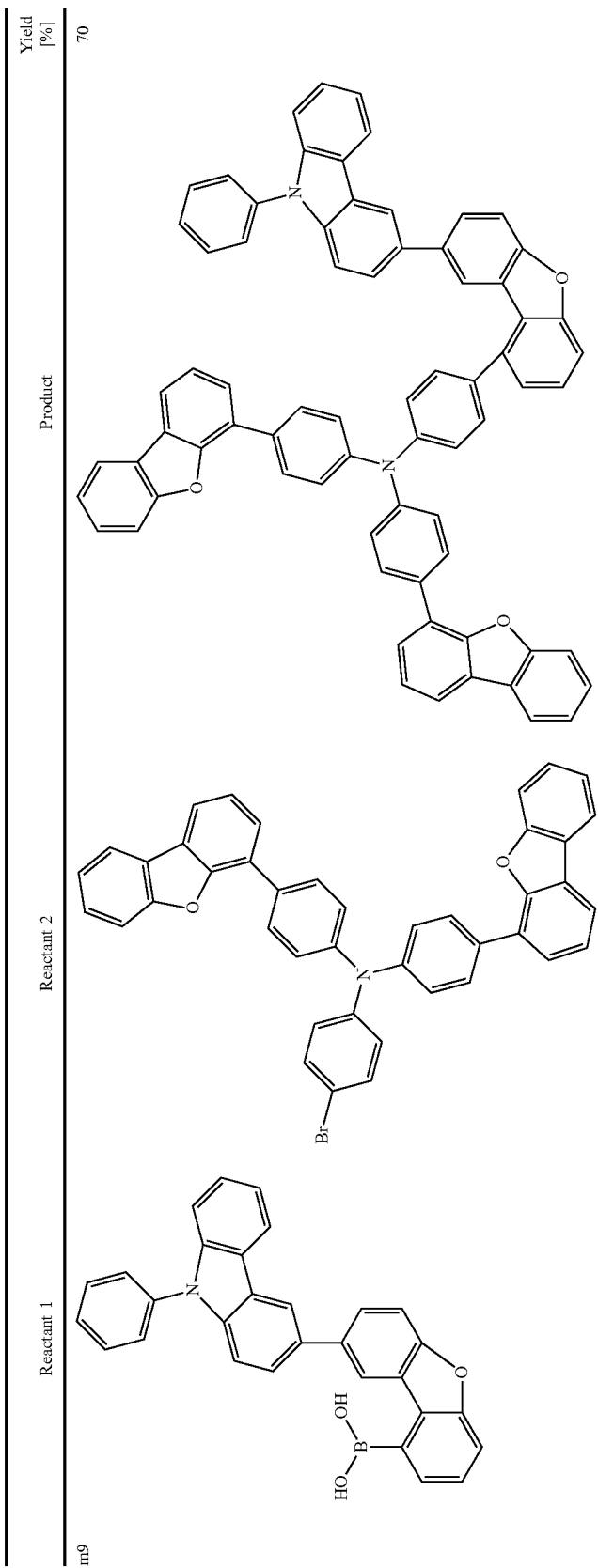

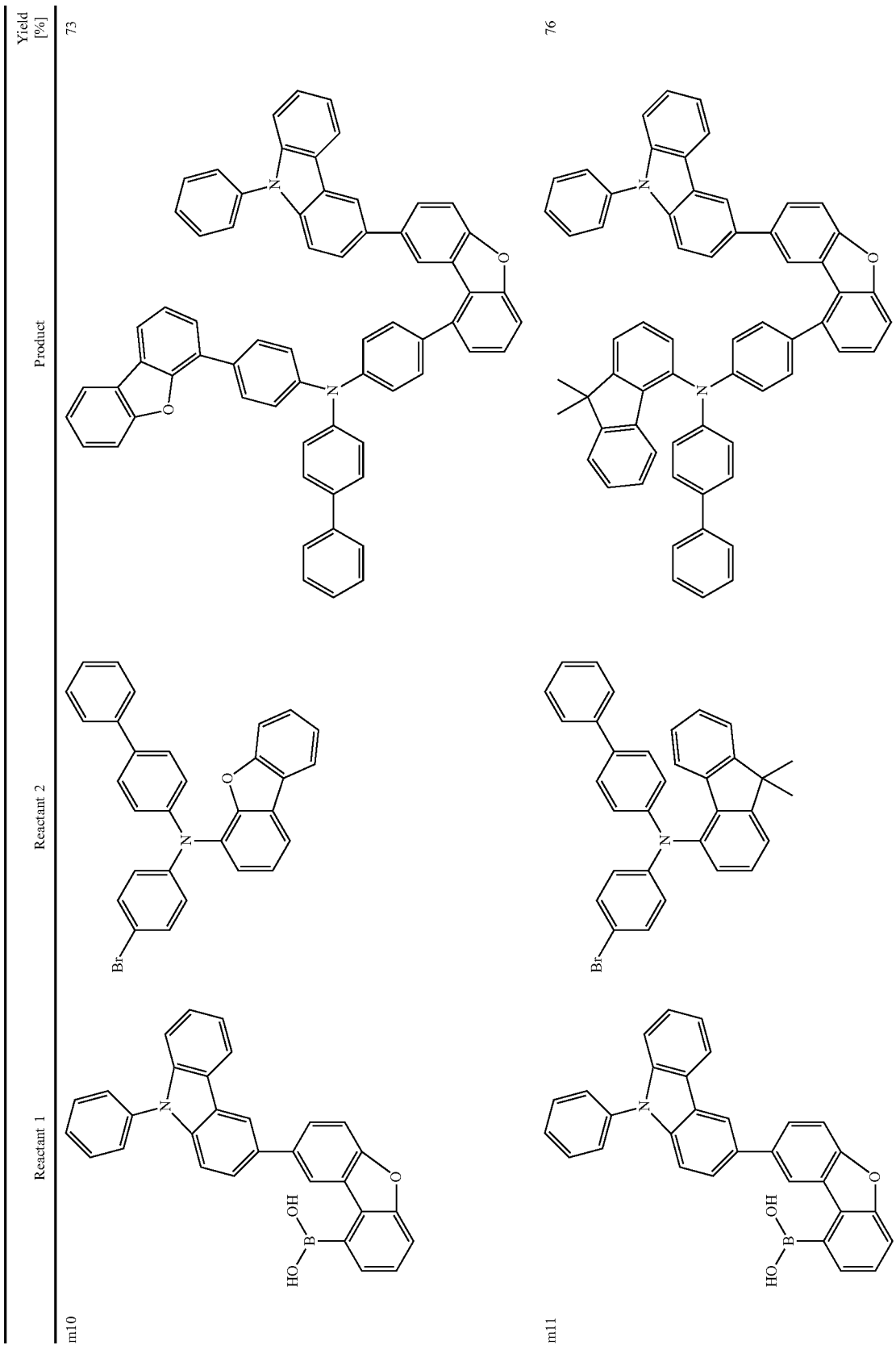

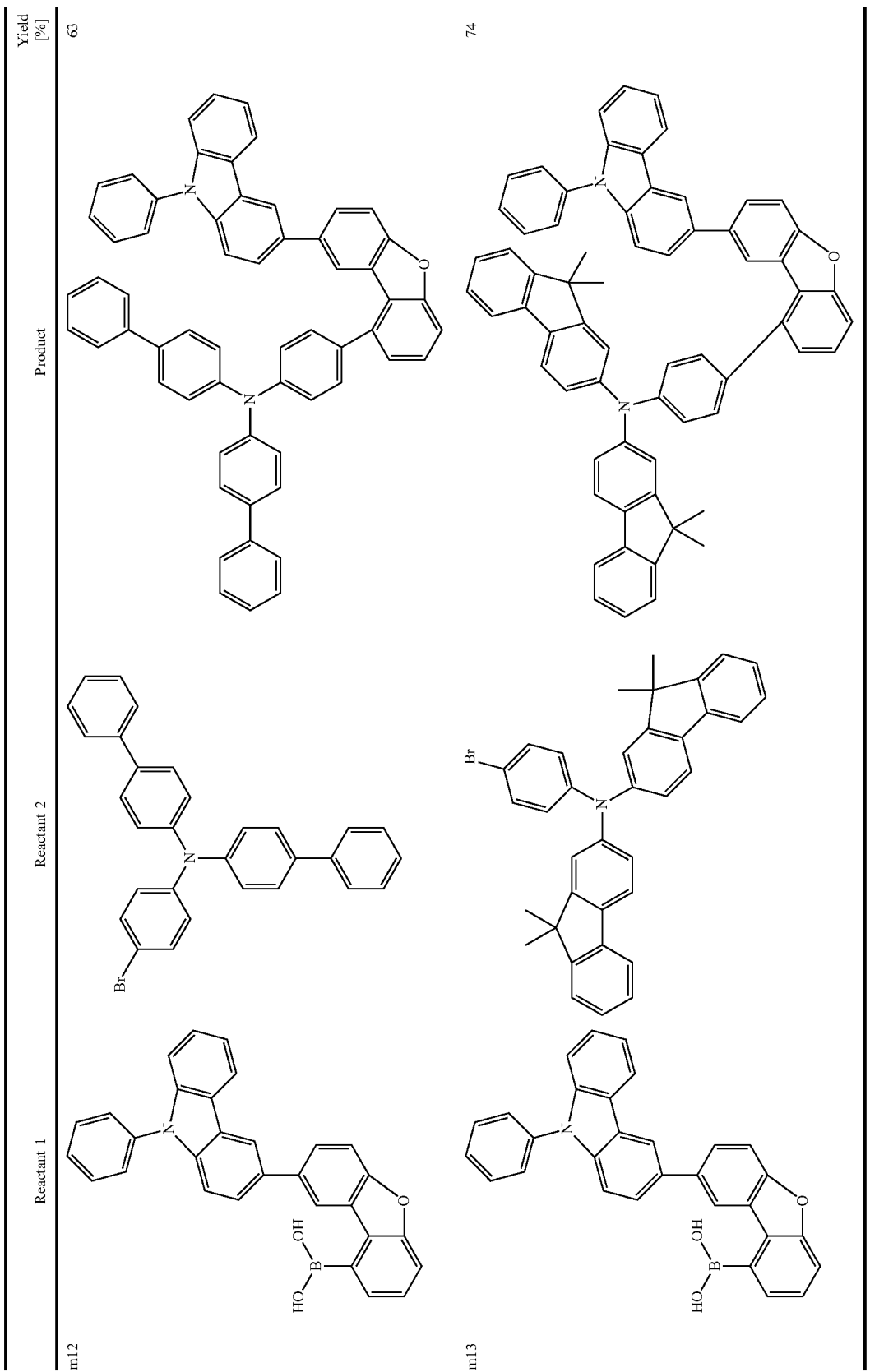

Production of the OLEDs

In Examples C1 to I10 which follow (see Tables 1 and 2), the data of various OLEDs are presented.

Pretreatment for Examples C1-I10: Glass plaques coated with structured ITO (indium tin oxide) of thickness 50 nm, prior to coating, are treated with an oxygen plasma, followed by an argon plasma. These plasma-treated glass plaques form the substrates to which the OLEDs are applied.

The OLEDs basically have the following layer structure: substrate/hole injection layer (HIL)/hole transport layer (HTL)/electron blacker layer (EBL) emission layer (EML)/ optional hole blacker layer (HBL)/electron transport layer (ETL)/optional electron injection layer (EIL) and finally a cathode. The cathode is formed by an aluminium layer of thickness 100 nm. The exact structure of the OLEDs can be found in Table 1. The materials required for production of the OLEDs are shown in Table 3.

All materials are applied by thermal vapour deposition in a vacuum chamber. In this case, the emission layer always consists of at least one matrix material (host material) and an emitting dopant (emitter) which is added to the matrix material(s) in a particular proportion by volume by co-evaporation. Details given in such a form as IC1:PA:TEG1 (55%:35%:10%) mean here that the material IC1 is present in the layer in a proportion by volume of 55%, PA in a proportion of 35% and TEG1 in a proportion of 10%. Analogously, the electron transport layer may also consist of a mixture of two materials.

The OLEDs are characterized in a standard manner. For this purpose, the electroluminescence spectra, the voltage and the external quantum efficiency (EQE, measured in percent) are determined as a function of luminance, calculated from current-voltage-luminance characteristics (IUL characteristics) assuming Lambertian radiation characteristics, and the lifetime. The electroluminescence spectra are determined at a luminance of 1000 cd/m$^2$. The parameter U1000 in Table 2 refers here to the voltage which is required for a luminance of 1000 cd/m$^2$, and the CIE 1931 x and y colour coordinates are calculated therefrom. SE1000 refers to the power efficiency which is achieved at 1000 cd/m$^2$. Finally, EQE1000 refers to the external quantum efficiency at an operating luminance of 1000 cd/m$^2$.

The data for the various OLEDs are collated in Table 2. Examples C1 to C4 are comparative examples according to the prior art; Examples I1-I10 show data of OLEDs of the invention.

Some of the examples are elucidated in detail hereinafter, in order to illustrate the advantages of the OLEDs of the invention.

Use of Mixtures of the Invention in the Emission Layer of Phosphorescent OLEDs

The materials of the invention, when used as matrix material in combination with an electron-conducting compound (for example compound IC5 in the examples used below) in the emission layer (EML) in phosphorescent OLEDs, give rise to significant improvements over the prior art, particularly with regard to the external quantum efficiency of the OLEDs. Through use of the inventive compounds K55 and K59, it is possible to observe an improvement in the EQE by about 5-10% compared to the compounds from the prior art PA1, PA2, PA3 and PA4 (comparison of examples C1, C2 and C3 with example I1 and comparison of C4 with I2).

TABLE 1

Structure of the OLEDs

| Ex. | HIL thickness | HTL thickness | EBL thickness | EML thickness | HBL thickness | ETL thickness | EIL thickness |
|---|---|---|---|---|---|---|---|
| C1 | HATCN 5 nm | SpMA1 230 nm | SpMA3 20 nm | IC5:SdT1:TEG2 (40%:50%:10%) 30 nm | — | ST2:LiQ (50%:50%) 40 nm | — |
| C2 | HATCN 5 nm | SpMA1 230 nm | SpMA3 20 nm | IC5:SdT2:TEG2 (40%:50%:10%) 30 nm | — | ST2:LiQ (50%:50%) 40 nm | — |
| C3 | HATCN 5 nm | SpMA1 230 nm | SpMA3 20 nm | IC5:SdT3:TEG2 (40%:50%:10%) 30 nm | — | ST2:LiQ (50%:50%) 40 nm | — |
| C4 | HATCN 5 nm | SpMA1 230 nm | SpMA3 20 nm | IC5:SdT4:TEG2 (40%:50%:10%) 30 nm | — | ST2:LiQ (50%:50%) 40 nm | — |
| I1 | HATCN 5 nm | SpMA1 230 nm | SpMA3 20 nm | IC5:K55:TEG2 (40%:50%:10%) 30 nm | — | ST2:LiQ (50%:50%) 40 nm | — |
| I2 | HATCN 5 nm | SpMA1 230 nm | SpMA3 20 nm | IC5:K59:TEG2 (40%:50%:10%) 30 nm | — | ST2:LiQ (50%:50%) 40 nm | — |
| I3 | HATCN 5 nm | SpMA1 240 nm | K51 10 nm | IC5:IC3:TEG2 (60%:40%:10%) 30 nm | — | ST2:LiQ (50%:50%) 40 nm | — |
| I4 | HATCN 5 nm | SpMA1 230 nm | SpMA3 20 nm | IC5:K52:TEG2 (40%:45%:15%) 30 nm | — | ST2:LiQ (50%:50%) 40 nm | — |
| I5 | HATCN 5 nm | SpMA1 230 nm | SpMA3 20 nm | IC5:K47:TEG2 (40%:45%:15%) 30 nm | — | ST2:LiQ (50%:50%) 40 nm | — |
| I6 | HATCN 5 nm | SpMA1 240 nm | K53 10 nm | IC5:IC3:TEG2 (60%:40%:10%) 30 nm | — | ST2:LiQ (50%:50%) 40 nm | — |
| I7 | HATCN 5 nm | SpMA1 230 nm | SpMA3 20 nm | IC5:K54:TEG2 (40%:45%:15%) 30 nm | — | ST2:LiQ (50%:50%) 40 nm | — |

TABLE 1-continued

Structure of the OLEDs

| Ex. | HIL thickness | HTL thickness | EBL thickness | EML thickness | HBL thickness | ETL thickness | EIL thickness |
|---|---|---|---|---|---|---|---|
| I8 | HATCN 5 nm | SpMA1 230 nm | SpMA3 20 nm | IC5:K55:TEG2 (40%:50%:10%) 30 nm | — | ST2:LiQ (50%:50%) 40 nm | — |
| I9 | HATCN 5 nm | SpMA1 240 nm | M13 10 nm | IC5:IC3:TEG2 (60%:40%:10%) 30 nm | — | ST2:LiQ (50%:50%) 40 nm | — |
| I10 | HATCN 5 nm | SpMA1 240 nm | M12 10 nm | IC5:IC3:TEG2 (60%:40%:10%) 30 nm | — | ST2:LiQ (50%:50%) 40 nm | — |

TABLE 2

Data of the OLEDs

| Ex. | U1000 (V) | SE1000 (cd/A) | EQE 1000 | CIE x/y at 1000 cd/m² |
|---|---|---|---|---|
| C1 | 3.4 | 62 | 16.4% | 0.33/0.63 |
| C2 | 3.3 | 59 | 16.1% | 0.32/0.63 |
| C3 | 3.5 | 58 | 15.6% | 0.34/0.62 |
| C4 | 3.6 | 59 | 16.0% | 0.33/0.63 |
| I1 | 3.3 | 64 | 17.3% | 0.33/0.63 |
| I2 | 3.7 | 63 | 17.2% | 0.33/0.63 |
| I3 | 3.3 | 54 | 14.6% | 0.34/0.63 |
| I4 | 3.3 | 63 | 16.8% | 0.33/0.63 |
| I5 | 3.5 | 63 | 16.9% | 0.33/0.63 |
| I6 | 3.2 | 56 | 14.9% | 0.32/0.63 |
| I7 | 3.4 | 62 | 16.7% | 0.33/0.63 |
| I8 | 3.3 | 64 | 17.5% | 0.32/0.64 |
| I9 | 3.1 | 56 | 15.1% | 0.33/0.63 |
| I10 | 3.3 | 56 | 15.2% | 0.32/0.63 |

TABLE 3

Structural formulae of the materials for the OLEDs

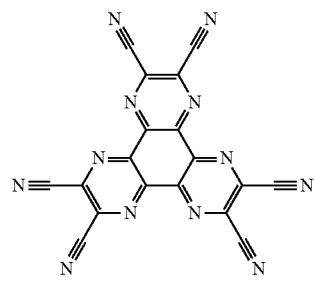

HATCN

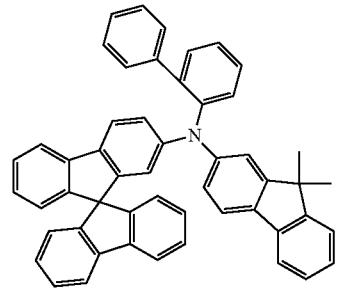

SpMA1

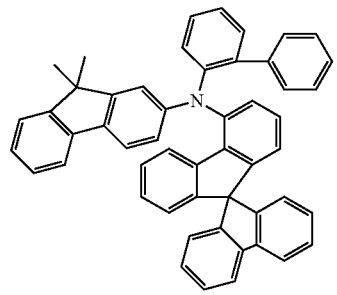

SpMA3

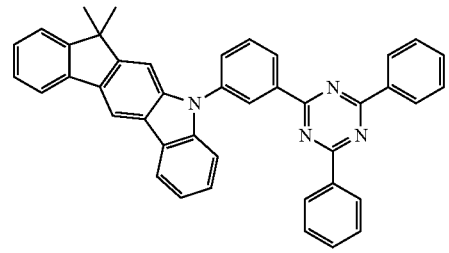

IC5

TABLE 3-continued
Structural formulae of the materials for the OLEDs
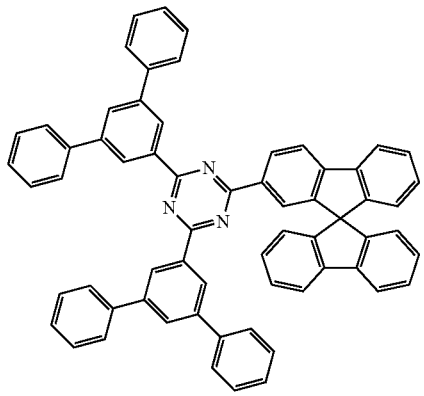
ST2
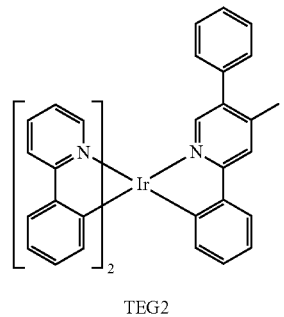
TEG2
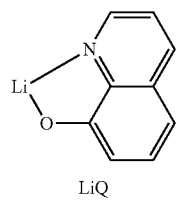
LiQ
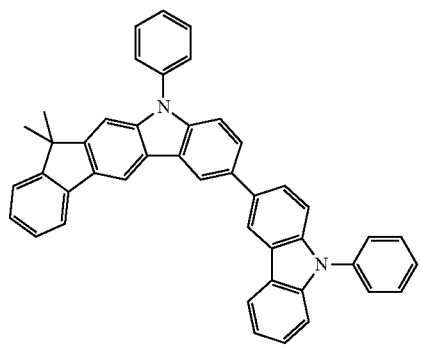
IC3
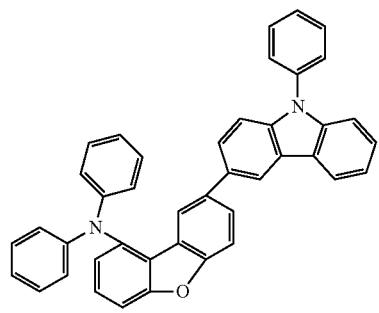
K55
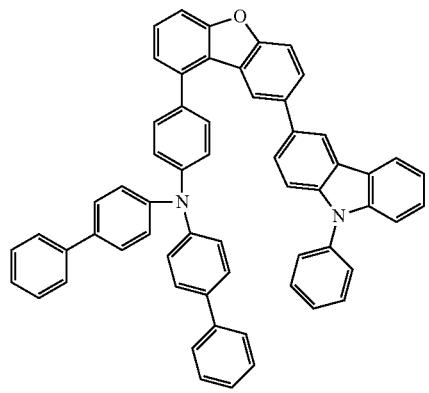
M12

TABLE 3-continued
Structural formulae of the materials for the OLEDs
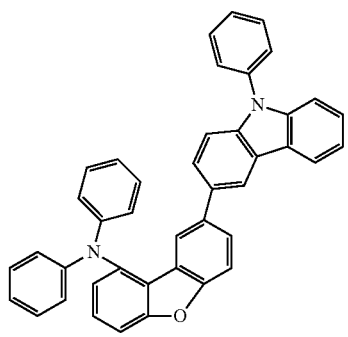
JP 2012-049518
PA1
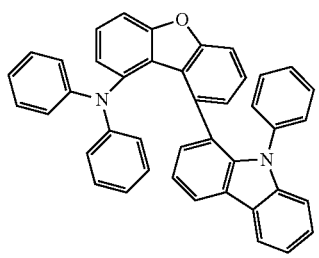
JP 2012-049518
PA2
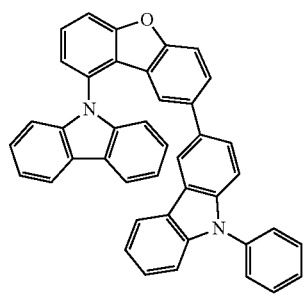
JP 2012-049518
PA3
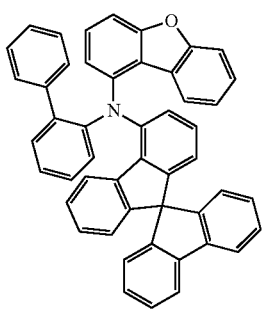
WO 2013/120577
PA4
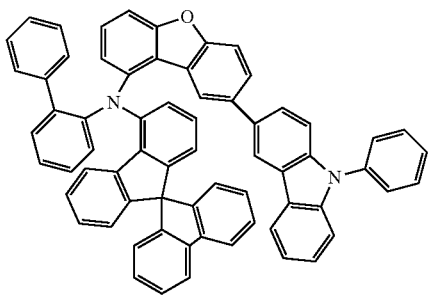
K59
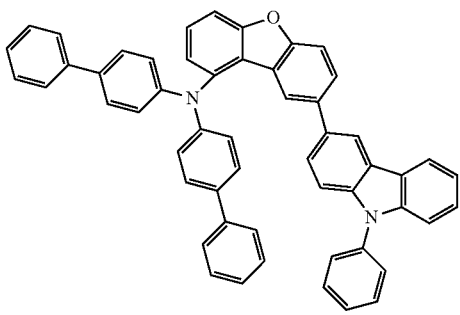
K51
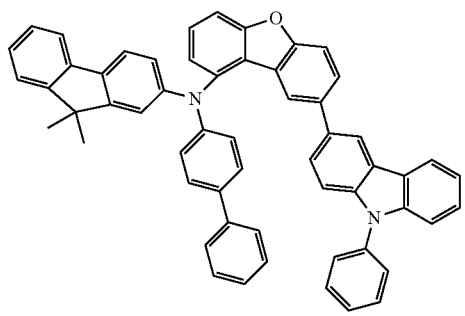
K52
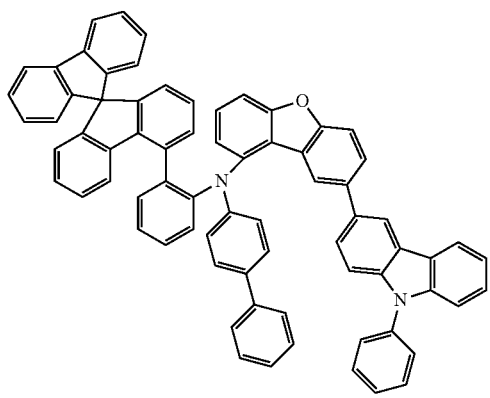
K47

TABLE 3-continued
Structural formulae of the materials for the OLEDs
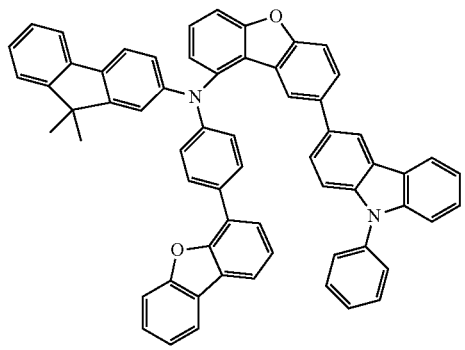
K53
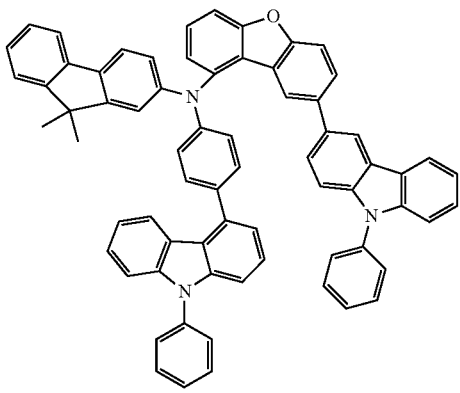
K54
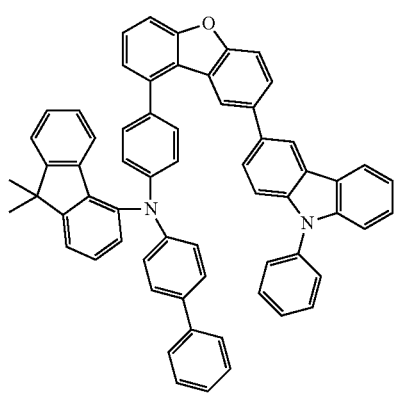
K16
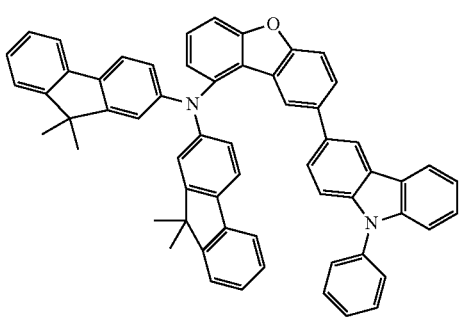
M13
The invention claimed is:
1. A compound of formula (1) or formula (2)
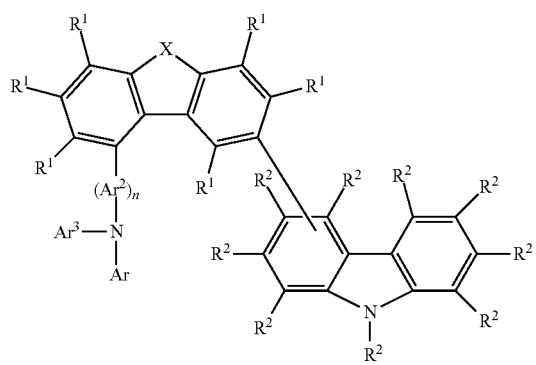
Formula (1)
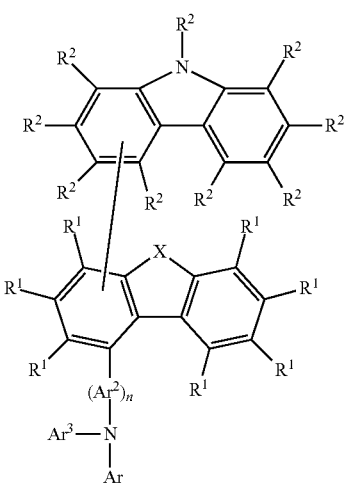
Formula (2)
where the symbols used are as follows:
X is O or S;
Ar is an aromatic or heteroaromatic ring system which has 5 to 40 aromatic ring atoms and may be substituted by one or more R radicals;

Ar¹ is the same or different at each instance and is an aromatic or heteroaromatic ring system which has 5 to 40 aromatic ring atoms and may be substituted by one or more R⁴ radicals;

Ar² is a divalent aromatic or heteroaromatic ring system which has 5 to 40 aromatic ring atoms and may be substituted by one or more R radicals;

Ar³ is an aromatic or heteroaromatic ring system which has 5 to 40 aromatic ring atoms and may be substituted by one or more R radicals;

R is the same or different at each instance and is selected from the group consisting of H, D, F, Cl, Br, I, CN, NO₂, C(=O)Ar¹, C(=O)R⁴, P(=O)(Ar¹)₂, P(Ar¹)₂, B(Ar¹)₂, N(R⁴)₂, N(Ar¹)₂, a straight-chain alkyl, alkoxy or thioalkyl group having 1 to 20 carbon atoms or a branched or cyclic alkyl, alkoxy or thioalkyl group having 3 to 20 carbon atoms or an alkenyl group having 2 to 20 carbon atoms, each of which may be substituted by one or more R⁴ radicals, where one or more nonadjacent CH₂ groups may be replaced by R⁴C=CR⁴, C=O, C=S, C=NR⁴, P(=O)(R⁴), SO, SO₂, NR⁴, O, S or CONR⁴ and where one or more hydrogen atoms may be replaced by D, F, Cl, Br, I, CN or NO₂, an aromatic or heteroaromatic ring system which has 5 to 40 aromatic ring atoms and may be substituted in each case by one or more R⁴ radicals, an aryloxy or heteroaryloxy group which has 5 to 40 aromatic ring atoms and may be substituted by one or more R⁴ radicals, or an aralkyl or heteroaralkyl group which has 5 to 40 aromatic ring atoms and may be substituted by one or more R⁴ radicals; at the same time, it is optionally possible for two R substituents bonded to the same carbon atom or to adjacent carbon atoms to form a monocyclic or polycyclic aliphatic or aromatic ring system which may be substituted by one or more R⁴ radicals;

R¹ is the same or different at each instance and is selected from the group consisting of H, D, F, Cl, Br, I, CN, NO₂, C(=O)Ar¹, C(=O)R⁴, P(=O)(Ar¹)₂, P(Ar¹)₂, B(Ar¹)₂, a straight-chain alkyl, alkoxy or thioalkyl group having 1 to 20 carbon atoms or a branched or cyclic alkyl, alkoxy or thioalkyl group having 3 to 20 carbon atoms or an alkenyl group having 2 to 20 carbon atoms, each of which may be substituted by one or more R⁴ radicals, where one or more nonadjacent CH₂ groups may be replaced by R⁴C=CR⁴, C=O, C=S, C=NR⁴, P(=O)(R⁴), SO, SO₂, NR⁴, O, S or CONR⁴ and where one or more hydrogen atoms may be replaced by D, F, Cl, Br, I, CN or NO₂, an aromatic or heteroaromatic ring system which has 5 to 40 aromatic ring atoms and may be substituted in each case by one or more R⁴ radicals, an aryloxy or heteroaryloxy group which has 5 to 40 aromatic ring atoms and may be substituted by one or more R⁴ radicals, or an aralkyl or heteroaralkyl group which has 5 to 40 aromatic ring atoms and may be substituted by one or more R⁴ radicals; at the same time, it is optionally possible for two R¹ substituents bonded to adjacent carbon atoms to form a monocyclic or polycyclic, aliphatic, aromatic or heteroaromatic ring system which may be substituted by one or more R⁴ radicals;

R² is the same or different at each instance and is selected from the group consisting of H, D, F, Cl, Br, I, CN, NO₂, C(=O)Ar¹, C(=O)R⁴, P(=O)(Ar¹)₂, P(Ar¹)₂, B(Ar¹)₂, N(R⁴)₂, a straight-chain alkyl, alkoxy or thioalkyl group having 1 to 20 carbon atoms or a branched or cyclic alkyl, alkoxy or thioalkyl group having 3 to 20 carbon atoms or an alkenyl group having 2 to 20 carbon atoms, each of which may be substituted by one or more R⁴ radicals, where one or more nonadjacent CH₂ groups may be replaced by R⁴C=CR⁴, C=O, C=S, C=NR⁴, P(=O)(R⁴), SO, SO₂, NR⁴, O, S or CONR⁴ and where one or more hydrogen atoms may be replaced by D, F, Cl, Br, I, CN or NO₂, an aromatic or heteroaromatic ring system which has 5 to 40 aromatic ring atoms and may be substituted in each case by one or more R⁴ radicals, an aryloxy or heteroaryloxy group which has 5 to 40 aromatic ring atoms and may be substituted by one or more R⁴ radicals, or an aralkyl or heteroaralkyl group which has 5 to 40 aromatic ring atoms and may be substituted by one or more R⁴ radicals; at the same time, it is optionally possible for two R² substituents bonded to adjacent carbon atoms to form a monocyclic or polycyclic, aliphatic, aromatic or heteroaromatic ring system which may be substituted by one or more R⁴ radicals;

R⁴ is the same or different at each instance and is selected from the group consisting of H, D, F, Cl, Br, I, CN, NO₂, N(R⁵)₂, C(=O)R⁵, a straight-chain alkyl, alkoxy or thioalkyl group having 1 to 20 carbon atoms or a branched or cyclic alkyl, alkoxy or thioalkyl group having 3 to 20 carbon atoms or an alkenyl group having 2 to 20 carbon atoms, each of which may be substituted by one or more R⁵ radicals, where one or more nonadjacent CH₂ groups may be replaced by R⁵C=CR⁵, C=O, C=S, C=NR⁵, P(=O)(R⁵), SO, SO₂, NR⁵, O, S or CONR⁵ and where one or more hydrogen atoms may be replaced by D, F, Cl, Br, I, CN or NO₂, an aromatic or heteroaromatic ring system which has 5 to 40 aromatic ring atoms and may be substituted in each case by one or more R⁵ radicals, an aryloxy or heteroaryloxy group which has 5 to 40 aromatic ring atoms and may be substituted by one or more R⁵ radicals, or an aralkyl or heteroaralkyl group which has 5 to 40 aromatic ring atoms and may be substituted by one or more R⁵ radicals; at the same time, it is optionally possible for two R⁴ substituents bonded to the same carbon atom or adjacent carbon atoms to form a monocyclic or polycyclic, aliphatic, aromatic or heteroaromatic ring system which may be substituted by one or more R⁵ radicals;

R⁵ is the same or different at each instance and is selected from the group consisting of H, D, F, CN, an aliphatic hydrocarbyl radical having 1 to 20 carbon atoms, or an aromatic or heteroaromatic ring system having 5 to 30 aromatic ring atoms in which one or more hydrogen atoms may be replaced by D, F, Cl, Br, I or CN and which may be substituted by one or more alkyl groups each having 1 to 4 carbon atoms; at the same time, it is possible for two or more adjacent R⁵ substituents together to form a mono- or polycyclic, aliphatic ring system;

n is 0 or 1;

where one R² in formula (1) and one R² and one R¹ bonded to a carbon atom in formula (2) are replaced by the single bond.

2. The compound according to claim 1, wherein the compound is a compound of the formula (1-1) or formula (2-1)

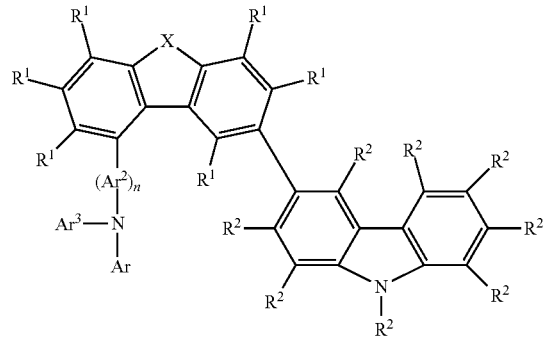

Formula (1-1)

Formula (2-1)

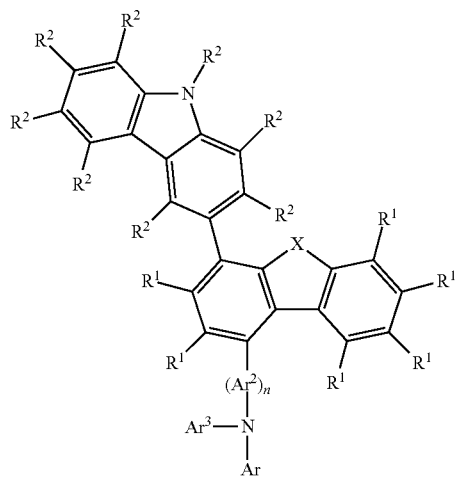

where the indices and symbols have the definitions given in claim 1.

3. A mixture comprising at least one compound according to claim 1 and at least one further compound and/or at least one solvent.

4. A method comprising utilizing the compound according to claim 1 or the mixture according to claim 3 in an electronic device.

5. An electronic device comprising at least one compound according to claim 1 or a mixture according to claim 3.

6. The electronic device according to claim 5, wherein it is an organic electroluminescent device.

7. The electronic device according to claim 6, wherein the compound according to claim 1 is used in an emitting layer, preferably in combination with a phosphorescent dopant and optionally one or more further matrix materials, or in a hole transport layer or in an electron blocker layer.

\* \* \* \* \*